(12) United States Patent
Hong et al.

(10) Patent No.: US 7,923,457 B2
(45) Date of Patent: *Apr. 12, 2011

(54) QUINOLINE DERIVATIVES

(75) Inventors: Yufeng Hong, San Diego, CA (US); Robert Steven Kania, San Diego, CA (US)

(73) Assignee: Agouron Pharmaceuticals Inc., San Diego, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 12/058,983

(22) Filed: Mar. 31, 2008

(65) Prior Publication Data

US 2009/0069316 A1  Mar. 12, 2009

Related U.S. Application Data

(63) Continuation of application No. 11/015,508, filed on Dec. 16, 2004, now Pat. No. 7,381,824.

(60) Provisional application No. 60/532,725, filed on Dec. 23, 2003.

(51) Int. Cl.
  *A61K 31/04* (2006.01)
  *C07D 215/38* (2006.01)

(52) U.S. Cl. .................................. 514/312; 546/153

(58) Field of Classification Search .................. 546/153, 546/159, 160; 514/312
See application file for complete search history.

(56) References Cited

U.S. PATENT DOCUMENTS

| | | | |
|---|---|---|---|
| 3,376,195 | A | 4/1968 | Allais et al. |
| 3,755,332 | A | 8/1973 | Wasley et al. |
| 3,936,461 | A | 2/1976 | Schwender et al. |
| 4,421,920 | A | 12/1983 | Baudouin et al. |
| 4,764,454 | A | 8/1988 | Ichijima et al. |
| 5,792,783 | A | 8/1998 | Tang et al. |
| 5,834,504 | A | 11/1998 | Tang et al. |
| 5,883,113 | A | 3/1999 | Tang et al. |
| 5,886,020 | A | 3/1999 | Tang et al. |
| 6,071,935 | A | 6/2000 | Lyssikatos |
| 6,143,764 | A | 11/2000 | Kubo et al. |
| 6,225,318 | B1 | 5/2001 | Sobolov-Jaynes et al. |
| 6,492,383 | B1 | 12/2002 | Munchhof et al. |
| 6,797,823 | B1 | 9/2004 | Kubo et al. |
| 7,381,824 | B2 * | 6/2008 | Hong et al. .............. 546/160 |
| 2004/0053908 | A1 | 3/2004 | Funahashi et al. |
| 2004/0132727 | A1 | 7/2004 | Sakai et al. |
| 2004/0209905 | A1 | 10/2004 | Kubo et al. |
| 2005/0049264 | A1 | 3/2005 | Miwa et al. |
| 2005/0187236 | A1 | 8/2005 | Tsuruoka et al. |

FOREIGN PATENT DOCUMENTS

| | | |
|---|---|---|
| EP | 0326330 | 8/1989 |
| EP | 0602851 | 6/1994 |
| EP | 1086705 | 3/2001 |
| EP | 0 860 433 B1 | 7/2002 |
| EP | 1251130 | 10/2002 |
| EP | 1 447 405 A1 | 8/2004 |
| EP | 1 522 540 A1 | 4/2005 |
| EP | 1548008 A1 | 6/2005 |
| FR | 2.077.455 | 9/1969 |
| JP | 11-158149 | 9/2002 |
| WO | WO92/21660 | 12/1992 |
| WO | WO93/03030 | 2/1993 |
| WO | WO93/13097 | 7/1993 |
| WO | WO95/15758 | 6/1995 |
| WO | WO95/19970 | 7/1995 |
| WO | WO95/21613 | 8/1995 |
| WO | WO95/23141 | 8/1995 |
| WO | WO96/09294 | 3/1996 |
| WO | WO96/15118 | 5/1996 |
| WO | WO96/30347 | 10/1996 |
| WO | WO96/40142 | 12/1996 |
| WO | WO97/03069 | 1/1997 |
| WO | WO97/13771 | 4/1997 |
| WO | WO97/17329 | 5/1997 |
| WO | WO97/22596 | 6/1997 |
| WO | WO97/32856 | 9/1997 |
| WO | WO97/49688 | 12/1997 |
| WO | WO98/02437 | 1/1998 |

(Continued)

OTHER PUBLICATIONS

Abuzar, S., CA 105:42720, abstract only of Indian Journal of Chemistry, Section B; Organic Chem include Med Chem, Col. 24B(8), pp. 848-852, 1985.

(Continued)

*Primary Examiner* — D. Margaret Seaman
(74) *Attorney, Agent, or Firm* — Jeffrey H. Tidwell

(57) ABSTRACT

The invention relates to compounds represented by Formula (I):

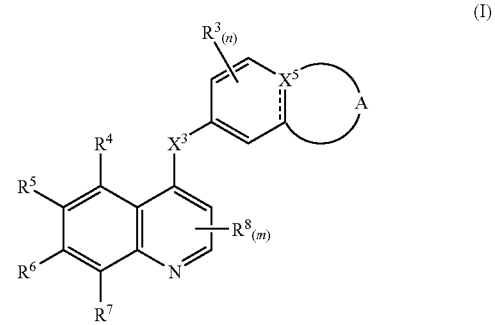

and to pharmaceutically acceptable salts or solvates of said compounds, wherein each of A, $R^{3-8}$, $X^3$, $X^5$, m, and n are defined herein. The invention also relates to pharmaceutical compositions containing the compounds of Formula (I) and to methods of treating hyperproliferative disorders in a mammal by administering compounds of Formula (I).

4 Claims, No Drawings

FOREIGN PATENT DOCUMENTS

| WO | WO98/02438 | 1/1998 |
|---|---|---|
| WO | WO98/13350 | 4/1998 |
| WO | WO98/23613 | 6/1998 |
| WO | WO98/37079 | 8/1998 |
| WO | WO98/50356 | 11/1998 |
| WO | WO98/51344 | 11/1998 |
| WO | WO98/54093 | 12/1998 |
| WO | WO99/10349 | 3/1999 |
| WO | WO99/16755 | 4/1999 |
| WO | WO99/24440 | 5/1999 |
| WO | WO99/61422 | 12/1999 |
| WO | WO 00/18761 | 4/2000 |
| WO | WO 00/35919 | 6/2000 |
| WO | WO00/38665 | 7/2000 |
| WO | WO00/43366 | 7/2000 |
| WO | WO 00/47212 | 8/2000 |
| WO | WO 00/50405 | 8/2000 |
| WO | WO01/47890 | 7/2001 |
| WO | WO01/47931 | 7/2001 |
| WO | WO01/70268 | 9/2001 |
| WO | WO01/74296 | 10/2001 |
| WO | WO01/74360 | 10/2001 |
| WO | WO01/85796 | 11/2001 |
| WO | WO 02/12226 | 2/2002 |
| WO | WO02/30453 | 4/2002 |
| WO | WO 02/30925 | 4/2002 |
| WO | WO 02/32872 A1 | 4/2002 |
| WO | WO02/41882 | 5/2002 |
| WO | WO02/064170 | 8/2002 |
| WO | WO03/006059 | 1/2003 |
| WO | WO 03/033472 A1 | 4/2003 |
| WO | WO03/035047 | 5/2003 |
| WO | WO 03/074529 | 9/2003 |
| WO | WO 2004/018430 | 3/2004 |
| WO | WO 2004/020434 | 3/2004 |

OTHER PUBLICATIONS

Bussolino, F. et al. "Role of Soluble Mediators in Angiogenesis," *European Journal of Cancer*, 1996, 32A:14, 2401-2412.

Chemical Abstract Accession No. 1981:407199. [Agrawal, V. et al., "Studies in Potential Filaraicides: Part XI. Synthesis of 2-(Dialkylaminomethyl)-4-Substituted Aminophenols aAs Amodiaquine Analogs," *Indian Journal of Chemistry, Section B*, 1981, 95:1, 68682.].

Chemical Abstract Accession No. 1969:68193. [Hamana, et al., "4-Substituted Quinoline Derivatives," *Japan Tokkyo Koho*, 1969, 70:15, 366.].

Chemical Abstract Accession No. 1994:217227. [Barlin, G. et al., "Potential Antimalarials. XVIII. Some Mono- and Di-Mannich Bases of 3-[7-Chloro(and Trifluoromethyl)Quinolin-4-ylamino]Phenol," *Australian Journal of Chemistry*, 1993, 46:11, 1685-93.].

Deplanque, G. et al. "Anti-angiogenic Agents: Clinical Trial Design and Therapies in Development," *European Journal of Cancer*, 2000, 36, 1713-1724.

Firsching, A. et al. "Antiproliferative and Angiostatic Activity of Suramin Analogues," *Cancer Research*, 1995, 55, 4957-4961.

Folkman, A. et al. "New Perspectives in Clinical Oncology From Angiogenesis Research," *European Journal of Cancer*, 1996, 32A:14, 2534-2539.

Gibson, K. H., CA 133:350152, abstract only of WO 2000/068200, Nov. 2000.

Gravatt, G. et al., "DNA-Directed Alkylating Agents. 4. 4-Anilinoquinoline-Based Minor Groove Directed Aniline Mustards," *Journal of Medicinal Chemistry*, 1991, 34, 1552-1560.

Henniquin, L.F., CA 136:178717, abstract only of WO 2002/12226, Feb. 2002.

Kotva, R. et al. "Substances With Antineoplastic Activity. LIII.* N-{δ-(4-Pyrrolo[2,3-d]Pyrimidinylthio)Valeryl}Amino Acids and Analogous Derivatives of Di- and Triglycine," *Collection Czechoslov Chemical Commun*, 1973, 38:5, 1438-1444.

Rewcastle, G. et al. "Tyrosine Kinase Inhibitors. 5. Synthesis and Structure-Activity Relationships for 4-[(Phenylmethyl)Amino]- and 4-(Phenylamino)Quinazolines as Potent Adenosine 5]-Triphosphate Binding Site Inhibitors of the Tyrosine Kinase Domain of the Epidermal Growth Factor Receptor," *Journal of Medicinal Chemistry*, 1995, 38, 3482-3487.

Spacey, G. et al. "Indolocarbazoles Potent and Selective Inhibitors of Platelet-Derived Growth Factor Receptor Autophosphorylation," *Biochemical Pharmacology*, 1998, 55, 261-271.

Wang, F. et al., "A Convenience Set of Bidentate Pyridine Ligands for Combinatorial Synthesis," *Tetrahedron Letters 40*, 1999, 4779-4782.

Aiello, L., et al., "Role of Vascular Endothelial Growth Factor in Diabetic Vascular Complications," *Kidney International*, 2000, S-113-S119, vol. 58, No. 77.

Eckhardt, S., et al., "Development of Angiogenesis Inhibitors for Cancer Therapy," *Investigational New Drugs*, 1997, 1-3, vol. 15.

Ferrara, N., et al., "The Biology of VEGF and its Receptors," *Nature Medicine*, 2003, 669-676, vol. 9, No. 6.

Fong, T., et al., SU5416 is a Potent and Selective Inhibitor of the Vascular Endothelial Growth Factor Receptor (FLK-1/KDR) That Inhibits Tyrosine Kinase Catalysis, Tumor Vascularization, and Growth of Multiple Tumor Types, *Cancer Research*, 1999, 99-106, vol. 59.

O'Reilly, M., "The Preclinical Evaluation of Angiogenesis Inhibitors," *Investigational New Drugs*, 1997, 5-13, vol. 15.

Parast, C., et al., "Characterization and Kinetic Mechanism of Catalytic Domain of Human Vascular Endothelial Growth Factor Receptor-2 Tyrosine Kinase (VEGFR2 TK), A Key Enzyme in Angiogenesis," *Biochemistry*, 1998, 16788-16801, vol. 37.

Wedge, S., et al., "ZD6474 Inhibits Vascular Endotheilial Growth Factor Signaling Angiogenesis, and Tumor Growth Following Oral Administration," *Cancer Research*, 2002, 4645-4655, vol. 62.

* cited by examiner

QUINOLINE DERIVATIVES

This application is a continuation of U.S. patent application Ser. No. 11/015,508, filed Dec. 16, 2004, now U.S. Pat. No. 7,381,824, which claims the benefit of U.S. Patent Application No. 60/532,725, filed Dec. 23, 2003, all of which are hereby incorporated by reference.

FIELD OF THE INVENTION

This invention relates to novel quinoline analogs and derivatives thereof, including pharmaceutically acceptable derivatives, such as salts, and solvates. The compounds of the present invention inhibit the activity of receptor kinases such as VEGFR and PDGRF that are required for cell growth and differentiation and angiogenesis. Particularly, the compounds in this invention inhibit VEGFR/KDR and therefore are useful for treatment of diseases and conditions that are associated with VEGFR/KDR activity, e.g., cancer and ophthalmic diseases such as age-related macular degeneration. This invention also relates to a method of using such compounds in the treatment of hyperproliferative diseases in mammals, especially humans, and to pharmaceutical compositions containing such compounds.

BACKGROUND OF THE INVENTION

A cell may become cancerous by virtue of the transformation of a portion of its DNA into an oncogene (i.e., a gene that upon activation leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Tyrosine kinases may be classified as growth factor receptor (e.g. EGFR, PDGFR, FGFR and erbB2) or non-receptor (e.g. c-src and bcr-abl) kinases. Such kinases may be aberrantly expressed in common human cancers such as breast cancer, gastrointestinal cancers such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. Studies indicate that epidermal growth factor receptor (EGFR) is mutated or overexpressed in many human cancers such as brain, lung, squamous cell, bladder, gastric, breast, head and neck, oesophageal, gynecological and thyroid cancers. Thus, inhibitors of receptor tyrosine kinases may be useful as selective inhibitors of the growth of mammalian cancer cells.

EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995), hereby incorporated by reference in its entirety.

Polypeptide growth factors, such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995), hereby incorporated by reference in its entirety. Agents that are capable of binding to or modulating the KDR/FLK-1 receptor may be used to treat disorders related to vasculogenesis or angiogenesis, such as diabetes, diabetic retinopathy, age related macular degeneration, hemangioma, glioma, melanoma, Kaposi's sarcoma and ovarian, breast, lung, pancreatic, prostate, colon and epidermoid cancer.

Compounds and methods that reportedly can be used to treat hyperproliferative diseases are disclosed in the following patents and applications: PCT international patent application publication number WO 00/38665 (published Jul. 6, 2001), PCT international patent application publication number WO 97/49688 (published Dec. 31, 1997), PCT international patent application publication number WO 98/23613 (published Jun. 4, 1998), U.S. patent application Ser. No. 09/502,129 (filed Feb. 10, 2000), U.S. patent application Ser. No. 08/953,078 (filed Oct. 17, 1997), U.S. Pat. No. 6,071,935 issued Jun. 6, 2000, PCT international patent application publication number WO 96/30347 (published Oct. 3, 1996), PCT international patent application publication number WO 96/40142 (published Dec. 19, 1996), PCT international patent application publication number WO 97/13771 (published Apr. 17, 1997), PCT international patent application publication number WO 95/23141 (published Aug. 31, 1995), PCT international patent application publication number WO 03/006059 (published Jan. 23, 2003), PCT international patent application publication number WO 03/035047 (published May 1, 2003), PCT international patent application publication number WO 02/064170 (published Aug. 22, 2002), PCT international patent application publication number WO 02/41882 (published May 30, 2002), PCT international patent application publication number WO 02/30453 (published Apr. 18, 2002), PCT international patent application publication number WO 01/85796 (published Nov. 15, 2001), PCT international patent application publication number WO 01/74360 (published Oct. 11, 2001), PCT international patent application publication number WO 01/74296 (published Oct. 11, 2001), PCT international patent application publication number WO 01/70268 (published Sep. 27, 2001), European patent application publication number EP 1086705 (published Mar. 28, 2001), and PCT international patent application publication number WO 98/51344 (published Nov. 19, 1998). The foregoing patent and applications are each incorporated herein by reference in their entirety.

SUMMARY OF THE INVENTION

Described herein are compounds capable of modulating the activity of receptor kinases such as VEGFR and PDGRF and methods for utilizing such modulation in the treatment of cancer and other proliferative disorders. Also described are compounds that mediate and/or inhibit the activity of protein kinases, and pharmaceutical compositions containing such compounds. Also described are therapeutic or prophylactic use of such compounds and compositions, and methods of treating cancer as well as other diseases associated with unwanted angiogenesis and/or cellular proliferation, by administering effective amounts of such compounds.

In one aspect are novel quinoline compounds. In another aspect provided are compounds that modulate the activity of receptor kinases such as KDR/VEGFR2 kinase in vitro and/or in vivo. According to a further aspect, provided are compounds that can selectively modulate the activity of receptor kinases such as KDR/VEGFR2 kinase. In yet another aspect, provided are pharmaceutical compositions of such VEGFR2-modulating compounds, including pharmaceutically acceptable salts thereof. According to yet another aspect, provided are syntheses schemes for the preparation of such VEGFR2-modulating compounds, and pharmaceutically acceptable salts thereof. In yet another aspect, methods are provided for modulating KDR/VEGFR2 kinase which comprise contacting the VEGFR2-modulating compounds, or pharmaceutically acceptable salts thereof, described herein, with KDR/VEGFR2 kinase. In yet another aspect, provided are methods for treating patients comprising administering a therapeutically effective amount of a VEGFR2-modulating compound, or a pharmaceutically acceptable salt thereof. In yet another aspect, are combination therapies involving administration of an anti-neoplastic agent and an effective amount of a VEGFR2-modulating compound, or a pharmaceutically acceptable salt thereof.

In one aspect are compounds of Formula (I):

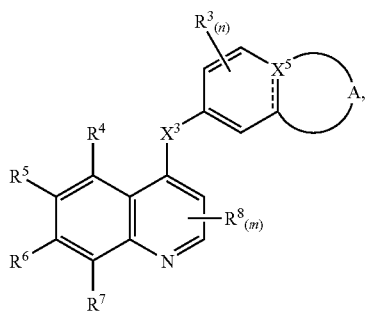

(I)

wherein
the ------ in Formula (I) indicates an optional bond;

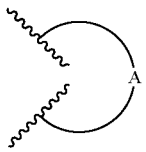

is selected from the group consisting of

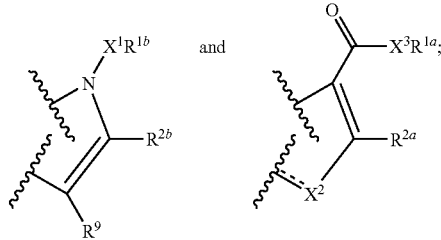

the ------ line indicates an optional bond;
$X^1$ is a bond or —C(O)NH—;
$X^2$ is O, S, or $NR^9$ where ----- is not a bond, or $X^2$ is N or CH where ----- is a bond;
$R^9$ is H or —$CH_3$;
$R^{1a}$ and $R^{1b}$ are selected from the group consisting of H, —$(CR^{10}R^{11})_j$CN, —$(CR^{10}R^{11})_j$—$(C_3-C_8)$cycloalkyl, —$(CR^{10}R^{11})_j$—$(C_5-C_8)$cycloalkenyl, $(C_2-C_6)$alkenyl, $(C_2$-$C_6)$alkynyl, —$(CR^{10}R^{11})_j$-aryl, —$(CR^{10}R^{11})_j$-heterocyclyl, and $(C_1-C_8)$alkyl, and wherein the C atoms of $R^{1a}$ and $R^{1b}$ can be optionally substituted with 1-3 independently selected $R^{12}$ groups;

$R^{2a}$ and $R^{2b}$ are selected from the group consisting of H, —$CH_3$, —$CF_3$, —CN, —$CH_2CH_3$, —$OCH_3$, and —$OCF_3$;

$R^3$ and $R^8$ are independently F;
$X^3$ is O or NH;
$X^5$ is C where ----- in Formula (I) is a bond, or, where ----- in Formula (I) is not a bond, is CH or N;
$R^4$ and $R^7$ are independently selected from H, halogen, —$CH_3$, and $CF_3$;
$R^5$ and $R^6$ are independently selected from the group consisting of H, halogen, —$CF_3$, —$N_3$, —$NO_2$, —OH, —$NH_2$, —$OCF_3$, —$X^4(CR^{10}R^{11})_j$CN, —$X^4(CR^{10}R^{11})_j$—$(C_3-C_8)$ cycloalkyl, —$X^4(CR^{10}R^{11})_j$—$(C_5-C_8)$ cycloalkenyl, —$X^4(C_2-C_6)$ alkenyl, —$X^4(C_2-C_6)$alkynyl, —$X^4(CR^{10}R^{11})_j$-aryl, —$X^4(CR^{10}R^{11})_j$-heterocyclyl, heterocyclyl, and —$X^4(C_1-C_8)$alkyl, and wherein the C and N atoms of $R^5$ and $R^6$ can be optionally substituted with 1 to 3 independently selected $R^{13}$ groups, or wherein $R^5$ and $R^6$ taken together may form a cyclic moiety selected from the group consisting of a 4-10 membered carbocyclyl and a 4-12 membered heterocyclyl which is optionally substituted with 1 to 3 independently selected $R^{13}$ groups;

$X^4$ is selected from the group consisting of a bond, O, NH, —C(O)—, —NHC(O)—, —OC(O)—, —C(O)O—, —C(O)NH—, and S;

each $R^{10}$ and $R^{11}$ are independently selected from the group consisting of H, F, and $(C_1-C_6)$alkyl, or $R^{10}$ and $R^{11}$ taken together may form a carbocyclyl, or two $R^{10}$ groups attached to adjacent carbon atoms may be selected together to form a carbocyclyl;

each $R^{12}$ and $R^{13}$ are independently selected from the group consisting of halogen, cyano, nitro, tetrazolyl, guanidino, amidino, methylguanidino, azido, —C(O)$R^{14}$—C(O), —$CF_3$, —$CF_2CF_3$, —$CH(CF_3)_2$, —C(OH)$(CF_3)_2$, —$OCF_3$, —$OCF_2H$, —$OCF_2CF_3$, —OC(O)$NH_2$, —OC(O)$NHR^{14}$, —OC(O)$NR^{14}R^{15}$, —NHC(O)$R^{14}$ —NHC(O)$NH_2$, —NHC(O)$NHR^{14}$—NHC(O)$NR^{14}R^{15}$, —C(O)OH, —C(O)$OR^{14}$—C(O)$NH_2$, —C(O)$NHR^{14}$, —C(O)$NR^{14}R^{15}$, —P(O)$_3H_2$, —P(O)$_3(R^{14})_2$, —S(O)$_3H$, —S(O)$_mR^{14}$, —$R^{14}$—$OR^{14}$, —OH, —$NH_2$, —NH, —$NHR^{14}$—$NR^{14}$ —$NR^{14}R^{15}$, —C(=NH)$NH_2$, —C(=NOH)$NH_2$, —N-morpholino, $(C_2-C_6)$alkyl, where any of the C atoms can be optionally substituted with an O atom, $(C_2-C_6)$alkenyl, $(C_2-C_6)$alkynyl, $(C_1-C_6)$haloalkyl, $(C_2-C_6)$haloalkenyl, $(C_2-C_6)$haloalkynyl, $(C_1-C_6)$haloalkoxy, —$(CR^{16}R^{17})_rNH_2$, —$(CR^{16}R^{17})_rNHR^{14}$, —$CNR^{14}R^{15}$, $(CR^{16}R^{17})_rNR^{14}R^{15}$ and —S(O)$_m(CF_2)_qCF_3$;

or any two $R^{12}$ or any two $R^{13}$ groups attached to adjacent carbon atoms may be selected together to be —O[C$(R^{16})(R^{17})]_rO$— or —O[C$(R^{16})(R^{17})]_{r+1}$—;

or any two $R^{12}$ or any two $R^{13}$ groups attached to the same or adjacent carbon atoms may be selected together to form a carbocyclyl or heterocyclyl;

each $R^{14}$ and $R^{15}$ are independently selected from the group consisting of $(C_1-C_{12})$ alkyl, $(C_3-C_8)$ cycloalkyl, $(C_6-C_{14})$ aryl, 4-12 membered heterocyclyl, —$(CR^{10}R^{11})_j$—$(C_6-C_{10})$ aryl, and —$(CR^{10}R^{11})_j$-(4-12 membered heterocyclyl);

each $R^{16}$ and $R^{17}$ are independently selected from the group consisting of hydrogen, $(C_1-C_{12})$ alkyl, $(C_6-C_{14})$ aryl, 4-12 membered heterocyclyl, —$(CR^{10}R^{11})_j$—$(C_6\text{-}C_{10})$ aryl, and —$(CR^{10}R^{11})_j$-(4-12 membered heterocyclyl);

and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from the group consisting of hydroxy, halogen, $(C_1\text{-}C_4)$alkyl, $(C_1\text{-}C_4)$alkoxy and —$N[(C_1\text{-}C_4)$alkyl$][(C_1\text{-}C_4)$alkyl];

and wherein j is 0, 1, 2, or 3 and when j is 2 or 3, each $CR^{10}R^{11}$ unit may be the same or different;

and wherein n is 0, 1, 2, or 3, and m is 0, 1 or 2;

and wherein q is an integer from 0 to 5, and r is an integer from 1 to 4;

or a pharmaceutically acceptable solvate or pharmaceutically acceptable salt thereof.

In one embodiment are compounds having the structure of Formula (I), wherein

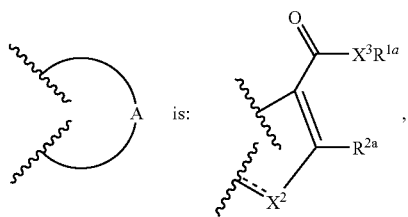

wherein $R^{1a}$, $R^{2a}$, $X^2$ and $X^3$ are as defined in connection with Formula (I). In further embodiments provided are compounds where (a) n and m are both 0; (b) $X^4$ is O; (c) $R^4$ and $R^7$ are both H; (d) $R^{2a}$ is $CH_3$; (e) $R^4$ and $R^7$ are both H, $R^{2a}$ is $CH_3$, and n and m are both 0 (and further, wherein $X^2$ is either O or S); (f) $X^2$ is either O or S; or (g) $R^4$, $R^5$, and $R^7$ are all H. Where $R^4$, $R^5$ and $R^7$ are H, an alternative embodiment is directed to compounds wherein $R^{2a}$ is $CH_3$, n and m are both 0, and $X^2$ is either O or S; this embodiment may further include compounds, wherein (1) $R^6$ is —$X^4(CR^{10}R^{11})_j$-heterocyclyl, and $X^4$ is a bond or O or (2) $R^6$ is —$X^4(C_1\text{-}C_8)$alkyl, and $X^4$ is a bond or O In another embodiment provided are compounds having the structure of Formula (I), wherein

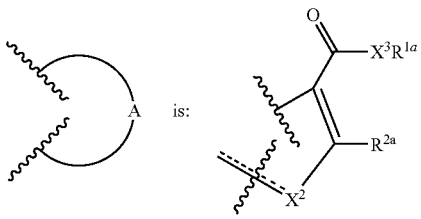

wherein $R^{1a}$, $R^{2a}$ and $X^2$ are as defined in connection with Formula (I) and j is 0. In a further embodiment of such compounds, $R^{1a}$ is selected from the group consisting of —$(C_3\text{-}C_8)$cycloalkyl, -aryl, -heterocyclyl, and $(C_1\text{-}C_8)$alkyl all of which may be optionally substituted with 1 to 3 independently selected $R^{12}$ groups.

In another embodiment are compounds having the structure of Formula (I), wherein

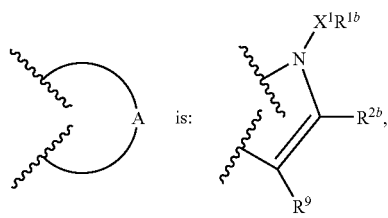

wherein $X^1$, $R^{1b}$, $R^{2b}$ and $R^9$ are as defined in connection with Formula (I).

In a further embodiment are compounds in which $X^3$ is NH. In yet further embodiments are such compounds in which (a) $X^1$ is —C(O)NH—; (b) $R^{2b}$ is —$CH_3$; or (c) $R^{2b}$ is $CH_3$ and n and m are both 0. Where $R^{2b}$ is $CH_3$ and n and m are both O, another embodiment is directed to compounds in which $X^1$ is —C(O)NH—. This embodiment may further include compounds where (1) $R^6$ is —$X^4(CR^{10}R^{11})_j$-heterocycle, and $X^4$ is a bond or O; or (2) $R^6$ is —$X^4(C_1\text{-}C_8)$alkyl, and $X^4$ is a bond or O.

In another embodiment are compounds having the structure of Formula (I) selected from the following group consisting of:

5-[(7-chloroquinazolini-4-yl)amino]-N,2-dimethyl-1H-indole-1-carboxamide,

6-[(7-iodoquinolin-4-yl)oxy]-N,2-dimethyl-1-benzofuran-3-carboxamide,

N-2-dimethyl-6-[(7-pyridin-4-ylquinolin-4-yl)oxy]-1-benzofuran-3-carboxamide,

N-2-dimethyl-6-[(7-pyridin-3-ylquinolin-4-yl)oxy]-1-benzofuran-3-carboxamide,

N-2-dimethyl-6-[(7-pyridin-2-ylquinolin-4-yl)oxy]-1-benzofuran-3-carboxamide,

N-2-dimethyl-6-[(7-pyridin-4-ylquinolin-4-yl)oxy]-1-benzothiophene-3-carboxamide, N-2-dimethyl-5-[(7-pyridin-4-ylquinolin-4-yl]amino]-1H-indole-1-carboxamide, N,2-dimethyl-5-[(7-pyridin-3-ylquinolin-4-yl)amino]-1H-indole-1-carboxamide, 6-{[7-(2-furyl)quinolin-4-yl]oxy}-N,2-dimethyl-1-benzofuran-3-carboxamide, N-2-dimethyl-6-[(7-pyridin-3-ylquinolin-4-yl)oxy]-1-benzothiophene-3-carboxamide, 6-[(7-{[(2S)-2-(methoxymethyl)pyrrolidin-1-yl]carbonyl}quinolin-4-yl)oxy]-N,2-dimethyl-1-benzofuran-3-carboxamide, 6-[(7-{[(2S)-2-(methoxymethyl)pyrrolidin-1-yl]carbonyl}quinolin-4-yl)oxy]-N,2-dimethyl-1-benzothiophene-3-carboxamide, N,2-dimethyl-6-[(7-pyrimidin-2-ylquinolin-4-yl)oxy]-1-benzothiophene-3-carboxamide, N,2-dimethyl-6-[(7-pyrimidin-2-ylquinolin-4-yl)oxy]-1-benzofuran-3-carboxamide, 6-[(7-bromoquinolin-4-yl)oxy]-N,2-dimethyl-1-benzofuran-3-carboxamide, 6-[(7-bromoquinolin-4-yl)oxy]-N,2-dimethyl-1-benzothiophene-3-carboxamide, 6-[(6-iodoquinolin-4-yl)oxy]-N,2-dimethyl-1-benzothiophene-3-carboxamide, 6-[(6-iodoquinolin-4-yl)oxy]-N,2-dimethyl-1-benzofuran-3-carboxamide, N,2-dimethyl-6-[(6-pyridin-4-ylquinolin-4-yl)oxy]-1-benzofuran-3-carboxamide, 6-[(6-methoxyquinolin-4-yl)oxy]-N,2-dimethyl-1-benzothiophene-3-carboxamide, 6-[(6-hydroxyquinolin-4-yl)oxy]-N,2-dimethyl-1-benzothiophene-3-carboxamide,
N,2-dimethyl-6-({6-[2-(1-methylpyrrolidinyl-2-yl)ethoxy]quinolin-4-yl}oxy)-1-benzothiophene-3-carboxamide,
6-[(7-methoxyquinoline-4-yl)oxy]-N,2-dimethyl-1-benzofuran-3-carboxamide,
6-[(7-hydroxyquinoline-4-yl)oxy]-N,2-dimethyl-1-benzofuran-3-carboxamide,
N,2-dimethyl-6-{(7-1,3-thiazol-2-yl)quinolin-4-yl)oxy}-1-benzofuran-3-carboxamide,
N,2-dimethyl-6-[(7-pyridin-2-yl)quinolin-4-yl)oxy]-1-benzothiaphene-3-carboxamide,
N,2-dimethyl-5-[(7-pyridin-2-yl)quinolin-4-yl)amino]-1H-indole-1-carboxamide,
N,2-dimethyl-6-{[7-(2-piperidin-1-ylethoxy)quinolin-4-yl]oxy}-1-benzofuran-3-carboxamide,
N,2-dimethyl-6-{[7-(pyridin-2-ylmethoxy)quinolin-4-yl]oxy}-1-benzofuran-3-carboxamide,
N,2-dimethyl-6-{[7-(thiazol-2-ylmethoxy)quinolin-4-yl]oxy}-1-benzofuran-3-carboxamide,
N,2-dimethyl-6-{[7-(2-pyrrolidin-1-ylethoxy)quinolin-4-yl]oxy}-1-benzofuran-3-carboxamide,
N,2-dimethyl-6-{[7-(2-morpholin-4-ylethoxy)quinolin-4-yl]oxy}-1-benzofuran-3-carboxamide,
6-({7-[2-(dimethylamino)ethoxy]quinolin-4-yl}oxy)-N,2-dimethyl-1-benzofuran-3-carboxamide,
N-butyl-6-[(7-methoxyquinolin-4-yl)oxy]-2-methyl-1-benzofuran-3-carboxamide,
6-[(7-methoxyquinolin-4-yl)oxy]-2-methyl-N-pyridin-2-yl-1-benzofuran-3-carboxamide,
N-butyl-6-[(7-hydroxyquinolin-4-yl)oxy]-2-methyl-1-benzofuran-3-carboxamide,
6-{[7-(allyloxy)quinolin-4-yl]oxy}-N,2-dimethyl-1-benzofuran-3-carboxamide,
N-isopropyl-6-[(7-methoxyquinolin-4-yl)oxy]-2-methyl-1-benzofuran-3-carboxamide,
N-butyl-2-methyl-6-{[7-(2-pyrrolidin-1-ylethoxy)quinolin-4-yl]oxy}-1-benzofuran-3-carboxamide,
N-butyl-2-methyl-6-{[7-(2-morpholin-4-ylethoxy)quinolin-4-yl]oxy}-1-benzofuran-3-carboxamide,
N-butyl-6-({7-[2-(dimethylamino)ethoxy]quinolin-4-yl}oxy)-2-methyl-1-benzofuran-3-carboxamide,
N-butyl-2-methyl-6-{[7-(2-piperidin-1-ylethoxy)quinolin-4-yl]oxy}-1-benzofuran-3-carboxamide,
N-cyclopropyl-6-[(7-methoxyquinolin-4-yl)oxy]-2-methyl-1-benzothiophene-3-carboxamide,
N-[2-(dimethylamino)ethyl]-6-[(7-methoxyquinolin-4-yl)oxy]-2-methyl-1-benzothiophene-3-carboxamide,
[(7-methoxyquinolin-4-yl)oxy]-2-methyl-N-propyl-1-benzothiophene-3-carboxamide,
N-[3-(dimethylamino)propyl]-6-[(7-methoxyquinolin-4-yl)oxy]-2-methyl-1-benzothiophene-3-carboxamide,
N-cyclohexyl-6-[(7-methoxyquinolin-4-yl)oxy]-2-methyl-1-benzothiophene-3-carboxamide,
N-cyclopentyl-6-[(7-methoxyquinolin-4-yl)oxy]-2-methyl-1-benzothiophene-3-carboxamide,
6-[(7-methoxyquinolin-4-yl)oxy]-2-methyl-N-(pyridin-3-ylmethyl)-1-benzothiophene-3-carboxamide,
6-[(7-hydroxyquinolin-4-yl)oxy]-2-methyl-N-propyl-1-benzothiophene-3-carboxamide,
N-[2-(dimethylamino)ethyl]-6-[(7-hydroxyquinolin-4-yl)oxy]-2-methyl-1-benzothiophene-3-carboxamide,
N-cyclopentyl-6-[(7-hydroxyquinolin-4-yl)oxy]-2-methyl-1-benzothiophene-3-carboxamide,
N-[3-(dimethylamino)propyl]-6-[(7-hydroxyquinolin-4-yl)oxy]-2-methyl-1-benzothiophene-3-carboxamide
6-[(7-hydroxyquinolin-4-yl)oxy]-2-methyl-N-(pyridin-3-ylmethyl)-1-benzothiophene-3-carboxamide,
N,2-dimethyl-6-{[7-(trifluoromethyl)quinolin-4-yl]oxy}-1-benzothiophene-3-carboxamide,
N,2-dimethyl-6-{[7-(trifluoromethyl)quinolin-4-yl]oxy}-1-benzofuran-3-carboxamide,
6-[(7-methoxyquinolin-4-yl)oxy]-2-methyl-N-(3-morpholin-4-ylpropyl)-1-benzothiophene-3-carboxamide,
N-cyclopropyl-6-[(7-methoxyquinolin-4-yl)oxy]-2-methyl-1-benzofuran-3-carboxamide,
6-[(7-methoxyquinolin-4-yl)oxy]-2-methyl-N-(3-morpholin-4-ylpropyl)-1-benzofuran-3-carboxamide,
6-[(7-methoxyquinolin-4-yl)oxy]-2-methyl-N-(pyridin-2-ylmethyl)-1-benzofuran-3-carboxamide,
6-[(7-methoxyquinolin-4-yl)oxy]-2-methyl-benzofuran-3-carboxylic acid (3-dimethylamino-propyl)-amide,
N-(3-hydroxypropyl)-6-[(7-methoxyquinolin-4-yl)oxy]-2-methyl-1-benzofuran-3-carboxamide,
N-(5-hydroxy-1H-pyrazol-3-yl)-6-[(7-methoxyquinolin-4-yl)oxy]-2-methyl-1-benzothiophene-3-carboxamide,
6-[(7-hydroxyquinolin-4-yl)oxy]-N-isopropyl-2-methyl-1-benzofuran-3-carboxamide,
6-[(7-hydroxyquinolin-4-yl)oxy]-N-isopropyl-2-methyl-1-benzothiophene-3-carboxamide,
N-isopropyl-6-[(7-methoxyquinolin-4-yl)oxy]-2-methyl-1-benzothiophene-3-carboxamide,
[(7-methoxyquinolin-4-yl)oxy]-N,1,2-trimethyl-1H-indole-3-carboxamide,
N-isopropyl-2-methyl-6-{[7-(trifluoromethoxy)quinolin-4-yl]oxy}-1-benzofuran-3-carboxamide,
N-cyclopropyl-2-methyl-6-{[7-(trifluoromethoxy)quinolin-4-yl]oxy}-1-benzofuran-3-carboxamide,
N-butyl-2-methyl-6-{[7-(trifluoromethoxy)quinolin-4-yl]oxy}-1-benzofuran-3-carboxamide,
6-[(7-methoxyquinolin-4-yl)oxy]-N,1,2-trimethyl-1H-indole-3-carboxamide,
N,1,2-trimethyl-6-{[7-(2-morpholin-4-ylethoxy)quinolin-4-yl]oxy}-1H-indole-3-carboxamide,
N,1,2-trimethyl-6-{[7-(2-pyrrolidin-1-ylethoxy)quinolin-4-yl]oxy}-1H-indole-3-carboxamide,
N-(2-hydroxypropyl)-6-[(7-methoxyquinolin-4-yl)oxy]-2-methyl-1-benzothiophene-3-carboxamide,
N-(2-hydroxybutyl)-6-[(7-methoxyquinolin-4-yl)oxy]-2-methyl-1-benzothiophene-3-carboxamide,
N-(3-hydroxybutyl)-6-[(7-methoxyquinolin-4-yl)oxy]-2-methyl-1-benzothiophene-3-carboxamide,
N,1,2-trimethyl-6-{[7-(2-piperidin-1-ylethoxy)quinolin-4-yl]oxy}-1H-indole-3-carboxamide,
6-{[7-(1,3-dioxolan-2-ylmethoxy)quinolin-4-yl]oxy}-N,2-dimethyl-1-benzofuran-3-carboxamide,
6-[(7-methoxyquinolin-4-yl)oxy]-2-methyl-N-[(2R)-tetrahydrofuran-2-ylmethyl]-1-benzofuran-3-carboxamide,
6-[(7-methoxyquinolin-4-yl)oxy]-2-methyl-N-[(2S)-tetrahydrofuran-2-ylmethyl]-1-benzofuran-3-carboxamide,
6-[(7-methoxyquinolin-4-yl)oxy]-2-methyl-N-[ethoxyethyl]-1-benzofuran-3-carboxamide,
6-[(7-methoxyquinolin-4-yl)oxy]-2-methyl-N-[2-methoxy-1-methyl-ethyl]-1-benzofuran-3-carboxamide,
N-(2-methoxyethyl)-6-[(7-methoxyquinolin-4-yl)oxy]-2-methyl-1-benzofuran-3-carboxamide,
N-cyclopropyl-2-methyl-6-[(7-pyrimidin-2-ylquinolin-4-yl)oxy]-1-benzofuran-3-carboxamide,
N-cyclopropyl-2-methyl-6-({7-[2-(methylamino)ethoxy]quinolin-4-yl}oxy)-1-benzofuran-3-carboxamide,
N-cyclopropyl-2-methyl-6-({7-[2-(diethylamino)ethoxy]quinolin-4-yl}oxy)-1-benzofuran-3-carboxamide, N-cyclopropyl-2-methyl-6-({7-[2-hydroxy-ethoxy]quinolin-4-yl}oxy)-1-benzofuran-3-carboxamide, 6-{[7-(2-bromoethoxy)quinolin-4-yl]oxy}-N-cyclopropyl-2-methyl-1-benzofuran-3-carboxamide,
N-cyclopropyl-2-methyl-6-{7-[2-(4-ethyl-piperazin-1-yl)ethoxy]quinolin-4-yloxy}-1-benzofuran-3-carboxamide,
N-cyclopropyl-6-({7-[2-(isopropylamino)ethoxy]quinolin-4-yl}oxy)-2-methyl-1-benzofuran-3-carboxamide,
N-cyclopropyl-6-({7-[2-(cyclopropylamino)ethoxy]quinolin-4-yl}oxy)-2-methyl-1-benzofuran-3-carboxamide,
N-cyclopropyl-6-[(7-{2-[(2-methoxy-1-methylethyl)amino]ethoxy}quinolin-4-yl)oxy]-2-methyl-1-benzofuran-3-carboxamide,
6-({7-[2-(tert-butylamino)ethoxy]quinolin-4-yl}oxy)-N-cyclopropyl-2-methyl-1-benzofuran-3-carboxamide,
N-cyclopropyl-2-methyl-6-{[7-(2-morpholin-4-ylethoxy)quinolin-4-yl]oxy}-1-benzofuran-3-carboxamide,
6-({7-[2-(cyclobutylamino)ethoxy]quinolin-4-yl}oxy)-N-cyclopropyl-2-methyl-1-benzofuran-3-carboxamide,
6-{[7-(benzyloxy)quinolin-4-yl]oxy}-N-(4,6-dimethylpyridin-2-yl)-2-methyl-1-benzofuran-3-carboxamide,
N-(4,6-dimethylpyridin-2-yl)-6-[(7-methoxyquinolin-4-yl)oxy]-2-methyl-1-benzofuran-3-carboxamide,
N-(4,6-dimethylpyridin-2-yl)-6-[(7-hydroxyquinolin-4-yl)oxy]-2-methyl-1-benzofuran-3-carboxamide,
N-cyclopropyl-2-methyl-6-{[7-(2-pyrrolidin-1-ylethoxy)quinolin-4-yl]oxy}-1-benzofuran-3-carboxamide,
N-cyclopropyl-2-methyl-6-{[7-(2-piperazin-1-ylethoxy)quinolin-4-yl]oxy}-1-benzofuran-3-carboxamide,
N-cyclopropyl-6-({7-[2-(dimethylamino)ethoxy]quinolin-4-yl}oxy)-2-methyl-1-benzofuran-3-carboxamide,
6-[(7-methoxyquinolin-4-yl)oxy]-2-methyl-N-{6-[(3-methylbutyl)amino]pyridin-3-yl}-1-benzofuran-3-carboxamide,
7-[(7-hydroxyquinolin-4-yl)oxy]-N,2-dimethylimidazo[1,2-α]pyridine-3-carboxamide,
N,2-dimethyl-7-{[7-(2-morpholin-4-ylethoxy)quinolin-4-yl]oxy}imidazo[1,2-α]pyridine-3-carboxamide,
N,2-dimethyl-6-({7-[(2-oxo-1,3-dioxolan-4-yl)methoxy]quinolin-4-yl}oxy)-1-benzofuran-3-carboxamide,
N-(2-methyl-1H-indol-5-yl)-7-(trifluoromethyl)quinoline-4-amine,
8-chloro-N-(2-methyl-1H-indol-5-yl)quinolin-4-amine,
N-(2-methyl-1H-indol-5-yl)quinolin-4-amine,
6-hydroxy-N,2-dimethyl-1-benzofuran-3-carboxamide,
N,2-dimethyl-6-[(6-pyridin-4-ylquinolin-4-yl)oxy]-1-benzothiophene-3-carboxamide,
N-cyclopropyl-6-({7-[2-(ethylamino)ethoxy]quinolin-4-yl}oxy)-2-methyl-1-benzofuran-3-carboxamide,
N-cyclopropyl-2-methyl-6-{[7-(2-piperidin-1-ylethoxy)quinolin-4-yl]oxy}-1-benzofuran-3-carboxamide,
7-fluoro-6-[(7-methoxyquinolin-4-yl)oxy]-2-methyl-N-(6-morpholin-4-ylpyridin-3-yl)-1-benzofuran-3-carboxamide,
7-fluoro-6-[(7-methoxyquinolin-4-yl)oxy]-2-methyl-N-(3-morpholin-4-ylpropyl)-1-benzofuran-3-carboxamide,
N-cyclopropyl-2-methyl-6-{[7-(2-piperazin-1-ylethoxy)quinolin-4-yl]oxy}-1 benzofuran-3-carboxamide,
6-{[7-(2,3-dihydroxypropoxy)quinolin-4-yl]oxy}-N,2-dimethyl-1-benzofuran-3-carboxamide,
N-[5-(aminomethyl)pyridin-2-yl]-6-[(7-methoxyquinolin-4-yl)oxy]-2-methyl-1-benzofuran-3-carboxamide,
N-[6-(aminomethyl)pyridin-3-yl]-6-[(7-methoxyquinolin-4-yl)oxy]-2-methyl-1-benzofuran-3-carboxamide,
4-{[4-({2-methyl-3-[(methylamino)carbonyl]-1-benzofuran-6-yl}oxy)quinolin-7-yl]oxy}butanoic acid,
{[4-({2-methyl-3-[(methylamino)carbonyl]-1-benzofuran-6-yl}oxy)quinolin-7-yl]oxy}acetic acid,
N-(4,6-dimethylpyridin-2-yl)-2-methyl-6-{[7-(2-pyrrolidin-1-ylethoxy)quinolin-4-yl]oxy}-1-benzofuran-3-carboxamide,
methyl 2-methyl-6-{[7-(2-morpholin-4-ylethoxy)quinolin-4-yl]oxy}-1-benzofuran-3-carboxylate,
6-({7-[2-hydroxy-3-(methylamino)propoxy]quinolin-4-yl}oxy)-N,2-dimethyl-1-benzofuran-3-carboxamide, and
methyl 4-{[4-({2-methyl-3-[(methylamino)carbonyl]-1-benzofuran-6-yl}oxy)quinolin-7-yl]oxy}butanoate,
or a pharmaceutically acceptable solvate or pharmaceutically acceptable salt thereof.

In another embodiment are compounds having the structure of Formula (I) selected from the group consisting of:

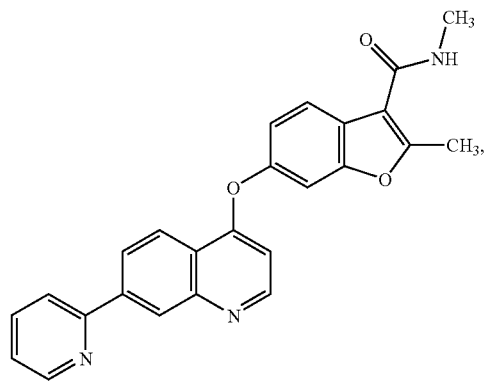

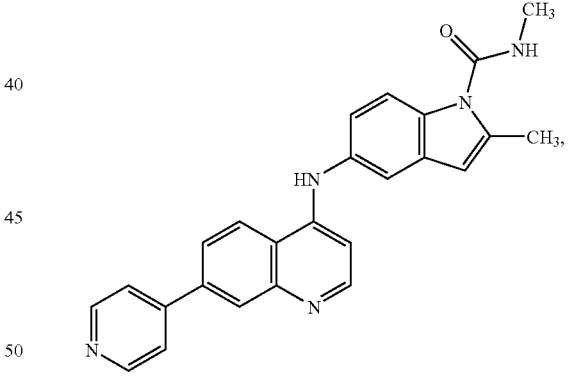

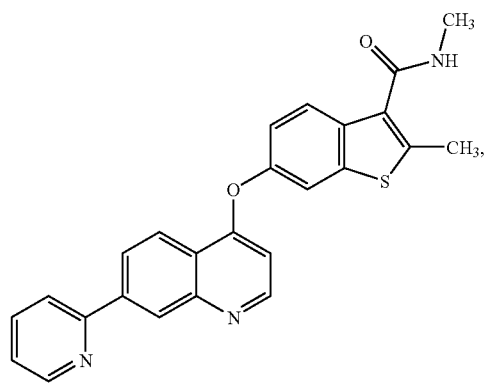

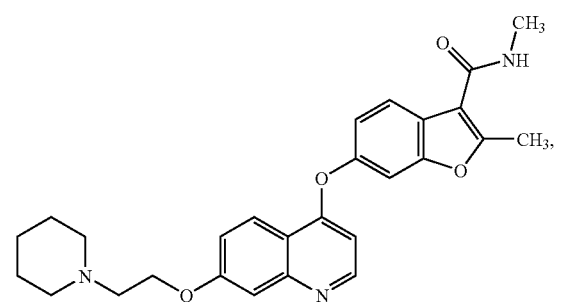
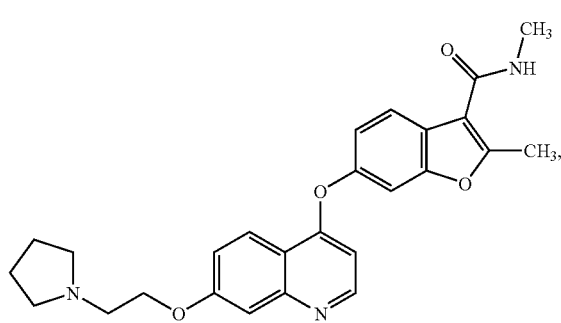
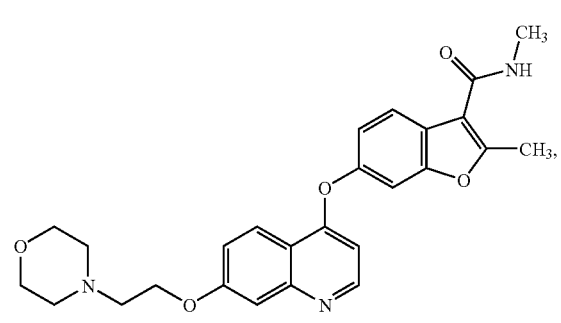
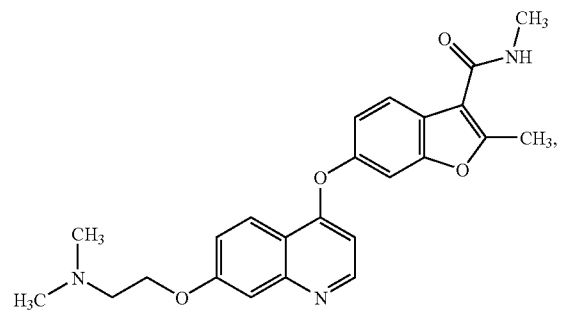
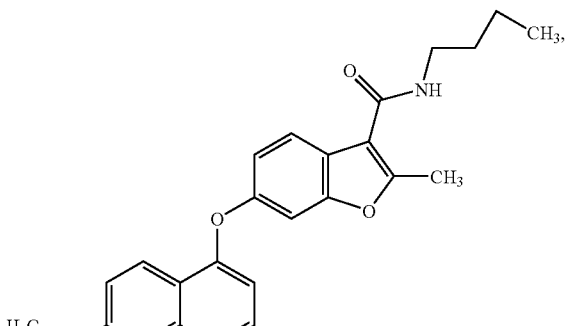
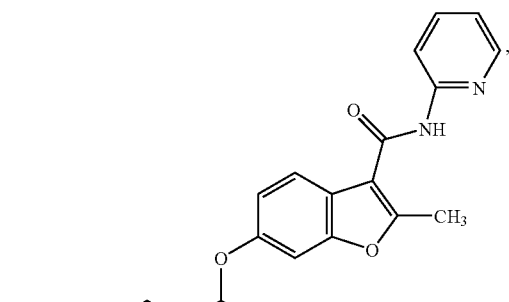
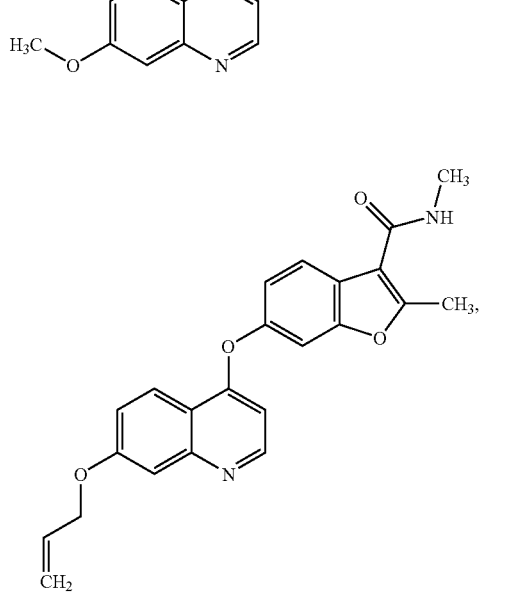
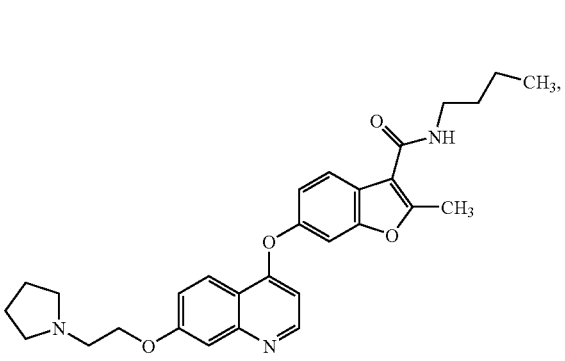
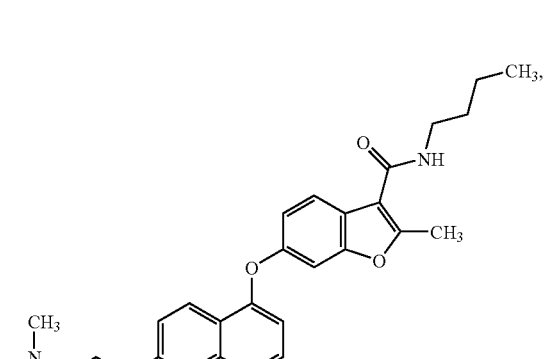

-continued

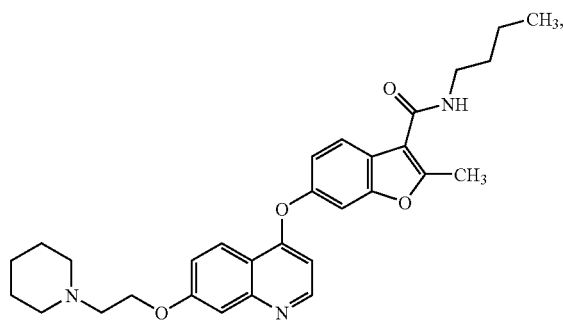

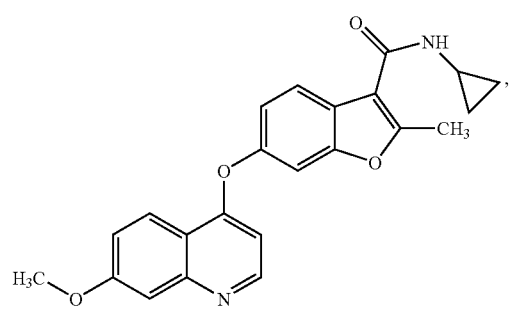

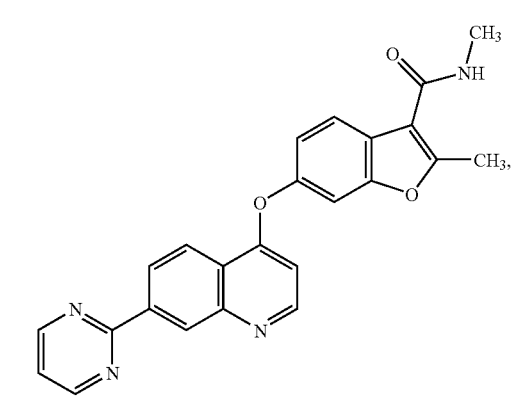

or a pharmaceutically acceptable solvate or pharmaceutically acceptable salt thereof.

In another embodiment are methods for producing a compound having the structure of Formula (I), wherein

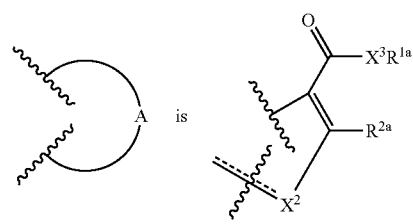

comprising (a) treating a carboxylic acid having the formula

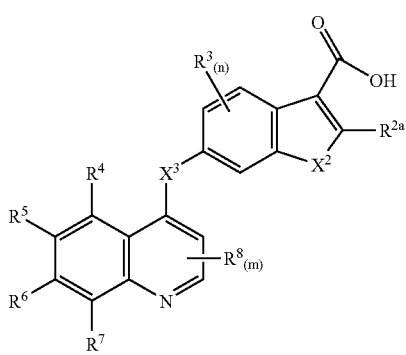

with an activating agent; and (b) contacting the corresponding product with $H_2NR^{1a}$. In a further embodiment of such methods, the activating agent is selected from the group consisting of thionyl chloride, oxalyl chloride, and O-(7-azabenzotriazol-1-yl)-1,1,3,3-tetramethyluronium hexafluorophosphate (HATU).

In another embodiment are methods for producing a compound having the structure of Formula (I), wherein

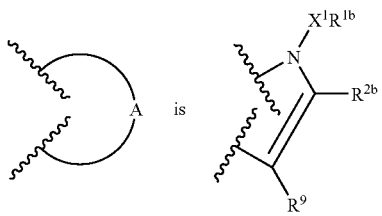

comprising treating a quinoline compound having the formula

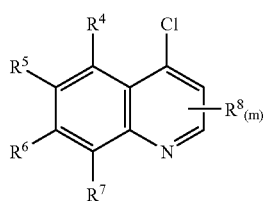

with a compound having the formula

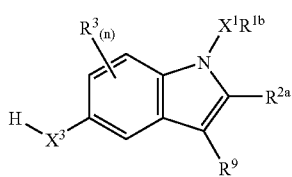

in the presence of an acid. In a further embodiment of such methods, $X^3$ is NH and said acid is HCl.

In another embodiment are methods for producing a compound having the structure of Formula (I), wherein

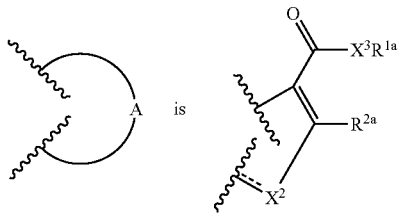

comprising treating a quinoline compound having the formula

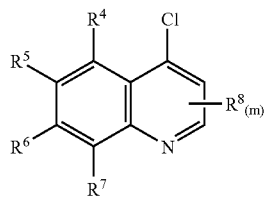

with a compound having the formula

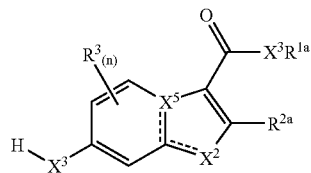

in the presence of a base.

Patients that can be treated with the compounds of formula (I), and pharmaceutically acceptable salts, or pharmaceutically acceptable solvates of said compounds, according to the methods of this invention include, for example, patients that have been diagnosed as having psoriasis, benign prostatic hypertrophy (BPH), lung cancer, eye cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The invention also relates to a pharmaceutical composition for the treatment of a hyperproliferative disorder in a mammal which comprises a therapeutically effective amount of a compound of formula (I), or pharmaceutically acceptable salts, or pharmaceutically acceptable solvates of said compounds, and a pharmaceutically acceptable carrier. In one embodiment, said pharmaceutical composition is for the treatment of cancer such as brain, lung, ophthalmic, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula (I), or pharmaceutically acceptable salts, or pharmaceutically acceptable solvates of said compounds, and a pharmaceutically acceptable carrier.

The invention also relates to a pharmaceutical composition for the prevention of blastocyte implantation in a mammal which comprises a therapeutically effective amount of a compound of formula (I), or pharmaceutically acceptable salts, or pharmaceutically acceptable solvates of said compounds, and a pharmaceutically acceptable carrier.

The invention also relates to a pharmaceutical composition for treating a disease related to vasculogenesis or angiogenesis in a mammal which comprises a therapeutically effective amount of a compound of formula (I), or pharmaceutically acceptable salts, or pharmaceutically acceptable solvates of said compounds, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula (I), or pharmaceutically acceptable salts, or pharmaceutically acceptable solvates of said compounds. In one embodiment, said method relates to the treatment of cancer such as brain, ophthalmic, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., BPH).

The invention also relates to a method for the treatment of a hyperproliferative disorder in a mammal which comprises administering to said mammal a therapeutically effective amount of a compound of formula (I), or pharmaceutically acceptable salts, or pharmaceutically acceptable solvates of said compounds, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The treatment of a hyperproliferative disorder in a mammal which comprises administering to said mammal a therapeutically effective amount of a VEGF receptor tyrosine kinase inhibitor may lead to a sustained increase in blood pressure.

The compounds of the present invention may be used in conjunction with an anti-hypertensive, such as NORVASC or PROCARDIA XL, commercially available from Pfizer, for use in the treatment of a hyperproliferative disorder in a mammal.

This invention also relates to a pharmaceutical composition for treating a disease related to vasculogenesis or angiogenesis in a mammal comprising (a) therapeutically effective amount of a compound of formula (I), or pharmaceutically acceptable salts, or pharmaceutically acceptable solvates of said compounds, (b) a therapeutically effective amount of a compound, salt or solvate of an antihypertensive agent, and (c) a pharmaceutically acceptable carrier.

This invention also relates to a pharmaceutical composition for treating a disease related to vasculogenesis or angiogenesis in a mammal comprising (a) therapeutically effective amount of a compound of formula (I), or pharmaceutically acceptable salts, or pharmaceutically acceptable solvates of said compounds, (b) a therapeutically effective amount of a compound, salt or solvate of an inhibitor of tumor necrosis factor alpha, and (c) a pharmaceutically acceptable carrier.

This invention also relates to a pharmaceutical composition for treating a disease related to undesired angiogenesis, endothelial cell migration or endothelial cell proliferation in a mammal comprising (a) therapeutically effective amount of a compound of formula (I), or pharmaceutically acceptable salts, or pharmaceutically acceptable solvates of said compounds, (b) a therapeutically effective amount of a compound, salt or solvate of a NADPH oxidase inhibitor, and (c) a pharmaceutically acceptable carrier.

This invention also relates to a pharmaceutical composition for inhibiting abnormal cell growth in a mammal, including a human, comprising an amount of a compound of formula (I), or pharmaceutically acceptable salts, or pharmaceutically acceptable solvates of said compounds, that is effective in inhibiting farnesyl protein transferase, and a pharmaceutically acceptable carrier.

This invention also relates to a pharmaceutical composition for inhibiting abnormal cell growth in a mammal which comprises an amount of a compound of formula (I), or pharmaceutically acceptable salts, or pharmaceutically acceptable solvates of said compounds, in combination with an amount of a chemotherapeutic, wherein the amounts of the compound, salt, or solvate, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, e.g. anti-androgens.

The compounds described herein may be used in a method for preventing or reducing the growth of tumor cells expressing functional VEGF-1 receptors by administering an effective amount of a small molecule VEGF-1 receptor antagonist to inhibit autocrine stimulation and an effective amount of a compound of Formula (I). Active ingredients in such compositions may be present in free form or in the form of a pharmaceutical acceptable salt and optionally at least one pharmaceutically acceptable carrier.

The compounds described herein also may be used in combination with a selective COX-2-inhibitor for simultaneous, separate or sequential use. The compounds described herein may also be used in combination with a truncated, soluble Flkl/KDR receptor to treat a subjects having disease or disorder associated with VEGF. Active ingredients in such compositions may be present in free form or in the form of a pharmaceutical acceptable salt and optionally at least one pharmaceutically acceptable carrier.

The compounds described herein also may be used in combination with a second active ingredient which decreases the activity of, binds to, or inhibits the epidermal growth factor (EGF). Active ingredients in such compositions may be present in free form or in the form of a pharmaceutical acceptable salt and optionally at least one pharmaceutically acceptable carrier.

The compounds described herein also may be used to inhibit VEGF-mediated angiogenesis in a tissue via several methods including but not limited to, contacting the tissue with an inhibitor of NADPH oxidase and an effective amount of a compound of Formula (I), by contacting the tissue with an inhibitor of reactive oxygen species (ROS) and an effective amount of a compound of Formula (I), or by contacting the tissue with an inhibitor of superoxide dismutase (SOD) and an effective amount of a compound of Formula (I). Active ingredients in such compositions may be present in free form or in the form of a pharmaceutical acceptable salt and optionally at least one pharmaceutically acceptable carrier.

The compounds described herein may also be used in combination with molecules which specifically bind to placenta growth factor in order to suppress or prevent placenta growth factor-induced pathological angiogenesis, vascular leakage (oedema), pulmonary hypertension, tumour formation and/or inflammatory disorders.

The compounds described herein also may be used in combination with molecules chosen from the group comprising: an antibody or any fragment thereof which specifically binds to placenta growth factor, a small molecule specifically binding to placenta growth factor or to vascular endothelial growth factor receptor-1, -vascular endothelial growth factor receptor-1 antagonists or any fragment thereof, -a ribozyme against nucleic acids encoding placenta growth factor or the vascular endothelial growth factor receptor-1, and -anti-sense nucleic acids hybridizing with nucleic acids encoding placenta growth factor or vascular endothelial growth factor receptor-1. Active ingredients in such compositions may be present in free form or in the form of a pharmaceutical acceptable salt and optionally at least one pharmaceutically acceptable carrier.

The compounds described herein may be used in a method of inhibiting the growth of non-solid tumor cells that are stimulated by a ligand of vascular endothelial growth factor receptor (including but not limited to VEGFR2 kinase) in mammals, the method comprising treating the mammals with an effective amount of a compound of Formula (I). The compounds described herein may be used in a method of inhibiting the growth of non-solid tumors that are stimulated by a ligand of vascular endothelial growth factor receptor (including but not limited to VEGFR2 kinase) in mammals, the method comprising treating the mammals with an effective amount of a compound of Formula (I) in combination with radiation.

The compounds described herein may also be used in combination with G2/M agents and with therapeutic agents whose therapeutic effectiveness is dependent, at least in part, on the presence of an internalizing cell surface structure on the target cell. Such G2/M agents include but are not limited to vinorelbine tartrate, cisplatin, carboplatin, paclitaxel, doxorubicin, 5FU, docetaxel, vinblastine, vincristine, cyclophosphamide, apigenin, genistein, cycloxazoline. The compounds described herein may also be used in combination with substances which inhibit signal transduction mediated by human VEGF receptor Flt-1.

The compounds described herein may also be used for treating or preventing a tumor necrosis factor-mediated disease comprising co-administering a tumor necrosis factor alpha antagonist and an effective amount of a compound of Formula (I) to a patient. Contemplated tumor necrosis factor-mediated diseases include but are not limited to autoimmune disease, acute or chronic immune disease, inflammatory disease and neurodegenerative disease.

This invention further relates to a method for inhibiting abnormal cell growth in a mammal which method comprises administering to the mammal an amount of a compound of formula (I), or pharmaceutically acceptable salts, or pharmaceutically acceptable solvates of said compounds, in combination with radiation therapy, wherein the amount of the compound, salt, or solvate is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula (I) can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula (I), or pharmaceutically acceptable salts, or pharmaceutically acceptable solvates of said compounds, which amount is effective in sensitizing abnormal cells to or enhancing the effects of treatment with radiation. The amount of the compound, salt, or solvate of formula (I) in this method can be determined according to the means for ascertaining effective amounts of such compounds described herein.

This invention also relates to a method of and to a pharmaceutical composition for inhibiting abnormal cell growth in a mammal which comprises an amount of a compound of formula (I), or pharmaceutically acceptable salts, or pharmaceutically acceptable solvates of said compounds, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula (I) and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are Prinomastat, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds. Other anti-angiogenesis agents, including other COX-II inhibitors and other MMP inhibitors, can also be used in the present invention.

This invention further relates to a method for treating a disease related to vasculogenesis or angiogenesis in a mammal comprising administering to said mammal a therapeutically effective amount of a compound of formula (I), or pharmaceutically acceptable salts, or pharmaceutically acceptable solvates of said compounds, in conjunction with a therapeutically effective amount of an anti-hypertensive agent.

A compound of formula (I) can also be used with signal transduction inhibitors, such as agents that can inhibit EGFR (epidermal growth factor receptor) responses, such as EGFR antibodies, EGF antibodies, and molecules that are EGFR inhibitors; VEGFR (vascular endothelial growth factor receptor) inhibitors, such as organic molecules or antibodies that bind to the VEGF receptor; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGFR inhibitors, for example SU-5416 and SU-6668 (Sugen Inc. of South San Francisco, Calif., USA), can also be combined with the compound of the present invention. VEGFR inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGFR inhibitors useful in the present invention are IM862 (Cytran Inc. of Kirkland, Wash., USA); anti-VEGFR monoclonal antibody of Genentech, Inc. of South San Francisco, Calif.; and angiozyme, a synthetic ribozyme from Ribozyme (Boulder, Colo.) and Chiron (Emeryville, Calif.). These and other VEGFR inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compounds of the present invention.

The compounds of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) that is incorporated by reference in its entirety, however other CTLA4 antibodies can be used in the present invention.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, and pharmaceutically acceptable salts of said compounds which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are noted for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be used in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The compounds of formula (I) or pharmaceutically acceptable salts, or pharmaceutically acceptable solvates of said compounds, can each independently also be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of present invention may in certain instances exist as tautomers. This invention relates to the use of all such tautomers and mixtures thereof.

Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulae are intended to cover solvated as well as unsolvated forms of the identified structures. For example, Formula I includes compounds of the indicated structure in both hydrated and non-hydrated forms. Additional examples of solvates include the structures in combination with isopropanol, ethanol, methanol, DMSO, ethyl acetate, acetic acid, or ethanolamine.

In the case of agents that are solids, it is understood by those skilled in the art that the inventive compounds and salts may exist in different crystal or polymorphic forms, all of which are intended to be within the scope of the present invention and specified formulas.

DEFINITIONS

As used herein, the following terms have the following meanings, unless expressly indicated otherwise.

The term "comprising" and "including" are used in their open, non-limiting sense.

The terms "abnormal cell growth" and "hyperproliferative disorder" are used interchangeably in this application.

"Abnormal cell growth" refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "acyl" includes alkyl, aryl, or heteroaryl substituents attached to a compound via a carbonyl functionality (e.g., —C(O)-alkyl, —C(O)-aryl, etc.).

The term "acylamino" refers to an acyl radical appended to an amino or alkylamino group, and includes —C(O)—NH$_2$ and —C(O)—NRR' groups where R and R' are as defined in conjunction with alkylamino.

The term "acyloxy" refers to the ester group —OC(O)—R, where R is H, alkyl, alkenyl, alkynyl, or aryl.

The term "alkenyl" includes alkyl moieties having at least one carbon-carbon double bond, including E and Z isomers of said alkenyl moiety. The term also includes cycloalkyl moieties having at least one carbon-carbon double bond, i.e., cycloalkenyl. Examples of alkenyl radicals include ethenyl, propenyl, butenyl, 1,4-butadienyl, cyclopentenyl, cyclohexenyl, prop-2-enyl, but-2-enyl, but-3-enyl, 2-methylprop-2-enyl, hex-2-enyl, and the like. An alkenyl group may be optionally substituted.

The term "alkenylene" refers to a divalent straight chain, branched chain or cyclic saturated aliphatic group containing at least one carbon-carbon double bond, and including E and Z isomers of said alkenylene moiety. An alkyenylene group may be optionally substituted.

The term "alkoxy" means an O-alkyl group. Examples of alkoxy radicals include methoxy, ethoxy, n-propoxy, isopropoxy, n-butoxy, iso-butoxy, sec-butoxy, tert-butoxy and the like.

The term "alkyl" means saturated monovalent hydrocarbon radicals having straight, cyclic or branched moieties. An "alkyl" group may include an optional carbon-carbon double or triple bond where the alkyl group comprises at least two carbon atoms. Cycloalkyl moieties require at least three carbon atoms. Examples of straight or branched alkyl radicals include methyl (Me), ethyl (Et), n-propyl, isopropyl, n-butyl, isobutyl, sec-butyl, tert-butyl, tert-amyl, pentyl, isopentyl, hexyl, heptyl, octyl and the like. An alkyl group may be optionally substituted.

The term "alkylamino" refers to the —NRR' group, where R and R' are independently selected from hydrogen (however, R and R' cannot both be hydrogen), alkyl, and aryl groups; or R and R', taken together, can form a cyclic ring system.

The term "alkylene" refers to a divalent straight chain, branched chain or cyclic saturated aliphatic group. The latter group may also be referred to more specifically as a cycloalkylene group. An alkylene group may be optionally substituted.

The term "alkylthio" alone or in combination, refers to an optionally substituted alkyl thio radical, alkyl-S—.

The term "alkynyl" refers to straight- and branched-chain alkynyl groups having from two to twelve carbon atoms, preferably from 2 to 6 carbons, and more preferably from 2 to 4 carbons. Illustrative alkynyl groups include prop-2-ynyl, but-2-ynyl, but-3-ynyl, 2-methylbut-2-ynyl, hex-2-ynyl, and the like. An alkynyl group may be optionally substituted.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl.

The term "amino" refers to the —NH$_2$ group.

The term "anti-neoplastic agent" refers to agents capable of inhibiting or preventing the growth of neoplasms, or checking the maturation and proliferation of malignant (cancer) cells.

The term "aromatic" refers to compounds or moieties comprising multiple conjugated double bonds. Examples of aromatic moieties include, without limitation, aryl or heteroaryl ring systems.

The term "aryl" (Ar) means an organic radical derived from a monocyclic or polycyclic aromatic hydrocarbon by removal of one hydrogen, such as phenyl or naphthyl. Preferred aryl groups have from 4 to 20 ring atoms, and more preferably from 6 to 14 ring atoms. An aryl group may be optionally substituted. Illustrative examples of aryl groups include the following moieties:

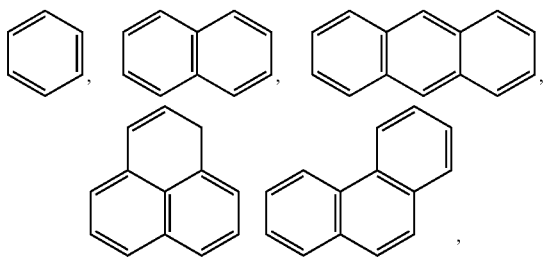

and the like.

The term "aryloxy" means aryl-O—.

The term "arylthio" means an aryl thio radical, aryl-S—.

The term "carbamoyl" or "carbamate" refers to the group —O—C(O)—NRR" where R and R" are independently selected from hydrogen, alkyl, and aryl groups; and R and R" taken together can form a cyclic ring system.

The term "carbocyclyl" includes optionally substituted cycloalkyl and aryl moieties. The term "carbocyclyl" also includes cycloalkenyl moieties having at least one carbon-carbon double bond.

The term "carboxy esters" refers to —C(O)OR where R is alkyl or aryl.

The term "cycloalkyl" refers to a monocyclic or polycyclic radical which contains only carbon and hydrogen, and may be saturated, partially unsaturated, or fully unsaturated. A cycloalkyl group may be optionally substituted. Preferred cycloalkyl groups include groups having from three to twelve ring atoms, more preferably from 5 to 10 ring atoms. Illustrative examples of cycloalkyl groups include the following moieties:

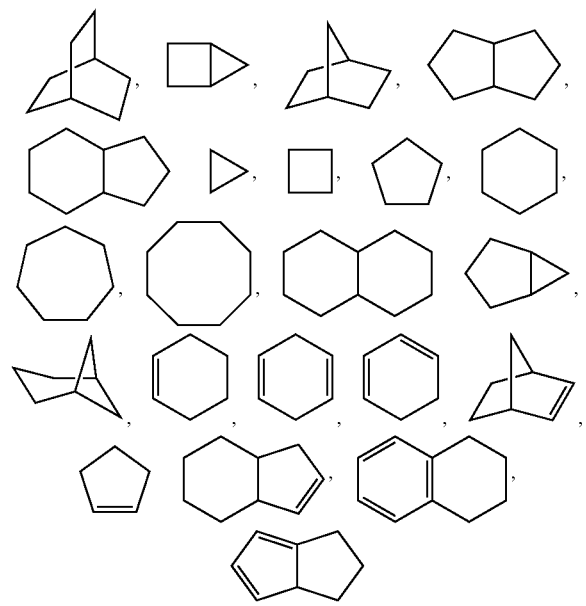

and compounds of the like.

The term "halo" or "halogen" means fluoro, chloro, bromo or iodo. Preferred halo groups are fluoro, chloro and bromo.

The terms haloalkyl, haloalkenyl, haloalkynyl and haloalkoxy include alkyl, alkenyl, alkynyl and alkoxy structures, that are substituted with one or more halo groups or with combinations thereof.

The terms "heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof.

The term "heteroaryl" (heteroAr) refers to an aryl group that includes one or more ring heteroatoms selected from nitrogen, oxygen and sulfur. A heteroaryl group may be optionally substituted. The polycyclic heteroaryl group may be fused or non-fused. Illustrative examples of aryl groups include the following moieties:

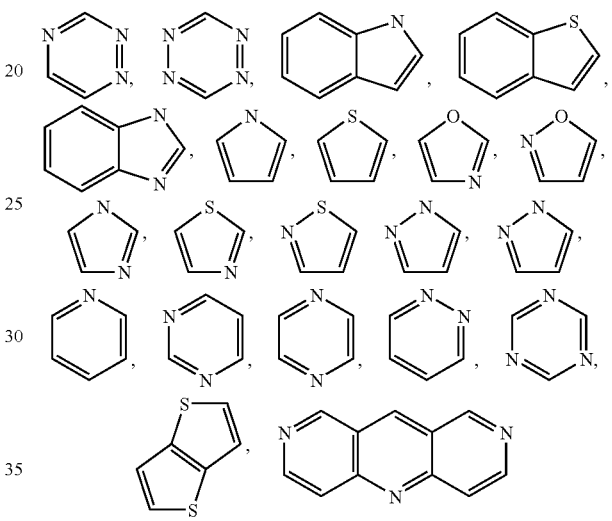

and the like.

The term "heterocyclyl" refers to aromatic and non-aromatic heterocyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl. An example of a 6 membered heterocyclic group is pyridyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. A heterocyclyl group may be optionally substituted.

The term "heterocyclic" comprises both heterocycloalkyl and heteroaryl groups.

A "heterocycloalkyl" group refers to a cycloalkyl group that includes at least one heteroatom selected from nitrogen, oxygen and sulfur. The radicals may be fused with an aryl or heteroaryl. Illustrative examples of heterocycloalkyl groups include

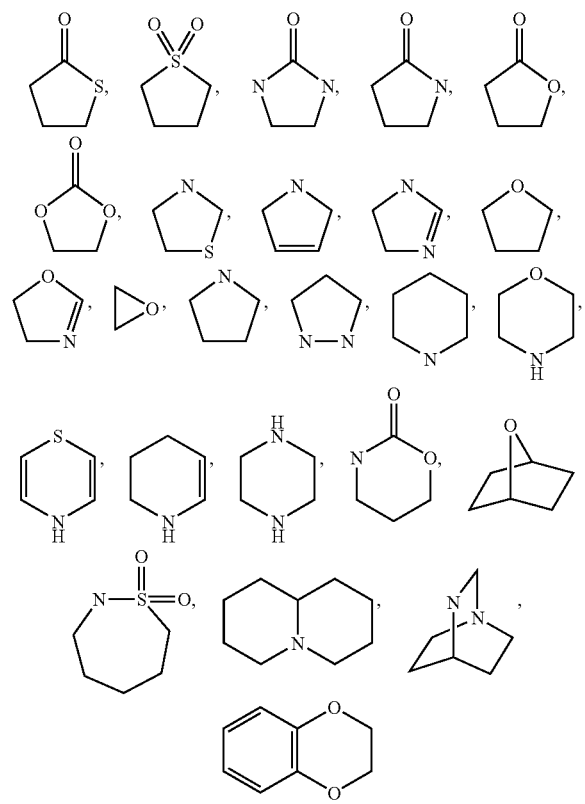

and the like.

The terms "5 membered heterocyclic", "5 or 6 membered heterocyclic", "5 to 8 membered heterocyclic", "5 to 10 membered heterocyclic" or "5 to 13 membered heterocyclic" includes aromatic and non-aromatic heterocyclic groups containing one to four heteroatoms each selected from O, S and N, wherein each heterocyclic group has from 5, 6, 5 to 8, 5 to 10 or 5 to 13 atoms in its ring system, respectively.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "neoplasm" is defined as in Stedman's *Medical Dictionary* 25th Edition (1990) and refers to an abnormal tissue that grows by cellular proliferation more rapidly than normal and continues to grow after the stimuli that initiated the new growth ceases. Neoplasms show partial or complete lack of structural organization and functional coordination compared with normal tissue, and usually form a distinct mass of tissue that may be either benign (benign tumor) or malignant (cancer).

"Optionally substituted" groups may be substituted or unsubstituted. When substituted, the substituents of an "optionally substituted" group may include, without limitation, one or more substituents independently selected from the following groups or designated subsets thereof: $(C_1-C_6)$ alkyl, $(C_2-C_6)$alkenyl, $(C_2-C_6)$alkynyl, $(C_1-C_6)$heteroalkyl, $(C_1-C_6)$haloalkyl, $(C_2-C_6)$haloalkenyl, $(C_2-C_6)$haloalkynyl, $(C_3-C_6)$cycloalkyl, phenyl, $(C_1-C_6)$alkoxy, phenoxy, $(C_1-C_6)$ haloalkoxy, amino, $(C_1-C_6)$alkylamino, $(C_1-C_6)$alkylthio, phenyl-S—, oxo, $(C_1-C_6)$carboxyester, $(C_1-C_6)$carboxamido, $(C_1-C_6)$acyloxy, H, halogen, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, pyridinyl, thiophene, furanyl, $(C_1-C_6)$carbamate, and $(C_1-C_6)$urea. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$).

The term "oxo" means an "O" group.

The term "perhalo" refers to groups wherein every C—H bond has been replaced with a C-halo bond on an aliphatic or aryl group. Examples of perhaloalkyl groups include —$CF_3$ and —$CFCl_2$.

The term "substituted" means that the group in question, e.g., alkyl group, etc., may bear one or more substituents.

The term "ureyl" or "urea" refers to the group —N(R)—C(O)—NR'R" where R, R', and R" are independently selected from hydrogen, alkyl, aryl; and where each of R—R', R'—R", or R—R" taken together can form a cyclic ring system.

Pharmaceutical Formulations and Compositions

In addition to compounds of Formula I, the invention includes N-oxides, pharmaceutically acceptable solvates, and pharmaceutically acceptable salts of such compounds and solvates.

The term "pharmaceutically acceptable" means pharmacologically acceptable and substantially non-toxic to the subject being administered the agent.

A "pharmacological composition" refers to a mixture of one or more of the compounds described herein, or physiologically acceptable salts thereof, with other chemical components, such as physiologically acceptable carriers and/or excipients. The purpose of a pharmacological composition is to facilitate administration of a compound to an organism.

A "physiologically acceptable carrier" refers to a carrier or diluent that does not cause significant or otherwise unacceptable irritation to an organism and does not unacceptably abrogate the biological activity and properties of the administered compound.

An "excipient" generally refers to substance, often an inert substance, added to a pharmacological composition or otherwise used as a vehicle to further facilitate administration of a compound. Examples of excipients include but are not limited to calcium carbonate, calcium phosphate, various sugars and types of starch, cellulose derivatives, gelatin, vegetable oils and polyethylene glycols.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid, 2-acetoxybenzoic acid or cinnamic acid, a sulfonic acid, such as p-toluenesulfonic acid, methanesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

Pharmaceutical compositions according to the invention may, alternatively or in addition to a compound of Formula (I), comprise as an active ingredient pharmaceutically acceptable salts of such compounds. Such compounds and salts are sometimes referred to herein collectively as "active agents" or "agents."

It will be appreciated that any solvate (e.g. hydrate) form of compounds of formula (I) can be used for the purpose of the present invention.

Therapeutically effective amounts of the active agents of the invention may be used to treat diseases mediated by modulation or regulation of protein kinases. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The compositions containing the compound(s) of the described herein can be administered for prophylactic and/or therapeutic treatments. In therapeutic applications, the compositions are administered to a patient already suffering from a proliferative disorder or condition (including, but not limited to, cancer), as described above, in an amount sufficient to cure or at least partially arrest the symptoms of the proliferative disorder or condition. An amount adequate to accomplish this is defined as "therapeutically effective amount or dose." Amounts effective for this use will depend on the severity and course of the proliferative disorder or condition, previous therapy, the patient's health status and response to the drugs, and the judgment of the treating physician. In prophylactic applications, compositions containing the compounds described herein are administered to a patient susceptible to or otherwise at risk of a particular proliferative disorder or condition. Such an amount is defined to be a "prophylactically effective amount or dose." In this use, the precise amounts also depend on the patient's state of health, weight, and the like. It is considered well within the skill of the art for one to determine such therapeutically effective or prophylactically effective amounts by routine experimentation (e.g., a dose escalation clinical trial).

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system (e.g., a tumor cell). An "enhancing-effective amount," as used herein, refers to an amount adequate to enhance the effect of another therapeutic agent in a desired system (including, by way of example only, a tumor cell in a patient). When used in a patient, amounts effective for this use will depend on the severity and course of the proliferative disorder (including, but not limited to, cancer), previous therapy, the patient's health status and response to the drugs, and the judgment of the treating physician. It is considered well within the skill of the art for one to determine such enhancing-effective amounts by routine experimentation.

Once improvement of the patient's conditions has occurred, a maintenance dose is administered if necessary. Subsequently, the dosage or the frequency of administration, or both, can be reduced, as a function of the symptoms, to a level at which the improved proliferative disorder or condition is retained. When the symptoms have been alleviated to the desired level, treatment can cease. Patients can, however, require intermittent treatment on a long-term basis upon any recurrence of the disease symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of one or more kinases, for example protein kinases such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Agents that potently regulate, modulate, or inhibit cell proliferation are preferred. For certain mechanisms, inhibition of the protein kinase activity associated with CDK complexes, among others, and those which inhibit angiogenesis and/or inflammation are preferred. The present invention is further directed to methods of modulating or inhibiting protein kinase activity, for example in mammalian tissue, by administering a compound of Formula (I). The activity of agents as anti-proliferatives is easily measured by known methods, for example by using whole cell cultures in an MTT assay. The activity of the compounds of Formula (I) as modulators of protein kinase activity, such as the activity of kinases, may be measured by any of the methods available to those skilled in the art, including in vivo and/or in vitro assays. Examples of suitable assays for activity measurements include those described in International Publication No. WO 99/21845; Parast, et al., *Biochemistry*, 37, 16788-16801 (1998); Connell-Crowley and Harpes, *Cell Cycle Materials and Methods*, (Michele Pagano, ed. Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the compounds of Formula (I) are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

A compound of Formula (I) can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a compound of Formula (I) can be dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethylcellulose, sodium carboxymethylcellulose, or polyvinylpyrrolidone (PVP). If desired, disintegrating agents may be added, such as crosslinked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of agents.

Pharmaceutical preparations that can be used orally include push-fit capsules made of gelatin, as well as soft, sealed capsules made of gelatin and a plasticizer, such as glycerol or sorbitol. The push-fit capsules can contain the agents in admixture with fillers such as lactose, binders such as starches, and/or lubricants such as talc or magnesium stearate, and, optionally, stabilizers. In soft capsules, the agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions take the form of tablets or lozenges formulated in conventional manners.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the agents in water-soluble form. Additionally, suspensions of the agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For administration to the eye, the agent is delivered in a pharmaceutically acceptable ophthalmic vehicle such that the compound is maintained in contact with the ocular surface for a sufficient time period to allow the compound to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

The agents may also be administered in conjunction with other accepted ophthalmic disease treatments, such as photodynamic therapy (PDT).

Alternatively, the agents may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the agents may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The agents of the invention may be useful in combination with known anti-cancer treatments such as: DNA interactive agents such as cisplatin or doxorubicin; topoisomerase II inhibitors such as etoposide; topoisomerase I inhibitors such as CPT-11 or topotecan; tubulin interacting agents such as paclitaxel, docetaxel or the epothilones; hormonal agents such as tamoxifen; thymidilate synthase inhibitors such as 5-fluorouracil; and anti-metabolites such as methotrexate. They may be administered together or sequentially, and when administered sequentially, the agents may be administered either prior to or after administration of the known anticancer or cytotoxic agent.

The term "chemotherapeutic agent" as used herein includes, for example, hormonal agents, antimetabolites, DNA interactive agents, tubilin-interactive agents, and others such as aspariginase or hydroxyureas.

DNA-interactive agents include alkylating agents, such as cisplatin, cyclophosphamide, altretamine; DNA strand-breakage agents, such as bleomycin; intercalating topoisomerase II inhibitors, e.g., dactinomycin and doxorubicin); nonintercalating topoisomerase II inhibitors such as, etoposide and teniposide; and the DNA minor groove binder plicamydin, for example.

Alkylating agents may form covalent chemical adducts with cellular DNA, RNA, or protein molecules, or with smaller amino acids, glutathione, or similar chemicals. Examples of typical alkylating agents include, but are not limited to, nitrogen mustards, such as chlorambucil, cyclophosphamide, isofamide, mechlorethamine, melphalan, uracil mustard; aziridine such as thiotepa; methanesulfonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine. DNA strand-breaking agents include bleomycin, for example.

DNA topoisomerase II inhibitors may include intercalators such as the following: amsacrine, dactinomycin, daunorubicin, doxorubicin (adriamycin), idarubicin, and mitoxantrone; as well as nonintercalators such as etoposide and teniposide.

An example of a DNA minor groove binder is plicamycin.

Antimetabolites generally interfere with the production of nucleic acids and thereby growth of cells by one of two major mechanisms. Certain drugs inhibit production of deoxyribonucleoside triphosphates that are the precursors for DNA synthesis, thus inhibiting DNA replication. Examples of these compounds are analogues of purines or pyrimidines and are incorporated in anabolic nucleotide pathways. These analogues are then substituted into DNA or RNA instead of their normal counterparts.

Antimetabolites useful as chemotherapeutic agents include, but are not limited to: folate antagonists such as methotrexate and trimetrexate; pyrimidine antagonists, such as fluorouracil, fluorodeoxyuridine, CB3717, azacitidine, cytarabine, and floxuridine; purine antagonists such as mercaptopurine, 6-thioguanine, fludarabine, pentostatin; and ribonucleotide reductase inhibitors such as hydroxyurea.

Tubulin interactive agents act by binding to specific sites on tubulin, a protein that polymerizes to form cellular microtubules. Microtubules are critical cell structure units and are required for cell division. These therapeutic agents disrupt the formation of microtubules. Exemplary tubulin-interactive agents include vincristine and vinblastine, both alkaloids and paclitaxel (Taxol).

Hormonal agents are also useful in the treatment of cancers and tumors, but only rarely in the case of B cell malignancies. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone and are used to treat B cell malignancies. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Other agents include hydroxyurea (which appears to act primarily through inhibition of the enzyme ribonucleotide reductase), and asparaginase (an enzyme which converts asparagine to aspartic acid and thus inhibits protein synthesis).

Included within the scope of cancer therapy agents are radiolabeled antibodies, including but not limited to, Zevalin™ (IDEC Pharmaceuticals Corp.) and Bexxar (Corixa, Inc.); the use of any other radioisotope (e.g., $^{90}Y$ and $^{131}I$) coupled to an antibody or antibody fragment that recognizes an antigen expressed by a neoplasm; external beam radiation or any other method for administration of radiation to a patient.

Further included within the scope of cancer therapy agents are cytotoxins, including but not limited to an antibody or antibody fragment linked to a cytotoxin, or any other method for selectively delivering a cytotoxic agent to a tumor cell.

Further included within the scope of cancer therapy agents are selective methods for destroying DNA, or any method for delivering heat to a tumor cells, including by way of example only, nanoparticles.

Further included within the scope of cancer therapy agents is the use of unlabeled antibodies or antibody fragments capable of killing or depleting tumor cells, including by way of example only, Rituxan™ (IDEC Pharmaceuticals Corp.) and Herceptin™ (Genentech).

The agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other anti-proliferatives or protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

DETAILED DESCRIPTION OF THE INVENTION

The compounds of Formula (I) can act as antagonists of the VEGFR2. Without being bound to any particular theory, the linked rings are thought to provide favorable space-filling and electrostatic complementarity in the active site of the targeted protein: the presence of a quinoline moiety offers structure advantages exemplified by the introduction of ether linked solubilizing groups on 6, or 7-position of the quinoline ring (depicted below):

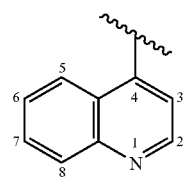

In addition, and without being bound to any particular theory, physico-chemical changes which result from introducing substituents at the 6 and 7 positions of the quinoline ring include but are not limited to: increased water solubility and selectivity (against FGF) of the prepared compounds and a favorable change in pharmaco-kinetics, dynamics and metabolism (PDM) properties In the examples described below, unless otherwise indicated, all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF), N,N-dimethylformamide (DMF), dichloromethane, toluene, and dioxane were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47-61 μm) and a silica gel: crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

General Synthetic Schemes Used for the Preparation of Quinoline ANALOGS

SCHEME I: GENERAL PREPARATION OF 4-CHLOROQUINOLINE ANALOGS (I-F)

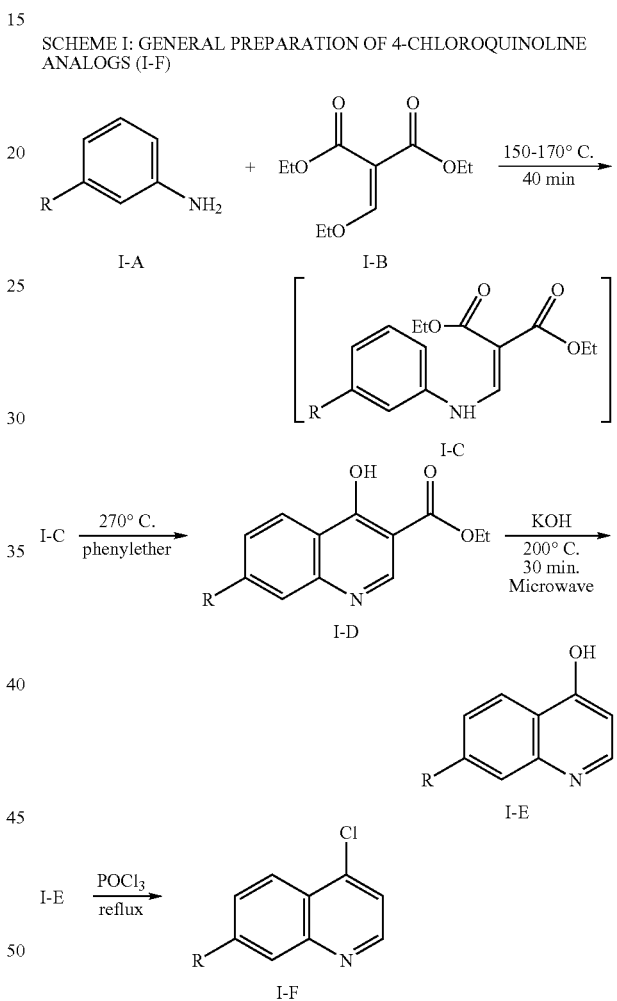

In this scheme R is an $R^6$ substituent as defined in connection with Formula (I). Reference: 1). *J. Am. Chem. Soc.*, 68, 1204-1208, (1946). 2). *J. Am. Chem. Soc.*, 68, 113-116, 1946.

A. Preparation of Compound I-D

A mixture of a substituted aniline I-A (1 eq.), and diethyl (ethoxymethylene) malonate I-B (1 eq.) was placed in a round bottom flask and heated in an oil bath. When the temperature of oil bath reached ~135° C. EtOH was generated and collected with a condenser. The reaction was heated at 160° C. for 40 minutes to give I-C. The reaction flask was removed from the oil bath. Phenyl ether (about two times volume of the reaction mixture) was added into the flask. The reaction flask was placed in the oil bath, which was preheated to 270° C. The reaction mixture was stirred and heated to 240-245° C. (temperature of reactants inside the flask) for 15 minutes. The reaction flask was removed from heating and slowly poured into hexane. Compound I-D was collected by filtration and washed by hexane to remove phenyl ether. The yields of reactions starting from compound I-A to compound I-D were usually in the range of 60 to 90%.

B. Preparation of Compound I-E

A solution of compound I-D (5 g) and KOH (3 eq.) in 60 ml of $H_2O/OH(CH_2)_2OH$ (1:1) was placed in a sealed vessel (XP-500 Plus vessel). The reaction was heated by microwave (MARS 5 Microwave System) at 200° C., under 220-240 psi pressure for 30 minutes. The reaction mixture was cooled to room temperature and poured into $H_2O$ (100 ml). The solution was acidified with 2N HCl to pH~6, saturated with NaCl and extracted with THF (3×200 ml). The combined oil layer was washed with brine and concentrated to give compound I-E (>80% yield).

C. Preparation of Compound I-F

Compound I-E was dissolved in neat $POCl_3$ (excess). The solution was heated to reflux for 2 hours. The excess amount of $POCl_3$ was removed by evaporation under vacuum. The residue was basified with $NH_4OH$ and extracted with EtOAc. The organic layer was concentrated. The residue was purified by column chromatography using 3:1 to 1:1 hexane/EtOAc to give compound I-F (70-90%).

SCHEME II: GENERAL PREPARATION OF (QUINOLIN-4-YL)OXY-1-BENZOFURAN (OR BENZOTHIOPHENE, OR INDOLE) ANALOGS (II-C)

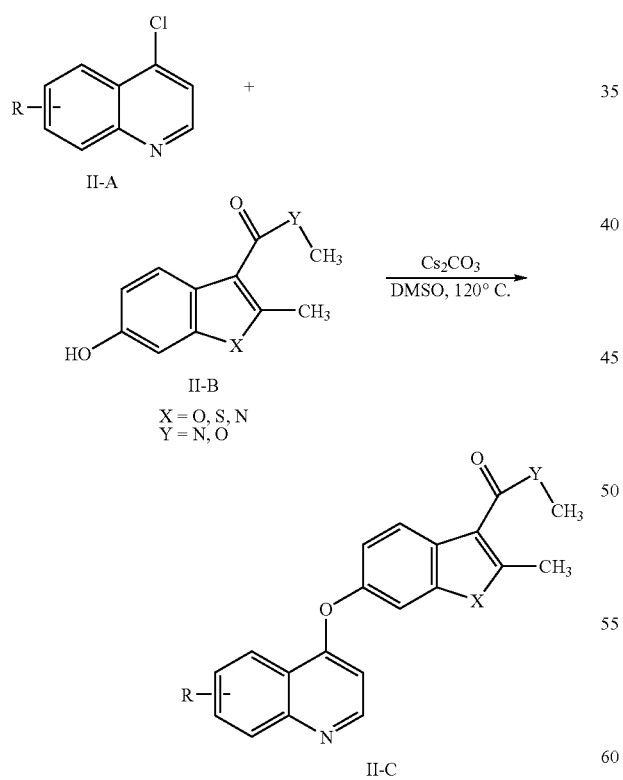

A solution of 4-chloroqunoline II-A (1 eq.), 4-hydroxyl-benzofuran (where X=O) II-B (1 eq.) and $Cs_2CO_3$ (1.5-2 eq.) in dry DMSO was heated to 120-130° C. for 2 hours. The dark brown solution was extracted with EtOAc. The organic layer was washed with brine, dried ($MgSO_4$) and concentrated. The residue was purified by silica gel column chromatography using 2-5% MeOH in $CH_2Cl_2$ to give compound II-C in 50-90% yield.

SCHEME III: GENERAL PREPARATION OF (INDOL-5-YL) QUINOLIN-4-AMINE (III-C)

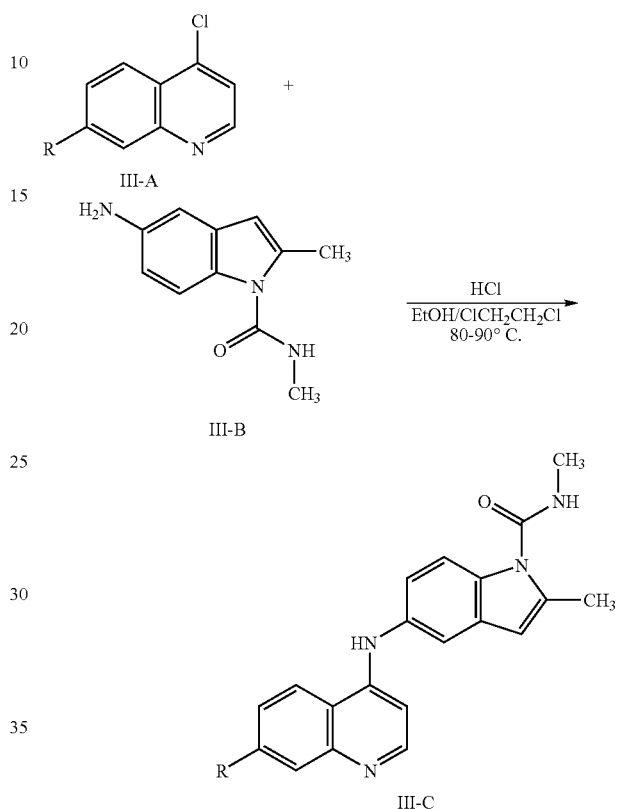

A solution of 4-chloroquinoline III-A (1 eq.), 5-amino-N, 2-dimethyl-1H-indole-1-carboxamide II-B (1 eq.) and HCl in dioxane (1.0 eq.) in a mixed solvent of $EtOH/ClCH_2CH_2Cl$ (1:1) was heated to 80-90° C. for 2 to 6 hours. The solution was extracted with EtOAc. The organic layer was washed with brine, dried ($MgSO_4$) and concentrated. The residue was purified by silica gel column chromatography using 2-5% MeOH in $CH_2Cl_2$ to give compound III-C in 50-90% yield.

SCHEME IV: GENERAL PREPARATION OF CARBOXAMIDE ANALOGS (IV-B)

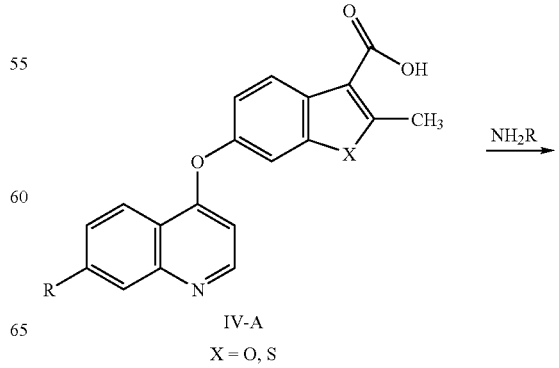

-continued

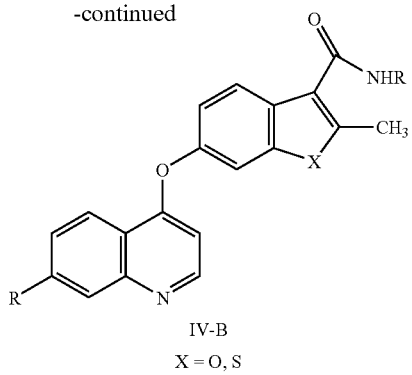

IV-B
X = O, S (i) Method IV(i)

Compound IV-A (1 eq.) was heated to reflux in net SOCl$_2$ (excess) for 2 minutes. The excess amount of SOCl$_2$ was removed by evaporation under vacuum. The residue was dissolved in dichloromethane. To this solution Et$_3$N (3 eq.) and corresponding amine were added. The solution was stirred at room temperature for 30 minutes, extracted with EtOAc, washed (brine) and concentrated. The residue was purified by silica gel column chromatography using 2-10% MeOH/CH$_2$Cl$_2$ or by HPLC (20-70% CH$_3$CN/H$_2$O) to give compound IV-B.

(ii) Method IV(ii)

To a solution of compound IV-A (1 eq.) in dichloromethane was added oxalyl chloride (5 eq.) at room temperature. The solution was stirred for 1 hour and concentrated under vacuum. The residue was dissolved in dichloromethane. To this solution Et$_3$N (3 eq.) and corresponding amine were added into. The solution was stirred at room temperature for 30 minutes, extracted with EtOAc, washed (brine) and concentrated. The residue was purified by silica gel column chromatography using 2-10% MeOH/CH$_2$Cl$_2$ or by HPLC (20-70% CH$_3$CN/H$_2$O) to give compound IV-B.

(iii) Method IV(iii)

To a solution of compound IV-A (1 eq.) in DMF was added Et$_3$N (1.5 eq.) and HATU (1.2 eq.) at room temperature. After being stirred for 10 minutes to the solution was added corresponding amine. The solution was stirred at room temperature for 30 minutes, extracted with EtOAc, washed (brine) and concentrated. The residue was purified by silica gel column chromatography using 2-10% MeOH/CH$_2$Cl$_2$ or by HPLC (20-70% CH$_3$CN/H$_2$O) to give compound IV-B.

EXAMPLES

Example 1

Preparation of N-(2-methyl-1H-indol-5-yl)-7-(trifluoromethyl)quinoline-4-amine

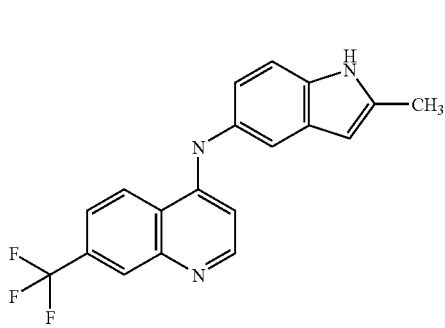

This compound was prepared according to the synthetic scheme depicted and described below.

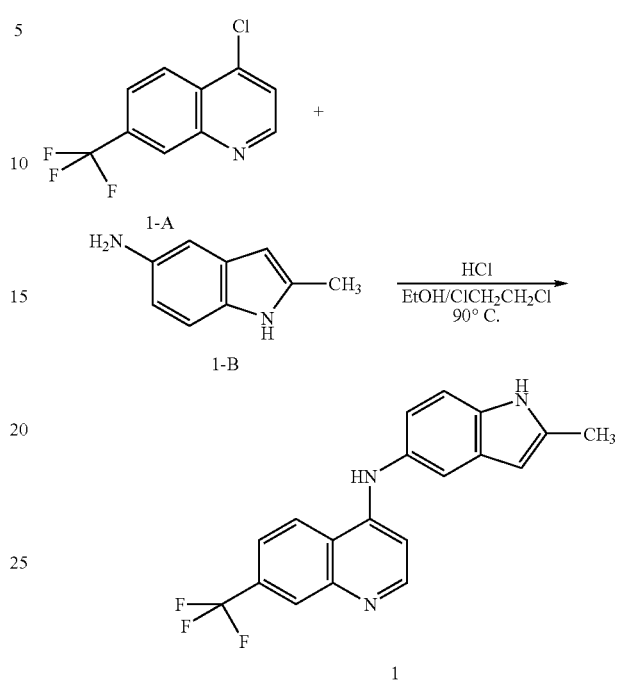

A suspension of 4-chloro-7-(trifluoromethyl)quinoline 1-A (158 mg, 0.68 mmol), 2-methyl-1H-indol-5-amine 1-B (100 mg, 0.68 mmol) and 4N HCl in dioxane (0.25 ml, 1.0 mmol) in a mixed solvent (EtOH/dichloroethane, 1:1, 6 ml) was heated to 90° C. in a sealed tube overnight. The reaction mixture was concentrated and dissolved in 2 ml of DMSO. The solution was purified by HPLC (DionexSystem, 20-60% CH$_3$CN/H$_2$O over 30 minutes). 40 mg of N-(2-methyl-1H-indol-5-yl)-7-(trifluoromethyl)quinolin-4-amine 1 was obtained.

$^1$H NMR (300 MHz, DMSO-d6) δ ppm 2.50 (s, 3H) 6.26 (s, 1H) 6.75 (d, J=5.46 Hz, 1H) 7.08 (d, J=8.48 Hz, 1H) 7.46 (m, 2H) 7.87 (d, J=8.85 Hz, 1H) 8.24 (s, 1H) 8.54 (d, J=5.27 Hz, 1H) 8.77 (s, 1H) 9.32 (s, 1H) 11.14 (s, 1H). LC/MS (APCI, pos.): 342.1 (M$^+$H).

Example 2

Preparation of 8-chloro-N-(2-methyl-1H-indol-5-yl)quinolin-4-amine

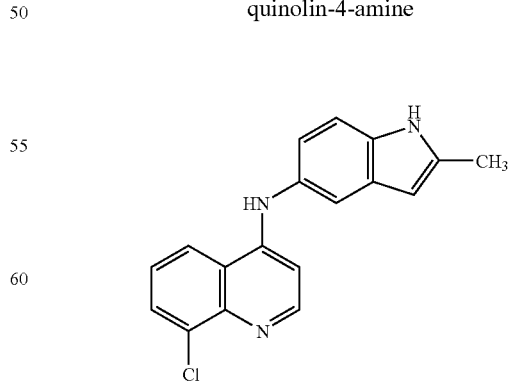

This compound was prepared by methods analogous to those described in Example 1.

¹H NMR (300 MHz, DMSO-d6) δ ppm 2.58 (s, 3H) 6.33 (s, 1H) 6.78 (d, J=5.46 Hz, 1H) 7.16 (m, 1H) 7.53 (m, 1H) 7.62 (d, J=7.35 Hz, 1H) 8.04 (d, J=7.35 Hz, 1H) 8.59 (m, 2H) 9.21 (s, 1H) 11.21 (s, 1H). LC/MS (APCI, pos.): 308.1 (M+H).

Example 3

Preparation of N-(2-methyl-1H-indol-5-yl)quinolin-4-amine

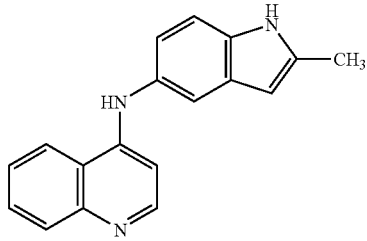

This compound was prepared using methods analogous to those described in Example 1 and Scheme III.

¹H NMR (300 MHz, DMSO-d6) δ ppm 2.15 (s, 3H) 5.89 (s, 1H) 6.32 (m, 1H) 6.73 (d, J=8.10 Hz, 1H) 7.09 (d, J=6.97 Hz, 2H) 7.23 (s, 1H) 7.40 (d, J=8.10 Hz, 1H) 7.59 (s, 1H) 8.11 (m, 2H) 8.64 (s, 1H) 10.76 (s, 1H). LC/MS (APCI, pos.): 274.1 (M+H).

Example 4

Preparation of 5-[(7-chloroquinazolini-4-yl)amino]-N,2-dimethyl-1H-indole-1-carboxamide

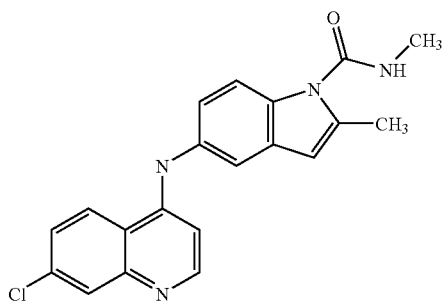

This compound was prepared using methods analogous to those described in Example 1 and Scheme III.

¹H NMR (300 MHz, DMSO-d6) δ ppm 2.44 (s, 3H) 2.83 (s, 3H) 7.40 (m, 1H) 7.54 (m, 1H) 7.74 (s, 1H) 7.85 (s, 1H) 8.12 (s, 1H) 8.46 (s, 1H) 8.53 (d, J=9.42 Hz, 1H) 9.88 (s, 1H). LC/MS (APCI, pos.): 366.1 (M+H).

Example 5

Preparation of 6-hydroxy-N,2-dimethyl-1-benzofuran-3-carboxamide

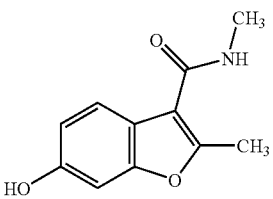

This compound was prepared according to the synthetic scheme depicted and described below.

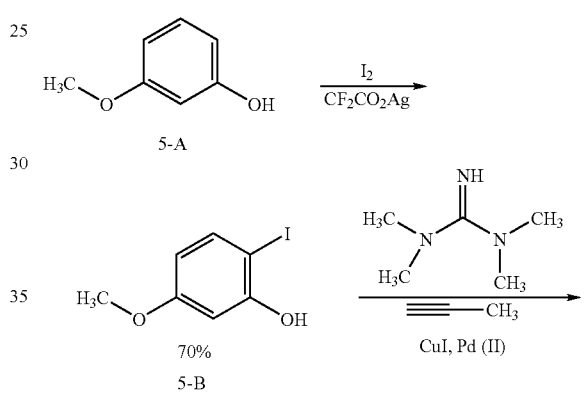

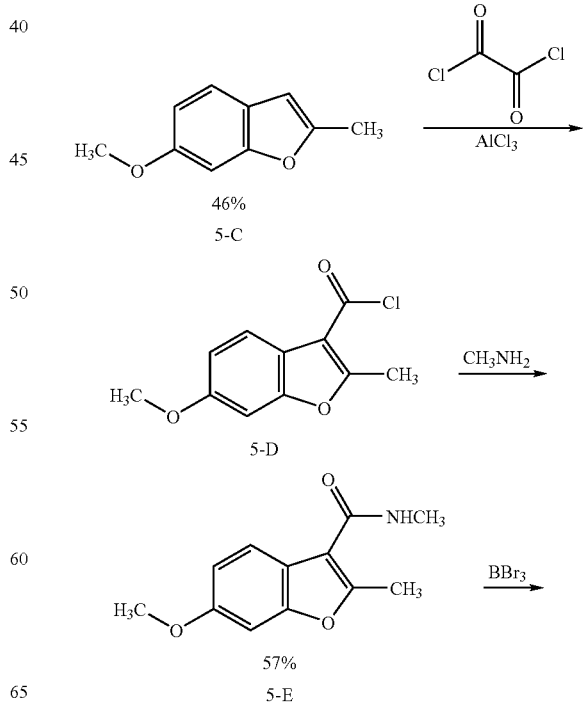

-continued

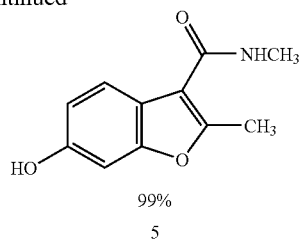

5
99%

I$_2$ (40.9 g, 161.1 mmol) was dissolved in CHCl$_3$ (850 mL) with stirring over 1 hour. The solution was added slowly into a reaction mixture of 3-methoxyphenol 5-A (20 g, 161.1 mmol) and silver trifluoroacetate in 200 mL CHCl$_3$ over 1.5 hours. The reaction was stirred at room temperature for 16 hours. Solids were removed by filtration. The filtrate was washed with 5% Na$_2$S$_2$O$_3$(500 mL), saturated NaHCO$_3$, brine, dried over MgSO$_4$ and concentrated. The crude mixture was triturated with carbon tetrachloride to give 2-iodo-5-methoxyphenol 5-B (13.6 g) as a white solid. The remaining crude products were purified by silica gel column chromatography eluted with CH$_2$Cl$_2$ to give 28.2 g of compound 5-B.

A solution of compound 5-B (14.6 g, 58.5 mmol), CuI (0.56 g, 2.9 mmol), N,N,N',N'- tetramethylguanidine (74 mL, 585 mmol) and dichlorobis(triphenyl phosphine) palladium (II) (3.9 g, 5.5 mmol) in 200 mL anhydrous DMF was cooled to −78° C. Propyne gas was bubbled in for 25 minutes. A balloon was placed to catch propyne. The reaction mixture was stirred for 17 hours, allowing temperature to go from −78° C. to room temperature. The solution was poured into 200 mL water and extracted with EtOAc, washed with water, brine and dried over MgSO$_4$. Silica gel column chromatography eluted with hexane/ethyl acetate (9:1) gave 6-methoxy-2-methyl-1-benzofuran 5-C (4.4 g, 46% yield).

A suspension of AlCl$_3$ (18 g, 135 mmol) in dichloromethane (250 mL) was cooled to 0° C. To this suspension oxalyl chloride (12 mL, 135 mmol) was added and stirred for 30 minutes. A solution of 5-C (4.38 g, 27 mmol) in 100 mL of dichloromethane was then added over 10 minutes. The ice bath was removed. The reaction was allowed to be stirred for 2 hours. at room temperature. The reaction mixture was poured into a saturated NaCl/ice and separated. Aqueous layer was extracted with CH$_2$Cl$_2$. The combined organic layer was dried over MgSO$_4$ and concentrated to give a crude mixture of compound 5-D (6.5 g).

Without purification the crude 5-D (6.5 g) obtained was dissolved in 50 mL of THF. To this solution was added a solution of methylamine (68 mL, 2.0M in THF). The reaction was stirred at room temperature for 1 hour. The reaction mixture was extracted with EtOAc, washed with brine, dried (MgSO$_4$), concentrated and purified by a silica gel chromatography, eluted with CH$_2$Cl$_2$/EtOAc (2:1) to give compound 5-E (3.38 g, 57% yield from 5-C).

A solution of 5-E (3.38 g, 15.4 mmol) in 50 mL of dichloromethane was cooled to −5° C. To this a solution of BBr$_3$ (31 mL, 30.8 mmol) in CH$_2$Cl$_2$ (1.0 M) was added. The solution was stirred at −5° C. for 1 hour. Additional 15 mL of BBr$_3$ solution was added and the reaction was stirred for 1 hour at 0° C. The solution was poured into saturated NaHCO$_3$/ice. The organic layer was then separated. The water layer was extracted with EtOAc. The combined organic layer was washed (brine), dried over MgSO$_4$ and concentrated to give the title compound 5 (3.16 g, 99%) as a solid.

Reference: Het. 45 (6), 1997, 1137.

Example 6

Preparation of 6-[(7-iodoquinolin-4-yl)oxy]-N,2-dimethyl-1-benzofuran-3-carboxamide

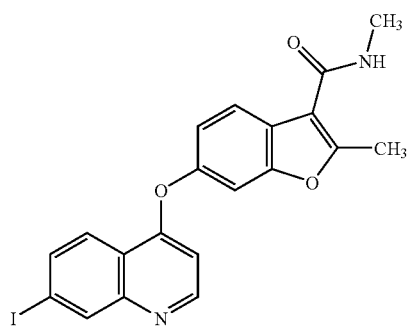

This compound was prepared according to the synthetic scheme depicted and described below.

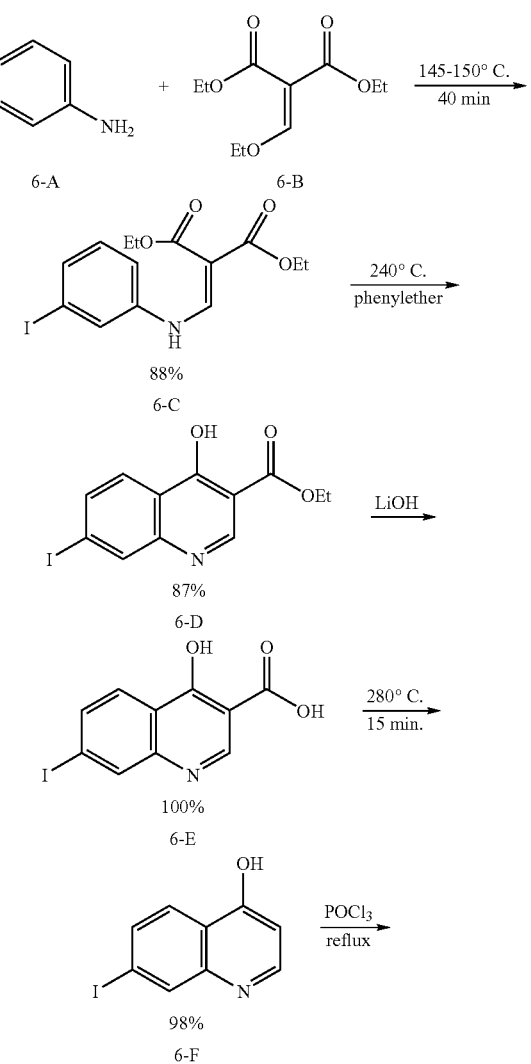

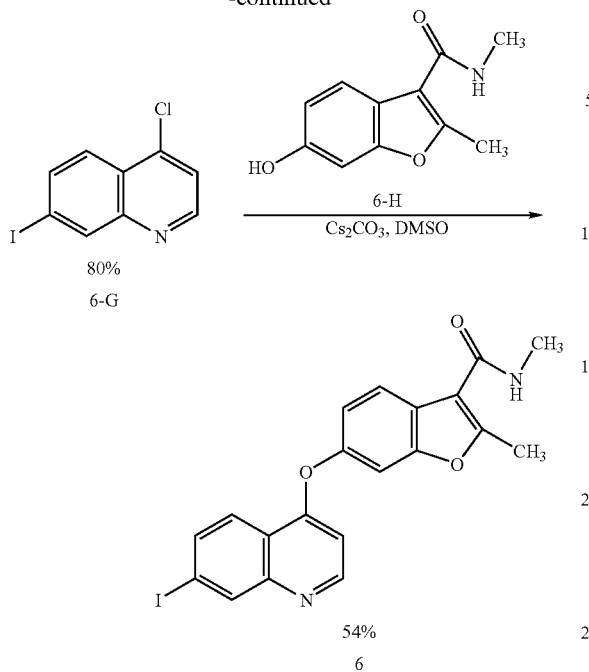

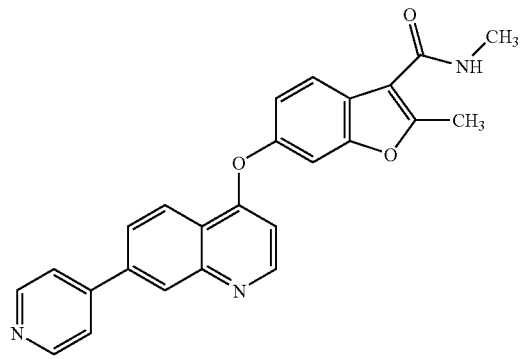

chromatography eluted with hexane/ethyl acetate (3:1 to 1:1) gave the title compound 6 (427 mg, 54% yield).

$^1$H NMR (300 MHz, CHLOROFORM-d) δ ppm 2.67 (s, 3H) 3.00 (d, J=4.90 Hz, 3H) 5.82 (s, 1H) 6.48 (d, J=5.27 Hz, 1H) 7.07 (dd, J=8.57, 2.17 Hz, 1H) 7.23 (d, J=2.07 Hz, 1H) 7.81 (dd, J=8.76, 1.60 Hz, 1H) 8.04 (d, J=8.85 Hz, 1H) 8.51 (d, J=1.32 Hz, 1H) 8.56 (d, J=5.27 Hz, 1H). LC/MS (APCI, pos.): 459.0 (M$^+$H).

Example 7

Preparation of N-2-dimethyl-6-[(7-pyridin-4-ylquinolin-4-yl)oxy]-1-benzofuran-3-carboxamide

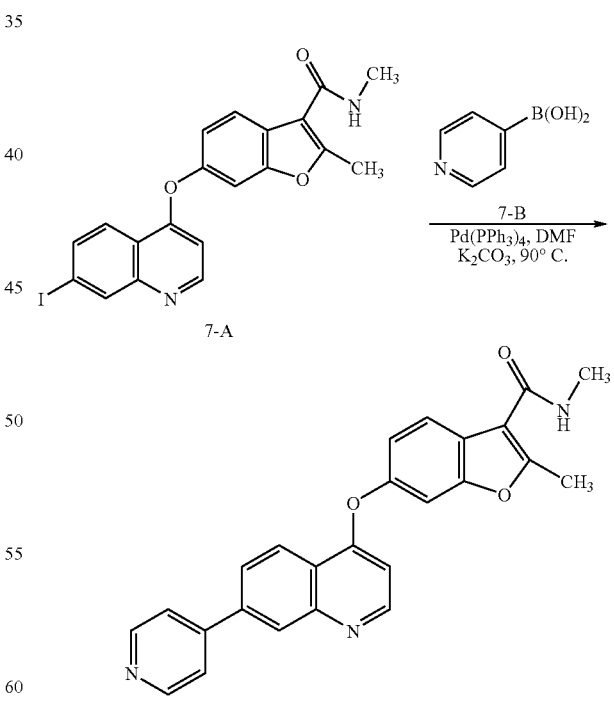

This compound was prepared according to the synthetic scheme depicted and described below.

A mixture of 3-iodoaniline 6-A (10 g, 45.6 mmol) and diethyl (ethoxymethylene) malonate 6-B (10 g, 45.6 mmol) was heated in an oil bath to 150° C. for 40 minutes. The reaction mixture was poured into 500 mL EtOH slowly with stirring. Diethyl {[(3-iodophenyl)amino]methylene}malonate 6-C (14.5 g, 88% yield) was collected as a white precipitate by filtration.

Compound 6-C (14.5 g) was placed in a round bottom flask equipped with a trap to collect EtOH generated during the reaction. Phenyl ether (60 mL) was added into the flask. When the suspension was heated to 230° C. the solution became clear and EtOH was generated. The reaction mixture was allowed to stay at 240-250° C. for 45 minutes, was cooled to 160° C. and slowly poured into 600 mL of hexane. Ethyl 4-hydroxy-7-iodoquinoline-3-carboxylate 6-D (11.1 g, 87% yield) was precipitated, filtrated, washed with hexane (2 times) and dried.

Compound 6-D (6.0 g) was treated with 20% LiOH (100 mL) in a mixed solvent of MeOH (100 mL) and THF (30 mL) at room temperature overnight. The solution was acidified with AcOH. 4-hydroxy-7-iodoquinoline-3-carboxylic acid 6-E (5.6 g, 100% yield) was obtained as a solid by filtration.

Compound 6-E (5.5 g) was placed I a 100 mL round bottom flask and heated under N$_2$ in an oil bath to 280° C. for 15 minutes. 7-iodoquinolin-4-ol 6-F (4.6 g, 99% yield) was obtained as a solid.

Compound 6-F (4.5 g) was dissolved in 30 mL of POCl$_3$. The solution was heated to reflux for 2 hours. The excess amount of POCl$_3$ was removed by evaporation under vacuum. The residue was basified with NH$_4$OH and extracted with EtOAc. The organic layer was concentrated to give 3.95 g (80% yield) of 4-chloro-7-iodoquinoline 6-G as a yellow solid.

A mixture of compound 6-G (500 mg, 1.7 mmol), 6-hydroxy-N,2-dimethyl-1-benzofuran-3-carboxamide 6-H (354 mg, 1.7 mmol) (the product of Example 5) and Cs$_2$CO$_3$ (920 mg, 2.6 mmol) in DMSO (5 mL) was heated to 120° C. for 1 hours. The solution was extracted with Silica gel column A solution of 6-[(7-iodoquinolin-4-yl)oxy]-N,2-dimethyl-1-benzofuran-3-carboxamide 7-A (60 mg, 0.13 mmol), pyridin-4-ylboronic acid 7-B (18 mg, 0.14 mmol), 2M K$_2$CO$_3$ solution (0.2 ml, 0.39 mmol) and [(C$_6$H$_5$)$_3$P]$_4$Pd (10 mg) in DMF (2 ml) was heated to 90° C. for 4 hours. The solution was filtrated and purified by a HPLC (Dionex System) using CH$_3$CN/H$_2$O (ACOH 0.1%) 40-80% over 30 minutes to yield the title compound 7 (13 mg).

$^1$H NMR (300 MHz, DMSO-d6) δ ppm 2.59 (s, 3H) 2.77 (d, J=4.52 Hz, 3H) 6.58 (d, J=5.27 Hz, 1H) 7.22 (dd, J=8.48, 2.07 Hz, 1H) 7.61 (d, J=2.07 Hz, 1H) 7.81 (d, J=8.48 Hz, 1H) 7.88 (m, 2H) 7.94 (d, J=4.52 Hz, 1H) 8.05 (dd, J=8.85, 1.70 Hz, 1H) 8.42 (m, 2H) 8.67 (m, 3H). LC/MS (APCI, pos.): 410.1 (M+H).

Example 8

Preparation of N-2-dimethyl-6-[(7-pyridin-3-ylquinolin-4-yl)oxy]-1-benzofuran-3-carboxamide

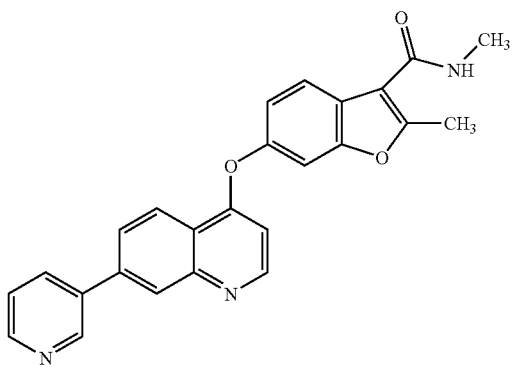

This compound was prepared according to methods analogous to those described in Example 7, using the appropriate boronic acid (pyridin-3-ylboronic acid).

$^1$H NMR (300 MHz, DMSO-d6) δ ppm 2.58 (s, 3H) 2.77 (d, J=4.52 Hz, 3H) 6.57 (d, J=5.27 Hz, 1H) 7.21 (dd, J=8.48, 2.07 Hz, 1H) 7.51 (dd, J=7.91, 4.71 Hz, 1H) 7.60 (d, J=2.07 Hz, 1H) 7.81 (d, J=8.48 Hz, 1H) 7.93 (d, J=4.52 Hz, 1H) 8.00 (dd, J=8.67, 1.70 Hz, 1H) 8.25 (m, 1H) 8.33 (d, J=1.51 Hz, 1H) 8.40 (d, J=8.67 Hz, 1H) 8.60 (dd, J=4.90, 1.51 Hz, 1H) 8.67 (d, J=5.09 Hz, 1H) 9.05 (d, J=2.26 Hz, 1H) LC/MS (APCI, pos.): 410.1 (M$^+$H).

Example 9

Preparation of N-2-dimethyl-6-[(7-pyridin-2-ylquinolin-4-yl)oxy]-1-benzofuran-3-carboxamide

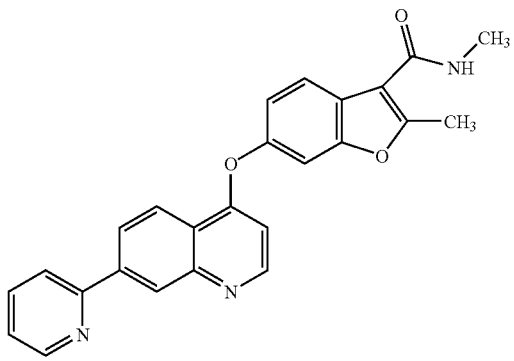

This compound was prepared according to the synthetic scheme depicted and described below.

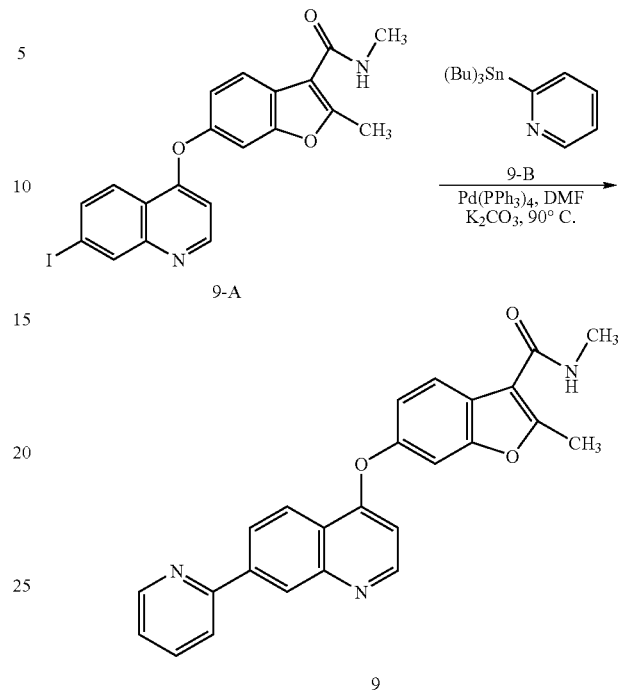

A solution of 6-[(7-iodoquinolin-4-yl)oxy]-N,2-dimethyl-1-benzofuran-3-carboxamide 9-A (60 mg, 0.13 mmol), 2-(tributylstannyl)pyridine 9-B (16 mg, 0.14 mmol) and [(C$_6$H$_5$)$_3$P]$_4$Pd (10 mg) in DMF (2 ml) was heated to 100° C. for 3 hours. The solution was filtrated and purified by a HPLC (Dionex System) using CH$_3$CN/H$_2$O (ACOH 0.1%) 40-80% over 30 minutes to yield the title compound 9.

$^1$H NMR (300 MHz, DMSO-d6) δ ppm 2.59 (s, 3H) 2.77 (d, J=4.52 Hz, 3H) 6.55 (d, J=5.27 Hz, 1H) 7.22 (dd, J=8.48, 2.07 Hz, 1H) 7.39 (dd, J=7.06, 5.18 Hz, 1H) 7.62 (d, J=2.26 Hz, 1H) 7.81 (d, J=8.67 Hz, 1H) 7.93 (m, 2H) 8.18 (d, J=8.10 Hz, 1H) 8.39 (s, 2H) 8.66 (m, 2H) 8.71 (m, 1H). LC/MS (APCI, pos.): 410.1 (M$^+$H).

Example 10

Preparation of N-2-dimethyl-6-[(7-pyridin-4-yl)quinolin-4-yl]oxy]-1-benzothiophene-3-carboxamide

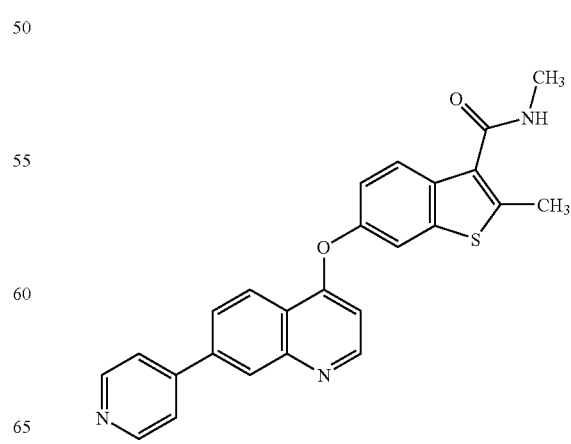

This compound was prepared according to the methods of Schemes I, II and IV and methods analogous to those described in Examples 5 to 7.

¹H NMR (300 MHz, DMSO-d6) δ ppm 2.55 (s, 3H) 2.77 (d, J=4.53 Hz, 3H) 6.60 (d, J=4.91 Hz, 1H) 7.28 (dd, J=8.48, 2.07 Hz, 1H) 7.81 (d, J=8.67 Hz, 1H) 7.87 (m, 2H) 8.05 (d, J=8.69 Hz, 1H) 8.21 (d, J=4.91 Hz, 1H) 8.41 (dd, J=5.10, 3.59 Hz, 1H) 8.68 (dd, J=9.82, 5.67 Hz, 1H). LC/MS (APCI, pos.): 426.0 (M⁺H).

Example 11

Preparation of N-2-dimethyl-5-[(7-pyridin-4-ylquinolin-4-yl]amino]-1H-indole-1-carboxamide

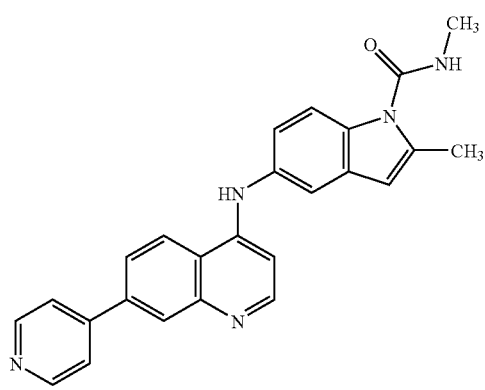

This compound was prepared according to the synthetic schemes depicted and described below.

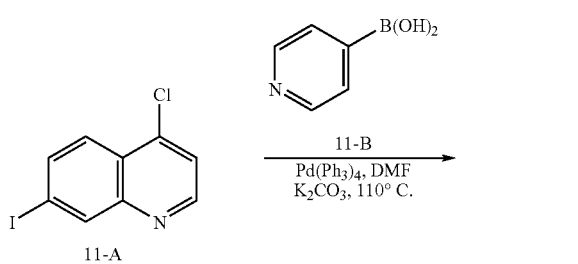

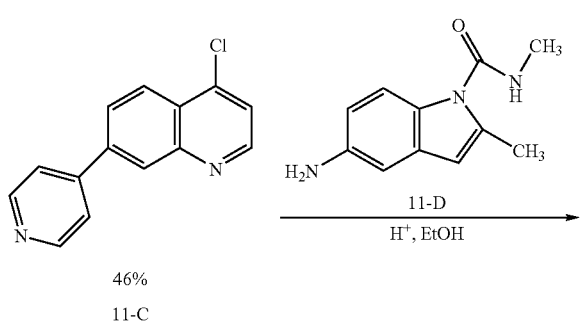

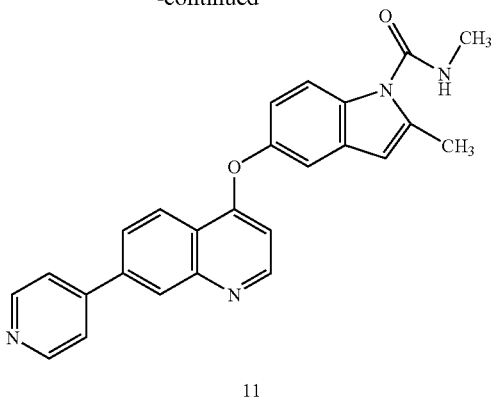

A solution of 4-chloro-7-iodoquinoline 11-A (500 mg, 1.73 mmol), pyridin-4-ylboronic acid 11-B (212 mg, 1.73 mmol), 2M K₂CO₃ solution (2.6 ml, 5.19 mmol) and [(C₆H₅)₃P]₄Pd (100 mg) in DMF (5 ml) were heated to 90° C. for 4 hours. The solution was filtrated and extracted with EtOAc. The organic layer was concentrated and purified by column chromatography using hexane/EtOAc (1/1) to give 193 mg of compound 11-C.

A mixture of compound 11-C (70 mg, 0.29 mmol), 5-amino-N,2-dimethyl-1H-indole-1-carboxamide 11-D (59 mg, 0.29 mmol) and 2N HCl (0.2 ml, 0.34 mmol) in 3 ml of a mixed solution of EtOH/Cl (CH₂)₂Cl (1/1) was heated to 80° C. for 1 hour. The title compound 11 (20 mg) was isolated by HPLC (Dionex System) using 30-60% CH₃CN/H₂O (0.1% AcOH) over 30 minutes.

¹H NMR (300 MHz, DMSO-d6) δ ppm 2.44 (s, 3H) 2.83 (d, J=4.53 Hz, 3H) 6.33 (s, 1H) 6.63 (d, J=5.67 Hz, 1H) 7.11 (d, J=8.69 Hz, 1H) 7.39 (s, 1H) 7.60 (d, J=8.69 Hz, 1H) 7.85 (d, J=5.67 Hz, 2H) 7.91 (d, J=8.69 Hz, 1H) 8.14 (d, J=4.53 Hz, 1H) 8.20 (s, 1H) 8.36 (d, J=5.29 Hz, 1H) 8.53 (d, J=9.07 Hz, 1H) 8.64 (d, J=5.67 Hz, 2H) 9.07 (s, 1H). LC/MS (APCI, pos.): 408.1 (M+H).

Example 12

Preparation of N,2-dimethyl-5-[(7-pyridin-3-ylquinolin-4-yl)amino]-1H-indole-1-carboxamide

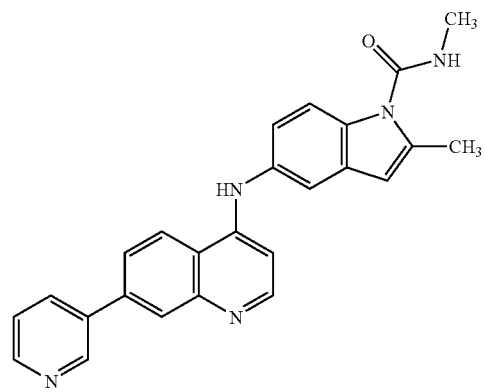

This compound was prepared according to the synthetic scheme depicted below and using methods analogous to those described in Example 11.

53

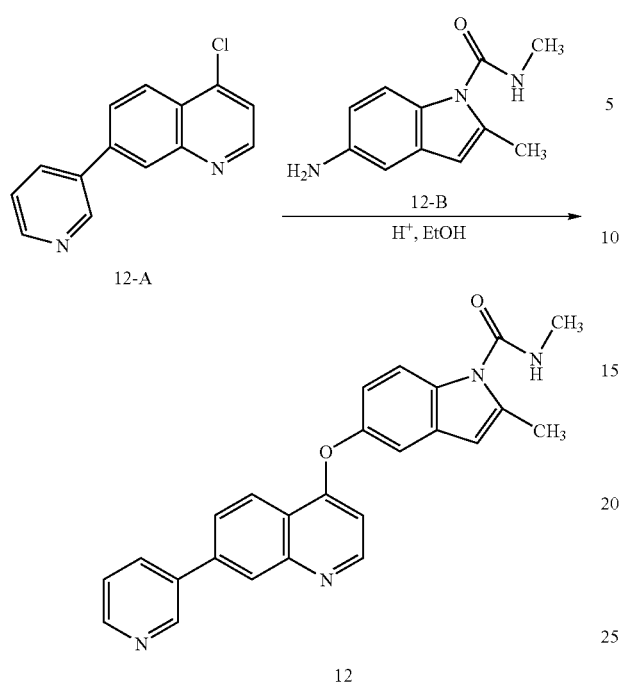

12

¹H NMR (400 MHz, DMSO-d6) δ ppm 2.45 (s, 3H) 2.84 (d, J=4.29 Hz, 3H) 6.36 (s, 1H) 6.62 (d, J=5.81 Hz, 1H) 7.13 (dd, J=8.84, 2.02 Hz, 1H) 7.44 (d, J=2.02 Hz, 1H) 7.53 (dd, J=8.08, 4.80 Hz, 1H) 7.64 (d, J=8.59 Hz, 1H) 7.98 (dd, J=8.72, 1.64 Hz, 1H) 8.13 (d, J=1.77 Hz, 1H) 8.22 (m, 1H) 8.39 (d, J=6.06 Hz, 1H) 8.62 (m, 2H) 9.03 (d, J=2.02 Hz, 1H). LC/MS (APCI, pos.): 408.1 (M+H).

Example 13

Preparation of 6-{[7-(2-furyl)quinolin-4-yl]oxy}-N,2-dimethyl-1-benzofuran-3-carboxamide

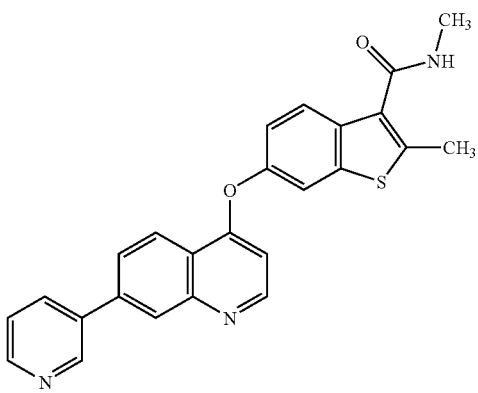

This compound was prepared using methods analogous to those described for preparing Examples 7-9.

¹H NMR (400 MHz, DMSO-d6) δ ppm 2.58 (s, 3H) 2.76 (d, J=4.55 Hz, 3H) 6.49 (m, 1H) 6.64 (dd, J=3.54, 1.77 Hz, 1H) 7.21 (m, 2H) 7.60 (d, J=2.02 Hz, 1H) 7.82 (m, 2H) 7.95 (m, 2H) 8.22 (d, J=1.52 Hz, 1H) 8.30 (m, 1H) 8.61 (d, J=5.31 Hz, 1H). LC/MS (APCI, pos.): 408.1 (M+H).

54

Example 14

Preparation of N-2-dimethyl-6-[(7-pyridin-3-ylquinolin-4-yl)oxy]-1-benzothiophene-3-carboxamide This compound was prepared according to the synthetic scheme depicted and described below.

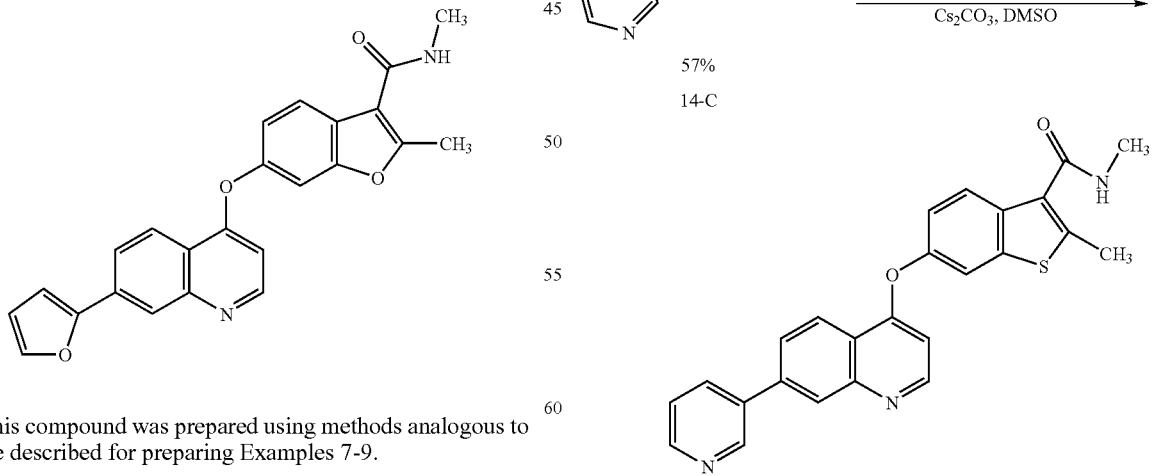

A solution of 4-chloro-7-iodoquinoline 14-A (500 mg, 1.73 mmol), pyridin-3-ylboronic acid 14-B (212 mg, 1.73 mmol), 2M K₂CO₃ solution (2.6 ml, 5.19 mmol) and [(C₆H₅)₃P]₄Pd (100 mg) in DMF (5 ml) were heated to 90° C. for 4 hours. The solution was filtrated and extracted with EtOAC. The organic layer was concentrated and purified by column chromatography using hexane/EtOAC (1/1) to give 234 mg of the compound 14-C.

A mixture of compound 14-C (70 mg, 0.29 mmol), 6-hydroxy-N,2-dimethyl-1-benzothiophene-3-carboxamide 14-D (64 mg, 0.29 mmol) and Cs₂CO₃ (141 mg, 0.43 mmol) in 3 ml of a mixed solution of EtOH/Cl(CH₂)₂Cl (1/1) was heated to 120° C. for 2 hours. The title compound 14 (20 mg) was isolated by HPLC (Dionex System) using 40-70% CH₃CN/H₂O (0.1% AcOH) over 30 minutes.

¹H NMR (400 MHz, DMSO-d6) δ ppm 2.53 (s, 3H) 2.76 (d, J=4.80 Hz, 3H) 6.56 (d, J=5.05 Hz, 1H) 7.27 (dd, J=8.59, 2.27 Hz, 1H) 7.49 (dd, J=7.83, 4.80 Hz, 1H) 7.81 (d, J=8.84 Hz, 1H) 7.89 (d, J=2.02 Hz, 1H) 7.99 (dd, J=8.72, 1.89 Hz, 1H) 8.23 (m, 2H) 8.31 (d, J=1.52 Hz, 1H) 8.37 (d, J=8.84 Hz, 1H) 8.57 (s, 1H) 8.66 (d, J=5.31 Hz, 1H) 9.03 (s, 1H). LC/MS (APCI, pos.): 426.1 (M⁺H).

Example 15

Preparation of 6-[(7-{[(2S)-2-(methoxymethyl)pyrrolidin-1-yl]carbonyl}quinolin-4-yl)oxy]-N,2-dimethyl-1-benzofuran-3-carboxamide

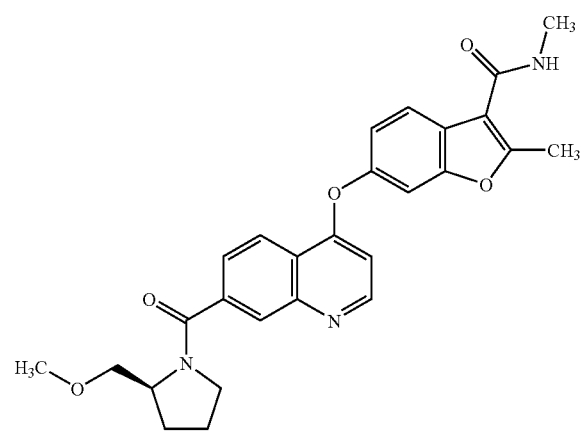

This compound was prepared according to the synthetic scheme depicted and described below.

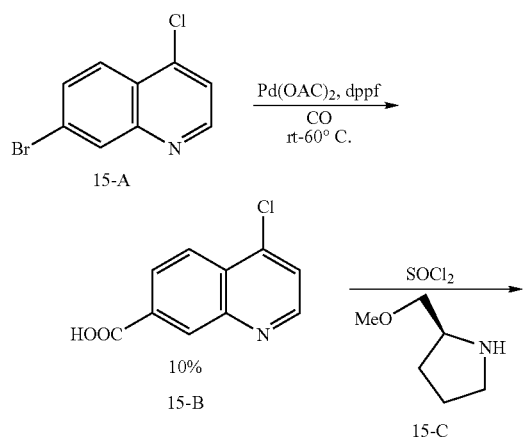

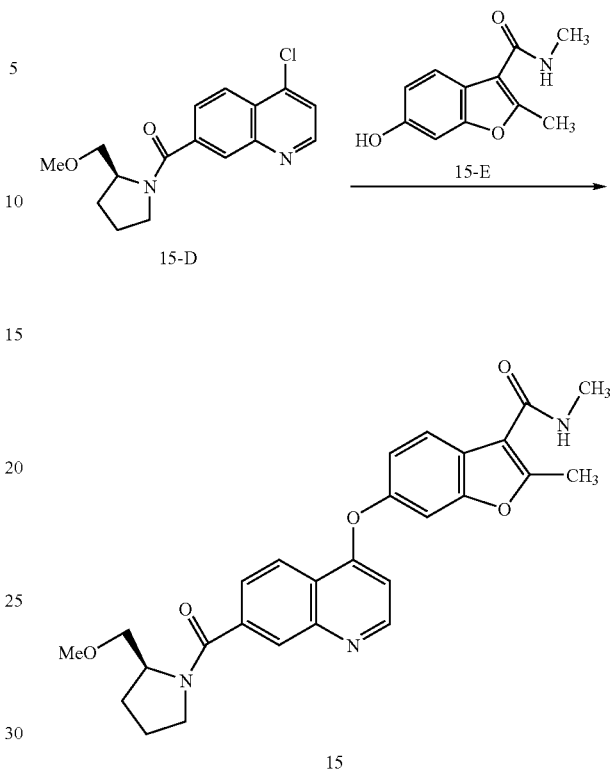

Into a solution of 15-A (1 g, 4.1 mmol), Pd(OAc)₂ (46 mg, 0.2 mmol), dppf (455 mg, 0.82 mmol) and KOAc (1.6 g, 16.4 mmol) in DMSO (20 ml) was bubbled CO gas at room temperature for 5 minutes. The solution was heated and stirred at 65° C. under CO gas (a balloon filled with CO gas was used) for 3 hours, poured into water and extracted with EtOAc. The concentrated residue was purified by silica gel column chromatography using hexane/ethylacetate/AcOH (70:30:1) to yield compound 15-B (120 mg).

A solution of compound 15-B (120 mg, 0.57 mmol) in net SOCl₂ (excess) was heated to reflux for 2 minutes. SOCl₂ was removed by evaporation under vacuum. The residue was dissolved in CH₂Cl₂. To the solution was added Et₃N (87 mg, 0.86 mmol) and (2S)-2-(methoxymethyl)pyrrolidine 15-C (78 mg). The solution was stirred at room temperature for 30 minutes. Compound 15-D (140 mg) was isolated by silica gel column chromatography using hexane/EtOAc (1:1).

A solution of compound 15-D (70 mg, 0.23 mmol), 15-E (47 mg, 0.23 mmol) and Cs₂CO₃ (90 mg, 0.27 mmol) was in DMSO (2 ml) was heated to 120° C. for 2 hours. The title compound 15 was isolated by HPLC (Dionex System) using 40-80% CH₃CN/H₂O (0.1% AcOH) over 30 minutes.

¹H NMR (300 MHz, DMSO-d6) δ ppm 1.84 (m, 4H) 2.58 (s, 3H) 2.76 (d, J=4.33 Hz, 3H) 2.97 (m, 2H) 3.42 (m, 2H) 3.57 (m, 1H) 6.58 (d, J=5.09 Hz, 1H) 7.23 (s, 1H) 7.64 (m, 2H) 7.81 (d, J=8.48 Hz, 1H) 7.93 (m, 1H) 8.01 (s, 1H) 8.34 (d, J=8.67 Hz, 1H) 8.66 (d, J=5.09 Hz, 1H). LC/MS (APCI, pos.): 474.2 (M+H).

Example 16

Preparation of 6-[(7-{[(2S)-2-(methoxymethyl)pyrrolidin-1-yl]carbonyl}quinolin-4-yl)oxy]-N,2-dimethyl-1-benzothiophene-3-carboxamide

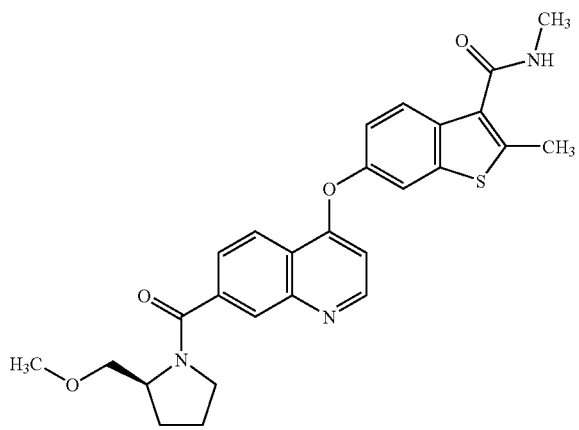

This compound was prepared according to the methods described in Example 15, substituting the appropriate benzothiophene intermediate for the benzofuran intermediate (15-E).

$^1$H NMR (300 MHz, DMSO-d6) δ ppm 1.92 (m, 4H) 2.56 (s, 3H) 2.78 (d, J=4.52 Hz, 3H) 2.97 (m, 2H) 3.41 (m, 2H) 3.58 (m, 1H) 6.59 (d, J=5.09 Hz, 1H) 7.28 (dd, J=8.76, 1.98 Hz, 1H) 7.63 (m, 2H) 7.82 (d, J=8.67 Hz, 1H) 7.91 (d, J=2.07 Hz, 1H) 8.01 (s, 1H) 8.22 (d, J=4.52 Hz, 1H) 8.33 (d, J=8.67 Hz, 1H) 8.67 (d, J=5.27 Hz, 1H). LC/MS (APCI, pos.): 490.2 (M$^+$H).

Example 17

Preparation of N,2-dimethyl-6-[(7-pyrimidin-2-ylquinolin-4-yl)oxy]-1-benzofuran-3-carboxamide

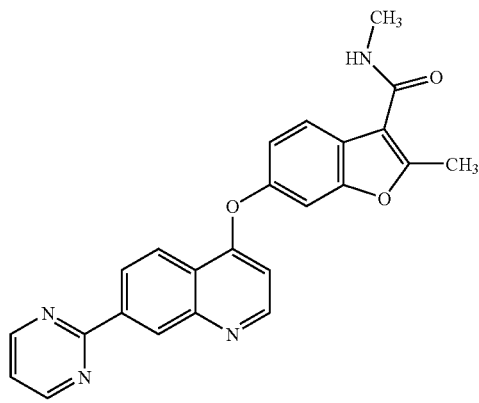

This compound was prepared according to the synthetic scheme depicted and described below.

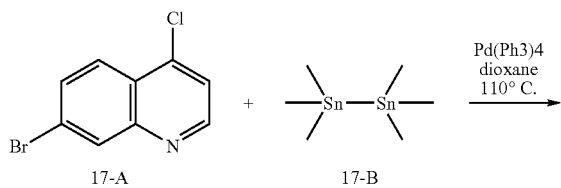

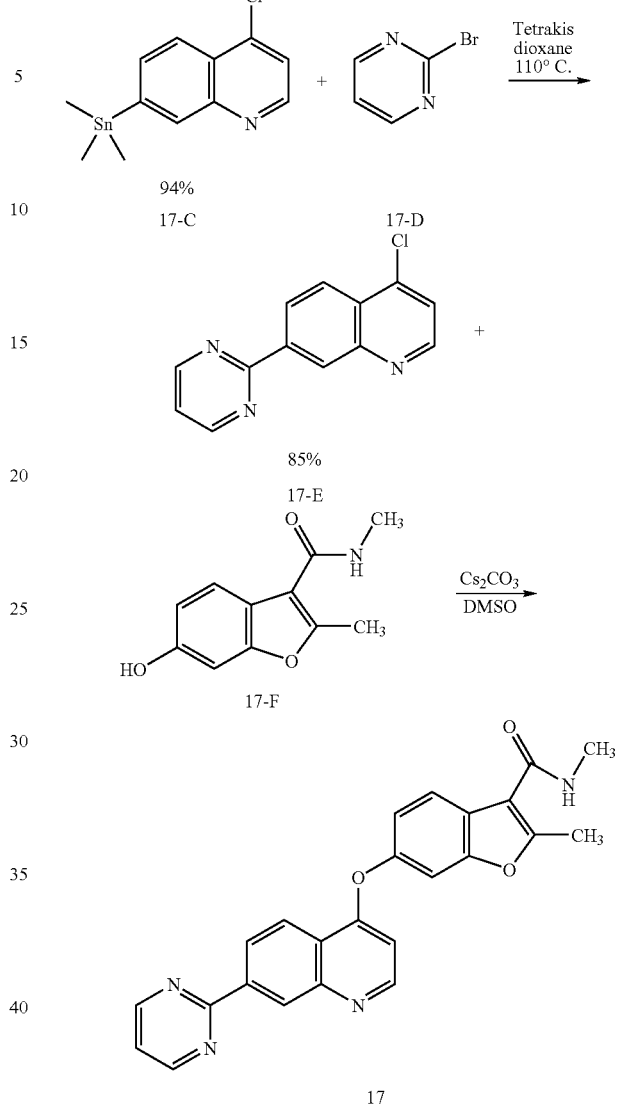

A solution of 4-chloro-7-bromoquinoline 17-A (1 g, 4.1 mmol) (see Scheme I: general preparation of quinolines), hexamethyldistannane 17-B (1.35 g, 4.1 mmol) and [(C$_6$H$_5$)$_3$P]$_4$Pd (237 mg) in 1,4-dioxane (10 ml) was heated to 105-110° C. for 2 hours. The solution was cooled to room temperature. Column chromatography (hexane/EtOAc 5:1) gave 4-chloro-7-(trimethylstannyl)quinoline 17-C (1.26 g, 94%).

A mixture of compound 17-C (500 mg, 1.5 mmol), 2-bromopyrimidine 17-D (366 mg, 2.3 mmol) and [(C$_6$H$_5$)$_3$P]$_4$Pd (87 mg) in 1,4-dioxane (5 ml) was heated to 110° C. for 2 hours, cooled to room temperature and crystallized from dioxane to give 308 mg of 4-chloro-7-pyrimidin-2-ylquinoline 17-E.

A mixture of 17-E (70 mg, 0.29 mmol), 6-hydroxy-N,2-dimethyl-1-benzofuran-3-carboxamide 17-F (60 mg, 0.29 mmol) and Cs$_2$CO$_3$ (141 mg, 0.43 mmol) in 2 ml of DMSO was heated to 120° C. for 2 hours. The title compound (23 mg) was isolated by HPLC (Dionex System) using 20-90% CH$_3$CN/H$_2$O (0.1% AcOH) over 30 minutes.

$^1$H NMR (300 MHz, DMSO-d6) δ ppm 2.59 (s, 3H) 2.77 (d, J=4.14 Hz, 3H) 6.59 (d, J=4.90 Hz, 1H) 7.22 (d, J=8.48 Hz, 1H) 7.58 (m, 2H) 7.81 (d, J=8.67 Hz, 1H) 8.07 (m, J=8.67

Hz, 1H) 8.43 (d, J=11.30 Hz, 2H) 8.69 (d, J=4.71 Hz, 1H) 9.21 (s, 1H) 9.31 (s, 2H). LC/MS (APCI, pos.): 411.1 (M+H).

Example 18

Preparation of N,2-dimethyl-6-[(7-pyrimidin-2-ylquinolin-4-yl)oxy]-1-benzothiophene-3-carboxamide

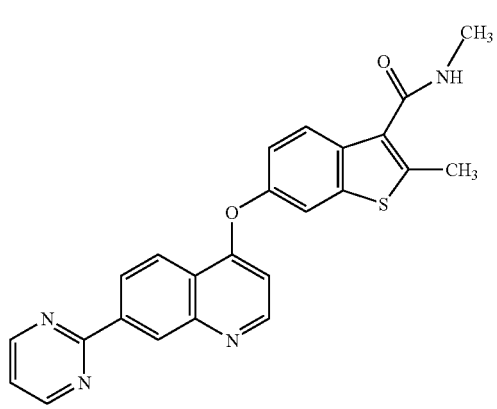

This compound was prepared according to methods analogous to those described in Example 17, substituting the appropriate benzothiophene intermediate for the benzofuran intermediate (17-F).

$^1$H NMR (300 MHz, DMSO-d6) δ ppm 2.56 (s, 3H) 2.78 (d, J=4.52 Hz, 3H) 6.61 (d, J=5.27 Hz, 1H) 7.29 (dd, J=8.85, 2.26 Hz, 1H) 7.83 (d, J=8.85 Hz, 1H) 7.91 (d, J=2.26 Hz, 1H) 8.07 (dd, J=8.67, 1.70 Hz, 1H) 8.23 (d, J=4.71 Hz, 1H) 8.42 (d, J=8.67 Hz, 1H) 8.46 (d, J=1.70 Hz, 1H) 8.70 (d, J=5.09 Hz, 1H) 9.21 (s, 1H) 9.31 (s, 2H). LC/MS (APCI, pos.): 427.1 (M$^+$H).

Example 19

Preparation of 6-[(7-bromoquinolin-4-yl)oxy]-N,2-dimethyl-1-benzofuran-3-carboxamide

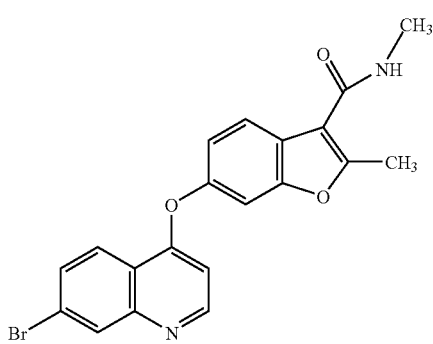

This compound was prepared using methods analogous to those described in Examples 5 and 6.

$^1$H NMR (300 MHz, DMSO-d6) δ ppm 2.58 (s, 3H) 2.76 (s, 3H) 6.56 (s, 1H) 7.20 (d, J=8.29 Hz, 1H) 7.60 (s, 1H) 7.77 (dd, J=14.51, 8.85 Hz, 2H) 7.92 (s, 1H) 8.22 (m, 2H) 8.63 (s, 1H). LC/MS (APCI, pos.): 411.0 (M+H).

Example 20

Preparation of 6-[(7-bromoquinolin-4-yl)oxy]-N,2-dimethyl-1-benzothiophene-3-carboxamide

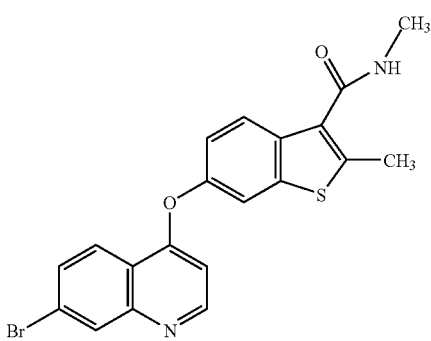

This compound was prepared using the methods analogous to those described in Examples 5 and 6.

$^1$H NMR (300 MHz, DMSO-d6) δ ppm 2.55 (s, 3H) 2.78 (d, J=4.52 Hz, 3H) 6.58 (d, J=5.09 Hz, 1H) 7.27 (dd, J=8.67, 2.26 Hz, 1H) 7.77 (m, 2H) 7.89 (d, J=2.07 Hz, 1H) 8.22 (m, 3H) 8.64 (d, J=5.27 Hz, 1H). LC/MS (APCI, pos.): 428.0 (M$^+$H).

Example 21

Preparation of 6-[(6-iodoquinolin-4-yl)oxy]-N,2-dimethyl-1-benzothiophene-3-carboxamide

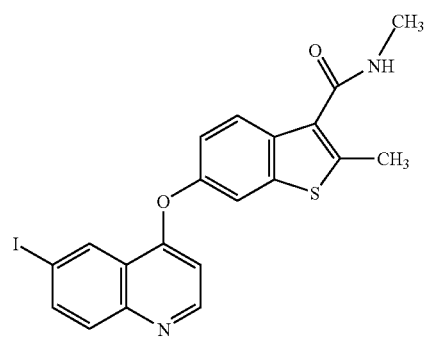

This compound was prepared according to the synthetic scheme depicted and described below.

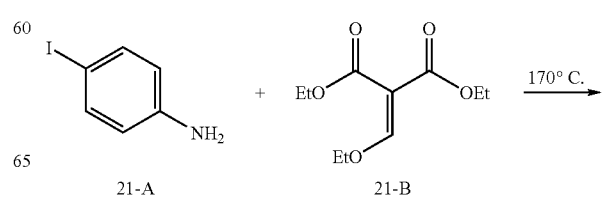

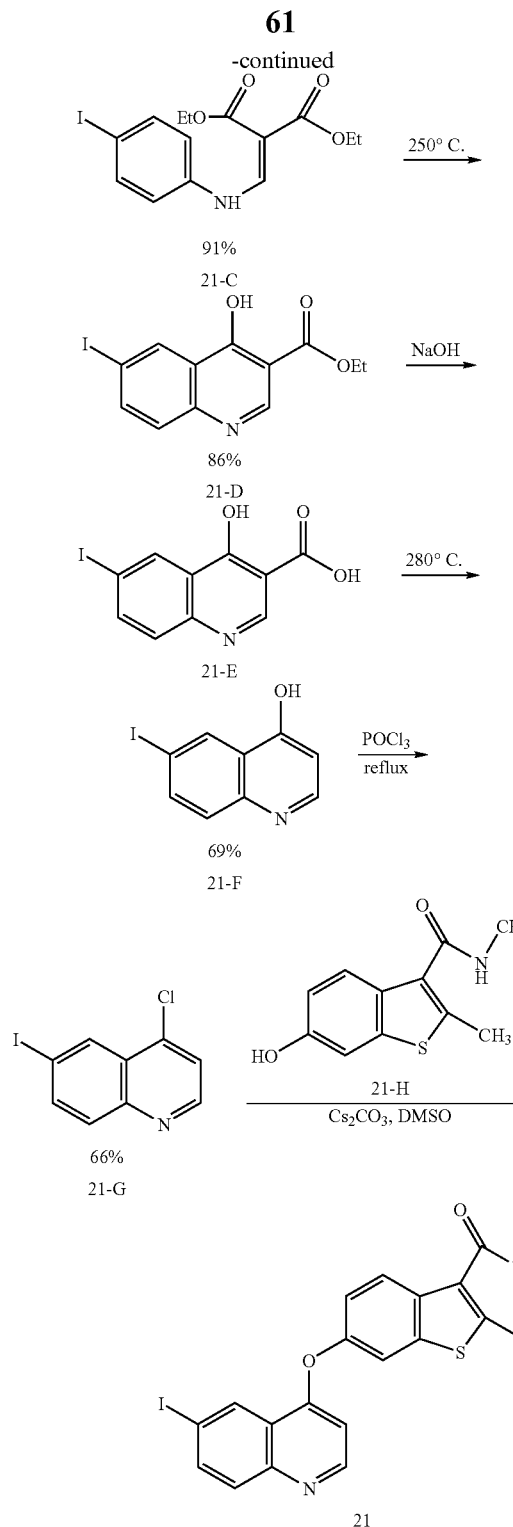

and EtOH was generated. The reaction was allowed to stay at 250° C. for 45 minutes, cooled to 160° C. and slowly poured into 500 ml of hexane. Ethyl 4-hydroxy-6-iodoquinoline-3-carboxylate (18.2 g, 86% yield) 21-D was precipitated, filtrated, washed with hexane (2 times) and dried.

Compound 21-D (6.0 g) was treated with 20% NaOH (100 ml) in a mixed solvent of MeOH (200 ml) and THF (80 ml) at room temperature overnight. The solution was acidified with 2N HCl to pH~6. 4-Hydroxy-6-iodoquinoline-3-carboxylic acid 21-E (13.3 g) was obtained as a solid by filtration.

Compound 21-E (5.5 g) was placed in a 100 ml round bottom flask and heated under $N_2$ in an oil bath to 280° C. for 10 minutes. 6-iodoquinolin-4-ol 21-F (9.9 g, 69% yield from 21-D) was obtained as a solid.

Compound 21-F (4.5 g) was dissolved in 50 ml of $POCl_3$. The solution was heated to reflux for 2 hours. The excess amount of $POCl_3$ was removed by evaporation under vacuum. The residue was neutralized with $NH_4OH$ to pH ~7 and extracted with EtOAc. The organic layer was concentrated and purified by chromatography on a silica gel column using hexane/ethylacetate (3:1) to give 7.1 g (66% yield) of 4-chloro-6-iodoquinoline 21-G as a yellow solid.

A mixture of compound 21-G (70 mg, 0.24 mmol), 6-hydroxy-N,2-dimethyl-1-benzothiophene-3-carboxamide 21-H (54 mg, 0.24 mmol) and $Cs_2CO_3$ (117 mg, 0.36 mmol) in DMSO (2 ml) was heated to 120° C. for 2 hours. The solution was extracted with EtOAc and purified by HPLC (Dionex System) using 40-80% $CH_3CN/H_2O$ over 30 min to give the title compound 21.

$^1$H NMR (300 MHz, DMSO-d6) δ ppm 2.55 (s, 3H) 2.78 (d, J=4.52 Hz, 3H) 6.55 (d, J=5.27 Hz, 1H) 7.28 (dd, J=8.85, 2.07 Hz, 1H) 7.79 (dd, J=16.39, 8.85 Hz, 2H) 7.89 (d, J=2.07 Hz, 1H) 8.04 (m, 1H) 8.22 (s, 1H) 8.63 (m, 2H). LC/MS (APCI, pos.): 475.0 ($M^+H$).

Example 22

Preparation of 6-[(6-iodoquinolin-4-yl)oxy]-N,2-dimethyl-1-benzofuran-3-carboxamide

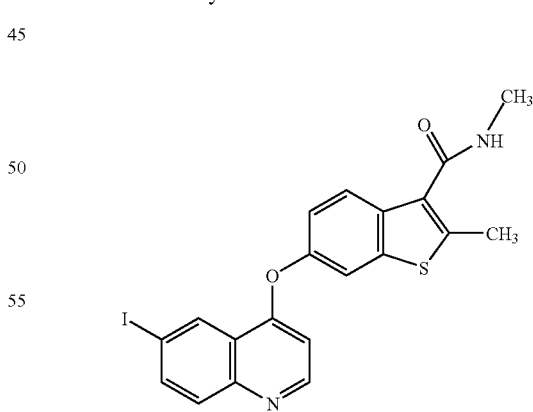

This compound was prepared according to methods analogous to those described in Example 21, substituting the appropriate benzofuran intermediate for the benzothiophene intermediate 21-H.

$^1$H NMR (300 MHz, DMSO-d6) δ ppm 2.58 (s, 3H) 2.76 (d, J=4.52 Hz, 3H) 6.54 (d, J=5.27 Hz, 1H) 7.21 (dd, J=8.48, A mixture of 4-iodoaniline 21-A (14.5 g, 66.2 mmol) and diethyl (ethoxymethylene) malonate 21-B (14.5 g, 66.2 mmol) was heated in an oil bath to 170° C. for 40 minutes. The reaction mixture was poured into 200 ml of EtOH slowly with stirring. Diethyl {[(4-iodophenyl)amino]methylene}malonate 21-C (23.5 g, 91% yield) was collected as a white solid by filtration.

Compound (23.5 g) 21-C was placed in a round bottom flask. Phenyl ether (60 ml) was added into the flask. When the suspension was heated to 230° C. the solution became clear 2.07 Hz, 1H) 7.60 (d, J=2.07 Hz, 1H) 7.78 (m, 2H) 7.93 (d, J=4.33 Hz, 1H) 8.03 (m, 1H) 8.62 (m, 2H). LC/MS (APCI, pos.): 459.0 (M+H).

Example 23

Preparation of N,2-dimethyl-6-[(6-pyridin-4-ylquinolin-4-yl)oxy]-1-benzothiophene-3-carboxamide

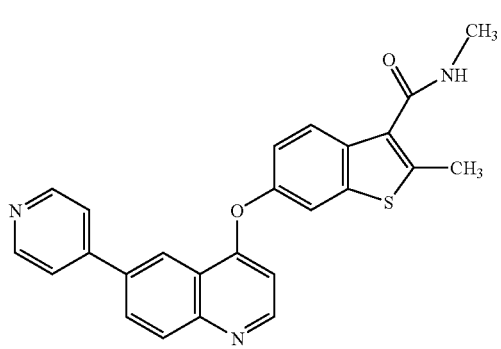

This compound was prepared according to the synthetic scheme depicted below.

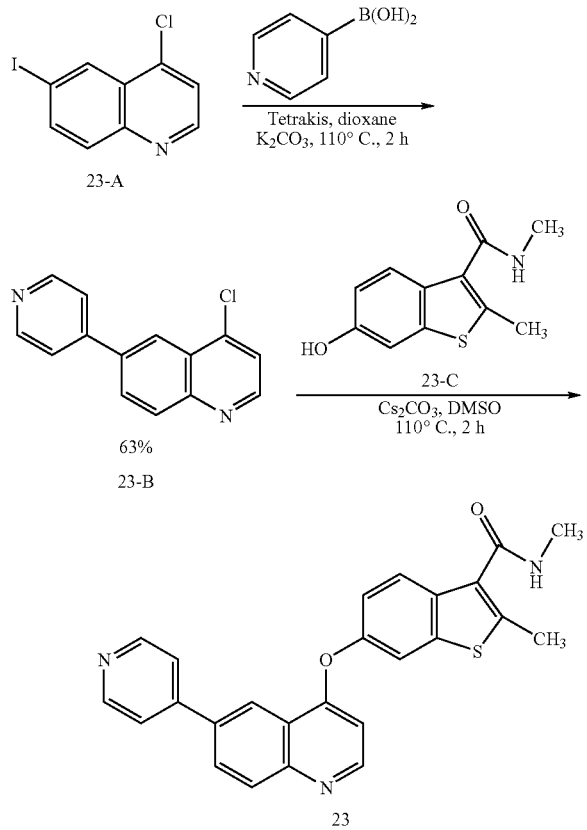

$^1$H NMR (300 MHz, DMSO-d6) δ ppm 2.62 (s, 3H) 2.85 (d, J=4.52 Hz, 3H) 6.66 (d, J=5.27 Hz, 1H) 7.38 (dd, J=8.85, 2.26 Hz, 1H) 7.91 (m, 3H) 8.00 (d, J=2.07 Hz, 1H) 8.18 (d, J=8.85 Hz, 1H) 8.28 (m, 2H) 8.72 (m, 4H). LC/MS (APCI, pos.): 426.10 (M+H).

Example 24

Preparation of N,2-dimethyl-6-[(6-pyridin-4-ylquinolin-4-yl)oxy]-1-benzofuran-3-carboxamide

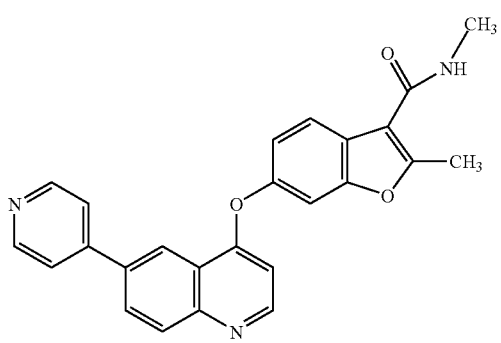

This compound was prepared according to the method described in Example 23, substituting the appropriate benzofuran intermediate for the benzothiophene intermediate 23-C.
$^1$H NMR (300 MHz, DMSO-d6) δ ppm 2.62 (s, 3H) 2.84 (m, 3H) 2.85 (d, J=4.52 Hz, 3H) 6.66 (d, J=5.27 Hz, 1H) 7.38 (dd, J=8.85, 2.26 Hz, 1H) 7.91 (m, 3H) 8.00 (d, J=2.07 Hz, 1H) 8.18 (d, J=8.85 Hz, 1H) 8.28 (m, 2H) 8.72 (m, 4H). LC/MS (APCI, pos.): 410.10 (M+H).

Example 25

Preparation of N,2-dimethyl-6-({6-[2-(1-methylpyrrolidinyl-2-yl)ethoxy]quinolin-4-yl}oxy)-1-benzothiophene-3-carboxamide

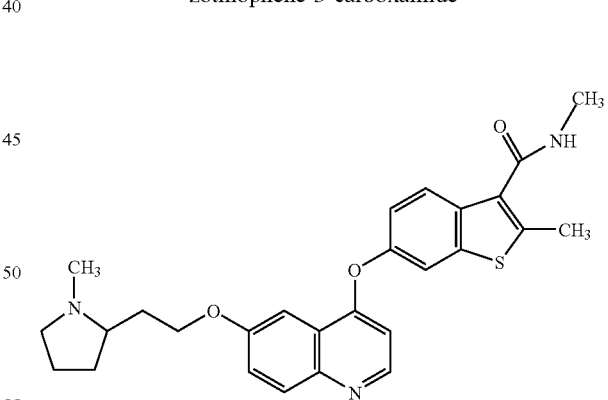

This compound was prepared according to the synthetic scheme depicted and described below.

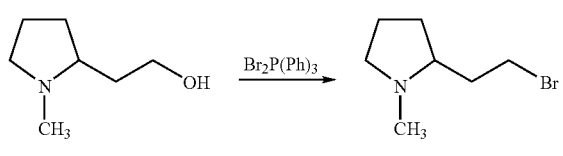

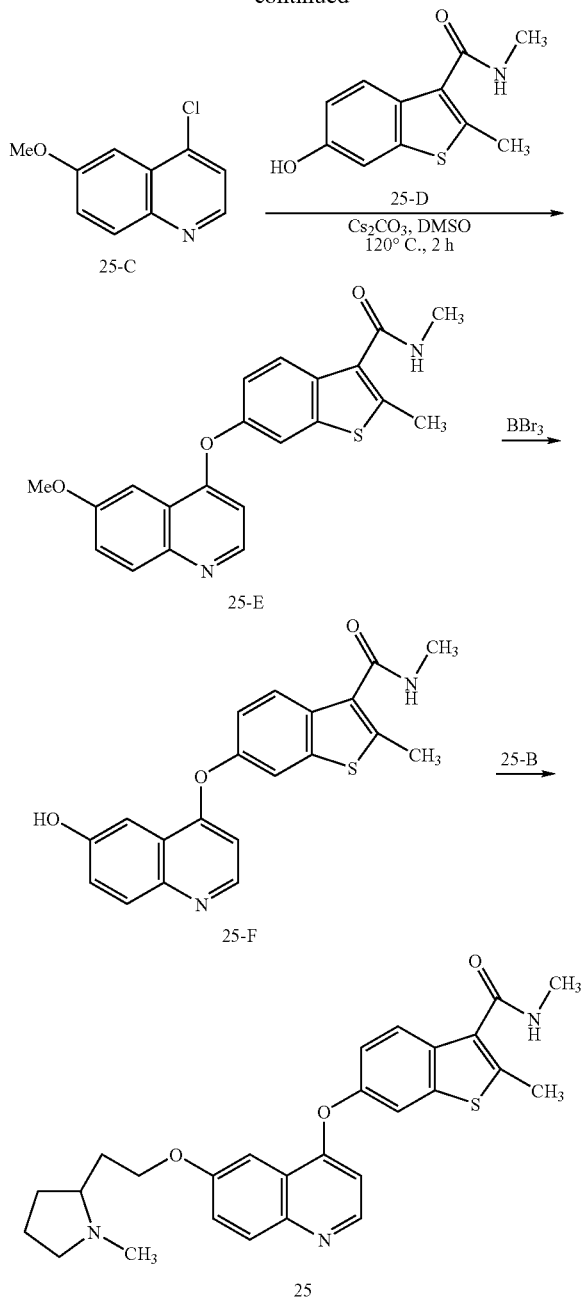

To a solution of 25-A (100 mg, 0.8 mmol) in dichloromethane (4 ml) was added Br₂P(Ph)₃ (330 mg, 0.8 mmol). The solution was stirred at room temperature for 30 minutes. The solution was poured into water, acidified with Hal to pH~2 and extracted with Teac. The water layer was basified with NH₄OH to pH~9 and extracted with Teac, dried (MgSO₄) and concentrated to give a crude compound 25-B (110 mg).

A mixture of compound 25-C (500 mg, 2.6 mol), 6-hydroxy-N,2-dimethyl-1-benzothiophene-3-carboxamide 25-D (573 mg, 2.6 mol) and Cs₂CO₃ (1.3 g, 3.9 mol) in 6 ml of DMSO was heated to 120° C. for 2 hours. The concentrated residue was purified by silica gel chromatography column using Hexane/Teac (2/1 to 100% Teac) to offer 6-[(6-methoxyquinolin-4-yl)oxy]-N,2-dimethyl-1-benzothiophene-3-carboxamide 25-E (361 mg, 37% yield) as a yellow solid.

To a solution of 25-E (320 mg) in dichloromethane (2 ml) was added 1.7 ml solution of BBr₃ (1M in dichloromethane) at −78° C. The solution was stirred at room temperature overnight. The reaction was quenched with MeOH. The residue was purified by a silica gel column using 2-5% MeOH in CH₂Cl₂ to give 6-[(6-hydroxyquinolin-4-yl)oxy]-N,2-dimethyl-1-benzothiophene-3-carboxamide 25-F (250 mg, 77% yield).

A solution of 25-F (70 mg, 0.19 mmol), 2-(2-bromoethyl)-1-methylpyrrolidine 25-B (110 mg crude and Cs₂CO₃ (94 mg, 1.5 mmol) in DMSO (2 ml) was heated to 120° C. for 2 hours. The title compound, N,2-dimethyl-6-({6-[2-(1-methylpyrrolidin-2-yl)ethoxy]quinolin-4-yl}oxy)-1-benzothiophene-3-carboxamide 25 (21 mg) was isolated by HPLC (Dionex System) using 20-60% CH₃CN/H₂O (0.1% AcOH) over 30 minutes.

¹H NMR (300 MHz, DMSO-d6) δ ppm 1.60-1.84 (m, 4H) 2.06 (m, 2H) 2.30 (s, 3H) 2.55 (s, 3H) 2.63 (m, 2H) 2.78 (d, J=4.52 Hz, 3H) 3.29 (m, 2H) 4.12 (m, 0.5H) 4.77 (m, 0.5H) 6.50 (dd, J=8.67, 3.58 Hz, 1H) 7.24 (m, 1H) 7.39 (m, 1H) 7.50 (m, 2H) 7.84 (m, 3H) 8.22 (s, 1H) 8.46 (d, J=5.09 Hz, 1H). LC/MS (APCI, pos.): 376.20 (M+H).

Example 26

Preparation of 6-[(6-methoxyquinolin-4-yl)oxy]-N,2-dimethyl-1-benzothiophene-3-carboxamide

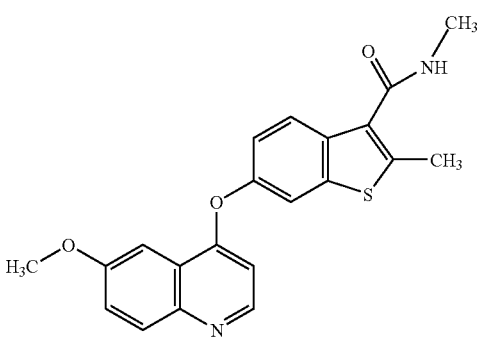

This compound was prepared according to methods analogues to those depicted and described in Example 25.

¹H NMR (300 MHz, DMSO-d6) δ ppm 2.55 (s, 3H) 2.78 (d, J=4.52 Hz, 3H) 3.87 (s, 3H) 6.50 (d, J=5.09 Hz, 1H) 7.25 (dd, J=8.76, 2.17 Hz, 1H) 7.41 (dd, J=9.23, 2.83 Hz, 1H) 7.53 (d, J=2.83 Hz, 1H) 7.81 (d, J=8.67 Hz, 1H) 7.88 (m, 2H) 8.22 (d, J=4.52 Hz, 1H) 8.46 (d, J=5.09 Hz, 1H). LC/MS (APCI, pos.): 379.10 (M⁺H).

Example 27

Preparation of 6-[(6-hydroxyquinolin-4-yl)oxy]-N,2-dimethyl-1-benzothiophene-3-carboxamide

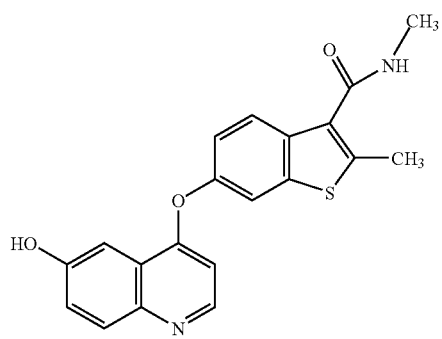

This compound was prepared according to methods analogous to those depicted and described in Example 25 using the appropriate 4-chloro-quinoline intermediate.

$^1$H NMR (300 MHz, DMSO-d6) δ ppm 2.61 (s, 3H) 2.84 (d, J=4.52 Hz, 3H) 6.55 (d, J=5.09 Hz, 1H) 7.29 (dd, J=8.85, 2.26 Hz, 1H) 7.36 (dd, J=9.14, 2.73 Hz, 1H) 7.49 (d, J=2.64 Hz, 1H) 7.88 (m, 3H) 8.28 (d, J=4.52 Hz, 1H) 8.47 (d, J=4.90 Hz, 1H) 10.14 (s, 1H). LC/MS (APCI, pos.): 365.10 (M$^+$H).

Example 28

Preparation of 6-[(7-hydroxyquinoline-4-yl)oxy]-N,2-dimethyl-1-benzofuran-3-carboxamide

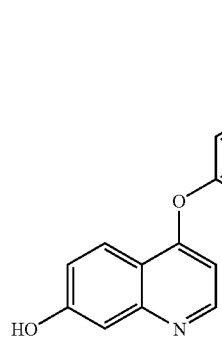

This compound was prepared according to the synthetic scheme depicted and described below.

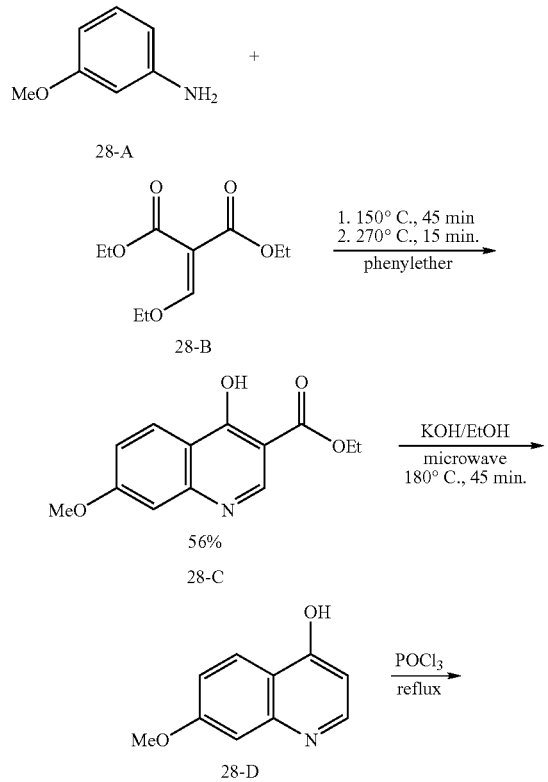

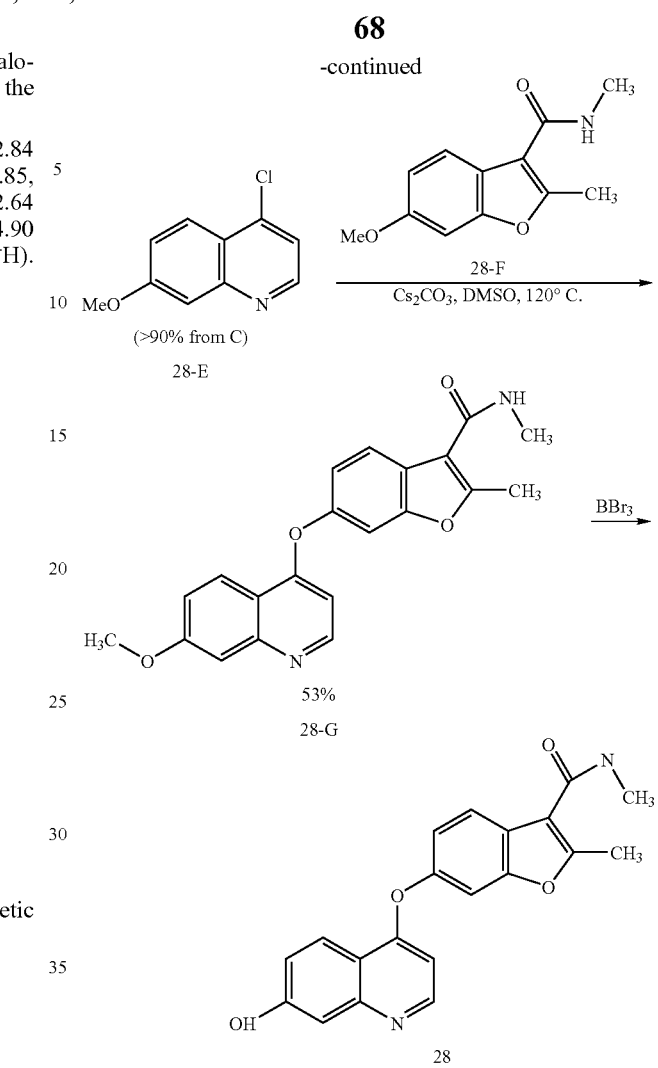

A mixture of 3-methoxyaniline (25 g, 204 mmol) 28-A and diethyl (ethoxymethylene) malonate (44 g, 204 mmol) 28-B was heated in an oil bath to 150° C. for 40 minutes. EtOH was generated when the temperature reached 132° C. and collected. The reaction flask was moved away from oil bath and phenyl ether (70 ml) was added into the reaction mixture. The oil bath was preheated to 270° C. The reaction was heated at 270° C. (oil bath temperature) for 15 minutes. The reaction mixture was poured slowly into 800 ml of hexane with stirring. Ethyl 4-hydroxy-7-methoxyquinoline-3-carboxylate 28-C was precipitated, filtrated, washed with hexane and dried (28.4 g, 56% yield).

A solution of compound 28-C (4.2 g) and KOH (3 g, 3 eq.) in 40 ml of EtOH/H$_2$O (1:1) was heated by microwave to 180° C. for 50 minutes. The mixture was cooled to room temperature, poured into water (100 ml), neutralized with AcOH to pH 7 and saturated with NaCl. The solution was extracted with THF (3×300 ml) and concentrated to yield 3.1 g of 7-methoxyquinolin-4-ol 28-D as a solid.

Compound 28-D (7.4 g) was dissolved in 20 ml of POCl$_3$. The solution was heated to reflux for 2 hours. The excess amount of POCl$_3$ was removed by evaporation under vacuum. The residue was neutralized with NH$_4$OH to pH ~7 and extracted with EtOAc. The organic layer was concentrated and purified by chromatography on a silica gel column using hexane/ethylacetate (3:1) to give 6.5 g of 4-chloro-7-methoxyquinoline as 28-E as a yellow solid.

A mixture of 28-E (1.4 g, 7.3 mmol), 6-hydroxy-N,2-dimethyl-1-benzofuran-3-carboxamide 28-F (1.5 g, 7.3 mmol) and Cs₂CO₃ (3.6, 11 mmol) in 12 ml of DMSO was heated to 120° C. for 2 hours, poured into water and extracted with EtOAc. Silica gel chromatography using 2% MeOH/CH₂Cl₂ offered 1.4 g of 6-[(7-methoxyquinolin-4-yl)oxy]-N,2-dimethyl-1-benzofuran-3-carboxamide 28-G.

To a suspension of 6-[(7-methoxyquinolin-4-yl)oxy]-N,2-dimethyl-1-benzofuran-3-carboxamide 28-G (1.4 g, 3.8 mmol) in CH₂Cl₂ was added 10 ml of BBr₃ (1M in CH₂Cl₂) at −78° C. The solution was stirred at room temperature for 6 hours. To the solution 20 ml of toluene was added into, heated to reflux for 4 hours, cooled to 0° C. and quenched with water, extracted with EtOAc and concentrated to give the title compound 28 (1.2 g) as a solid.

¹H NMR (300 MHz, DMSO-d6) δ ppm 2.56 (d, J=7.35 Hz, 3H) 2.76 (d, J=4.52 Hz, 3H) 6.28 (d, J=5.27 Hz, 1H) 7.14 (m, 2H) 7.19 (d, J=2.26 Hz, 1H) 7.53 (d, J=2.07 Hz, 1H) 7.77 (d, J=8.48 Hz, 1H) 7.92 (d, J=4.52 Hz, 1H) 8.11 (d, J=9.04 Hz, 1H) 8.45 (d, J=5.27 Hz, 1H) 10.23 (s, 1H). LC/MS (APCI, pos.): 349.10 (M+H).

Example 29

Preparation of 6-[(7-methoxyquinoline-4-yl)oxy]-N,2-dimethyl-1-benzofuran-3-carboxamide

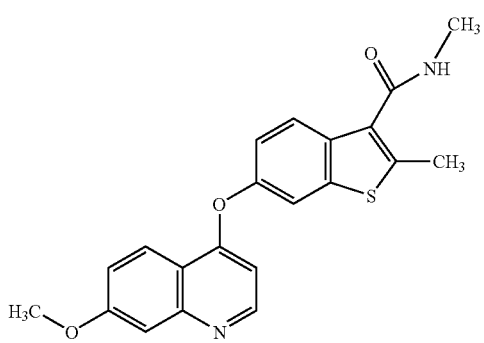

This compound was prepared according to methods analogous to those described in Example 28.

¹H NMR (300 MHz, DMSO-d6) δ ppm 2.57 (s, 3H) 2.76 (d, J=4.52 Hz, 3H) 3.87 (s, 3H) 6.37 (d, J=5.27 Hz, 1H) 7.20 (m, 2H) 7.35 (d, J=2.45 Hz, 1H) 7.56 (d, J=2.07 Hz, 1H) 7.78 (d, J=8.48 Hz, 1H) 7.92 (d, J=4.52 Hz, 1H) 8.17 (d, J=9.04 Hz, 1H) 8.53 (d, J=5.27 Hz, 1H). LC/MS (APCI, pos.): 363.10 (M+H).

Example 30

Preparation of N,2-dimethyl-6-{(7-1,3-thiazol-2-yl)quinolin-4-yl)oxy}-1-benzofuran-3-carboxamide

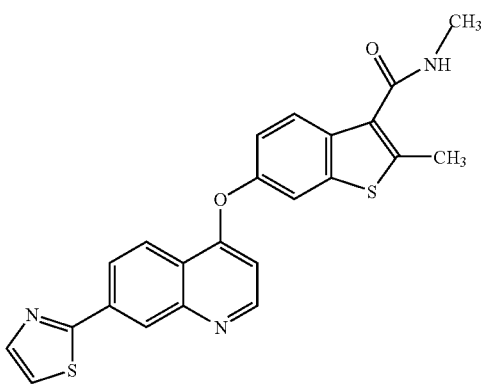

This compound was prepared according to methods analogous to those described in Examples 7-9, 13, and 17.

¹H NMR (300 MHz, DMSO-d6) δ ppm 2.59 (s, 3H) 2.77 (d, J=4.33 Hz, 3H) 7.23 (d, J=9.61 Hz, 2H) 7.63 (s, 1H) 7.81 (d, J=8.48 Hz, 1H) 7.89 (d, 2H) 8.00 (d, J=2.83 Hz, 1H) 8.20 (d, J=8.67 Hz, 1H) 8.41 (d, J=8.67 Hz, 1H) 8.48 (s, 1H) 8.68 (d, J=5.27 Hz, 1H). LC/MS (APCI, pos.): 426.10 (M+H).

Example 31

Preparation of N,2-dimethyl-6-[(7-pyridin-2-yl)quinolin-4-yl)oxy}-1-benzothiaphene-3-carboxamide

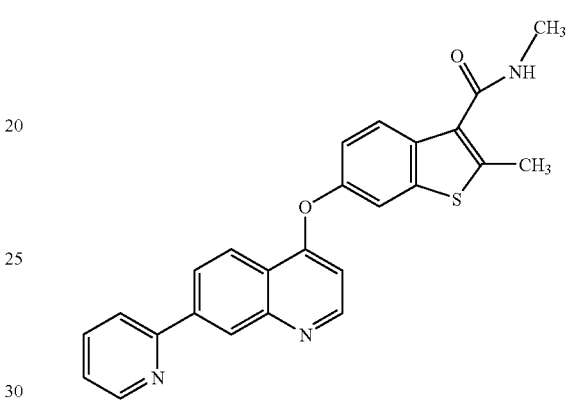

This compound was prepared according to methods analogous to those described in Example 10.

¹H NMR (300 MHz, DMSO-d6) δ ppm 2.56 (s, 3H) 2.78 (d, J=4.52 Hz, 3H) 7.30 (dd, J=8.85, 2.26 Hz, 1H) 7.39 (dd, J=7.54, 4.71 Hz, 1H) 7.83 (d, J=8.85 Hz, 1H) 7.92 (m, 2H) 8.18 (d, J=7.91 Hz, 1H) 8.23 (d, J=4.90 Hz, 1H) 8.38 (s, 2H) 8.67 (m, 2H) 8.71 (dd, J=4.80, 0.85 Hz, 1H). LC/MS (APCI, pos.): 426.10 (M+H).

Example 32

Preparation of N,2-dimethyl-5-[(7-pyridin-2-yl)quinolin-4-yl)amino]-1H-indole-1-carboxamide

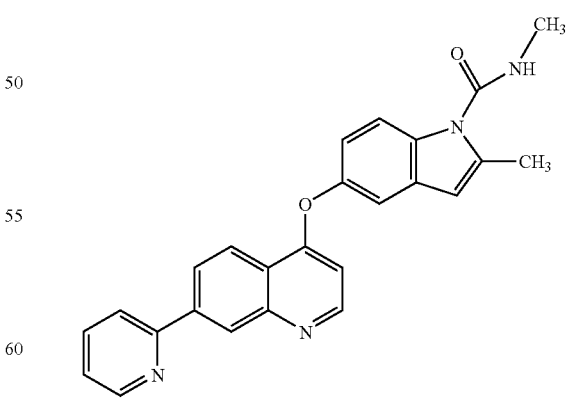

This compound was prepared according to methods analogous to those described in Example 11.

¹H NMR (300 MHz, DMSO-d6) δ ppm 2.43 (s, 3H) 2.83 (d, J=4.33 Hz, 3H) 6.36 (s, 1H) 6.62 (d, J=6.03 Hz, 1H) 7.13

(dd, J=8.76, 1.98 Hz, 1H) 7.42 (m, 2H) 7.64 (d, J=8.67 Hz, 1H) 7.92 (m, 1H) 8.17 (m, 2H) 8.29 (d, J=8.67 Hz, 1H) 8.38 (d, J=6.03 Hz, 1H) 8.55 (s, 1H) 8.60 (d, J=9.04 Hz, 1H) 8.71 (m, 1H) 9.71 (s, 1H). LC/MS (APCI, pos.): 408.20 (M+H).

Example 33

Preparation of N,2-dimethyl-6-{[7-(pyridin-2-yl-methoxy)quinolin-4-yl]oxy}-1-benzofuran-3-carboxamide

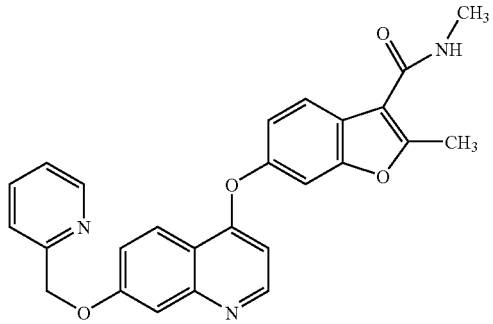

This compound was prepared according to the reaction scheme depicted below.

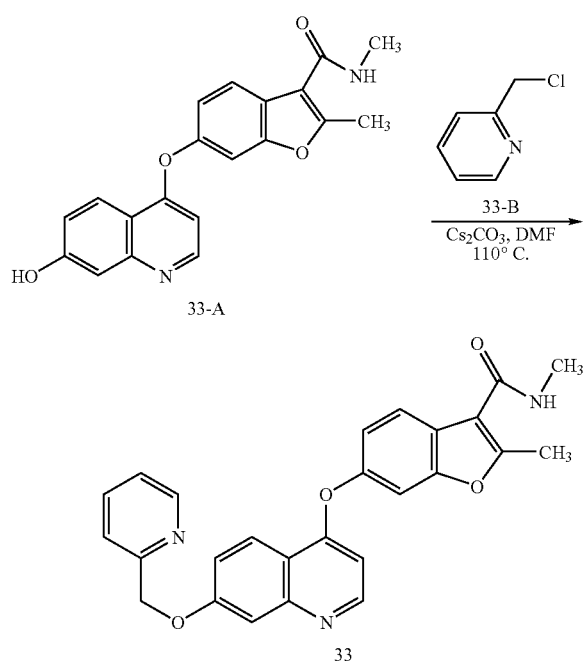

$^1$H NMR (300 MHz, DMSO-d6) δ ppm 2.57 (s, 3H) 2.76 (d, J=4.52 Hz, 3H) 5.35 (s, 2H) 6.39 (d, J=5.27 Hz, 1H) 7.17 (dd, J=8.48, 2.07 Hz, 1H) 7.36 (m, 1H) 7.41 (d, J=2.45 Hz, 1H) 7.45 (d, J=5.84 Hz, 2H) 7.56 (d, J=1.88 Hz, 1H) 7.78 (d, J=8.48 Hz, 1H) 7.92 (d, J=4.52 Hz, 1H) 8.21 (d, J=9.23 Hz, 1H) 8.53 (m, 3H). LC/MS (APCI, pos.): 441.20 (M+H).

Example 34

Preparation of N,2-dimethyl-6-{[7-(thiazol-2-yl-methoxy)quinolin-4-yl]oxy}-1-benzofuran-3-carboxamide

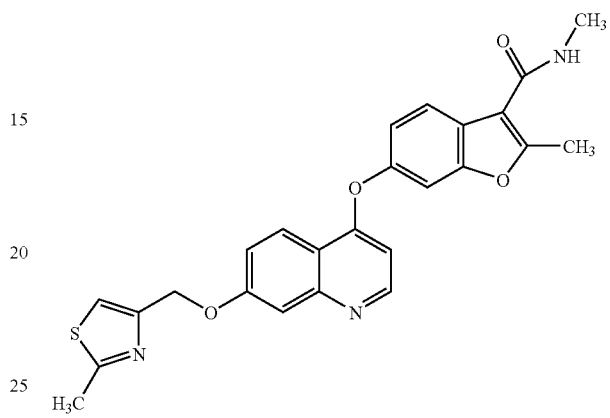

This compound was prepared according to the methods depicted in Example 33, substituting the appropriate thiazolyl intermediate for the pyridyl intermediate (33-B).

$^1$H NMR (300 MHz, DMSO-d6) δ ppm 2.57 (s, 3H) 2.62 (s, 3H) 2.76 (d, J=4.52 Hz, 3H) 5.23 (s, 2H) 6.38 (d, J=5.27 Hz, 1H) 7.17 (dd, J=8.57, 2.17 Hz, 1H) 7.29 (dd, J=9.04, 2.45 Hz, 1H) 7.49 (d, J=2.64 Hz, 1H) 7.56 (d, J=2.07 Hz, 1H) 7.58 (s, 1H) 7.78 (d, J=8.48 Hz, 1H) 7.93 (s, 1H) 8.18 (d, J=9.23 Hz, 1H) 8.53 (d, J=5.27 Hz, 1H). LC/MS (APCI, pos.): 461.20 (M+H).

General Synthetic Scheme for the Preparation of the Compounds of Examples 35 to 38

A solution of amine B (0.27 mmol) and Cs$_2$CO$_3$ (175 mg, 0.54 mmol) in DMF (2 ml) was stirred at room temperature for 1 hour. To this solution was added a solution of 6-[(7-hydroxyquinolin-4-yl)oxy]-N,2-dimethyl-1-benzofuran-3-carboxamide A (70 mg, 0.18 mmol) in DMF (1 ml). The solution was heated to 120° C. for 2 hours. The solids were removed by filtration. The residue was purified by HPLC using 20-60% CH$_3$CN/H$_2$O over 30 minutes to yield compound C.

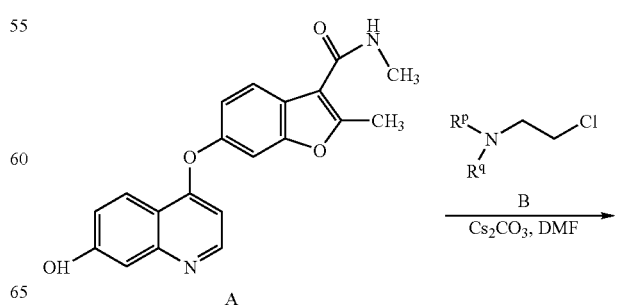

-continued

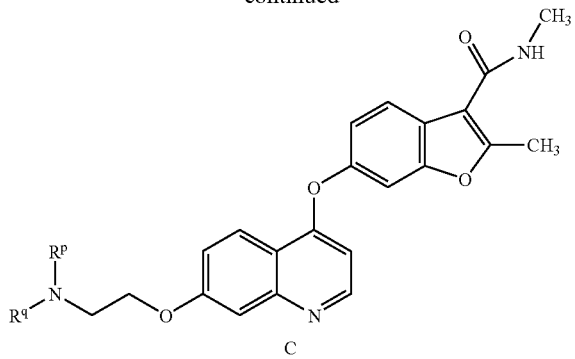

C

Example 35

Preparation of N,2-dimethyl-6-{[7-(2-pyrrolidin-1-ylethoxy)quinolin-4-yl]oxy}-1-benzofuran-3-carboxamide

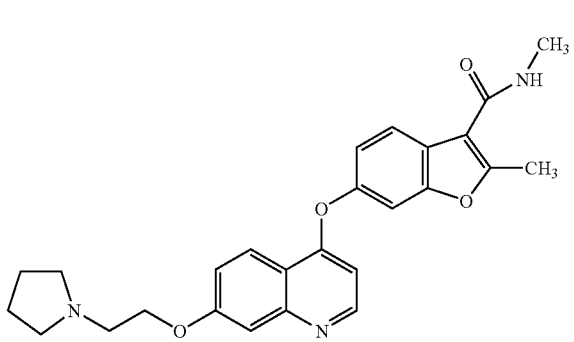

$^1$H NMR (300 MHz, DMSO-d6) δ ppm 1.63 (m, 4H) 2.45 (m, 4H) 2.79 (m, 5H) 4.19 (t, J=5.75 Hz, 2H) 6.37 (d, J=5.27 Hz, 1H) 7.16 (dd, J=8.57, 2.17 Hz, 1H) 7.23 (dd, J=9.14, 2.54 Hz, 1H) 7.35 (d, J=2.45 Hz, 1H) 7.55 (d, J=2.07 Hz, 1H) 7.79 (m, 1H) 7.92 (d, J=4.52 Hz, 1H) 8.16 (d, J=9.23 Hz, 1H) 8.52 (d, J=5.27 Hz, 1H). LC/MS (APCI, pos.): 447.25 (M+H).

Example 36

Preparation of N,2-dimethyl-6-{[7-(2-morpholin-4-ylethoxy)quinolin-4-yl]oxy}-1-benzofuran-3-carboxamide

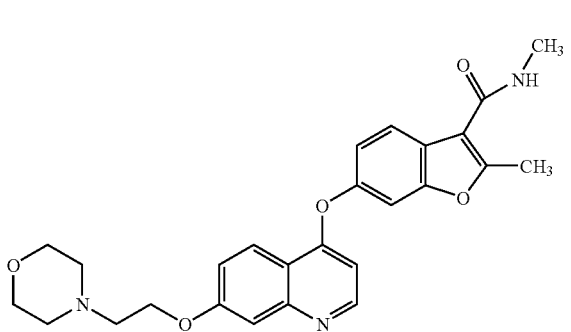

$^1$H NMR (300 MHz, DMSO-d6) δ ppm 2.57 (s, 3H) 2.73 (m, 5H) 3.30 (m, 4H) 3.53 (m, 4H) 4.21 (t, J=5.37 Hz, 2H) 6.37 (d, J=5.27 Hz, 1H) 7.19 (m, 2H) 7.37 (d, J=2.07 Hz, 1H) 7.55 (d, J=1.88 Hz, 1H) 7.78 (d, J=8.67 Hz, 1H) 7.92 (d, J=4.33 Hz, 1H) 8.16 (d, J=9.23 Hz, 1H) 8.52 (d, J=5.27 Hz, 1H). LC/MS (APCI, pos.): 462.10 (M+H).

Example 37

Preparation of 6-({7-[2-(dimethylamino)ethoxy]quinolin-4-yl}oxy)-N,2-dimethyl-1-benzofuran-3-carboxamide

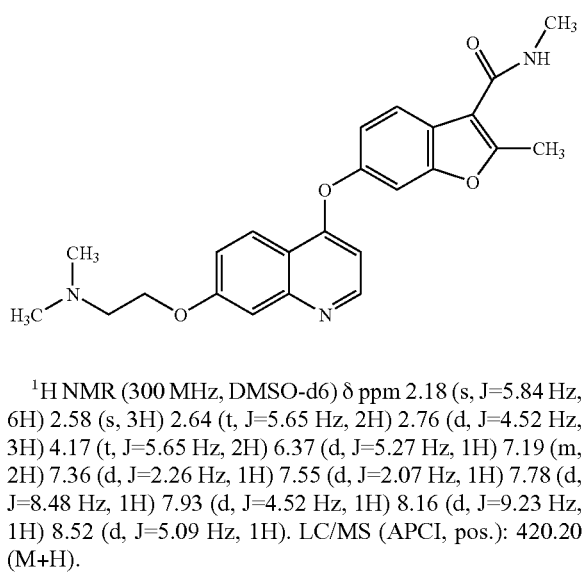

$^1$H NMR (300 MHz, DMSO-d6) δ ppm 2.18 (s, J=5.84 Hz, 6H) 2.58 (s, 3H) 2.64 (t, J=5.65 Hz, 2H) 2.76 (d, J=4.52 Hz, 3H) 4.17 (t, J=5.65 Hz, 2H) 6.37 (d, J=5.27 Hz, 1H) 7.19 (m, 2H) 7.36 (d, J=2.26 Hz, 1H) 7.55 (d, J=2.07 Hz, 1H) 7.78 (d, J=8.48 Hz, 1H) 7.93 (d, J=4.52 Hz, 1H) 8.16 (d, J=9.23 Hz, 1H) 8.52 (d, J=5.09 Hz, 1H). LC/MS (APCI, pos.): 420.20 (M+H).

Example 38

Preparation of N,2-dimethyl-6-{[7-(2-piperidin-1-ylethoxy)quinolin-4-yl]oxy}-1-benzofuran-3-carboxamide

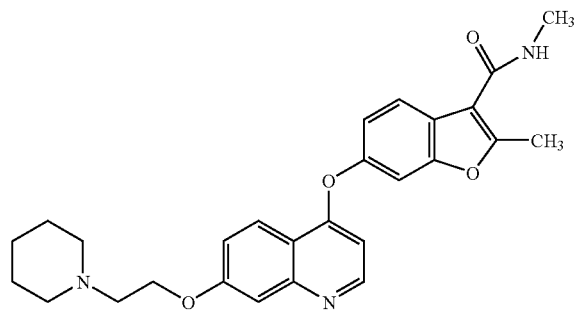

This compound was prepared according to methods analogous to those described in Examples 33-37.

$^1$H NMR (300 MHz, DMSO-d6) δ ppm 1.32 (m, 2H) 1.45 (m, 4H) 2.42 (m, 4H) 2.57 (s, 3H) 2.67 (t, J=5.84 Hz, 2H) 2.76 (d, J=4.52 Hz, 3H) 4.18 (t, J=5.84 Hz, 2H) 6.37 (d, J=5.27 Hz, 1H) 7.16 (dd, J=8.48, 2.26 Hz, 1H) 7.22 (dd, J=9.14, 2.54 Hz, 1H) 7.35 (d, J=2.45 Hz, 1H) 7.55 (d, J=2.07 Hz, 1H) 7.78 (d, J=8.67 Hz, 1H) 7.92 (d, J=4.71 Hz, 1H) 8.15 (d, J=9.23 Hz, 1H) 8.52 (d, J=5.09 Hz, 1H). LC/MS (APCI, pos.): 460.20 (M+H).

Example 39

Preparation of N-butyl-6-[(7-methoxyquinolin-4-yl)oxy]-2-methyl-1-benzofuran-3-carboxamide

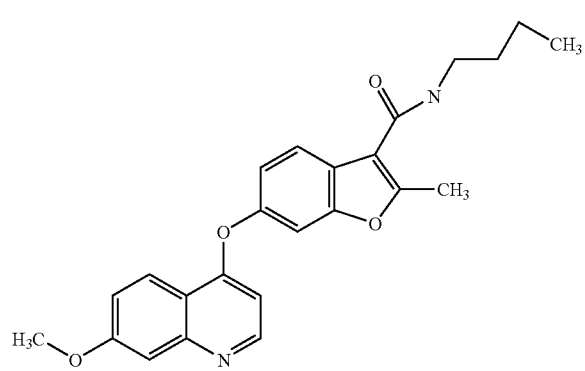

This compound was prepared according to methods analogous to those described in Examples 33-38.

$^1$H NMR (400 MHz, DMSO-d6) δ ppm 0.76 (t, J=7.45 Hz, 3H) 1.22 (m, 2H) 1.38 (m, 2H) 2.46 (s, 3H) 3.13 (m, 2H) 3.77 (s, 3H) 6.27 (d, J=5.31 Hz, 1H) 7.07 (dd, J=8.46, 2.15 Hz, 1H) 7.13 (dd, J=9.09, 2.53 Hz, 1H) 7.25 (d, J=2.53 Hz, 1H) 7.45 (d, J=2.02 Hz, 1H) 7.63 (d, J=8.59 Hz, 1H) 7.89 (t, J=5.68 Hz, 1H) 8.07 (d, J=9.10 Hz, 1H) 8.43 (d, J=5.31 Hz, 1H). LC/MS (APCI, pos.): 405.20 (M+H).

Example 40

Preparation of 6-[(7-methoxyquinolin-4-yl)oxy]-2-methyl-N-pyridin-2-yl-1-benzofuran-3-carboxamide

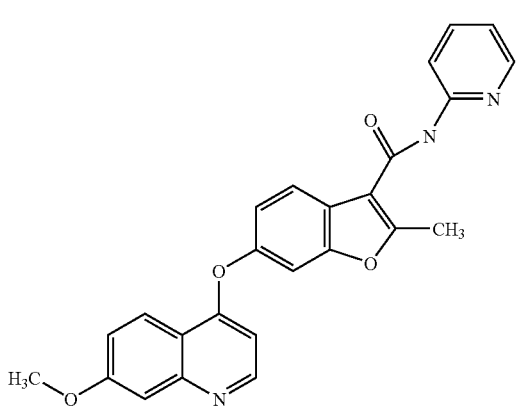

This compound was prepared according to methods analogous to those described in Examples 33-39.

$^1$H NMR (400 MHz, DMSO-d6) δ ppm 2.64 (s, 3H) 3.88 (s, 3H) 6.40 (m, 1H) 7.11 (m, 1H) 7.21 (m, 2H) 7.35 (d, J=2.53 Hz, 1H) 7.60 (d, J=2.27 Hz, 1H) 7.79 (m, 2H) 8.13 (d, J=8.34 Hz, 1H) 8.17 (m, 1H) 8.32 (dd, J=4.80, 1.01 Hz, 1H) 8.53 (t, J=4.29 Hz, 1H) 10.53 (s, 1H). LC/MS (APCI, pos.): 426.10 (M+H).

Example 41

Preparation of N-butyl-6-[(7-hydroxyquinolin-4-yl)oxy]-2-methyl-1-benzofuran-3-carboxamide

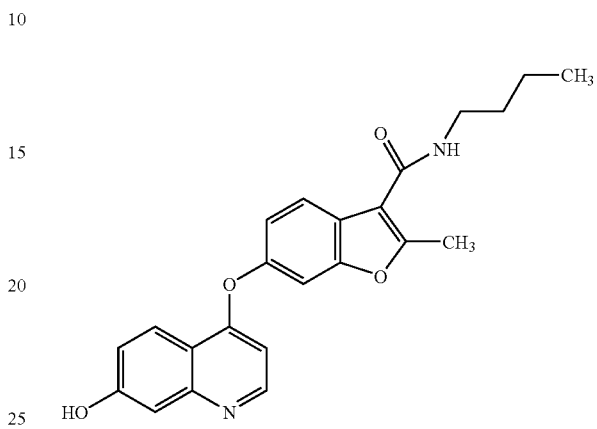

This compound was prepared according to methods analogous to those described in Example 28.

$^1$H NMR (400 MHz, DMSO-d$_6$) δ ppm 0.86 (t, J=7.45 Hz, 3H) 1.31 (m, 2H) 1.47 (m, 2H) 2.56 (s, 3H) 3.23 (m, 2H) 6.28 (d, J=5.05 Hz, 1H) 7.14 (m, 2H) 7.19 (d, J=2.53 Hz, 1H) 7.53 (d, J=2.02 Hz, 1H) 7.73 (d, J=8.59 Hz, 1H) 7.99 (t, J=5.68 Hz, 1H) 8.11 (d, J=9.10 Hz, 1H) 8.45 (d, J=5.31 Hz, 1H) 10.19 (s, 1H). LC/MS (APCI, pos.): 391.20 (M+H).

Example 42

Preparation of 6-{[7-(allyloxy)quinolin-4-yl]oxy}-N,2-dimethyl-1-benzofuran-3-carboxamide

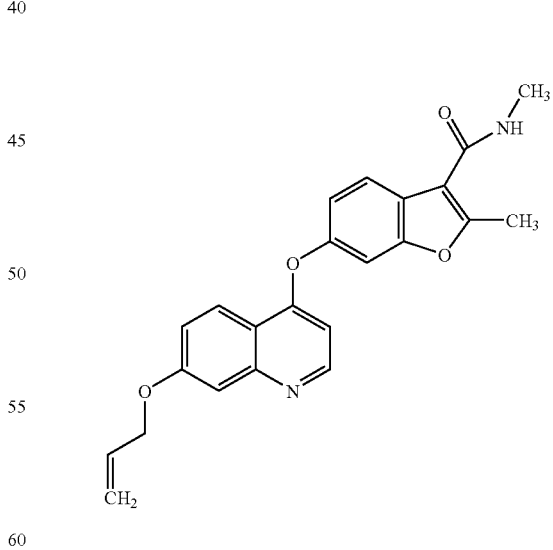

This compound was prepared according to methods analogous to those described in Examples 33-40.

$^1$H NMR (400 MHz, DMSO-d$_6$) δ ppm 2.65 (s, 3H) 2.84 (d, J=4.55 Hz, 3H) 4.78 (d, J=5.31 Hz, 2H) 5.34 (d, J=10.61 Hz, 1H) 5.49 (m, 1H) 6.13 (m, 1H) 6.45 (d, J=5.31 Hz, 1H) 7.24 (dd, J=8.46, 2.15 Hz, 1H) 7.33 (dd, J=9.09, 2.27 Hz, 1H) 7.44 (d, J=2.27 Hz, 1H) 7.63 (d, J=2.02 Hz, 1H) 7.86 (d, J=8.34 Hz, 1H) 7.98 (d, J=4.29 Hz, 1H) 8.25 (d, J=9.35 Hz, 1H) 8.60 (d, J=5.31 Hz, 1H). LC/MS (APCI, pos.): 389.10 (M+H).

Example 43

Preparation of N-isopropyl-6-[(7-methoxyquinolin-4-yl)oxy]-2-methyl-1-benzofuran-3-carboxamide

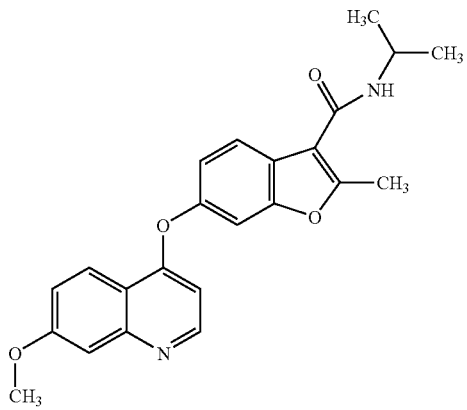

This compound was prepared according to methods analogous to those described in Examples 33-40 and 42.

$^1$H NMR (400 MHz, DMSO-d6) δ ppm 1.20 (m, 6H) 2.62 (s, 3H) 3.33 (s, 3H) 3.95 (s, 3H) 4.14 (m, 1H) 6.44 (m, 1H) 7.25 (d, J=2.02 Hz, 1H) 7.31 (dd, J=9.22, 2.40 Hz, 1H) 7.42 (s, 1H) 7.62 (s, 1H) 7.78 (d, J=8.59 Hz, 1H) 7.96 (d, J=7.58 Hz, 1H) 8.25 (m, 1H) 8.60 (d, J=5.05 Hz, 1H). LC/MS (APCI, pos.): 391.10 (M+H).

Example 44

Preparation of N-butyl-2-methyl-6-{[7-(2-pyrrolidin-1-ylethoxy)quinolin-4-yl]oxy}-1-benzofuran-3-carboxamide

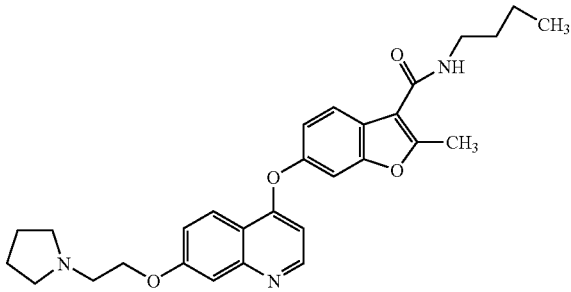

This compound was prepared according to methods analogous to those described in Examples 33-40 and 42-43.

$^1$H NMR (400 MHz, DMSO-d6) δ ppm 0.94 (t, J=7.33 Hz, 3H) 1.37 (m, 2H) 1.56 (m, 2H) 1.71 (m, 4H) 2.57 (m, 4H) 2.64 (s, 3H) 2.89 (t, J=5.68 Hz, 2H) 3.30 (m, 2H) 4.27 (t, J=5.94 Hz, 2H) 6.45 (d, J=5.31 Hz, 1H) 7.24 (dd, J=8.46, 2.15 Hz, 1H) 7.30 (dd, J=9.10, 2.53 Hz, 1H) 7.43 (d, J=2.53 Hz, 1H) 7.62 (d, J=2.27 Hz, 1H) 7.81 (d, J=8.34 Hz, 1H) 8.07 (t, J=6.06 Hz, 1H) 8.24 (d, J=9.10 Hz, 1H) 8.60 (d, J=5.31 Hz, 1H). LC/MS (APCI, pos.): 488.20 (M+H).

Example 45

Preparation of N-butyl-2-methyl-6-{[7-(2-morpholin-4-ylethoxy)quinolin-4-yl]oxy}-1-benzofuran-3-carboxamide

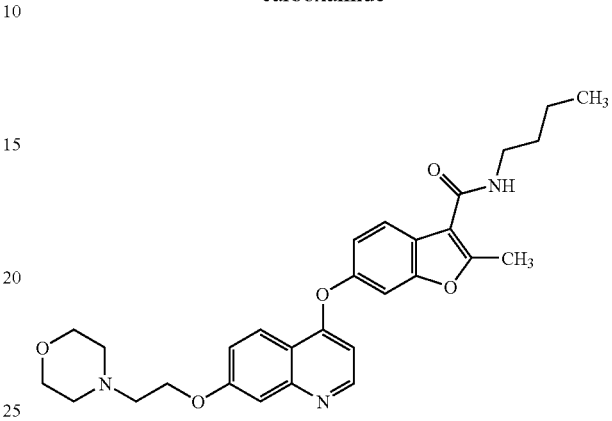

This compound was prepared according to methods analogous to those described in Examples 33-40 and 42-44.

$^1$H NMR (400 MHz, DMSO-d6) δ ppm 0.86 (t, J=7.33 Hz, 3H) 1.31 (m, 2H) 1.48 (m, 2H) 2.56 (s, 3H) 2.72 (t, J=5.56 Hz, 2H) 3.53 (m, 4H) 4.21 (t, J=5.68 Hz, 2H) 6.37 (d, J=5.05 Hz, 1H) 7.16 (dd, J=8.59, 2.02 Hz, 1H) 7.23 (dd, J=9.35, 2.53 Hz, 1H) 7.37 (d, J=2.27 Hz, 1H) 7.55 (d, J=2.02 Hz, 1H) 7.73 (d, J=8.59 Hz, 1H) 8.01 (t, J=5.81 Hz, 1H) 8.16 (d, J=9.35 Hz, 1H) 8.52 (d, J=5.05 Hz, 1H). LC/MS (APCI, pos.): 504.20 (M+H).

Example 46

Preparation of N-butyl-6-({7-[2-(dimethylamino)ethoxy]quinolin-4-yl}oxy)-2-methyl-1-benzofuran-3-carboxamide

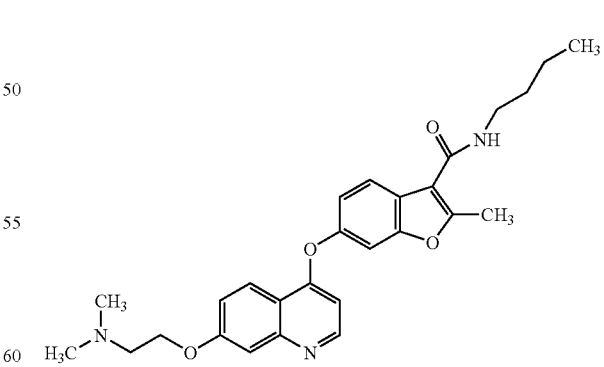

This compound was prepared according to methods analogous to those described in Examples 33-40 and 42-45.

$^1$H NMR (400 MHz, DMSO-D6) δ ppm 0.86 (t, 3H), 1.32 (m, 2H), 1.48 (m, 2H), 2.18 (s, 6H), 2.40 (m, 2H), 2.56 (s, 3H), 2.63 (t, 2H), 4.18 (t, 2H), 6.36 (d, 1H), 7.17 (dd, 1H), 7.22 (dd, 1H), 7.36 (d, 2H), 7.55 (d, 1H), 7.73 (d, 1H), 8.01 (t, 1H), 8.16 (d, 1H), 8.52 (d, 1H). LC/MS (APCI, pos.): 462.20 (M+H).

Example 47

Preparation of N-butyl-2-methyl-6-{[7-(2-piperidin-1-ylethoxy)quinolin-4-yl]oxy}-1-benzofuran-3-carboxamide

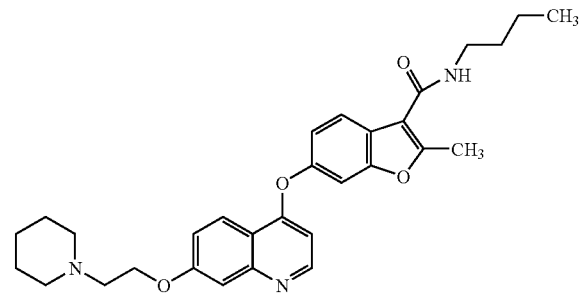

This compound was prepared according to methods analogous to those described in Examples 33-40 and 42-46.

¹H NMR (400 MHz, DMSO-d6) δ ppm 0.86 (t, J=7.45 Hz, 3H) 1.31 (m, 2H) 1.47 (m, 2H) 2.18 (s, 6H) 2.56 (s, 3H) 2.63 (m, 2H) 4.17 (t, J=5.68 Hz, 2H) 6.37 (d, J=5.05 Hz, 1H) 7.17 (dd, J=8.46, 2.15 Hz, 1H) 7.22 (dd, J=9.10, 2.53 Hz, 1H) 7.36 (d, J=2.27 Hz, 1H) 7.55 (d, J=2.27 Hz, 1H) 7.73 (d, J=8.59 Hz, 1H) 8.01 (t, J=5.56 Hz, 1H) 8.16 (d, J=9.10 Hz, 1H) 8.52 (d, J=5.05 Hz, 1H). LC/MS (APCI, pos.): 502.20 (M+H).

Example 48

Preparation of N-cyclopropyl-6-[(7-methoxyquinolin-4-yl)oxy]-2-methyl-1-benzothiophene-3-carboxamide

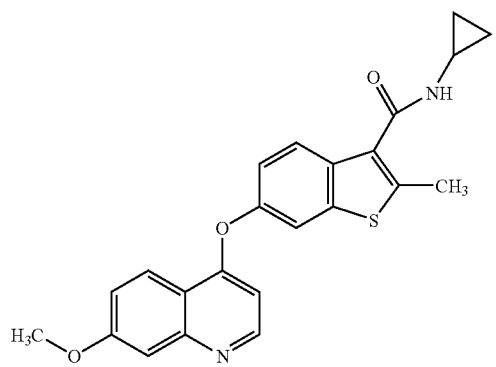

This compound was prepared according to the synthetic scheme depicted and described below.

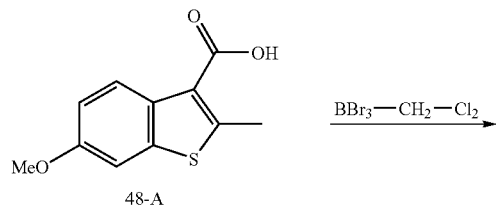

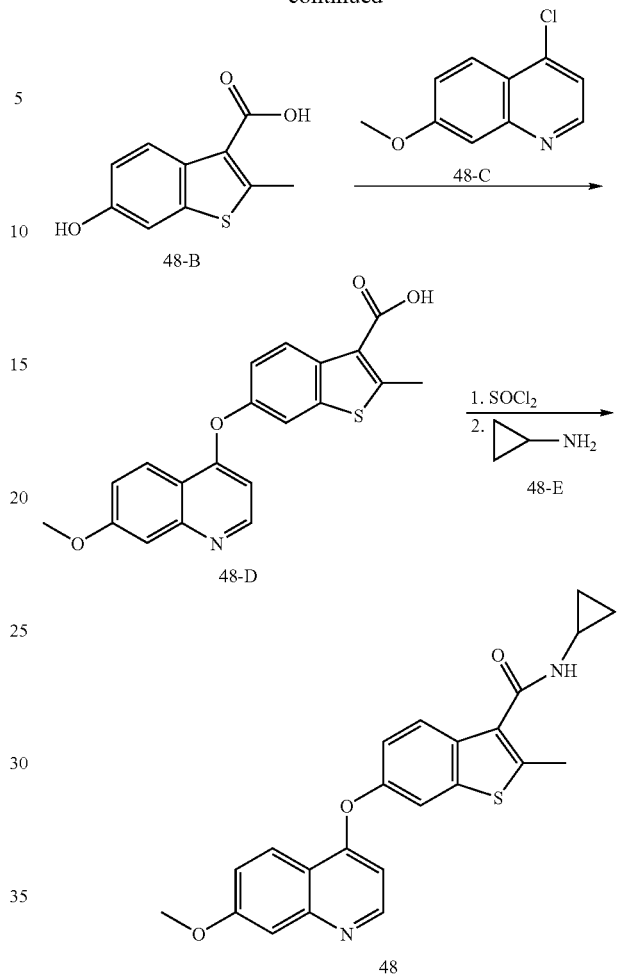

To a solution of 6-methoxy-2-methyl-1-benzothiophene-3-carboxylic acid 48-A (5 g, 22.5 mmol) in CH₂Cl₂ (50 ml) was added BBr₃ (33 ml, 1M CH₂Cl₂ solution) at −78° C. After being stirred for 1 hour the cooling bath was removed. The reaction was stirred at room temperature overnight. The reaction was quenched with water at 0° C. The mixture was extracted with EtOAc. Insoluble was collected by filtration to yield 2.1 g of 6-hydroxy-2-methyl-1-benzothiophene-3-carboxylic acid (B). The organic layer was washed with brine, dried (MgSO₄) and concentrated to give 2.7 g of 48-B.

A mixture of 48-B (1.5 g, 7.2 mmol), 4-chloro-7-methoxyquinoline 48-C (1.4 g, 7.2 mmol) and Cs₂CO₃ (7 g, 21.6 mmol) in 40 ml of DMSO was heated to 120° C. for 2 hours, poured into water, acidified with AcOH to pH~6 and extracted with EtOAc (3×100 ml) and concentrated. The residue was purified by silica gel chromatography using 5% AcOH in EtOAc to offered 1.4 g of 6-[(7-methoxyquinolin-4-yl)oxy]-2-methyl-1-benzothiophene-3-carboxylic acid 48-D.

Compound 48-D (90 mg, 0.24 mmol) was dissolved in SOCl₂ (2 ml). The solution was heated to reflux to 5 minutes. SOCl₂ was removed under vacuum. The residue was dissolved in 2 ml of CH₂Cl₂ and cyclopropanamine 48-E (34 mg, 0.6 mmol) was added into. The solution was stirred at room temperature for 20 minutes. The title compound 48 (79 mg) was isolated by silica gel column using 5% MeOH in CH₂Cl₂.

¹H NMR (300 MHz, DMSO-d6) δ ppm 0.51 (m, 2H) 0.65 (m, 2H) 2.51 (s, 3H) 2.83 (m, 1H) 3.93 (s, 3H) 6.67 (d, J=6.41 Hz, 1H) 7.32 (dd, J=8.76, 2.17 Hz, 1H) 7.46 (m, 1H) 7.49 (m, 1H) 7.80 (d, J=8.85 Hz, 1H) 7.96 (d, J=2.07 Hz, 1H) 8.37 (d, J=4.33 Hz, 1H) 8.40 (s, 1H) 8.78 (d, J=6.41 Hz, 1H). LC/MS (APCI, pos.): 405.10 (M+H).

Example 49

Preparation of N-[2-(dimethylamino)ethyl]-6-[(7-methoxyquinolin-4-yl)oxy]-2-methyl-1-benzothiophene-3-carboxamide

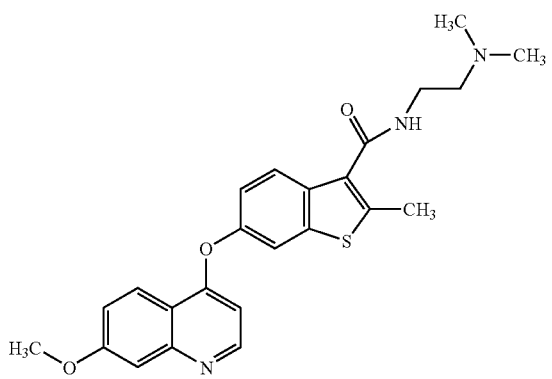

This compound was prepared according to methods analogous to those depicted and described in connection with Example 48, substituting the appropriate amine intermediate for cyclopropylamine (48-E).

$^1$H NMR (300 MHz, DMSO-d6) δ ppm 2.25 (s, 6H) 2.63 (s, 3H) 3.33 (m, 2H) 3.43 (q, J=6.15 Hz, 2H) 3.95 (s, 3H) 6.46 (d, J=5.09 Hz, 1H) 7.31 (m, 2H) 7.43 (d, J=2.26 Hz, 1H) 7.91 (m, 2H) 8.23 (d, J=9.04 Hz, 1H) 8.30 (t, J=5.37 Hz, 1H) 8.61 (d, J=5.27 Hz, 1H). LC/MS (APCI, pos.): 436.10 (M+H).

Example 50

Preparation of [(7-methoxyquinolin-4-yl)oxy]-2-methyl-N-propyl-1-benzothiophene-3-carboxamide

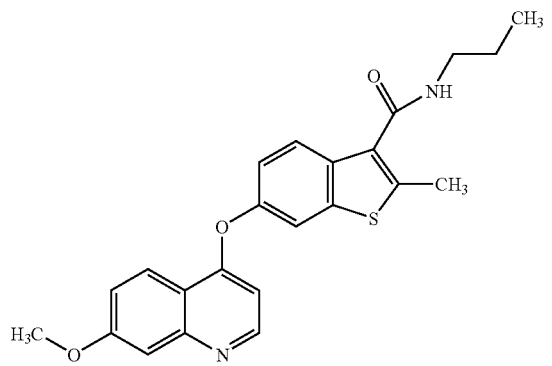

This compound was prepared according to methods analogous to those depicted and described in connection with Example 48, substituting the appropriate amine intermediate for cyclopropylamine (48-E).

$^1$H NMR (300 MHz, DMSO-d6) δ ppm 0.95 (t, J=7.35 Hz, 3H) 1.58 (m, 2H) 2.61 (s, 3H) 3.28 (m, 2H) 3.94 (s, 3H) 6.46 (d, J=5.27 Hz, 1H) 7.30 (m, 2H) 7.42 (d, J=2.45 Hz, 1H) 7.83 (d, J=8.85 Hz, 1H) 7.92 (d, J=2.26 Hz, 1H) 8.23 (d, J=9.04

Hz, 1H) 8.38 (t, J=5.75 Hz, 1H) 8.60 (d, J=5.27 Hz, 1H). LC/MS (APCI, pos.): 407.10 (M+H).

Example 51

Preparation of N-[3-(dimethylamino)propyl]-6-[(7-methoxyquinolin-4-yl)oxy]-2-methyl-1-benzothiophene-3-carboxamide

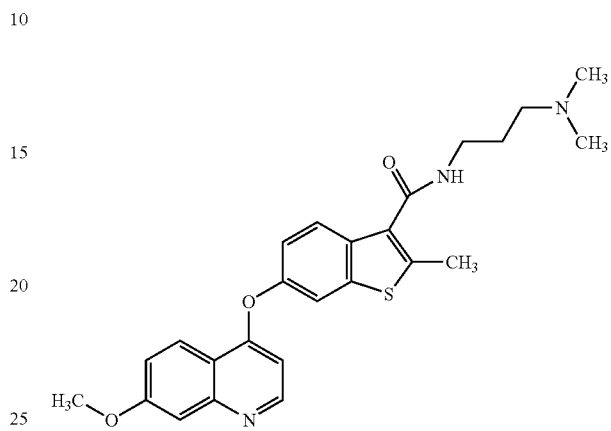

This compound was prepared according to methods analogous to those depicted and described in connection with Example 48, substituting the appropriate amine intermediate for cyclopropylamine (48-E).

$^1$H NMR (300 MHz, DMSO-d6) δ ppm 1.80 (m, 2H) 2.36 (s, 6H) 2.58 (m, 2H) 2.63 (s, 3H) 3.34 (m, 2H) 3.95 (s, 3H) 7.30 (m, 2H) 7.42 (s, 1H) 7.87 (d, J=8.48 Hz, 1H) 7.93 (s, 1H) 8.22 (m, 1H) 8.45 (m, 1H) 8.61 (m, 1H). LC/MS (APCI, pos.): 451.20 (M+H).

Example 52

Preparation of N-cyclohexyl-6-[(7-methoxyquinolin-4-yl)oxy]-2-methyl-1-benzothiophene-3-carboxamide

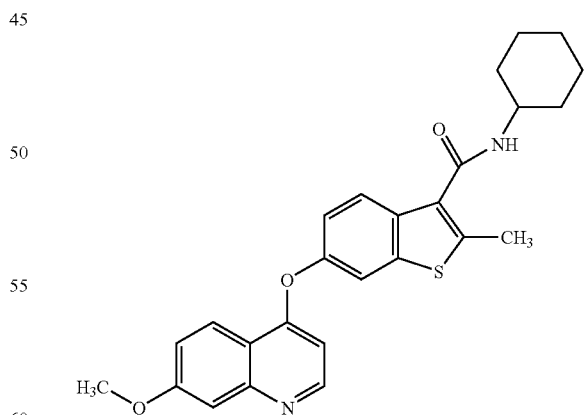

This compound was prepared according to methods analogous to those depicted and described in connection with Example 48, substituting the appropriate amine intermediate for cyclopropylamine (48-E).

$^1$H NMR (400 MHz, DMSO-d6) δ ppm 1.33 (m, 4H) 1.61 (m, 2H) 1.75 (m, J=2.78 Hz, 2H) 1.93 (m, 2H) 2.62 (s, 3H)

3.84 (m, 1H) 4.01 (s, 3H) 6.68 (d, J=6.06 Hz, 1H) 7.39 (dd, J=8.84, 2.27 Hz, 1H) 7.48 (dd, J=9.22, 2.40 Hz, 1H) 7.55 (d, J=2.53 Hz, 1H) 7.87 (d, J=8.59 Hz, 1H) 8.02 (d, J=2.27 Hz, 1H) 8.30 (d, J=8.08 Hz, 1H) 8.41 (d, J=9.35 Hz, 1H) 8.80 (d, J=6.06 Hz, 1H). LC/MS (APCI, pos.): 447.10 (M+H).

Example 53

Preparation of N-cyclopentyl-6-[(7-methoxyquinolin-4-yl)oxy]-2-methyl-1-benzothiophene-3-carboxamide

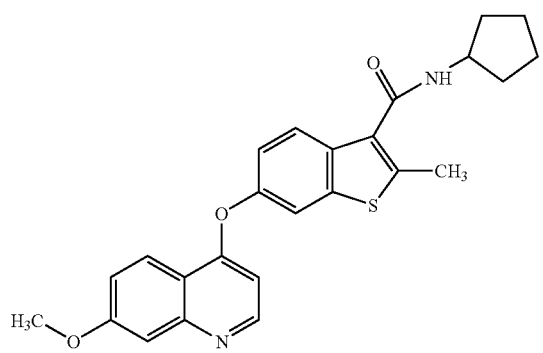

This compound was prepared according to methods analogous to those depicted and described in connection with Example 48, substituting the appropriate amine intermediate for cyclopropylamine (48-E).

$^1$H NMR (400 MHz, DMSO-d$_6$) δ ppm 1.57 (m, 4H) 1.71 (m, 2H) 1.93 (m, 2H) 2.60 (s, 3H) 3.95 (s, 3H) 4.31 (m, 1H) 6.46 (d, J=5.05 Hz, 1H) 7.31 (m, 2H) 7.43 (d, J=2.53 Hz, 1H) 7.81 (d, J=8.59 Hz, 1H) 7.91 (d, J=2.27 Hz, 1H) 8.24 (d, J=9.10 Hz, 1H) 8.36 (d, J=7.33 Hz, 1H) 8.61 (d, J=5.31 Hz, 1H). LC/MS (APCI, pos.): 433.10 (M$^+$H).

Example 54

Preparation of 6-[(7-methoxyquinolin-4-yl)oxy]-2-methyl-N-(pyridin-3-ylmethyl)-1-benzothiophene-3-carboxamide

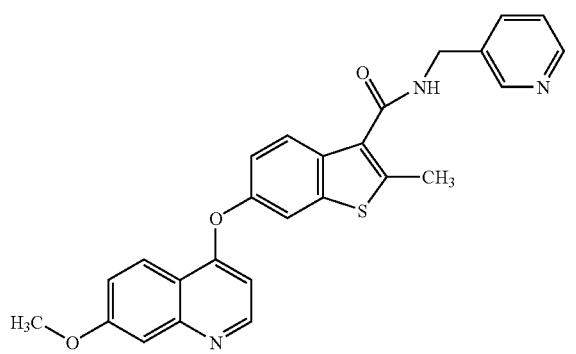

This compound was prepared according to methods analogous to those depicted and described in connection with Example 48, substituting the appropriate amine intermediate for cyclopropylamine (48-E).

$^1$H NMR (400 MHz, DMSO-d6) δ ppm 2.63 (s, 3H) 3.95 (s, 3H) 4.57 (d, J=6.06 Hz, 1H) 6.48 (d, J=5.31 Hz, 1H) 7.32 (m, 2H) 7.41 (m, 1H) 7.43 (d, J=2.27 Hz, 1H) 7.82 (m, 1H) 7.86 (d, J=8.84 Hz, 1H) 7.94 (d, J=2.27 Hz, 1H) 8.23 (d, J=9.09 Hz, 1H) 8.50 (dd, J=4.80, 1.52 Hz, 1H) 8.61 (d, J=5.05 Hz, 1H) 8.63 (d, J=1.77 Hz, 1H) 8.97 (t, J=5.94 Hz, 1H). LC/MS (APCI, pos.): 456.10 (M$^+$H).

Example 55

Preparation of 6-[(7-hydroxyquinolin-4-yl)oxy]-2-methyl-N-propyl-1-benzothiophene-3-carboxamide

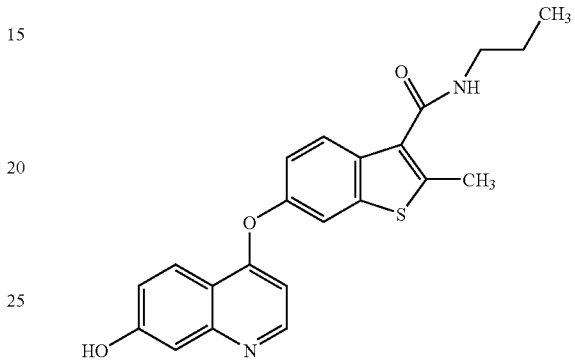

This compound was prepared using methods analogous to those depicted and described in Examples 48, 33 and 28, using the appropriate starting materials.

$^1$H NMR (400 MHz, DMSO-d6) δ ppm 0.99 (q, J=7.16 Hz, 3H) 1.62 (m, 2H) 2.65 (d, J=6.06 Hz, 3H) 3.32 (m, 2H) 6.41 (t, J=5.68 Hz, 1H) 7.24 (m, 1H) 7.32 (m, 2H) 7.86 (m, 1H) 7.93 (d, J=4.29 Hz, 1H) 8.21 (dd, J=8.59, 6.57 Hz, 1H) 8.40 (s, 1H) 8.57 (t, J=5.68 Hz, 1H) 10.29 (d, J=6.32 Hz, 1H). LC/MS (APCI, pos.): 393.1 (M+H).

Example 56

Preparation of N-cyclopentyl-6-[(7-hydroxyquinolin-4-yl)oxy]-2-methyl-1-benzothiophene-3-carboxamide

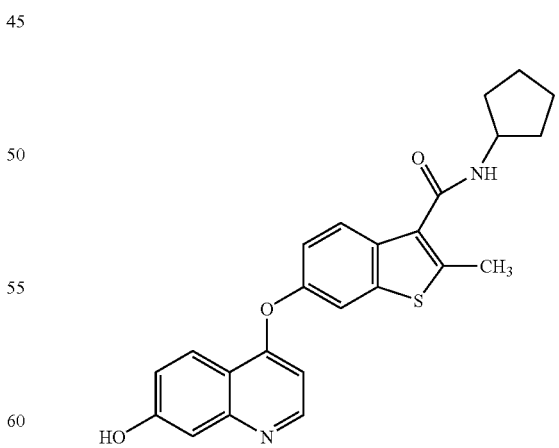

This compound was prepared using methods analogous to those depicted and described in Examples 48, 33 and 28, using the appropriate starting materials.

$^1$H NMR (400 MHz, DMSO-d6) δ ppm 1.50 (m, 4H) 1.61 (m, 2H) 1.85 (m, 2H) 2.52 (s, 3H) 4.23 (m, 1H) 6.30 (d, J=5.05 Hz, 1H) 7.13 (dd, J=8.97, 2.40 Hz, 1H) 7.21 (m, 2H) 7.73 (d, J=8.84 Hz, 1H) 7.82 (d, J=2.27 Hz, 1H) 8.28 (d, J=7.33 Hz, 1H) 8.46 (d, J=5.05 Hz, 1H) 10.18 (s, 1H). LC/MS (APCI, pos.): 419.1 (M+H).

Example 57

Preparation of N-[2-(dimethylamino)ethyl]-6-[(7-hydroxyquinolin-4-yl)oxy]-2-methyl-1-benzothiophene-3-carboxamide

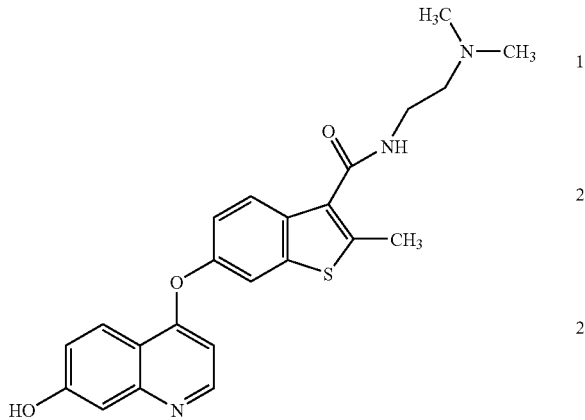

This compound was prepared using methods analogous to those depicted and described in Examples 48, 33 and 28, using the appropriate starting materials.

¹H NMR (400 MHz, CHLOROFORM-d) δ ppm 2.46 (d, J=4.04 Hz, 6H) 2.68 (d, J=4.55 Hz, 3H) 2.83 (s, 2H) 3.76 (m, 2H) 6.30 (s, 1H) 6.98 (s, 1H) 7.10 (s, 1H) 7.26 (d, J=5.05 Hz, 1H) 7.37 (s, 2H) 7.49 (d, J=2.53 Hz, 1H) 7.90 (dd, J=8.34, 4.80 Hz, 1H) 8.06 (d, J=4.04 Hz, 1H) 8.30 (s, 1H). LC/MS (APCI, pos.): 422.1 (M+H).

Example 58

Preparation of N-[3-(dimethylamino)propyl]-6-[(7-hydroxyquinolin-4-yl)oxy]-2-methyl-1-benzothiophene-3-carboxamide

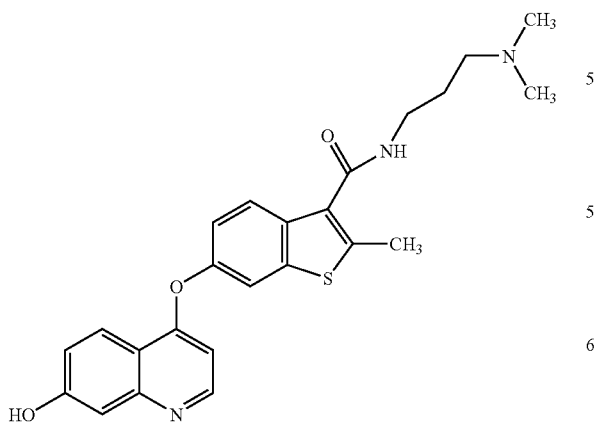

This compound was prepared using methods analogous to those depicted and described in Examples 48, 33 and 28, using the appropriate starting materials.

¹H NMR (400 MHz, DMSO-d6) δ ppm 1.74 (m, 2H) 2.43 (s, 6H) 2.56 (s, 3H) 2.62 (m, J=6.32 Hz, 2H) 3.29 (m, 2H) 6.30 (d, J=5.31 Hz, 1H) 7.13 (dd, J=9.10, 2.27 Hz, 1H) 7.22 (m, 3H) 7.78 (d, J=8.84 Hz, 1H) 7.84 (d, J=2.27 Hz, 1H) 8.10 (d, J=9.10 Hz, 1H) 8.36 (t, J=5.56 Hz, 1H) 8.46 (d, J=5.31 Hz, 1H) 10.19 (s, 1H). LC/MS (APCI, pos.): 422.1 (M+H).

Example 59

Preparation of 6-[(7-hydroxyquinolin-4-yl)oxy]-2-methyl-N-(pyridin-3-ylmethyl)-1-benzothiophene-3-carboxamide

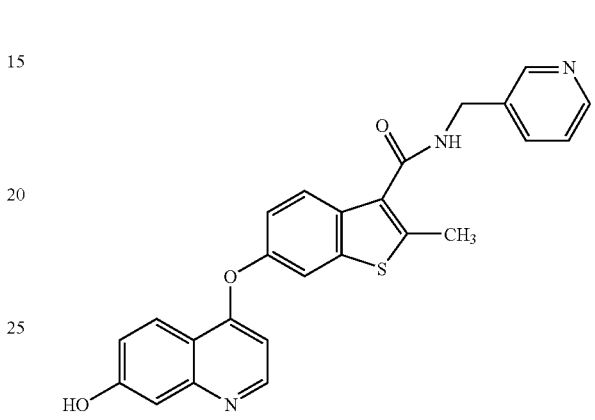

This compound was prepared using methods analogous to those depicted and described in Examples 48, 33 and 28, using the appropriate starting materials.

¹H NMR (400 MHz, DMSO-d6) δ ppm 2.56 (s, 3H) 4.49 (d, J=6.06 Hz, 2H) 6.37 (d, J=5.05 Hz, 1H) 7.17 (dd, J=8.97, 1.64 Hz, 1H) 7.21 (s, 1H) 7.25 (dd, J=8.84, 1.77 Hz, 1H) 7.34 (dd, J=7.83, 4.80 Hz, 1H) 7.74 (d, J=8.08 Hz, 1H) 7.79 (d, J=8.59 Hz, 1H) 7.86 (s, 1H) 8.15 (d, J=9.09 Hz, 1H) 8.43 (d, J=4.29 Hz, 1H) 8.51 (d, J=5.31 Hz, 1H) 8.55 (s, 1H) 8.89 (t, J=6.06 Hz, 1H) 10.38 (s, 1H). LC/MS (APCI, pos.): 442.1 (M+H).

Example 60

Preparation of N,2-dimethyl-6-{[7-(trifluoromethyl)quinolin-4-yl]oxy}-1-benzothiophene-3-carboxamide

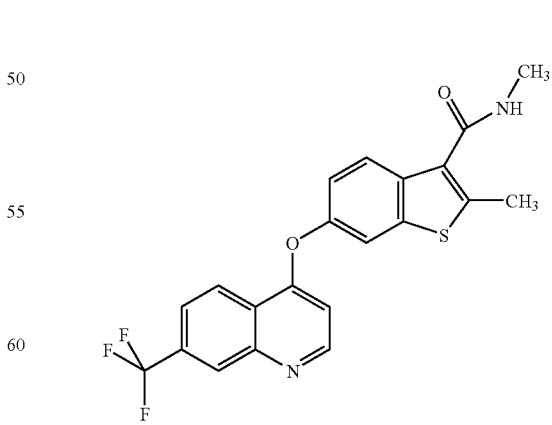

This compound was prepared according to methods analogous to those described in Scheme I and Example 21, using the appropriate starting materials.

¹H NMR (400 MHz, DMSO-d6) δ ppm 2.63 (s, 3H) 2.85 (t, J=4.93 Hz, 3H) 6.78 (d, J=5.05 Hz, 1H) 7.37 (dd, J=8.84, 2.27 Hz, 1H) 7.91 (d, J=8.84 Hz, 1H) 7.95 (dd, J=8.84, 1.52 Hz, 1H) 7.99 (d, J=2.27 Hz, 1H) 8.27 (m, 1H) 8.41 (s, 1H) 8.60 (d, J=8.84 Hz, 1H) 8.85 (d, J=5.31 Hz, 1H). LC/MS (APCI, pos.): 417.1 (M+H).

Example 61

Preparation of N,2-dimethyl-6-{[7-(trifluoromethyl)quinolin-4-yl]oxy}-1-benzofuran-3-carboxamide

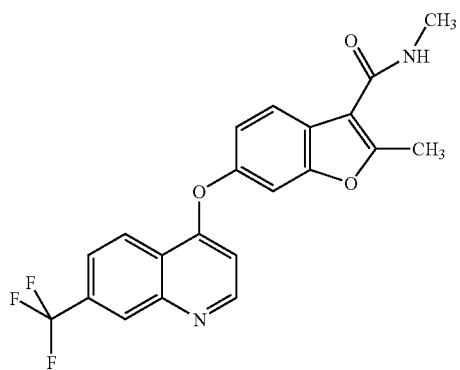

This compound was prepared according to methods analogous to those described in Schemes I and II and Examples 5 and 6 and using the appropriate starting materials.

¹H NMR (400 MHz, CHLOROFORM-d) δ ppm 2.75 (d, J=1.77 Hz, 3H) 3.09 (s, 3H) 5.90 (s, 1H) 6.63 (s, 1H) 7.17 (d, J=8.34 Hz, 1H) 7.32 (s, 1H) 7.78 (d, J=7.33 Hz, 2H) 8.41 (s, 1H) 8.53 (d, J=7.07 Hz, 1H) 8.75 (s, 1H). LC/MS (APCI, pos.): 401.1 (M+H).

Example 62

Preparation of 6-[(7-methoxyquinolin-4-yl)oxy]-2-methyl-N-(3-morpholin-4-ylpropyl)-1-benzothiophene-3-carboxamide

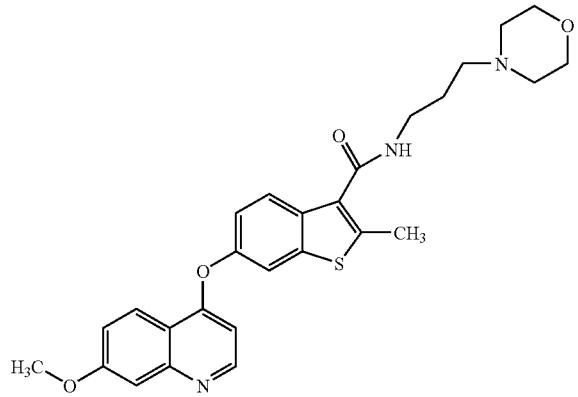

This compound was prepared using methods analogous to those depicted and described in Examples 48, 33 and 28, using the appropriate starting materials.

¹H NMR (300 MHz, DMSO-d6) δ ppm 1.99 (m, 2H) 2.66 (s, 3H) 3.19 (m, J=12.43 Hz, 4H) 3.41 (m, 6H) 3.65 (t, J=11.68 Hz, 2H) 4.00 (m, 3H) 6.64 (d, J=5.84 Hz, 1H) 7.39 (dd, J=8.76, 2.35 Hz, 1H) 7.44 (m, 1H) 7.47 (s, 1H) 7.91 (d, J=8.67 Hz, 1H) 8.03 (d, J=2.26 Hz, 1H) 8.37 (d, J=9.04 Hz, 1H) 8.52 (t, J=5.75 Hz, 1H) 8.77 (d, J=5.46 Hz, 1H) 9.52 (s, 1H). LC/MS (APCI, pos.): 491.2 (M+H).

Example 63

Preparation of N-cyclopropyl-6-[(7-methoxyquinolin-4-yl)oxy]-2-methyl-1-benzofuran-3-carboxamide

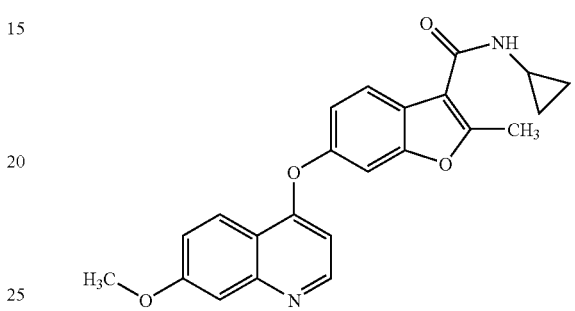

This compound was prepared using methods analogous to those depicted and described in Examples 48, 33 and 28, using the appropriate starting materials.

¹H NMR (300 MHz, DMSO-d6) δ ppm 0.55 (m, J=3.86, 3.86 Hz, 2H) 0.65 (m, 2H) 2.53 (s, 3H) 2.80 (m, 1H) 3.87 (s, 3H) 6.36 (d, J=5.09 Hz, 1H) 7.15 (dd, J=8.48, 2.07 Hz, 1H) 7.23 (dd, J=9.14, 2.54 Hz, 1H) 7.35 (d, J=2.45 Hz, 1H) 7.54 (d, J=2.07 Hz, 1H) 7.68 (d, J=8.48 Hz, 1H) 8.12 (d, J=3.77 Hz, 1H) 8.17 (d, J=9.23 Hz, 1H) 8.52 (d, J=5.09 Hz, 1H). LC/MS (APCI, pos.): 389.1 (M+H).

Example 64

Preparation of 6-[(7-methoxyquinolin-4-yl)oxy]-2-methyl-N-(3-morpholin-4-ylpropyl)-1-benzofuran-3-carboxamide

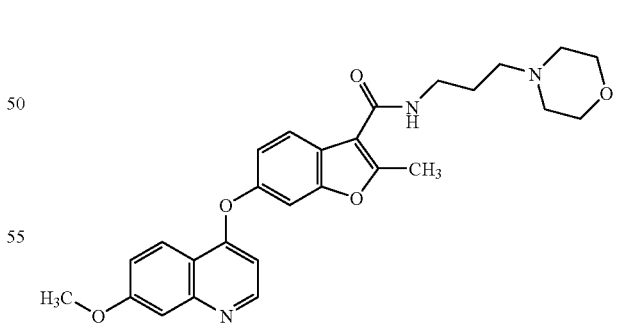

This compound was prepared using methods analogous to those depicted and described in Examples 48, 33 and 28, using the appropriate starting materials.

¹H NMR (300 MHz, DMSO-d6) δ ppm 1.83 (m, 2H) 2.42 (m, J=24.11 Hz, 8H) 2.74 (s, 3H) 3.66 (m, 4H) 4.04 (s, 3H) 6.54 (d, J=5.27 Hz, 1H) 7.34 (dd, J=8.57, 2.17 Hz, 1H) 7.40 (dd, J=9.14, 2.54 Hz, 1H) 7.52 (d, J=2.64 Hz, 1H) 7.73 (d, J=2.26 Hz, 1H) 7.92 (d, J=8.48 Hz, 1H) 8.19 (m, 1H) 8.34 (d, J=9.23 Hz, 1H) 8.69 (d, J=5.27 Hz, 1H). LC/MS (APCI, pos.): 476.2 (M+H).

Example 65

Preparation of 6-[(7-methoxyquinolin-4-yl)oxy]-2-methyl-benzofuran-3-carboxylic acid (3-dimethylamino-propyl)-amide

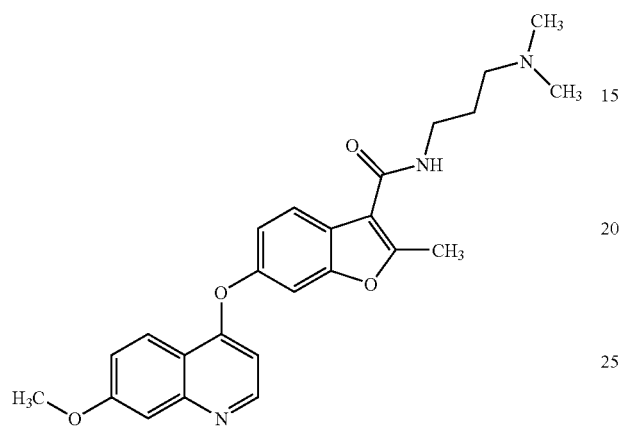

This compound was prepared using methods analogous to those depicted and described in Examples 48, 33 and 28, using the appropriate starting materials.
¹H NMR (300 MHz, DMSO-d6) δ ppm 1.70 (m, 2H) 2.15 (d, J=3.96 Hz, 6H) 2.65 (s, 3H) 3.32 (m, 4H) 3.95 (s, 3H) 6.45 (d, J=5.27 Hz, 1H) 7.25 (dd, J=8.48, 2.07 Hz, 1H) 7.30 (dd, J=9.14, 2.54 Hz, 1H) 7.42 (d, J=2.64 Hz, 1H) 7.63 (d, J=2.26 Hz, 1H) 7.83 (d, J=8.67 Hz, 1H) 8.16 (t, J=5.46 Hz, 1H) 8.24 (d, J=9.23 Hz, 1H) 8.60 (d, J=5.27 Hz, 1H). LC/MS (APCI, pos.): 434.2 (M+H).

Example 66

Preparation of 6-[(7-methoxyquinolin-4-yl)oxy]-2-methyl-N-(pyridin-2-ylmethyl)-1-benzofuran-3-carboxamide

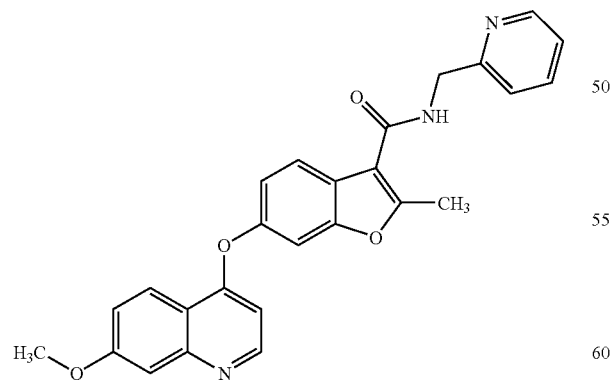

This compound was prepared using methods analogous to those depicted and described in Examples 48, 33 and 28, using the appropriate starting materials.
¹H NMR (300 MHz, DMSO-d6) δ ppm 2.63 (s, 3H) 3.87 (s, 3H) 4.56 (d, J=5.84 Hz, 2H) 6.39 (d, J=5.27 Hz, 1H) 7.21 (m, 3H) 7.35 (m, J=1.88 Hz, 2H) 7.58 (d, J=2.07 Hz, 1H) 7.73 (m, 1H) 7.85 (d, J=8.48 Hz, 1H) 8.17 (d, J=9.04 Hz, 1H) 8.48 (dd, J=4.05, 0.85 Hz, 1H) 8.53 (d, J=5.27 Hz, 1H) 8.58 (m, 1H). LC/MS (APCI, pos.): 440.1 (M+H).

Example 67

Preparation of N-(3-hydroxypropyl)-6-[(7-methoxyquinolin-4-yl)oxy]-2-methyl-1-benzofuran-3-carboxamide

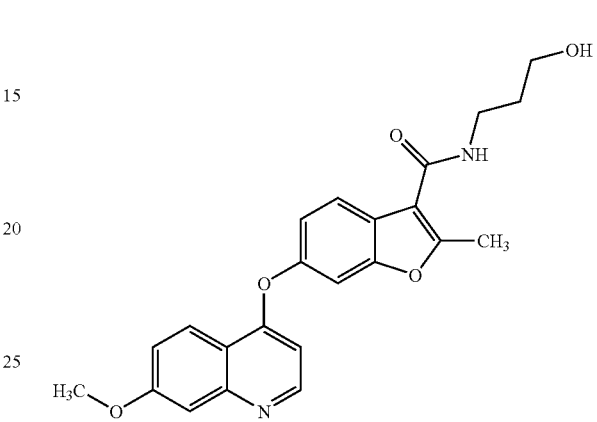

This compound was prepared using methods analogous to those depicted and described in Examples 48, 33 and 28, using the appropriate starting materials.
¹H NMR (300 MHz, DMSO-d6) δ ppm 1.75 (m, 2H) 2.64 (s, 3H) 3.34 (m, 4H) 3.94 (s, 3H) 4.57 (s, 1H) 6.44 (d, J=5.27 Hz, 1H) 7.23 (dd, J=8.57, 2.17 Hz, 1H) 7.30 (dd, J=9.04, 2.64 Hz, 1H) 7.42 (d, J=2.45 Hz, 1H) 7.62 (d, J=1.88 Hz, 1H) 7.82 (d, J=8.48 Hz, 1H) 8.06 (t, J=5.46 Hz, 1H) 8.24 (m, J=9.04 Hz, 1H) 8.59 (d, J=5.27 Hz, 1H). LC/MS (APCI, pos.): 407.1 (M+H).

Example 68

Preparation of N-(5-hydroxy-1H-pyrazol-3-yl)-6-[(7-methoxyquinolin-4-yl)oxy]-2-methyl-1-benzothiophene-3-carboxamide

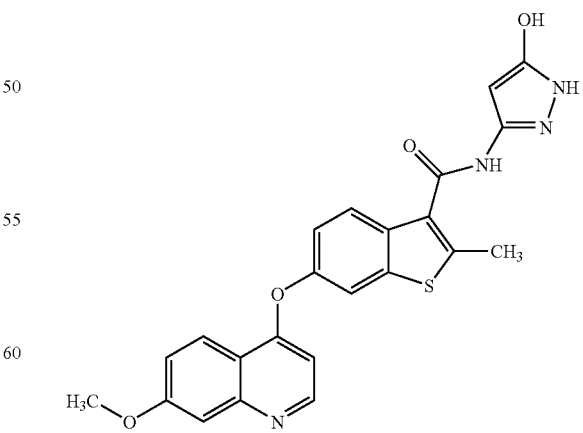

This compound was prepared using methods analogous to those depicted and described in Examples 48, 33 and 28, using the appropriate starting materials.

¹H NMR (300 MHz, DMSO-d6) δ ppm 2.54 (s, 3H) 3.96 (s, 3H) 4.87 (s, 1H) 6.54 (d, J=5.27 Hz, 1H) 6.86 (s, 1H) 7.33 (m, 2H) 7.44 (d, J=2.45 Hz, 1H) 7.58 (d, J=8.67 Hz, 1H) 7.96 (d, J=2.26 Hz, 1H) 8.26 (d, J=9.04 Hz, 1H) 8.66 (d, J=5.27 Hz, 1H). LC/MS (APCI, pos.): 447.0 (M+H).

Example 69

Preparation of 6-[(7-hydroxyquinolin-4-yl)oxy]-N-isopropyl-2-methyl-1-benzofuran-3-carboxamide

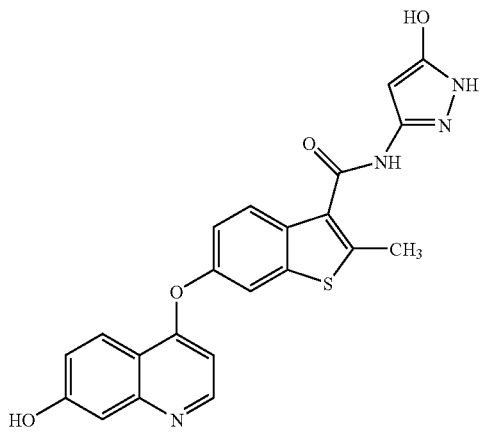

This compound was prepared using methods analogous to those depicted and described in Examples 48, 33 and 28 using the appropriate starting materials.

¹H NMR (300 MHz, DMSO-d6) δ ppm 1.02 (d, J=6.59 Hz, 6H) 2.42 (s, 3H) 3.96 (m, 1H) 6.16 (d, J=5.27 Hz, 1H) 7.02 (m, 3H) 7.07 (d, J=2.07 Hz, 1H) 7.41 (d, J=2.07 Hz, 1H) 7.57 (d, J=8.48 Hz, 1H) 7.76 (d, J=7.54 Hz, 1H) 8.00 (d, J=9.04 Hz, 1H) 8.33 (d, J=5.09 Hz, 1H) 10.10 (s, 1H). LC/MS (APCI, pos.): 477.1 (M+H).

Example 70

Preparation of 6-[(7-hydroxyquinolin-4-yl)oxy]-N-isopropyl-2-methyl-1-benzothiophene-3-carboxamide

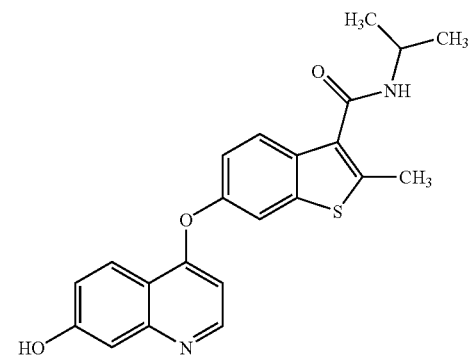

This compound was prepared using methods analogous to those depicted and described in Examples 48, 33 and 28, using the appropriate starting materials.

¹H NMR (300 MHz, DMSO-d6) δ ppm 1.17 (d, J=6.59 Hz, 6H) 2.57 (s, 3H) 3.30 (s, 3H) 4.14 (m, 1H) 6.35 (d, J=5.27 Hz, 1H) 7.23 (m, 3H) 7.79 (d, J=8.67 Hz, 1H) 7.88 (d, J=2.26 Hz, 1H) 8.16 (d, J=9.04 Hz, 1H) 8.25 (d, J=7.72 Hz, 2H) 8.52 (d, J=5.27 Hz, 1H) 10.31 (s, 1H). LC/MS (APCI, pos.): 393.1 (M+H).

Example 71

Preparation of N-isopropyl-6-[(7-methoxyquinolin-4-yl)oxy]-2-methyl-1-benzothiophene-3-carboxamide

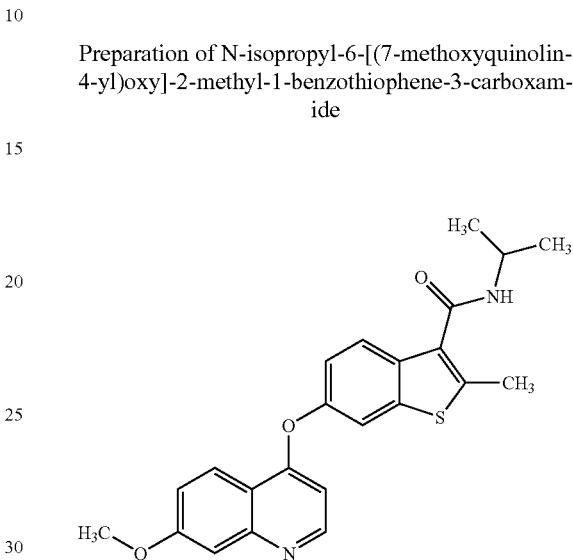

This compound was prepared using methods analogous to those depicted and described in Examples 48, 33 and 28, using the appropriate starting materials.

¹H NMR (300 MHz, DMSO-d6) δ ppm 1.27 (d, J=6.41 Hz, 6H) 2.67 (s, 3H) 4.01 (s, 3H) 4.22 (m, 1H) 6.52 (d, J=5.27 Hz, 1H) 7.38 (m, 2H) 7.49 (d, J=2.45 Hz, 1H) 7.89 (d, J=8.67 Hz, 1H) 7.99 (d, J=2.26 Hz, 1H) 8.30 (d, J=9.04 Hz, 1H) 8.35 (d, J=7.91 Hz, 1H) 8.68 (d, J=5.27 Hz, 1H). LC/MS (APCI, pos.): 407.1 (M+H).

General Preparation of the Compounds of Examples 72 to 74

These compounds were prepared according to the reaction scheme depicted below and using methods analogous to those described in connection with Schemes I and IV (described hereinabove).

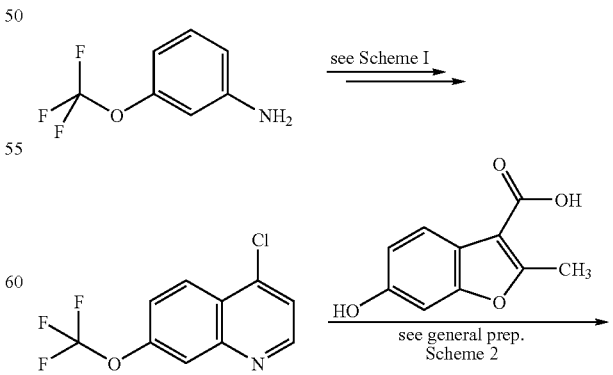

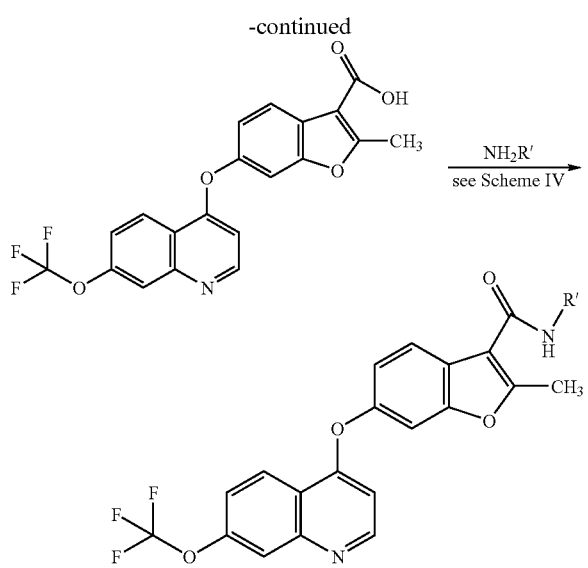

Example 72

Preparation of N-isopropyl-2-methyl-6-{[7-(trifluoromethoxy)quinolin-4-yl]oxy}-1-benzofuran-3-carboxamide

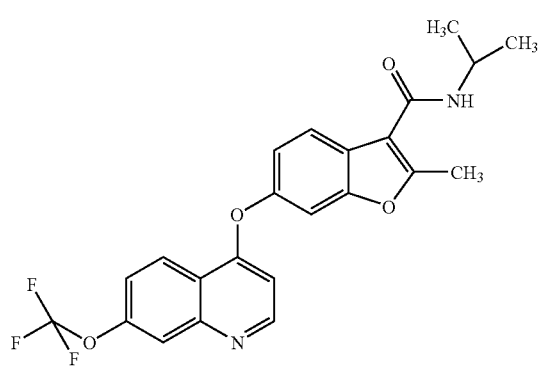

$^1$H NMR (300 MHz, CHLOROFORM-d) δ ppm 1.33 (d, J=6.41 Hz, 6H) 2.74 (s, 3H) 4.36 (m, J=6.41 Hz, 1H) 5.67 (d, J=7.72 Hz, 1H) 6.54 (d, J=4.90 Hz, 1H) 7.16 (dd, J=8.48, 2.07 Hz, 1H) 7.31 (s, 1H) 7.46 (d, J=9.23 Hz, 1H) 7.73 (d, J=8.29 Hz, 1H) 7.95 (s, 1H) 8.45 (d, J=9.04 Hz, 1H) 8.69 (d, J=4.71 Hz, 1H). LC/MS (APCI, pos.): 445.0 (M+H).

Example 73

Preparation of N-cyclopropyl-2-methyl-6-{[7-(trifluoromethoxy)quinolin-4-yl]oxy}-1-benzofuran-3-carboxamide

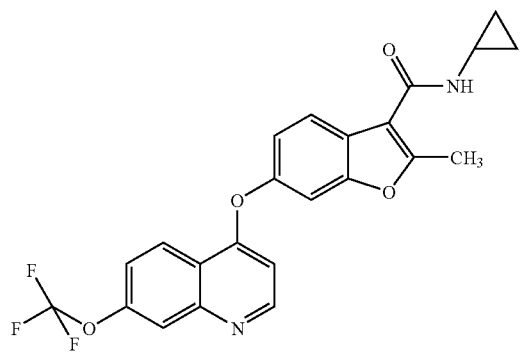

$^1$H NMR (300 MHz, CHLOROFORM-d) δ ppm 0.69 (m, 2H) 0.93 (m, J=6.97, 5.46 Hz, 2H) 2.75 (s, 3H) 2.94 (m, 1H) 6.02 (s, 1H) 6.53 (d, J=5.27 Hz, 1H) 7.15 (dd, J=8.48, 2.07 Hz, 1H) 7.31 (d, J=2.07 Hz, 1H) 7.46 (dd, J=9.14, 1.79 Hz, 1H) 7.70 (d, J=8.48 Hz, 1H) 7.95 (s, 1H) 8.45 (d, J=9.04 Hz, 1H) 8.69 (d, J=5.27 Hz, 1H). LC/MS (APCI, pos.): 443.0 (M+H).

Example 74

Preparation of N-butyl-2-methyl-6-{[7-(trifluoromethoxy)quinolin-4-yl]oxy}-1-benzofuran-3-carboxamide

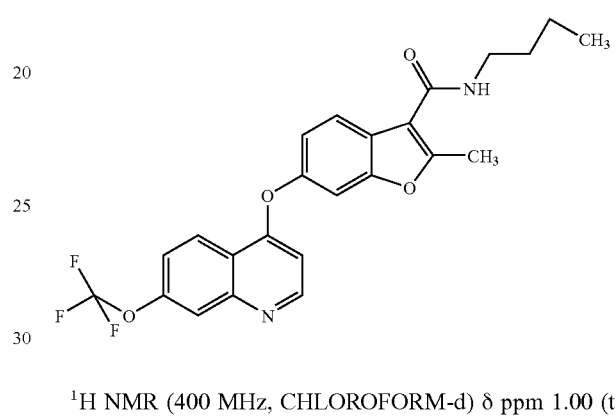

$^1$H NMR (400 MHz, CHLOROFORM-d) δ ppm 1.00 (t, J=7.33 Hz, 3H) 1.47 (m, 2H) 1.67 (m, 2H) 3.52 (m, 2H) 5.87 (s, 1H) 6.56 (d, J=4.80 Hz, 1H) 7.16 (dd, J=8.46, 1.89 Hz, 1H) 7.32 (d, J=2.02 Hz, 1H) 7.48 (d, J=9.35 Hz, 1H) 7.75 (d, J=8.34 Hz, 1H) 7.99 (s, 1H) 8.46 (d, J=9.10 Hz, 1H) 8.70 (d, J=4.04 Hz, 1H). LC/MS (APCI, pos.): 459.0 (M+H).

Preparation of Compounds of Example 75 to 77

These compounds were prepared according to the synthetic scheme depicted below and using methods described in connection with Scheme II.

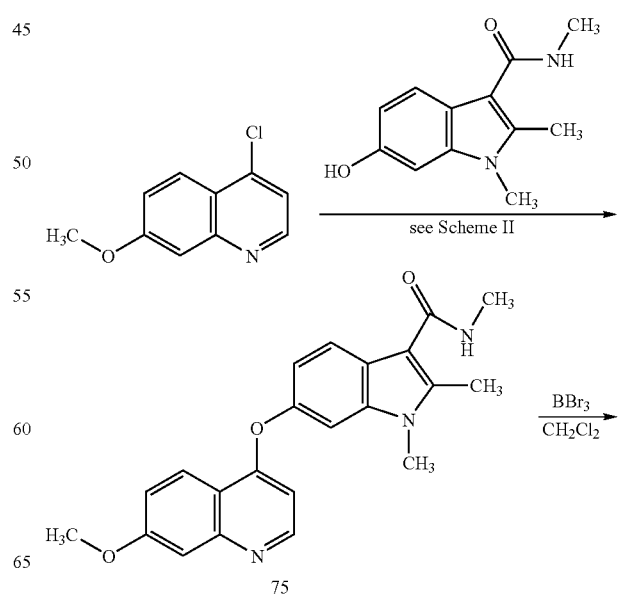

75

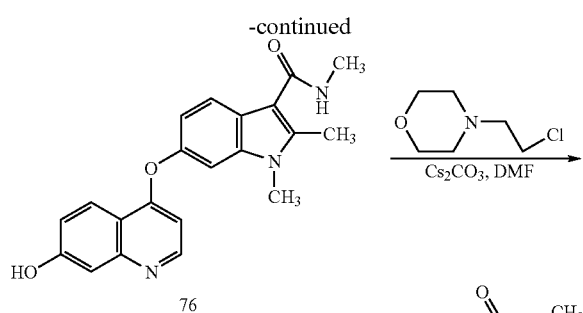

(dd, J=8.67, 2.07 Hz, 1H) 7.19 (m, 1H) 7.24 (d, J=2.26 Hz, 1H) 7.47 (d, J=2.26 Hz, 1H) 7.55 (m, J=4.52 Hz, 1H) 7.83 (d, J=8.48 Hz, 1H) 8.21 (d, J=9.04 Hz, 1H) 8.48 (d, J=5.27 Hz, 1H) 10.21 (s, 1H). MS (APCI, m/z) 362.1 (M+1) Anal. ($C_{21}H_{19}N_3O_3$_0.7$H_2O$)

Example 77

Preparation of N,1,2-trimethyl-6-{[7-(2-morpholin-4-ylethoxy)quinolin-4-yl]oxy}-1H-indole-3-carboxamide

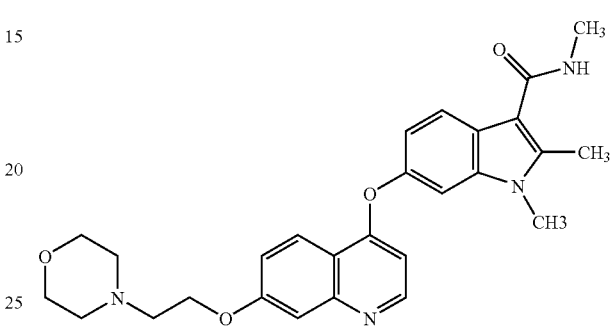

$^1$H NMR (300 MHz, CHLOROFORM-d) δ ppm 2.63 (d, J=4.71 Hz, 2H) 2.65 (d, J=4.52 Hz, 2H) 2.75 (s, 3H) 2.92 (t, J=5.56 Hz, 2H) 3.08 (d, J=4.90 Hz, 3H) 3.67 (s, 3H) 3.76 (d, J=4.71 Hz, 2H) 3.78 (d, J=4.52 Hz, 2H) 4.30 (t, J=5.56 Hz, 2H) 5.89 (m, 1H) 6.39 (d, J=5.27 Hz, 1H) 7.04 (dd, J=8.67, 2.07 Hz, 1H) 7.15 (d, J=1.88 Hz, 1H) 7.25 (dd, J=9, 3 Hz, 1H) 7.42 (d, J=2.45 Hz, 1H) 7.77 (d, J=8.67 Hz, 1H) 8.31 (d, J=9.04 Hz, 1H) 8.56 (d, J=5.27 Hz, 1H) MS (APCI, m/z) 475.1 (M+1) Anal. ($C_{27}H_{30}N_4O_4$_0.5$H_2O$□0.5 $CH_3COOH$)

Example 78

Preparation of N,1,2-trimethyl-6-{[7-(2-pyrrolidin-1-ylethoxy)quinolin-4-yl]oxy}-1H-indole-3-carboxamide

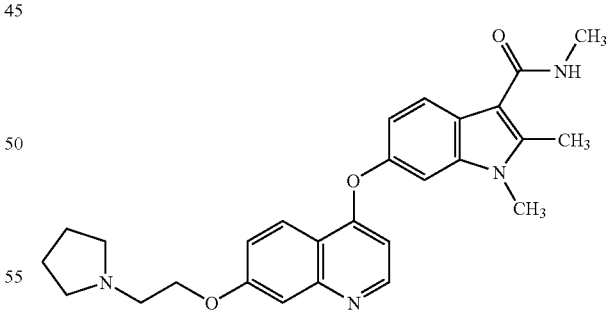

This compound was prepared according to methods analogous for those used to prepare the compounds of Example 75 to Example 77.

$^1$H NMR (300 MHz, DMSO-d6) δ ppm 1.70 (m, 4H) 2.54 (m, J=6.41 Hz, 4H) 2.60 (s, 3H) 2.80 (d, J=4.52 Hz, 3H) 2.87 (t, J=5.75 Hz, 2H) 3.67 (s, 3H) 4.25 (t, J=5.75 Hz, 2H) 6.35 (d, J=5.27 Hz, 1H) 7.00 (dd, J=8.48, 1.88 Hz, 1H) 7.29 (dd, J=9.14, 2.54 Hz, 1H) 7.40 (d, J=2.26 Hz, 1H) 7.49 (d, J=1.88 Hz, 1H) 7.56 (q, J=4.46 Hz, 1H) 7.84 (d, J=8.67 Hz, 1H) 8.25

Example 75

Preparation of [(7-methoxyquinolin-4-yl)oxy]-N,1,2-trimethyl-1H-indole-3-carboxamide

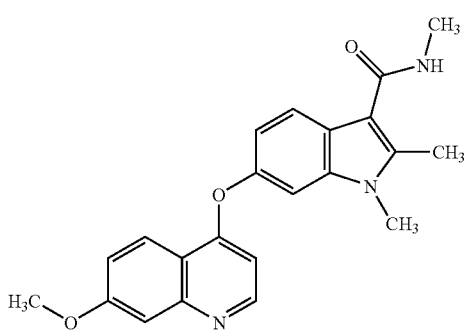

$^1$H NMR (300 MHz, DMSO-d6) δ ppm 2.61 (s, 3H) 2.80 (d, J=4.52 Hz, 3H) 3.67 (s, 3H) 3.93 (s, 3H) 6.36 (d, J=5.27 Hz, 1H) 7.00 (dd, J=8.57, 2.17 Hz, 1H) 7.29 (dd, J=9.14, 2.54 Hz, 1H) 7.40 (d, J=2.45 Hz, 1H) 7.49 (d, J=2.07 Hz, 1H) 7.56 (m, 1H) 7.84 (d, J=8.48 Hz, 1H) 8.26 (d, J=9.04 Hz, 1H) 8.56 (d, J=5.27 Hz, 1H) MS (APCI, m/z) 376.1 (M+1) Anal. ($C_{22}H_{21}N_3O_3$ 1.3$H_2O$)

Example 76

Preparation of 6-[(7-methoxyquinolin-4-yl)oxy]-N,1,2-trimethyl-1H-indole-3-carboxamide

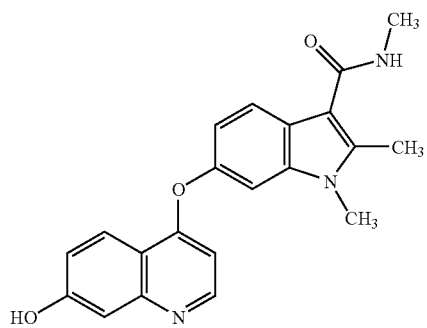

$^1$H NMR (300 MHz, DMSO-d6) δ ppm 2.60 (s, 3H) 2.80 (d, J=4.52 Hz, 3H) 3.67 (s, 3H) 6.27 (d, J=5.27 Hz, 1H) 6.98

(d, J=9.04 Hz, 1H) 8.55 (d, J=5.27 Hz, 1H) MS (APCI, m/z) 459.1 (M+1) Anal. ($C_{27}H_{30}N_4O_3$_0.5$H_2O$_1 $CH_3COOH$)

Example 79

Preparation of N,1,2-trimethyl-6-{[7-(2-piperidin-1-ylethoxy)quinolin-4-yl]oxy}-1H-indole-3-carboxamide

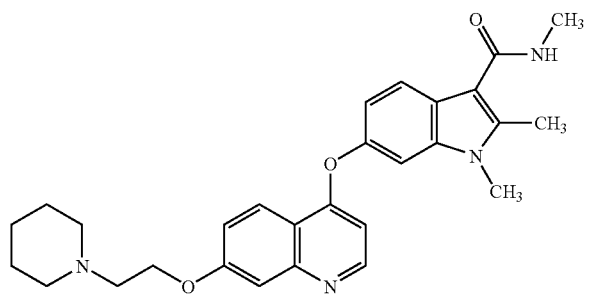

This compound was prepared according to methods analogous to those used to prepare the compounds of Example 75 to Example 77.

$^1$H NMR (300 MHz, CHLOROFORM-d) δ ppm 1.49 (m, 2H) 1.76 (s, 4H) 2.68 (s, 3H) 2.80 (s, 4H) 3.01 (d, J=4.90 Hz, 3H) 3.09 (m, 2H) 3.60 (s, 3H) 4.40 (m, 2H) 5.81 (m, 1H) 6.32 (d, J=5.27 Hz, 1H) 6.97 (dd, J=8.76, 1.60 Hz, 1H) 7.08 (s, 1H) 7.16 (d, J=2.07 Hz, 1H) 7.36 (d, J=1.88 Hz, 1H) 7.71 (d, J=8.67 Hz, 1H) 8.25 (d, J=9.23 Hz, 1H) 8.49 (d, J=5.27 Hz, 1H) MS (APCI, m/z) 473.1 (M+1) Anal. ($C_{28}H_{32}N_4O_3$_1.25$H_2O$_0.5 $CH_3COOH$)

Example 80

Preparation of N-(2-hydroxypropyl)-6-[(7-methoxyquinolin-4-yl)oxy]-2-methyl-1-benzothiophene-3-carboxamide

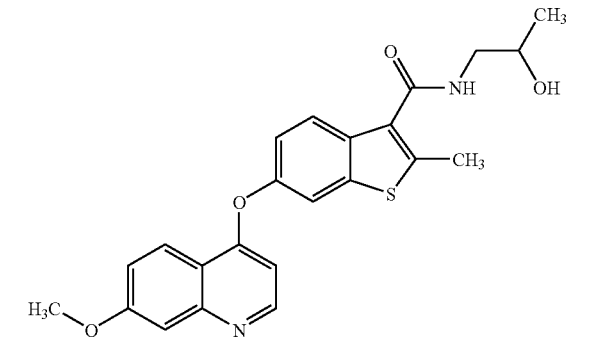

This compound was prepared using methods analogous to those depicted and described in Example 48, 33 and 28, using the appropriate starting materials.

$^1$H NMR (300 MHz, CHLOROFORM-d) δ ppm 1.31 (m, 3H) 2.71 (d, J=13.94 Hz, 3H) 3.38 (m, 1H) 3.79 (m, 1H) 3.98 (s, 3H) 4.13 (m, 1H) 6.34 (m, 1H) 6.42 (d, J=5.27 Hz, 1H) 7.22 (m, 2H) 7.44 (d, J=2.45 Hz, 1H) 7.56 (d, J=2.07 Hz, 1H) 8.01 (d, J=8.85 Hz, 1H) 8.26 (d, J=9.23 Hz, 1H) 8.57 (d, J=5.27 Hz, 1H)

Example 81

Preparation of N-(2-hydroxybutyl)-6-[(7-methoxyquinolin-4-yl)oxy]-2-methyl-1-benzothiophene-3-carboxamide

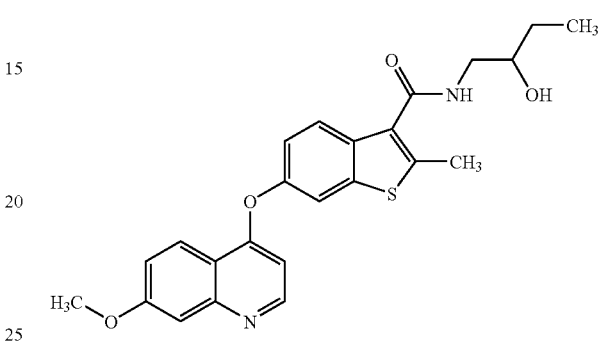

This compound was prepared using methods analogous to those depicted and described in Example 48, 33 and 28, using the appropriate starting materials.

$^1$H NMR (300 MHz, CHLOROFORM-d) δ ppm 1.05 (t, J=7.44 Hz, 3H) 1.61 (m, 2H) 2.74 (s, 3H) 3.40 (m, 1H) 3.81 (m, J=14.32 Hz, 2H) 3.98 (s, 3H) 6.31 (m, 1H) 6.42 (d, J=5.27 Hz, 1H) 7.22 (m, 2H) 7.43 (d, J=2.45 Hz, 1H) 7.56 (d, J=2.07 Hz, 1H) 8.00 (d, J=8.85 Hz, 1H) 8.26 (d, J=9.04 Hz, 1H) 8.58 (d, J=5.27 Hz, 1H)

Example 82

Preparation of N-(3-hydroxybutyl)-6-[(7-methoxyquinolin-4-yl)oxy]-2-methyl-1-benzothiophene-3-carboxamide

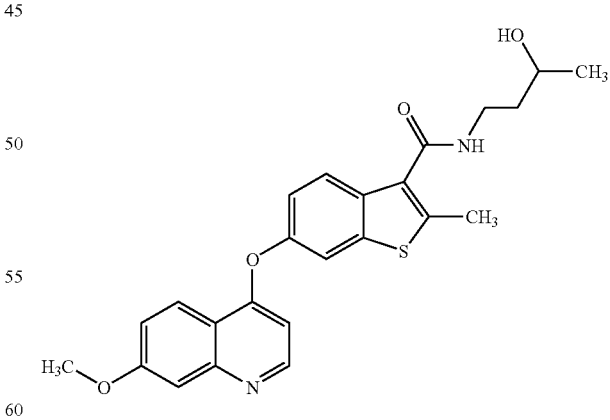

This compound was prepared using methods analogous to those depicted and described in Example 48, 33 and 28, using the appropriate starting materials.

$^1$H NMR (300 MHz, CHLOROFORM-d) δ ppm 1.29 (d, J=6.41 Hz, 3H) 1.76 (m, 2H) 2.73 (s, 3H) 3.41 (m, 1H) 3.98 (s, 3H) 4.01 (m, 2H) 6.42 (d, J=5.27 Hz, 1H) 6.47 (m, 1H)

7.23 (m, 2H) 7.43 (d, J=2.45 Hz, 1H) 7.56 (d, J=2.07 Hz, 1H) 7.99 (d, J=8.85 Hz, 1H) 8.26 (d, J=9.04 Hz, 1H) 8.58 (d, J=5.27 Hz, 1H)

Example 83

Preparation of 6-{[7-(1,3-dioxolan-2-ylmethoxy)quinolin-4-yl]oxy}-N,2-dimethyl-1-benzofuran-3-carboxamide

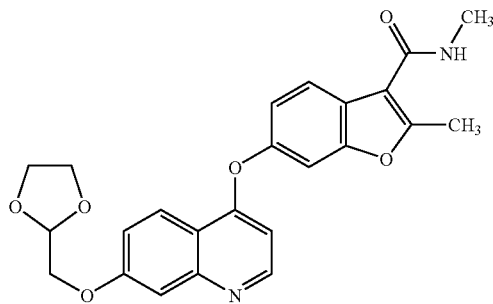

This compound was prepared using methods analogous to those depicted and described in Example 48, 33 and 28, using the appropriate starting materials.

$^1$H NMR (300 MHz, DMSO-d6) δ ppm 2.57 (s, 3H) 2.76 (d, J=4.52 Hz, 3H) 3.84 (m, 2H) 3.94 (m, 2H) 4.14 (d, J=3.77 Hz, 2H) 5.24 (m, 1H) 6.38 (d, J=5.09 Hz, 1H) 7.17 (dd, J=8.57, 2.17 Hz, 1H) 7.25 (dd, J=9.04, 2.45 Hz, 1H) 7.37 (d, J=2.26 Hz, 1H) 7.56 (d, J=1.88 Hz, 1H) 7.78 (d, J=8.48 Hz, 1H) 7.92 (d, J=4.33 Hz, 1H) 8.18 (d, J=9.04 Hz, 1H) 8.53 (d, J=5.09 Hz, 1H). LC/MS (APCI, pos.): 435.1 (M+H).

Example 84

Preparation of 6-[(7-methoxyquinolin-4-yl)oxy]-2-methyl-N-[(2R)-tetrahydrofuran-2-ylmethyl]-1-benzofuran-3-carboxamide

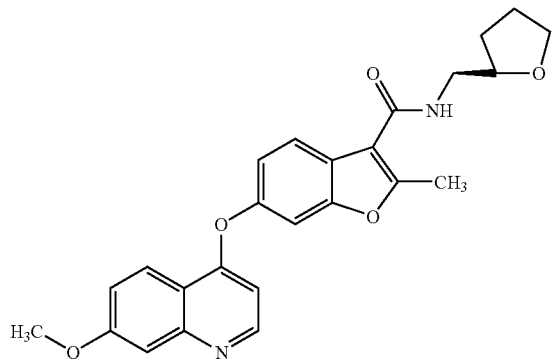

This compound was prepared using methods analogous to those depicted and described in Example 48, 33 and 28, using the appropriate starting materials.

$^1$H NMR (400 MHz, DMSO-d6) δ ppm 1.70 (m, 1H) 1.97 (m, 3H) 2.70 (s, 3H) 3.42 (t, J=5.94 Hz, 2H) 3.73 (m, 1H) 3.87 (m, 1H) 4.01 (s, 3H) 4.09 (m, 1H) 6.51 (d, J=5.31 Hz, 1H) 7.30 (dd, J=8.46, 2.15 Hz, 1H) 7.36 (dd, J=9.10, 2.53 Hz, 1H) 7.48 (d, J=2.53 Hz, 1H) 7.68 (d, J=2.02 Hz, 1H) 7.86 (d, J=8.59 Hz, 1H) 8.19 (t, J=5.94 Hz, 1H) 8.30 (d, J=9.10 Hz, 1H) 8.66 (d, J=5.31 Hz, 1H). LC/MS (APCI, pos.): 433.1 (M+H).

Example 85

Preparation of 6-[(7-methoxyquinolin-4-yl)oxy]-2-methyl-N-[(2S)-tetrahydrofuran-2-ylmethyl]-1-benzofuran-3-carboxamide

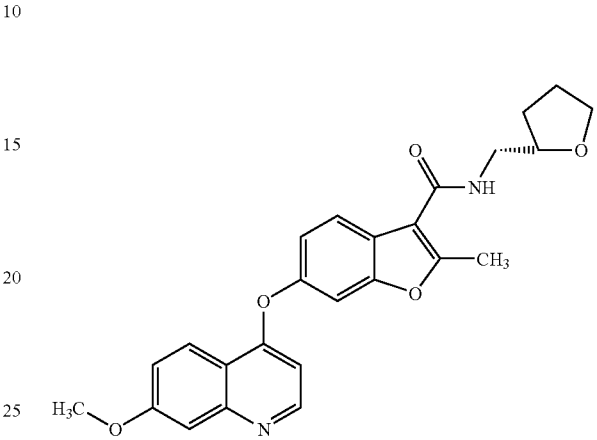

This compound was prepared using methods analogous to those depicted and described in Example 48, 33 and 28, using the appropriate starting materials.

$^1$H NMR (400 MHz, DMSO-d$_6$) δ ppm 1.57 (m, 1H) 1.84 (m, 3H) 2.57 (s, 3H) 3.29 (t, J=5.94 Hz, 2H) 3.60 (m, 1H) 3.74 (m, 1H) 3.88 (s, 3H) 3.96 (m, 1H) 6.38 (d, J=5.31 Hz, 1H) 7.17 (dd, J=8.46, 2.15 Hz, 1H) 7.23 (dd, J=9.09, 2.53 Hz, 1H) 7.35 (d, J=2.53 Hz, 1H) 7.55 (d, J=2.02 Hz, 1H) 7.73 (d, J=8.59 Hz, 1H) 8.06 (t, J=5.68 Hz, 1H) 8.17 (d, J=9.09 Hz, 1H) 8.53 (d, J=5.31 Hz, 1H). LC/MS (APCI, pos.): 433.1 (M+H).

Example 86

Preparation of 6-[(7-methoxyquinolin-4-yl)oxy]-2-methyl-N-[ethoxy-ethyl]-1-benzofuran-3-carboxamide

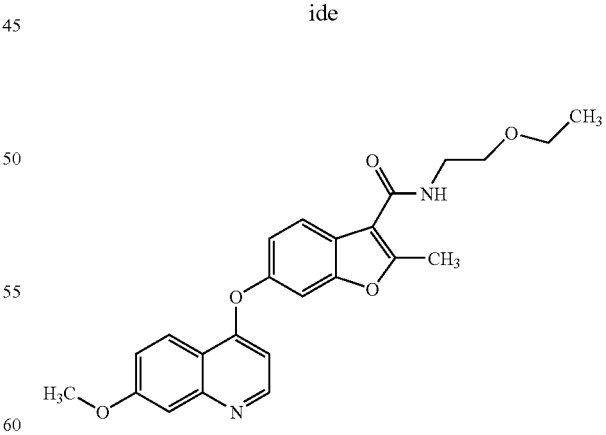

This compound was prepared using methods analogous to those depicted and described in Example 48, 33 and 28, using the appropriate starting materials.

$^1$H NMR (400 MHz, DMSO-d$_6$) δ ppm 1.21 (t, J=6.95 Hz, 3H) 2.70 (s, 3H) 3.55 (m, 6H) 4.01 (s, 3H) 6.51 (d, J=5.31 Hz, 1H) 7.30 (dd, J=8.59, 2.02 Hz, 1H) 7.37 (dd, J=9.09, 2.53 Hz, 1H) 7.49 (d, J=2.53 Hz, 1H) 7.69 (d, J=2.02 Hz, 1H) 7.88 (d, J=8.59 Hz, 1H) 8.15 (t, J=5.43 Hz, 1H) 8.31 (d, J=9.09 Hz, 1H) 8.66 (d, J=5.31 Hz, 1H). LC/MS (APCI, pos.): 421.10 (M+H).

Example 87

Preparation of 6-[(7-methoxyquinolin-4-yl)oxy]-2-methyl-N-[2-methoxy-1-methyl-ethyl]-1-benzofuran-3-carboxamide

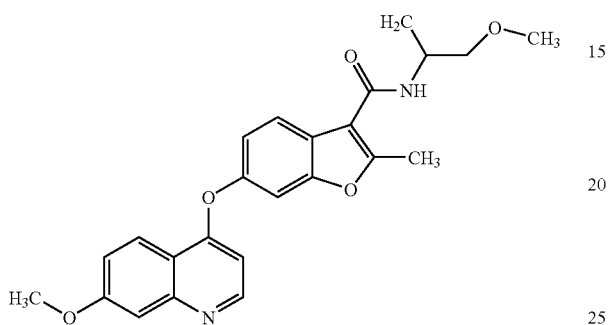

This compound was prepared using methods analogous to those depicted and described in Example 48, 33 and 28, using the appropriate starting materials.

¹H NMR (400 MHz, DMSO-d₆) δ ppm 1.11 (d, J=6.82 Hz, 3H) 2.55 (s, 3H) 3.27 (m, 5H) 3.38 (m, 1H) 3.88 (s, 3H) 4.16 (m, J=14.40, 6.57 Hz, 1H) 6.37 (d, J=5.31 Hz, 1H) 7.17 (dd, J=8.46, 2.15 Hz, 1H) 7.23 (dd, J=9.35, 2.53 Hz, 1H) 7.35 (d, J=2.53 Hz, 1H) 7.55 (d, J=2.02 Hz, 1H) 7.69 (d, J=8.34 Hz, 1H) 7.86 (d, J=8.34 Hz, 1H) 8.17 (d, J=9.09 Hz, 1H) 8.53 (d, J=5.31 Hz, 1H). LC/MS (APCI, pos.): 421.10 (M+H).

Example 88

Preparation of N-(2-methoxyethyl)-6-[(7-methoxyquinolin-4-yl)oxy]-2-methyl-1-benzofuran-3-carboxamide

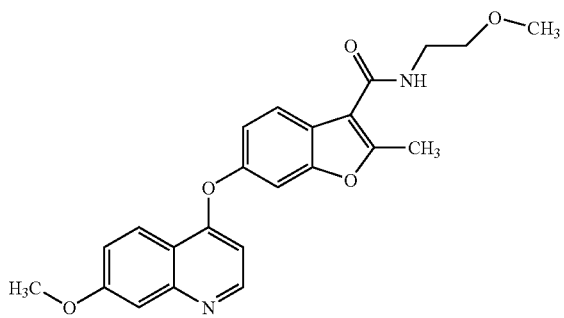

This compound was prepared using methods analogous to those depicted and described in Example 48, 33 and 28, using the appropriate starting materials.

¹H NMR (400 MHz, DMSO-d6) δ ppm 2.46 (s, 3H) 3.13 (s, 3H) 3.32 (m, 4H) 3.77 (s, 3H) 6.27 (d, J=5.31 Hz, 1H) 7.07 (dd, J=8.59, 2.02 Hz, 1H) 7.13 (dd, J=9.35, 2.53 Hz, 1H) 7.25 (d, J=2.53 Hz, 1H) 7.45 (d, J=2.02 Hz, 1H) 7.64 (d, J=8.59 Hz, 1H) 7.93 (t, J=5.05 Hz, 1H) 8.07 (d, J=9.35 Hz, 1H) 8.42 (d, J=5.31 Hz, 1H). LC/MS (APCI, pos.): 407.1 (M+H).

Example 89

Preparation of N-cyclopropyl-2-methyl-6-[(7-pyrimidin-2-ylquinolin-4-yl)oxy]-1-benzofuran-3-carboxamide

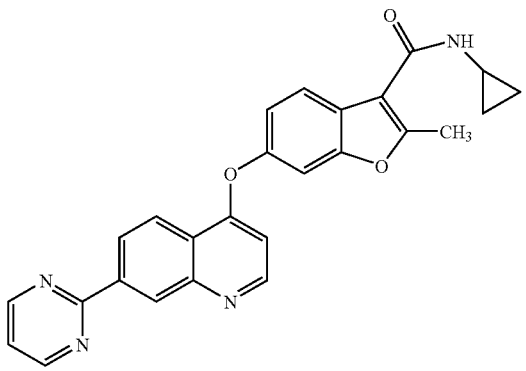

This compound was prepared using methods analogous to those depicted and described in Example 48, 33 and 28, using the appropriate starting materials.

¹H NMR (400 MHz, DMSO-d6) δ ppm 0.56 (m, 2H) 0.66 (m, 2H) 2.54 (s, 3H) 2.81 (m, 1H) 6.57 (d, J=4.80 Hz, 1H) 7.22 (m, 1H) 7.48 (m, 1H) 7.61 (d, J=1.52 Hz, 1H) 7.72 (d, J=8.59 Hz, 1H) 8.13 (m, 1H) 8.43 (d, J=9.09 Hz, 1H) 8.60 (d, J=9.60 Hz, 1H) 8.69 (d, J=4.80 Hz, 1H) 8.96 (d, J=4.80 Hz, 2H) 8.98 (m, 1H). LC/MS (APCI, pos.): 437.1 (M+H).

Example 90

Preparation of N-cyclopropyl-2-methyl-6-({7-[2-(methylamino)ethoxy]quinolin-4-yl}oxy)-1-benzofuran-3-carboxamide

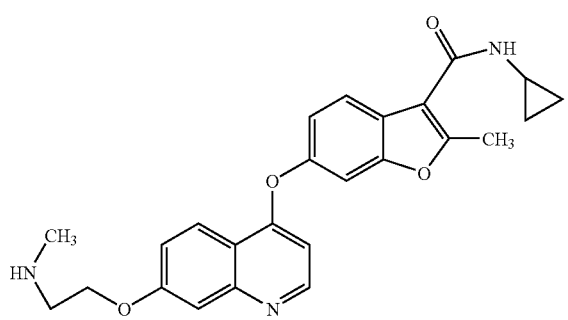

This compound was prepared according to the synthetic scheme depicted and described below.

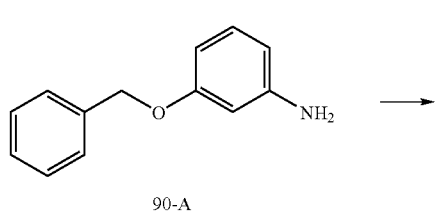

90-A

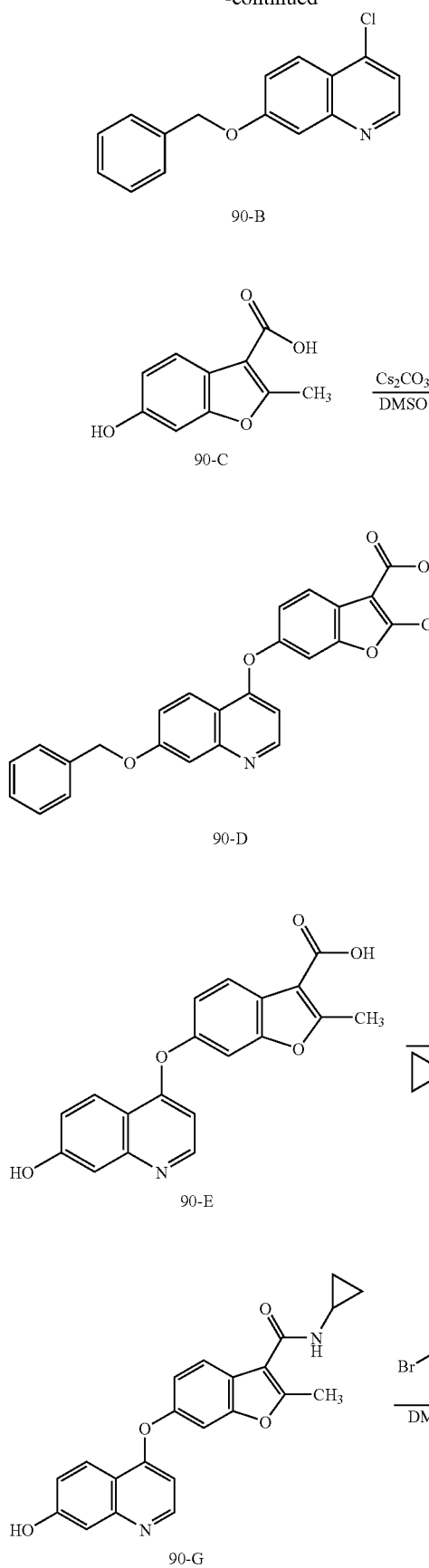

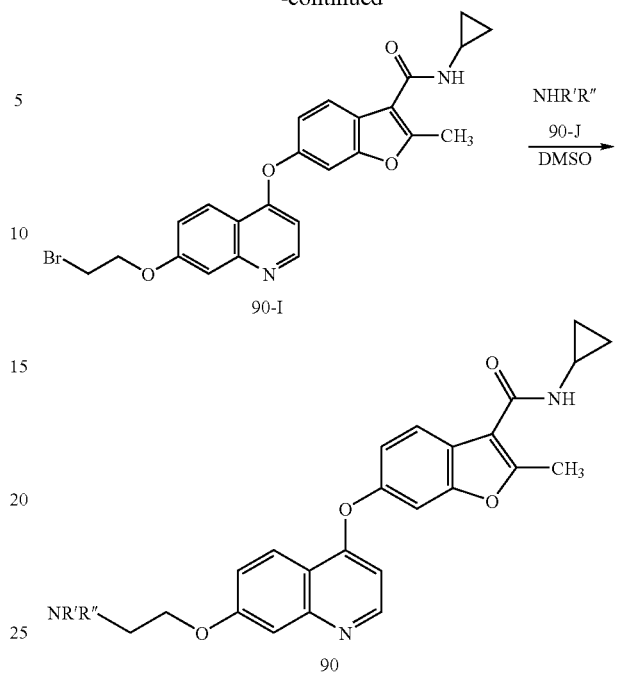

7-(benzyloxy)-4-chloroquinoline 90-B was prepared (see general synthesis Scheme I) from the commercially available compound 90-A (from Aldrich). A mixture of 90-B (2.8 g, 10.4 mmol), 6-hydroxy-2-methyl-1-benzofuran-3-carboxylic acid 90-C (2 g, 10.4 mmol) and Cs₂CO₃ (10.1 g, 31.4 mmol) in DMSO (70 ml) was heated to 130° C. for 2 hours. The solution was poured into water, neutralized with AcOH and extracted with EtOAc. The concentrated residue was purified by silica gel chromatography using 2-5% MeOH in CH₂Cl₂ to give 6-{[7-(benzyloxy)quinolin-4-yl]oxy}-2-methyl-1-benzofuran-3-carboxylic acid 90-D (4.2 g, 94% yield) as a solid.

Compound 90-D (2.4 g) was treated with TFA (net) by refluxing for 2 hours. The solution was cooled to room temperature, poured into water and extracted with EtOAc. The organic layer was washed (brine), dried (MgSO₄) and concentrated to give 6-[(7-hydroxyquinolin-4-yl)oxy]-2-methyl-1-benzofuran-3-carboxylic acid 90-E (1.4 g, 86% yield).

A solution of 90-E (1.6 g, 4.8 mmol), HATU (2.1 g, 5.7 mmol) and triethylamine (970 mg, 9.6 mmol) in DMF (10 ml) was stirred at room temperature for 20 minutes. To the solution was added cyclopropanamine 90-F (547 mg, 9.6 mmol). The reaction mixture was stirred for 30 minutes, poured into water and extracted with EtOAc. Silica gel column chromatography using 5% MeOH in CH₂Cl₂ yield N-cyclopropyl-6-[(7-hydroxyquinolin-4-yl)oxy]-2-methyl-1-benzofuran-3-carboxamide 90-G (1.4 g, 77% yield) as a solid.

A solution of 90-G (1.4 g, 3.7 mmol), Br(CH₂)₂Br 90-H (2.1 g, 11.2 mmol) and K₂CO₃ (1.5 g, 11.2 mmol) in DMF (40 ml) was heated to 50° C. overnight. The reaction mixture was extracted with EtOAc. The concentrated residue was purified by silica gel column chromatography using 5% MeOH/CH₂Cl₂ to yield 6-{[7-(2-bromoethoxy)quinolin-4-yl]oxy}-N-cyclopropyl-2-methyl-1-benzofuran-3-carboxamide 90-I (1.1 g, 61%).

A solution of compound 90-I (100 mg, 0.21 mmol) and 0.3 ml of methylamine 90-J (R'=CH₃, R'=H) in THF (2N) in DMSO (2 ml) was heated to 60° C. for 1 hour. The reaction mixture was purified by HPLC (Dionex System) using 10-50% CH₃CN/H₂O+0.1% AcOH over 30 minutes to give N-cyclopropyl-2-methyl-6-({7-[2-(methylamino)ethoxy]quinolin-4-yl}oxy)-1-benzofuran-3-carboxamide 90 (42 mg).

¹H NMR (400 MHz, DMSO-d6) δ ppm 0.55 (m, 2H) 0.65 (m, J=7.07, 4.55 Hz, 2H) 2.30 (s, 3H) 2.53 (s, 3H) 2.80 (m, 1H) 2.84 (t, J=5.56 Hz, 2H) 4.13 (t, J=5.56 Hz, 2H) 6.36 (d, J=5.05 Hz, 1H) 7.14 (dd, J=8.46, 2.15 Hz, 1H) 7.23 (dd, J=9.10, 2.53 Hz, 1H) 7.34 (d, J=2.27 Hz, 1H) 7.54 (d, J=2.02 Hz, 1H) 7.68 (d, J=8.59 Hz, 1H) 8.11 (d, J=4.29 Hz, 1H) 8.16 (d, J=9.35 Hz, 1H) 8.52 (d, J=5.05 Hz, 1H). LC/MS (APCI, pos.): 432.1 (M+H).

Example 91

Preparation of N-cyclopropyl-2-methyl-6-({7-[2-(diethylamino)ethoxy]quinolin-4-yl}oxy)-1-benzofuran-3-carboxamide

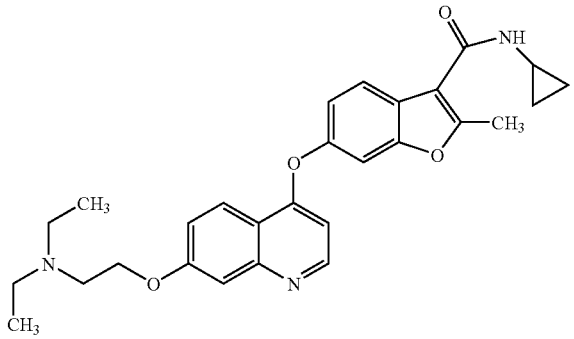

This compound was prepared using methods analogous to those depicted and described in Example 90, using the appropriate amine in place of methylamine (90-J).

¹H NMR (400 MHz, DMSO-d6) δ ppm 0.54 (m, 2H) 0.65 (m, 2H) 0.93 (t, J=7.07 Hz, 6H) 2.52 (m, 4H) 2.53 (s, 3H) 2.79 (m, 3H) 4.14 (t, J=6.06 Hz, 2H) 6.35 (d, J=5.05 Hz, 1H) 7.14 (dd, J=8.46, 2.15 Hz, 1H) 7.21 (dd, J=9.10, 2.53 Hz, 1H) 7.34 (d, J=2.53 Hz, 1H) 7.53 (d, J=2.02 Hz, 1H) 7.68 (d, J=8.34 Hz, 1H) 8.11 (d, J=4.04 Hz, 1H) 8.15 (d, J=9.10 Hz, 1H) 8.52 (d, J=5.05 Hz, 1H). LC/MS (APCI, pos.): 474.2 (M+H).

Example 92

Preparation of N-cyclopropyl-2-methyl-6-({7-[2-hydroxy-ethoxy]quinolin-4-yl}oxy)-1-benzofuran-3-carboxamide

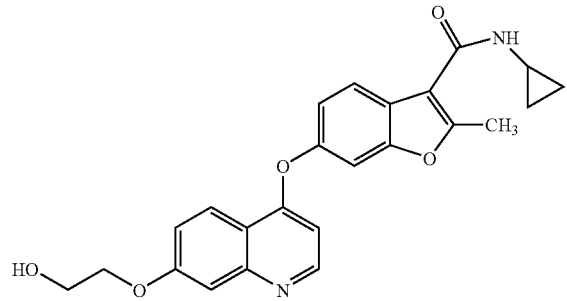

This compound was prepared using methods analogous to those depicted and described in Example 90.

¹H NMR (400 MHz, DMSO-d6) δ ppm 0.55 (m, 2H) 0.65 (m, 2H) 2.53 (s, 3H) 2.81 (d, J=3.79 Hz, 1H) 3.75 (s, 2H) 4.11 (t, J=5.05 Hz, 2H) 4.89 (m, 1H) 6.36 (d, J=5.05 Hz, 1H) 7.15 (dd, J=8.46, 2.15 Hz, 1H) 7.24 (dd, J=9.10, 2.53 Hz, 1H) 7.34 (d, J=2.27 Hz, 1H) 7.54 (d, J=2.02 Hz, 1H) 7.68 (d, J=8.34 Hz, 1H) 8.11 (d, J=3.79 Hz, 1H) 8.16 (d, J=9.10 Hz, 1H) 8.52 (d, J=5.31 Hz, 1H). LC/MS (APCI, pos.): 419.1 (M+H).

Example 93

Preparation of 6-{[7-(2-bromoethoxy)quinolin-4-yl]oxy}-N-cyclopropyl-2-methyl-1-benzofuran-3-carboxamide

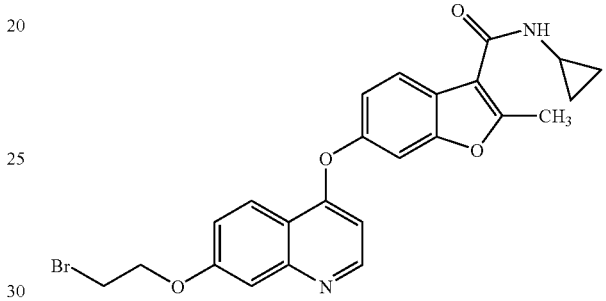

This compound was prepared using methods analogous to those depicted and described in Example 90.

¹H NMR (400 MHz, DMSO-d6) δ ppm 0.54 (m, 2H) 0.65 (m, 2H) 2.53 (s, 3H) 2.80 (m, 1H) 3.84 (m, 2H) 4.47 (m, 2H) 6.38 (d, J=5.31 Hz, 1H) 7.15 (dd, J=8.46, 2.15 Hz, 1H) 7.27 (dd, J=9.09, 2.53 Hz, 1H) 7.38 (d, J=2.53 Hz, 1H) 7.55 (d, J=2.02 Hz, 1H) 7.69 (d, J=8.34 Hz, 1H) 8.12 (d, J=3.79 Hz, 1H) 8.19 (d, J=9.09 Hz, 1H) 8.54 (d, J=5.31 Hz, 1H). LC/MS (APCI, pos.): 481.0 (M+H).

Example 94

Preparation of N-cyclopropyl-2-methyl-6-{7-[2-(4-ethyl-piperazin-1-yl)-ethoxy]quinolin-4-yloxy}-1-benzofuran-3-carboxamide

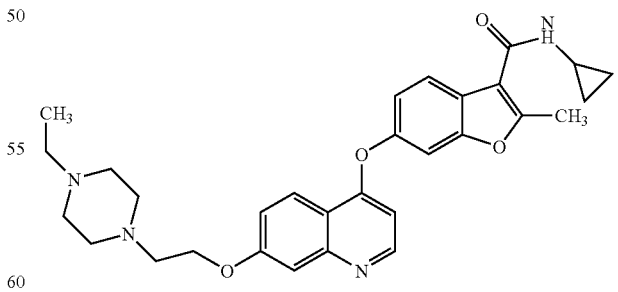

This compound was prepared using methods analogous to those depicted and described in Example 90, using the appropriate amine in place of methylamine (90-J).

¹H NMR (400 MHz, DMSO-d6) δ ppm 0.43 (m, 2H) 0.53 (m, 2H) 0.80 (t, J=7.20 Hz, 3H) 2.12 (q, J=7.33 Hz, 2H) 2.30 (m, 8H) 2.41 (s, 3H) 2.59 (t, J=5.68 Hz, 2H) 2.68 (m, 1H) 4.07

(t, J=5.56 Hz, 2H) 6.23 (d, J=5.31 Hz, 1H) 7.00 (dd, J=8.59, 2.02 Hz, 1H) 7.09 (dd, J=9.10, 2.53 Hz, 1H) 7.22 (d, J=2.27 Hz, 1H) 7.37 (d, J=2.02 Hz, 1H) 7.56 (d, J=8.34 Hz, 1H) 7.98 (d, J=4.04 Hz, 1H) 8.03 (d, J=9.10 Hz, 1H) 8.39 (d, J=5.31 Hz, 1H). LC/MS (APCI, pos.): 515.2 (M+H).

Example 95

Preparation of N-cyclopropyl-6-({7-[2-(isopropylamino)ethoxy]quinolin-4-yl}oxy)-2-methyl-1-benzofuran-3-carboxamide

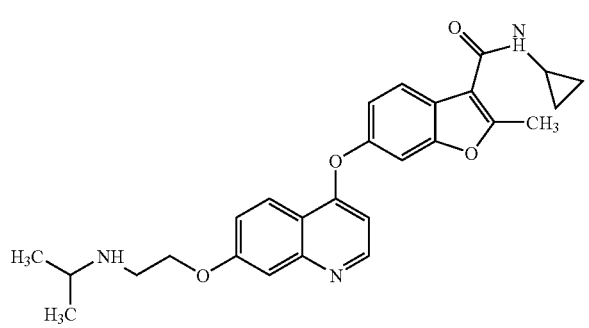

This compound was prepared using methods analogous to those depicted and described in Example 90, using the appropriate amine in place of methylamine (90-J).

$^1$H NMR (400 MHz, DMSO-d6) δ ppm 0.54 (m, 2H) 0.65 (m, 2H) 0.95 (d, J=6.32 Hz, 6H) 2.53 (s, 3H) 2.73 (m, J=12.38, 6.06 Hz, 1H) 2.80 (m, J=7.20, 3.92 Hz, 1H) 2.89 (t, J=5.56 Hz, 2H) 4.12 (t, J=5.56 Hz, 2H) 6.35 (d, J=5.31 Hz, 1H) 7.15 (dd, J=8.59, 2.02 Hz, 1H) 7.24 (dd, J=9.22, 2.40 Hz, 1H) 7.33 (m, 1H) 7.54 (d, J=2.02 Hz, 1H) 7.68 (d, J=8.59 Hz, 1H) 8.12 (d, J=3.79 Hz, 1H) 8.16 (d, J=9.10 Hz, 1H) 8.52 (d, J=5.05 Hz, 1H). LC/MS (APCI, pos.): 460.1 (M+H).

Example 96

Preparation of N-cyclopropyl-6-({7-[2-(cyclopropylamino)ethoxy]quinolin-4-yl}oxy)-2-methyl-1-benzofuran-3-carboxamide

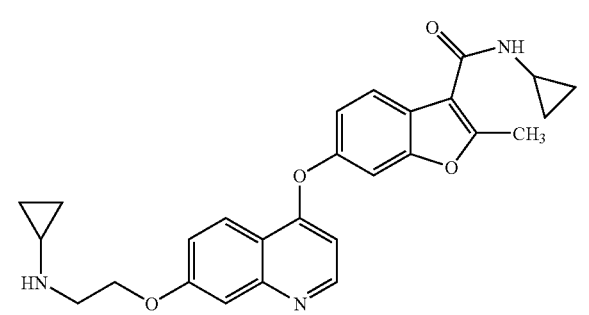

This compound was prepared using methods analogous to those depicted and described in Example 90, using the appropriate amine in place of methylamine (90-J).

$^1$H NMR (400 MHz, DMSO-d$_6$) δ ppm 0.02 (m, 2H) 0.16 (m, 2H) 0.37 (m, 2H) 0.47 (m, 2H) 1.94 (m, 1H) 2.36 (s, 3H) 2.64 (m, 1H) 2.79 (t, J=5.68 Hz, 2H) 3.96 (t, J=5.68 Hz, 2H) 6.18 (d, J=5.05 Hz, 1H) 6.98 (dd, J=8.46, 2.15 Hz, 1H) 7.06 (dd, J=9.09, 2.27 Hz, 1H) 7.16 (m, 1H) 7.37 (d, J=2.02 Hz, 1H) 7.51 (d, J=8.34 Hz, 1H) 7.95 (d, J=3.79 Hz, 1H) 7.99 (d, J=9.10 Hz, 1H) 8.35 (d, J=5.05 Hz, 1H). LC/MS (APCI, pos.): 458.1 (M+H).

Example 97

Preparation of N-cyclopropyl-6-[(7-{2-[(2-methoxy-1-methylethyl)amino]ethoxy}quinolin-4-yl)oxy]-2-methyl-1-benzofuran-3-carboxamide

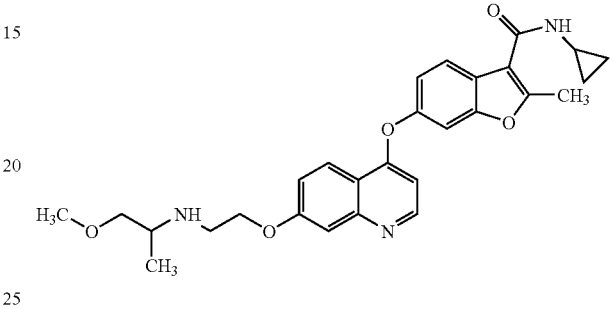

This compound was prepared using methods analogous to those depicted and described in Example 90, using the appropriate amine in place of methylamine (90-J).

$^1$H NMR (400 MHz, DMSO-d$_6$) δ ppm 0.54 (m, 2H) 0.65 (m, 2H) 0.91 (d, J=6.57 Hz, 3H) 2.53 (s, 3H) 2.81 (m, 2H) 2.92 (m, 2H) 3.15 (m, 2H) 3.18 (m, 4H) 3.20 (m, 3H) 4.13 (m, 2H) 6.35 (d, J=5.31 Hz, 1H) 7.15 (dd, J=8.46, 2.15 Hz, 1H) 7.23 (dd, J=9.10, 2.53 Hz, 1H) 7.34 (d, J=2.27 Hz, 1H) 7.54 (d, J=2.02 Hz, 1H) 7.68 (d, J=8.34 Hz, 1H) 8.12 (d, J=4.04 Hz, 1H) 8.16 (d, J=9.10 Hz, 1H) 8.52 (d, J=5.05 Hz, 1H). LC/MS (APCI, pos.): 490.1 (M+H).

Example 98

Preparation of 6-({7-[2-(tert-butylamino)ethoxy]quinolin-4-yl}oxy)-N-cyclopropyl-2-methyl-1-benzofuran-3-carboxamide

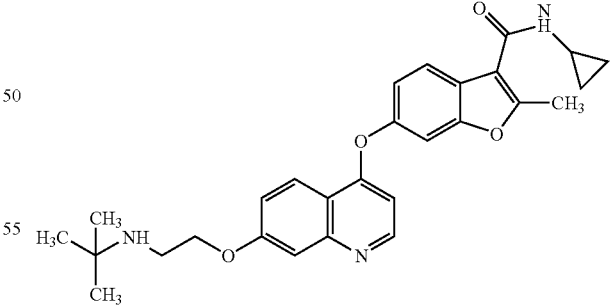

This compound was prepared using methods analogous to those depicted and described in Example 90, using the appropriate amine in place of methylamine (90-J).

$^1$H NMR (400 MHz, DMSO-d6) δ ppm 0.56 (m, 2H) 0.67 (m, 2H) 1.04 (s, 9H) 2.55 (s, 3H) 2.82 (m, 1H) 2.91 (t, J=5.81 Hz, 2H) 4.14 (t, J=5.68 Hz, 2H) 6.37 (d, J=5.31 Hz, 1H) 7.16 (dd, J=8.46, 2.15 Hz, 1H) 7.25 (dd, J=9.10, 2.53 Hz, 1H) 7.35 (d, J=2.53 Hz, 1H) 7.56 (d, J=2.27 Hz, 1H) 7.70 (d, J=8.59

Hz, 1H) 8.14 (d, J=4.04 Hz, 1H) 8.18 (d, J=9.10 Hz, 1H) 8.53 (d, J=5.31 Hz, 1H). LC/MS (APCI, pos.): 474.1 (M+H).

Example 99

Preparation of N-cyclopropyl-2-methyl-6-{[7-(2-morpholin-4-ylethoxy)quinolin-4-yl]oxy}-1-benzofuran-3-carboxamide

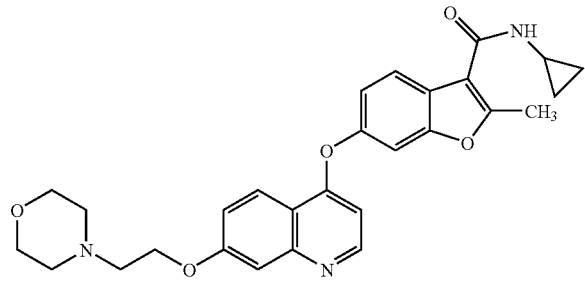

This compound was prepared using methods analogous to those depicted and described in Example 90, using the appropriate amine in place of methylamine (90-J).

$^1$H NMR (400 MHz, DMSO-d6) δ ppm 1.04 (m, 2H) 1.15 (m, 2H) 3.02 (s, 3H) 3.21 (t, J=5.56 Hz, 2H) 3.30 (m, 1H) 3.76 (m, 4H) 4.03 (m, 4H) 4.71 (t, J=5.68 Hz, 2H) 6.85 (d, J=5.31 Hz, 1H) 7.64 (dd, J=8.46, 2.15 Hz, 1H) 7.72 (dd, J=9.10, 2.53 Hz, 1H) 7.86 (d, J=2.53 Hz, 1H) 8.03 (d, J=2.27 Hz, 1H) 8.18 (d, J=8.34 Hz, 1H) 8.62 (m, 1H) 8.65 (d, J=9.10 Hz, 1H) 9.01 (d, J=5.05 Hz, 1H). LC/MS (APCI, pos.): 488.1 (M+H).

Example 100

Preparation of 6-({7-[2-(cyclobutylamino)ethoxy]quinolin-4-yl}oxy)-N-cyclopropyl-2-methyl-1-benzofuran-3-carboxamide

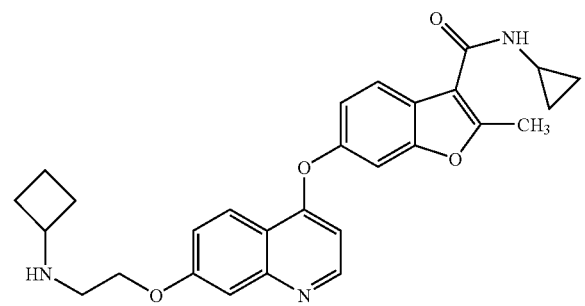

This compound was prepared using methods analogous to those depicted and described in Example 90, using the appropriate amine in place of methylamine (90-J).

$^1$H NMR (400 MHz, DMSO-d6) δ ppm 0.54 (m, 2H) 0.65 (m, 2H) 1.56 (m, 4H) 2.05 (m, 2H) 2.53 (s, 3H) 2.81 (t, J=5.68 Hz, 2H) 3.36 (m, 1H) 4.08 (m, J=5.68, 5.68 Hz, 2H) 6.35 (d, J=5.31 Hz, 1H) 7.15 (dd, J=8.46, 2.15 Hz, 1H) 7.23 (dd, J=9.10, 2.53 Hz, 1H) 7.32 (d, J=2.53 Hz, 1H) 7.54 (d, J=2.02 Hz, 1H) 7.68 (d, J=8.59 Hz, 1H) 8.12 (d, J=3.79 Hz, 1H) 8.16 (d, J=9.09 Hz, 1H) 8.52 (d, J=5.05 Hz, 1H). LC/MS (APCI, pos.): 472.1 (M+H).

Example 101

Preparation of N-cyclopropyl-2-methyl-6-{[7-(2-pyrrolidin-1-ylethoxy)quinolin-4-yl]oxy}-1-benzofuran-3-carboxamide

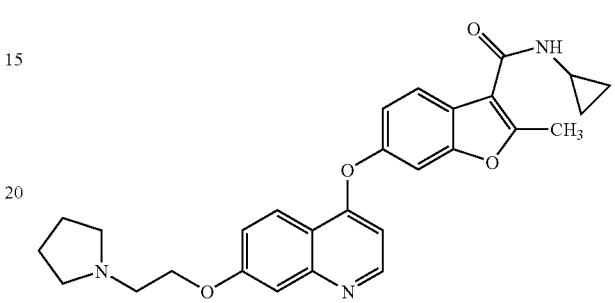

This compound was prepared using methods analogous to those depicted and described in Example 90, using the appropriate amine in place of methylamine (90-J).

$^1$H NMR (400 MHz, DMSO-d6) δ ppm 0.53 (m, 2H) 0.65 (m, 2H) 1.63 (m, 4H) 2.50 (m, 3H) 2.53 (m, 3H) 2.80 (m, 4H) 4.19 (t, J=5.81 Hz, 2H) 6.36 (d, J=5.31 Hz, 1H) 7.14 (m, 1H) 7.23 (dd, J=9.10, 2.53 Hz, 1H) 7.35 (d, J=2.53 Hz, 1H) 7.54 (d, J=2.02 Hz, 1H) 7.68 (m, 1H) 8.12 (m, 1H) 8.15 (d, J=9.10 Hz, 1H) 8.52 (d, J=5.31 Hz, 1H). LC/MS (APCI, pos.): 472.1 (M+H).

Example 102

Preparation of N-cyclopropyl-2-methyl-6-{[7-(2-piperazin-1-ylethoxy)quinolin-4-yl]oxy}-1-benzofuran-3-carboxamide

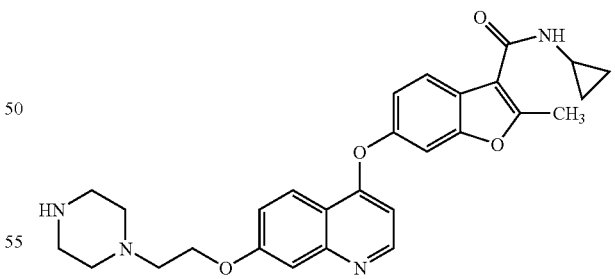

This compound was prepared using methods analogous to those depicted and described in Example 90, using the appropriate amine in place of methylamine (90-J).

$^1$H NMR (400 MHz, DMSO-d6) δ ppm 0.54 (m, 2H) 0.65 (m, 2H) 2.38 (m, 2H) 2.66 (m, 4H) 2.81 (m, 1H) 3.12 (m, 4H) 4.19 (t, J=5.68 Hz, 2H) 6.36 (d, J=5.31 Hz, 1H) 7.15 (m, 2H) 7.21 (m, 2H) 7.53 (dd, J=7.20, 2.15 Hz, 1H) 7.68 (m, 1H) 8.14 (m, 2H) 8.52 (d, J=5.31 Hz, 1H). LC/MS (APCI, pos.): 487.1 (M+H).

Example 103

Preparation of N-cyclopropyl-6-({7-[2-(ethylamino)ethoxy]quinolin-4-yl}oxy)-2-methyl-1-benzofuran-3-carboxamide

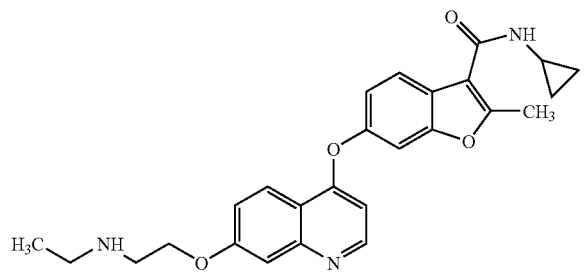

This compound was prepared using methods analogous to those depicted and described in Example 90, using the appropriate amine in place of methylamine (90-J).

$^1$H NMR (400 MHz, DMSO-d6) δ ppm 0.54 (m, 2H) 0.66 (m, 2H) 0.98 (t, J=7.07 Hz, 3H) 2.53 (s, 3H) 2.58 (m, 2H) 2.80 (m, 1H) 2.89 (m, 2H) 4.13 (t, J=5.56 Hz, 2H) 6.35 (d, J=5.31 Hz, 1H) 7.15 (d, J=8.59 Hz, 1H) 7.24 (d, J=8.84 Hz, 1H) 7.34 (s, 1H) 7.54 (s, 1H) 7.68 (d, J=8.34 Hz, 1H) 8.12 (d, J=3.54 Hz, 1H) 8.16 (d, J=9.09 Hz, 1H) 8.52 (d, J=5.05 Hz, 1H). LC/MS (APCI, pos.): 446.1 (M+H).

Example 104

Preparation of N-cyclopropyl-2-methyl-6-{[7-(2-piperidin-1-ylethoxy)quinolin-4-yl]oxy}-1-benzofuran-3-carboxamide

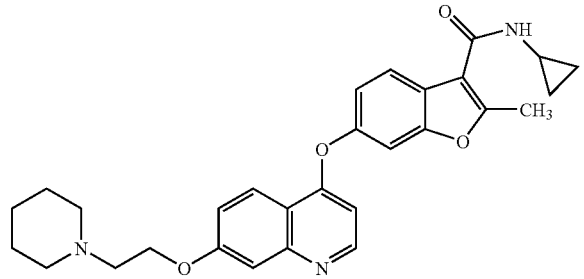

This compound was prepared using methods analogous to those depicted and described in Example 90, using the appropriate amine in place of methylamine (90-J).

$^1$H NMR (400 MHz, DMSO-d6) δ ppm 0.55 (m, 2H) 0.66 (m, J=5.05 Hz, 2H) 1.35 (m, 2H) 1.45 (m, 4H) 2.60 (m, 2H) 2.67 (m, 2H) 2.81 (m, 2H) 4.19 (t, J=5.68 Hz, 2H) 6.36 (d, J=5.31 Hz, 1H) 7.14 (m, 1H) 7.20 (d, J=10.36 Hz, 1H) 7.36 (s, 1H) 7.54 (s, 1H) 7.68 (m, 1H) 8.13 (d, J=9.35 Hz, 1H) 8.15 (d, J=9.10 Hz, 1H) 8.52 (d, J=5.05 Hz, 1H). LC/MS (APCI, pos.): 486.1 (M+H).

Example 105

Preparation of N-cyclopropyl-6-({7-[2-(dimethylamino)ethoxy]quinolin-4-yl}oxy)-2-methyl-1-benzofuran-3-carboxamide

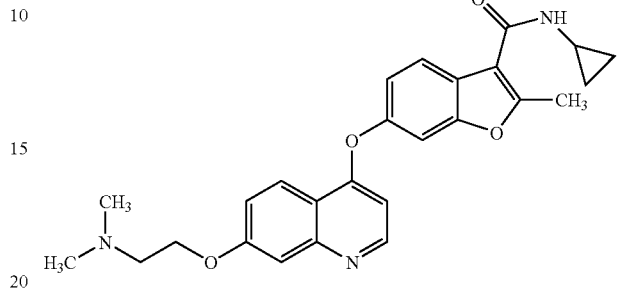

This compound was prepared using methods analogous to those depicted and described in Example 90, using the appropriate amine in place of methylamine (90-J).

$^1$H NMR (400 MHz, CD$_3$OD) δ ppm 0.58 (m, 2H) 0.75 (m, 2H) 2.33 (s, 6H) 2.53 (s, 3H) 2.79 (m, 1H) 2.84 (t, J=5.18 Hz, 2H) 4.21 (t, J=5.31 Hz, 2H) 6.40 (d, J=5.31 Hz, 1H) 7.08 (m, 1H) 7.24 (dd, J=9.22, 2.40 Hz, 1H) 7.29 (m, J=8.46, 2.15 Hz, 2H) 8.21 (d, J=9.35 Hz, 1H) 8.42 (d, J=5.31 Hz, 1H). LC/MS (APCI, pos.): 446.1 (M+H).

Example 106

Preparation of 6-[(7-methoxyquinolin-4-yl)oxy]-2-methyl-N-{6-[(3-methylbutyl)amino]pyridin-3-yl}-1-benzofuran-3-carboxamide

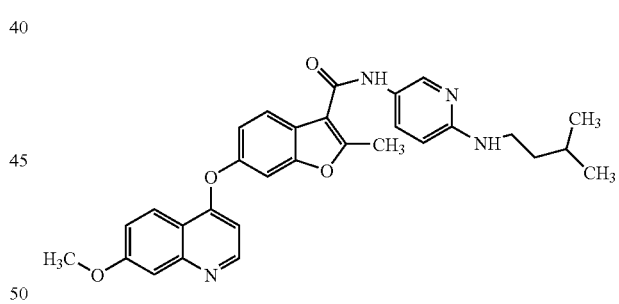

This compound was prepared according to the synthetic scheme depicted and described below.

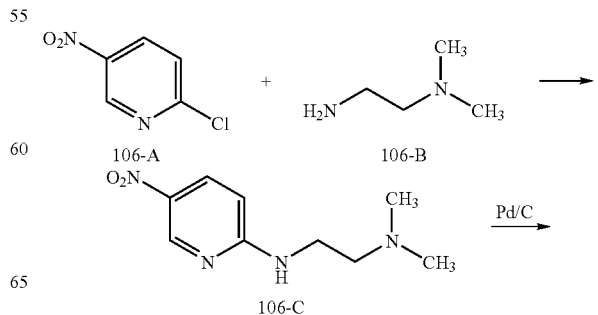

-continued

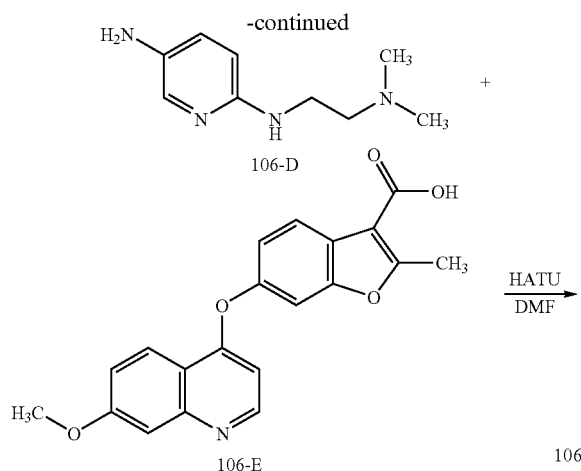

To a solution of 2-chloro-5-nitropyridine 106-A and EtN₃ (4.7 g, 46.5 mmol) in CH₃CN (150 ml) was added N,N-dimethylethlenediamine 106-B (4.1 g, 46.5 mmol). The solution was stirred at room temperature for 3 hours, extracted with EtOAc, washed (brine), dried(MgSO₄) and concentrated to give N,N-dimethyl-N'-(5-nitropyridin-2-yl)ethane-1,2-diamine 106-C (5.2 g) as a yellow solid.

Hydrogenation of compound 106-C (5.2 g) (with 10% Pd/C) in EtOH (150 ml) under [H₂] (40 psi) at room temperature for 15 hours gave compound 106-D (4.7 g) as dark brown oil.

To a solution of compound 106-D (120 mg) in DMF was added Et₃N (1.5 eq.) and HATU (1.2 eq.) at room temperature. After being stirred for 10 minutes, to the solution was added 6-[(6-methoxyquinolin-4-yl)oxy]-2-methyl-1-benzofuran-3-carboxylic acid 106-E (1.0 eq.) The solution was stirred at room temperature for 30 minutes, extracted with EtOAc, washed (brine) and concentrated. The residue was purified by HPLC (10-40% CH₃CN/H₂O, over 30 minutes) to give the title compound 106.

¹H NMR (400 MHz, CHLOROFORM-D) δ ppm 2.38 (s, 6H) 2.69 (m, 2H) 2.79 (s, 3H) 3.46 (t, J=5.81 Hz, 2H) 3.98 (s, 3H) 6.43 (t, J=5.43 Hz, 1H) 6.50 (d, J=8.84 Hz, 1H) 7.21 (m, 2H) 7.34 (d, J=2.02 Hz, 1H) 7.39 (s, 1H) 7.44 (d, J=2.53 Hz, 1H) 7.79 (m, 2H) 8.17 (d, J=2.27 Hz, 1H) 8.27 (m, 1H) 8.60 (m, 1H). LC/MS (APCI, pos.): 512.1.1 (M+H).

Example 107

Preparation of 6-{[7-(benzyloxy)quinolin-4-yl]oxy}-N-(4,6-dimethylpyridin-2-yl)-2-methyl-1-benzofuran-3-carboxamide

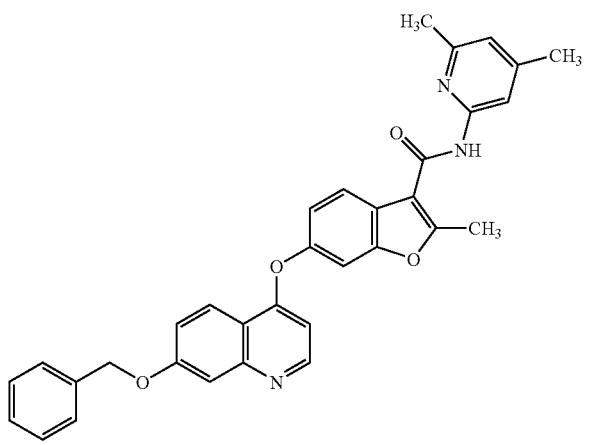

This compound was prepared using methods analogous to those depicted and described in Examples 106, 48, 33 and 28, using the appropriate starting materials.

¹H NMR (300 MHz, CHLOROFORM-d) δ ppm 2.42 (s, 3H) 2.50 (s, 3H) 2.85 (s, 3H) 5.30 (s, 2H) 6.61 (d, J=6.22 Hz, 1H) 6.85 (s, 1H) 7.22 (dd, J=8.48, 2.26 Hz, 1H) 7.41 (m, 5H) 7.54 (m, 2H) 8.03 (d, J=8.67 Hz, 2H) 8.09 (m, 1H) 8.39 (d, J=9.23 Hz, 1H) 8.59 (d, J=6.22 Hz, 1H). MS (APCI, m/z) 530.1 (M+1) HRMS Calculated Mass for C33H27N3O4 (M+): 530.2075 Observed Mass (M+): 530.2091 Mass Error: 3.08 ppm Example 108

Preparation of N-(4,6-dimethylpyridin-2-yl)-6-[(7-methoxyquinolin-4-yl)oxy]-2-methyl-1-benzofuran-3-carboxamide

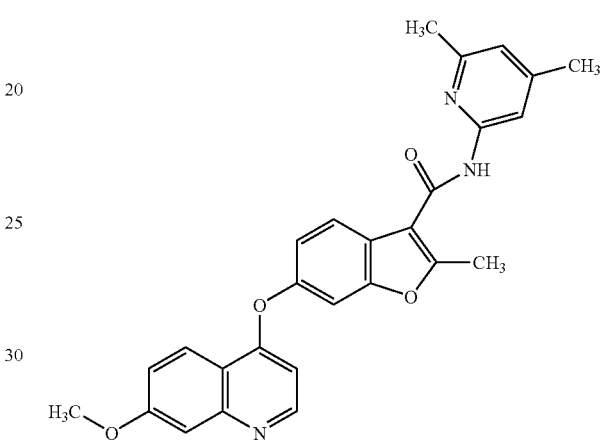

This compound was prepared using methods analogous to those depicted and described in Examples 106, 48, 33 and 28, using the appropriate starting materials.

¹H NMR (300 MHz, DMSO-d6) δ ppm 2.31 (s, 3H) 2.39 (s, 3H) 2.68 (s, 3H) 3.93 (s, 3H) 6.46 (d, J=4.33 Hz, 1H) 6.88 (s, 1H) 7.25 (d, J=9.98 Hz, 1H) 7.29 (d, J=8.85 Hz, 1H) 7.41 (s, 1H) 7.65 (s, 1H) 7.80 (d, J=9.61 Hz, 1H) 7.88 (s, 1H) 8.24 (d, J=8.29 Hz, 1H) 8.59 (d, J=4.14 Hz, 1H) 10.46 (s, 1H) MS (APCI, m/z) 454.1 (M+1) HRMS Calculated Mass for C27H23N3O4 (M+): 454.1762 Observed Mass (M+): 454.1769 Mass Error: 1.66 ppm Example 109

Preparation of N-(4,6-dimethylpyridin-2-yl)-6-[(7-hydroxyquinolin-4-yl)oxy]-2-methyl-1-benzofuran-3-carboxamide

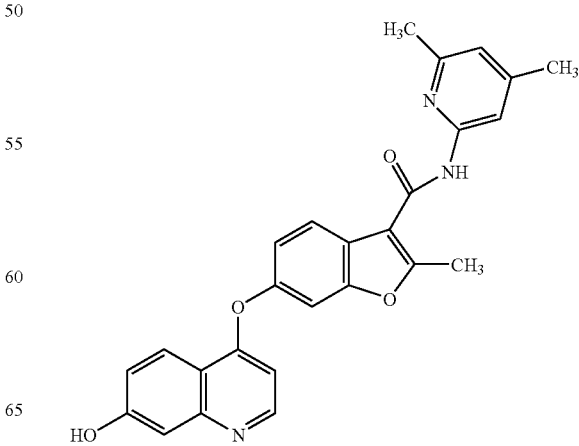

This compound was prepared using methods analogous to those depicted and described in Examples 106, 48, 33 and 28, using the appropriate starting materials.

¹H NMR (300 MHz, DMSO-d6) δ ppm 2.32 (s, 3H) 2.40 (s, 3H) 2.70 (s, 3H) 5.75 (s, 1H) 6.56 (s, 1H) 6.78 (d, J=6.59 Hz, 1H) 6.90 (s, 1H) 7.37 (dd, J=8.29, 1.51 Hz, 1H) 7.45 (m, 2H) 7.82 (s, 1H) 7.88 (d, J=6.03 Hz, 2H) 8.48 (d, J=8.85 Hz, 1H) 8.85 (d, J=6.59 Hz, 1H) 10.56 (s, 1H) MS (APCI, m/z) 440.1 (M+1) HRMS Calculated Mass for C26H21N3O4 (M+): 440.1605 Observed Mass (M+): 440.1617 Mass Error: 2.89 ppm

Example 110

Preparation of N,2-dimethyl-6-({7-[(2-oxo-1,3-dioxolan-4-yl)methoxy]quinolin-4-yl}oxy)-1-benzofuran-3-carboxamide

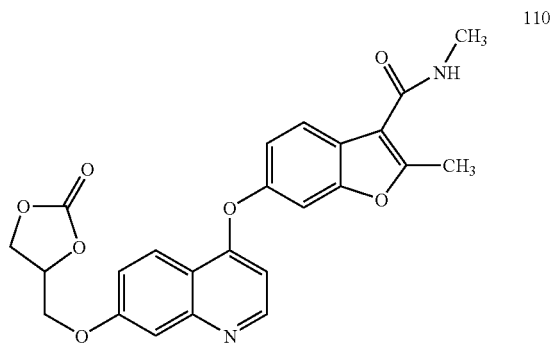

110

This compound was prepared according to the synthetic scheme depicted and described below.

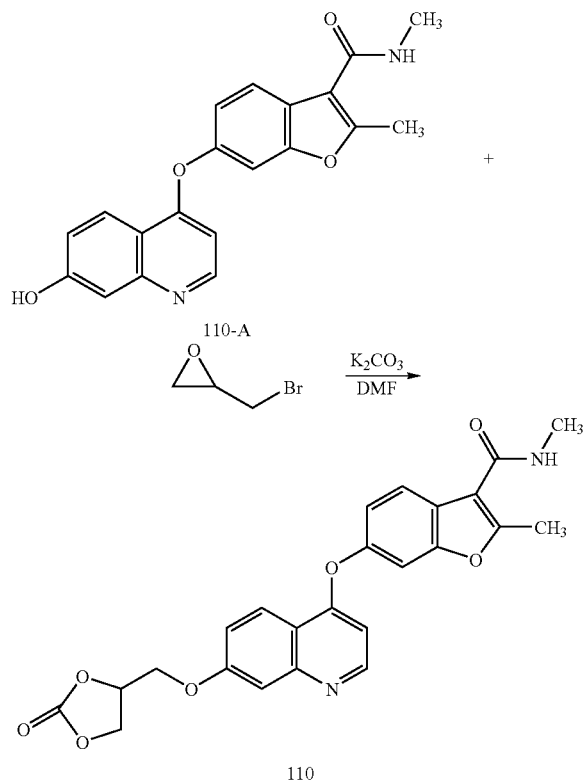

A solution of 6-[(7-hydroxyquinolin-4-yl)oxy]-N,2-dimethyl-1-benzofuran-3-carboxamide 110-A (500 mg, 1.43 mmol), 2-(bromomethyl)oxirane (286 mg, 2.1 mmol) and K₂CO₃ (386 mg, 2.8 mmol) in DMF (15 mL) was stirred at 90° C. for 3 h. The mixture was then extracted with EtOAc. The concentrated residue was purified by silica gel column chromatography using 0-5% MeOH/CH₂Cl₂ to give N,2-dimethyl-6-({7-[(2-oxo-1,3-dioxolan-4-yl)methoxy]quinolin-4-yl}oxy)-1-benzofuran-3-carboxamide 110 (323 mg).

¹H NMR (400 MHz, CHLOROFORM-D) d ppm 2.75 (s, 3H) 3.08 (d, J=4.80 Hz, 3H) 4.33 (dd, J=10.86, 3.54 Hz, 1H) 4.47 (m, 1H) 4.61 (dd, J=8.59, 6.06 Hz, 1H) 4.69 (t, J=8.59 Hz, 1H) 5.16 (m, J=8.34, 5.81 Hz, 1H) 5.88 (s, 1H) 6.49 (d, J=5.31 Hz, 1H) 7.16 (dd, J=8.59, 2.02 Hz, 1H) 7.31 (m, 2H) 7.55 (d, J=2.02 Hz, 1H) 7.76 (m, 1H) 8.34 (d, J=9.10 Hz, 1H) 8.62 (d, J=5.31 Hz, 1H). LC/MS (APCI, pos.): 449.1 (M+H).

Example 111

Preparation of 7-[(7-hydroxyquinolin-4-yl)oxy]-N,2-dimethylimidazo[1,2-α]pyridine-3-carboxamide

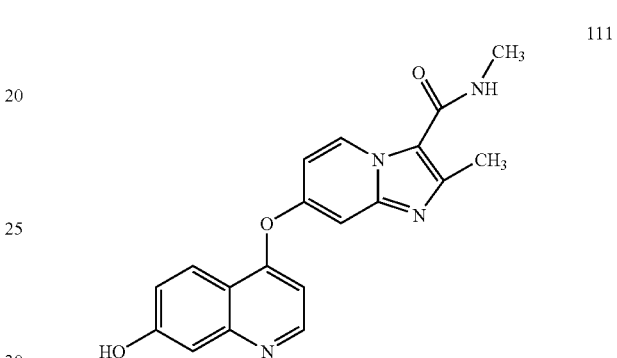

111

This compound was prepared according to the synthetic scheme depicted and described below.

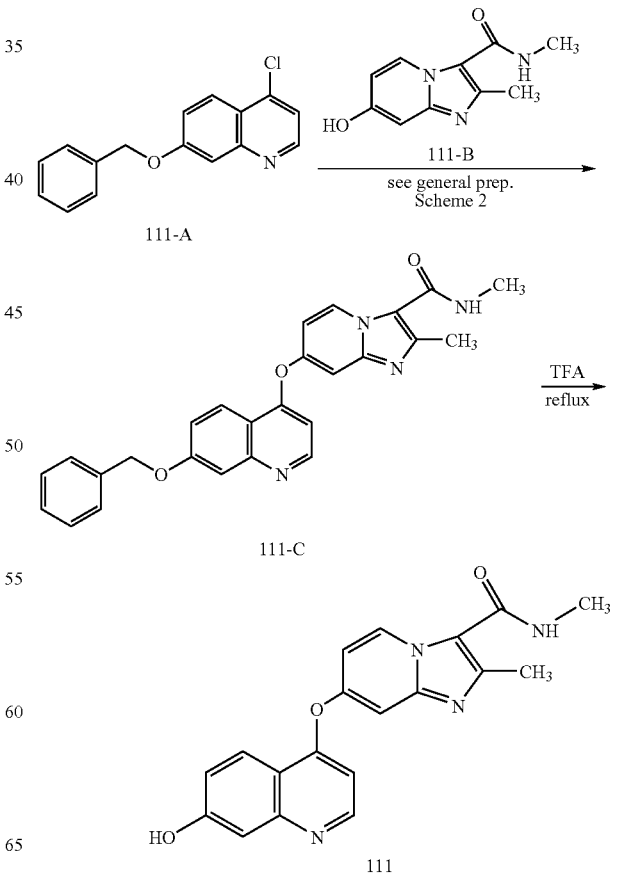

The first step of the reaction was carried out according to Scheme II discussed previously to yield 7-{[7-(benzyloxy) quinolin-4-yl]oxy}-N,2-dimethylimidazo[1,2-α]pyridine-3-carboxamide 111-C. Following the addition of TFA and reflux, 7-[(7-hydroxyquinolin-4-yl)oxy]-N,2-dimethylimidazo[1,2-α]pyridine-3-carboxamide 111 was obtained.

$^1$H NMR (400 MHz, DMSO-d6) δ ppm 2.50 (s, 3H) 2.79 (d, J=4.55 Hz, 3H) 6.75 (d, J=5.31 Hz, 1H) 6.98 (dd, J=7.58, 2.53 Hz, 1H) 7.19 (dd, J=9.10, 2.27 Hz, 1H) 7.25 (d, J=2.27 Hz, 1H) 7.37 (d, J=2.02 Hz, 1H) 7.73 (q, J=4.38 Hz, 1H) 8.10 (d, J=9.10 Hz, 1H) 8.62 (d, J=5.31 Hz, 1H) 9.08 (d, J=7.58 Hz, 1H) 10.55 (s, 1H). LC/MS (ACPI, pos.): 349.1 (M+H).

Note that 7-hydroxy-N,2-dimethylimidazo[1,2-α]pyridine-3-carboxamide 111-B was obtained by the following procedure. To a solution of 4-methoxypyridin-2-amine (prepared as in Org. Prep. & Proc. Int., 29, 1, 117-122, 1997) 2.8 g, 22.6 mmol in ethanol (100 ml) was added ethyl 2-chloro-3-oxobutanoate (6.2 ml, 45.2 mmol) and the resulting solution heated to reflux for 16 hours under a nitrogen atmosphere. The solvents were removed in-vacuo and the yellow solid was titrated with dichloromethane to extract the crude product. The dichloromethane extracts were concentrated and purified by flash chromatography (eluting with ethyl acetate) to yield ethyl 7-methoxy-2-methylimidazo[1,2-α]pyridine-3-carboxylate, 2 g, 38%, as a yellow solid.

$^1$H NMR 400 MHz (CDCl$_3$) δ 9.10 (1H, d, J=7.7 Hz), 6.87 (1H, d, J=2.5 Hz), 6.64 (1H, dd, J=2.7, 7.8 Hz), 4.39 (2H, q, J=7.0 Hz), 3.87 (3H, s), 2.65 (3H, s), 1.41 (3H, t, J=7.2 Hz). APCI (pos) m/z: 235.1 [MH+].

To a solution of ethyl 7-methoxy-2-methylimidazo[1,2-α]pyridine-3-carboxylate (1.8 g, 7.7 mmol) in THF (100 ml) and MeOH (50 ml) was added aq. NaOH (11.5 ml, 2M, 23.1 mmol) and the resulting emulsion heated to reflux for 2 hours. A further aliquot of NaOH was then added (3.8 ml, 2M, 7.7 mmol) and the resulting mixture heated for a further 2 hours. The solvents were removed in-vacuo and the residue was acidified with 1.5 N HCl to pH 3, and the resulting solid was filtered off, washed with water and dried in vacuo to yield 7-methoxy-2-methylimidazo[1,2-α]pyridine-3-carboxylic acid, 1.2 g, 76%, as an off white solid.

$^1$H NMR 400 MHz (DMSO D$_6$) δ 12.76 (1H, bs), 9.02 (1H, d, J=7.7 Hz), 6.99 (1H, d, J=2.5 Hz), 6.76 (1H, dd, J=2.6, 7.5 Hz), 3.82 (3H, s), 2.45 (3H, s). APCI pos) m/z: 207.1 [MH+].

To a stirred solution of 7-methoxy-2-methylimidazo[1,2-α]pyridine-3-carboxylic acid (1.2 g, 5.82 mmol) in DMF (25 ml) was added EDCl (1.23 g, 6.41 mmol), HOBt (0.87 g, 6.41 mmol), N-methyl morpholine (767 ul, 11.64 mmol), methylamine (2M in THF, 6 ml, 11.64 mmol) and DMAP (70 mg, 0.58 mmol) sequentially, and the resulting mixture stirred at ambient temperature for 16 hours. The resulting solution was concentrated in-vacuo and pre-absorbed onto SiO$_2$ and then purified by flash chromatography (eluting with 5-8% MeOH/DCM) to yield 7-Methoxy-N,2-dimethylimidazo[1,2-α]pyridine-3-carboxamide, 1.11 g, 87%, as a white solid.

$^1$H NMR 400 MHz (CDCl$_3$) δ 9.23 (1H, d, J=7.9 Hz), 6.84 (1H, d, J=2.5 Hz), 6.59 (1H, dd, J=2.5, 7.5 Hz), 5.70 (1H, bs), 3.86 (3H, s), 3.03 (3H, d, J=4.8 Hz), 2.64 (3H, s). APCI m/z: 220.1 [MH+].

To a solution of 7-methoxy-N,2-dimethylimidazo[1,2-α]pyridine-3-carboxamide (985 mg, 4.49 mmol) in DMF (20 ml) was added sodium thioethylate (80% pure, 1.86 g, 18 mmol) and the mixture heated to 120° C. for 2 hours. After cooling to ambient temperature, the reaction was neutralized to pH 6 with 1N HCl and concentrated in vacuo. The residue was dissolved in MeOH/H$_2$O, pre-absorbed onto SiO$_2$, and purified by flash chromatography (eluting with 90/10/1-80/20/5, DCM/MeOH/cNH$_3$) to yield the crude product as a yellow solid, which was titrated with MeOH to yield 7-hydroxy-N,2-dimethylimidazo[1,2-α]pyridine-3-carboxamide 111-B, 700 mg, 78%, as a pale yellow solid.

$^1$H NMR 400 MHz (DMSO d$_6$) δ 10.44 (1H, bs), 8.88 (1H, d, J=7.6 Hz), 7.46 (1H, d, J=4.6 Hz), 6.66 (1H, d, J=2.0 Hz), 6.60 (1H, dd, J=2.5, 7.3 Hz), 2.80 (3H, d, J=4.6 Hz), 2.46 (3H, s). APCI m/z: 206.1 [MH+].

Example 112

Preparation of N,2-dimethyl-7-{[7-(2-morpholin-4-ylethoxy)quinolin-4-yl]oxy}imidazo[1,2-α]pyridine-3-carboxamide

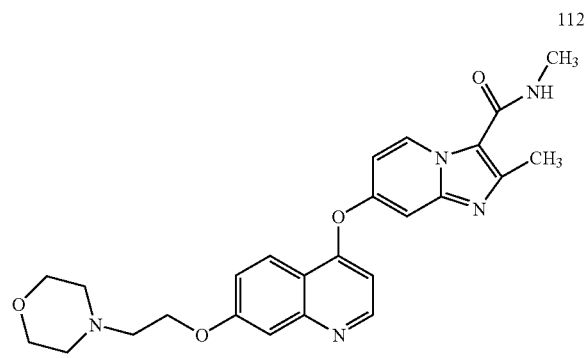

This compound was prepared according to the synthetic scheme depicted and described below.

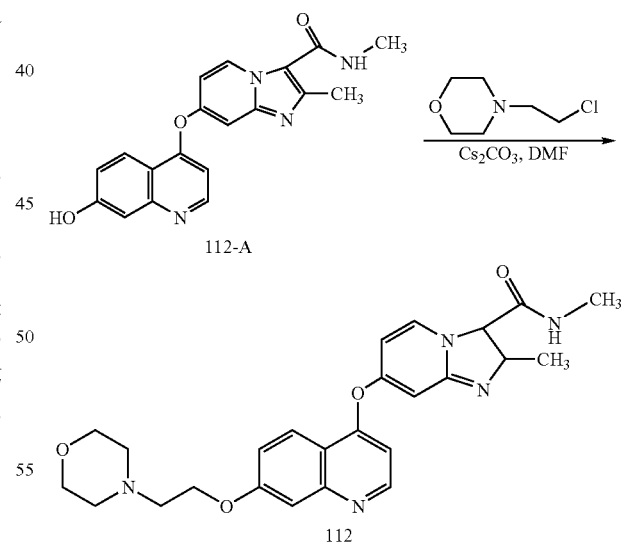

Note that 7-[(7-hydroxyquinolin-4-yl)oxy]-N,2-dimethylimidazo[1,2-α]pyridine-3-carboxamide 112-A was prepared according to Example 111.

$^1$H NMR (400 MHz, DMSO-d6) δ ppm 2.49 (s, 3H) 2.70 (m, 2H) 2.78 (d, J=4.80 Hz, 3H) 3.54 (m, 4H) 4.23 (m, 2H) 6.75 (d, J=5.05 Hz, 1H) 6.95 (dd, J=7.58, 2.53 Hz, 1H) 7.24 (dd, J=9.10, 2.53 Hz, 1H) 7.31 (d, J=2.53 Hz, 1H) 7.41 (d, J=2.02 Hz, 1H) 7.70 (d, J=4.55 Hz, 1H) 8.07 (d, J=9.09 Hz, 1H) 8.62 (d, J=5.31 Hz, 1H) 9.07 (d, J=7.58 Hz, 1H). LC/MS (PCPI, pos.): 462.2 (M+H).

Example 113

Preparation of 7-fluoro-6-[(7-methoxyquinolin-4-yl)oxy]-2-methyl-N-(6-morpholin-4-ylpyridin-3-yl)-1-benzofuran-3-carboxamide

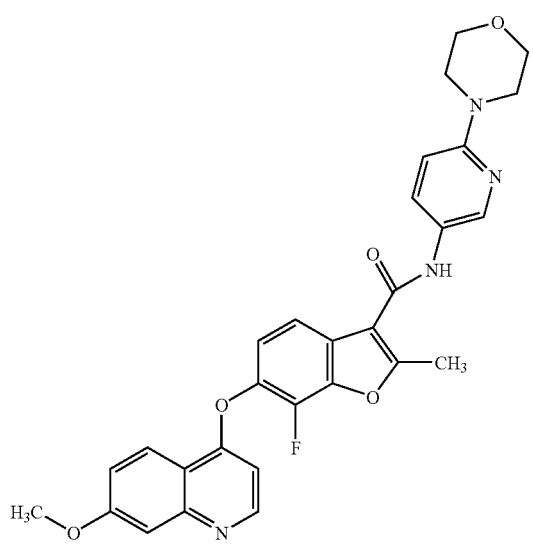

This compound was prepared according to the synthetic scheme depicted and described below.

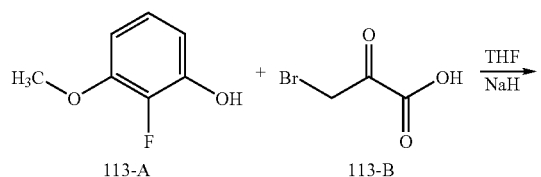

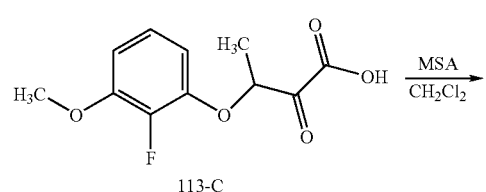

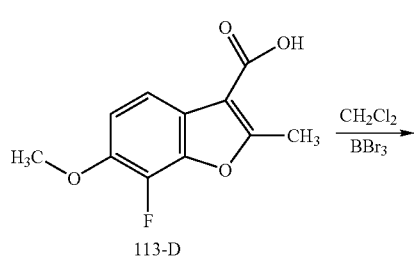

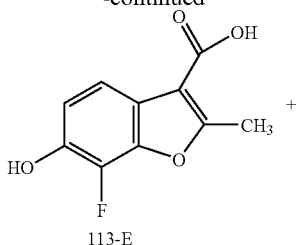

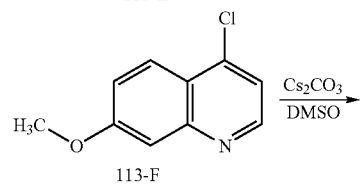

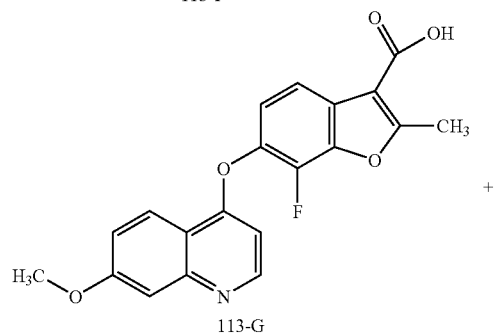

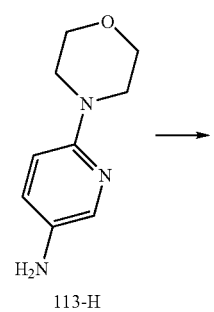

2-fluoro-3-methoxyphenol 113-A, which was prepared in a similar manner to a published procedure (Bioorg. Med. Chem. Lett.; EN; 10; 18; 2000; 2115-2118), was dissolved in anhydrous THF (75 mL) to which NaH (3.8 g, 95.0 mmol) was added and stirred for 0.5 h at 0° C. Next, 3-bromo-2-oxopropanoic acid 113-B was added to the reaction mixture. Note that 3-bromo-2-oxopropanoic acid was prepared according to a published procedure (J. Biol. Chem.; 164; 1946; 437) except that NBS was used in place of bromine. The reaction mixture was then stirred for 1.5 h. The solution was diluted with 100 mL with EtOAc and partitioned between H$_2$O (50 mL). The aqueous layer was neutralized with 3N HCl to about a pH of about 2, after which 100 mL of EtOAc was added and extracted with supplementary EtOAc (2×50 mL). The combined organic layers were dried over Na$_2$SO$_4$ and concentrated to give 3-(2-fluoro-3-methoxyphenoxy)-2-oxobutanoic acid 113-C.

The residue was taken up in 50 mL of CH$_2$Cl$_2$ and MSA (2.0 mL, 30.4 mmol) and stirred for 10 h. H$_2$O (50 mL) was then added to the solution and partitioned with EtOAc (50 mL) followed by concentration of the organic layer. The crude product was then dissolved in 20 mL of diethyl ether (20 mL) and n-heptane (50 mL) was added to the mixture to give 7-fluoro-6-methoxy-2-methyl-1-benzofuran-3-carboxylic acid 113-D (1.86 g, 28%) as a white solid. HPLC: R$_t$ 3.76 min. (95% area).

$^1$H NMR (DMSO-d$_3$, 400 MHz) δ: 13.12 (1H, bs), 7.62 (1H, d, J=8.8 Hz), 7.23, (1H, t, J=8.4 Hz), 3.93 (3H, s), 2.75 (3H, s). LRMS (ESI) (M+H$^+$) m/z: 223.1.

Dissolved 113-D (0.78 g, 3.49 mmol) in CH$_2$Cl$_2$(10 mL) and cooled to 0° C. BBr$_3$ (7.0 mL, 7.0 mmol, 1.0 M in CH$_2$Cl$_2$) was then added to the solution in a drop-wise fashion and stirred for 1 hour with a precipitate forming. The reaction was diluted with H$_2$O (20 mL) and filtered to yield 7-fluoro-6-hydroxy-2-methyl-1-benzofuran-3-carboxylic acid 113-E (0.65 g, 89%) as a tan solid. HPLC: R$_t$ 3.17 min. (98% area).

$^1$H NMR (DMSO-d$_3$, 400 MHz) δ: 13.01 (1H, bs), 10.01 (1H, bs), 7.44 (1H, d, J=8.8 Hz), 6.95, (1H, t, J=8.4 Hz), 2.08 (3H, s). LRMS (ESI) (M+H$^+$) m/z: 209.2.

4-chloro-7-methoxyquinoline 113-F (prepared according to Scheme I described previously) was then added according to Scheme II described previously to yield 7-fluoro-6-[(7-methoxyquinolin-4-yl)oxy]-2-methyl-1-benzofuran-3-carboxylic acid 113-G. 6-morpholin-4-ylpyridin-3-amine 113-H, which is commercially available from BIONET, was then added according to Scheme IV(iii) to yield the final product 7-fluoro-6-[(7-methoxyquinolin-4-yl)oxy]-2-methyl-N-(6-morpholin-4-ylpyridin-3-yl)-1-benzofuran-3-carboxamide 113.

$^1$H NMR (DMSO-d$_3$, 400 MHz) δ: 10.05 (1H, s), 8.56 (1H, d, J=5.3 Hz), 8.40 (1H, s), 8.22 (1H, d, J=9.1 Hz), 7.86 (1H, dd, J=9.0, 1.9 Hz), 7.60 (1H, d, J=8.6 Hz), 7.38-7.34 (2H, m), 7.28 (1H, dd, J=9.1, 2.5 Hz), 6.83 (1H, d, J=9.1 Hz), 6.43 (1H, d, J=5.1 Hz), 3.89 (3H, s), 3.65 (4H, t, J=5.0 Hz), 3.34 (4H, t, J=5.0 Hz), 2.66 (3H, s). HRMS (ESI) C$_{29}$H$_{26}$FN$_4$O$_5$ (M+H$^+$) m/z: Calc. 529.1887. Found: 529.1888. Anal. (C$_{29}$H$_{26}$FN$_4$O$_5$ 1.0H$_2$O) Calc'd: C, 63.73; H, 4.98; N, 10.25. Found: C, 63.49; H, 4.75; N, 9.94.

Example 114

Preparation of 7-fluoro-6-[(7-methoxyquinolin-4-yl)oxy]-2-methyl-N-(3-morpholin-4-ylpropyl)-1-benzofuran-3-carboxamide

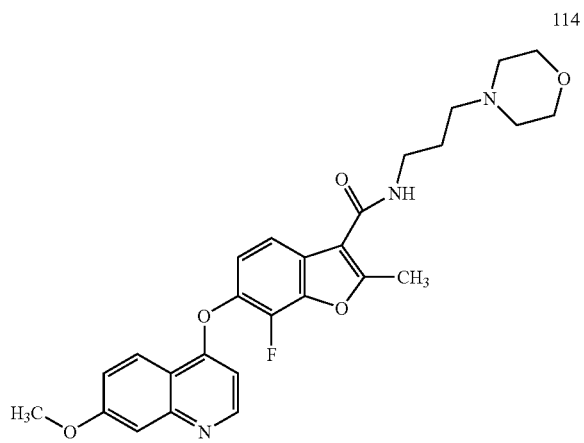

This compound was prepared using methods analogous to those depicted and described in Example 113, but where the appropriate amine (commercially available from ALDRICH) was added in place of 113-H.

$^1$H NMR (DMSO-d$_3$, 400 MHz) δ: $^1$H NMR (DMSO-d$_3$, 400 MHz) δ: 8.62 (1H, d, J=5.3 Hz), 8.30 (1H, d, J=9.1 Hz), 8.20 (1H, t, J=5.6 Hz), 7.64 (1H, d, J=8.6 Hz), 7.46-7.39 (2H, m), 7.34 (1H, dd, J=9.4, 2.5 Hz), 6.50 (1H, d, J=5.1 Hz), 3.96 (3H, s), 3.58 (4H, t, J=4.3 Hz), 3.46-3.30 (4H, m), 2.68 (3H, s), 2.61 (4H, t, J=6.6 Hz). HRMS (ESI) C$_{27}$H$_{29}$FN$_3$O$_5$ (M+H$^+$) m/z: Calc. 494.2091. Found: 494.2103. Anal. (C$_{27}$H$_{28}$FN$_3$O$_5$ 1.2H$_2$O) Calc'd: C, 62.95; H, 5.95; N, 8.16. Found: C, 62.59; H, 5.56; N, 8.09.

Example 115

Preparation of N-cyclopropyl-2-methyl-6-{[7-(2-piperazin-1-ylethoxy)quinolin-4-yl]oxy}-1 benzofuran-3-carboxamide

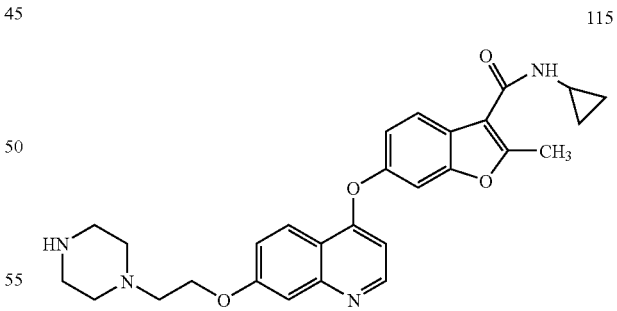

This compound was prepared using methods analogous to those depicted and described in Example 90, where the appropriate amine (commercially available from ALDRICH) was used in place of methylamine (90-J).

$^1$H NMR (400 MHz, DMSO-D6) d ppm 0.54 (m, 2H) 0.65 (m, 2H) 2.38 (m, 2H) 2.66 (m, 4H) 2.81 (m, 1H) 3.12 (m, 4H) 4.19 (t, J=5.68 Hz, 2H) 6.36 (d, J=5.31 Hz, 1H) 7.15 (m, 2H) 7.21 (m, 2H) 7.53 (dd, J=7.20, 2.15 Hz, 1H) 7.68 (m, 1H) 8.14 (m, 2H) 8.52 (d, J=5.31 Hz, 1H). LC/MS (APCI, pos.): 487.1 (M+H).

Example 116

Preparation of 6-{[7-(2,3-dihydroxypropoxy)quinolin-4-yl]oxy}-N,2-dimethyl-1-benzofuran-3-carboxamide

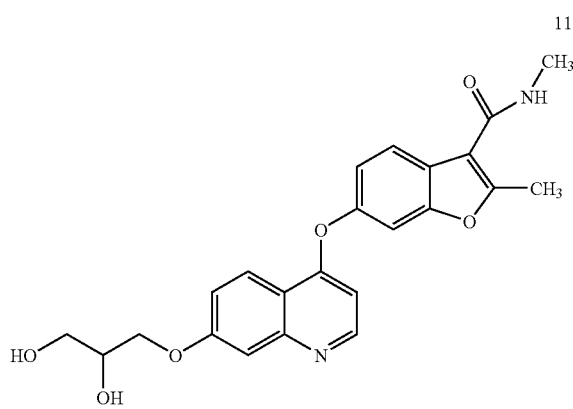

This compound was prepared according to the synthetic scheme depicted and described below.

120 mg of N,2-dimethyl-6-({7-[(2-oxo-1,3-dioxolan-4-yl)methoxy]quinolin-4-yl}oxy)-1-benzofuran-3-carboxamide 116-A (as prepared in Example 110) was treated with 20% NaOH (0.5 mL) in MeOH (2 mL) at room temperature for 1 h. The solution was then extracted with EtOAc. The concentrated residue was purified by HPLC using 10-40% $CH_3CN/H_2O$ over 30 min. to give 6-{[7-(2,3-dihydroxypropoxy)quinolin-4-yl]oxy}-N,2-dimethyl-1-benzofuran-3-carboxamide 116.

$^1$H NMR (400 MHz, DMSO-D6) δ ppm 2.57 (s, 3H) 2.76 (d, J=4.55 Hz, 3H) 3.44 (t, J=5.56 Hz, 2H) 3.82 (m, 1H) 3.98 (dd, J=10.11, 6.32 Hz, 1H) 4.13 (dd, J=10.11, 4.04 Hz, 1H) 4.68 (t, J=5.68 Hz, 1H) 4.99 (d, J=5.05 Hz, 1H) 6.37 (d, J=5.31 Hz, 1H) 7.16 (dd, J=8.46, 2.15 Hz, 1H) 7.24 (dd, J=9.10, 2.53 Hz, 1H) 7.33 (d, J=2.53 Hz, 1H) 7.56 (d, J=2.02 Hz, 1H) 7.78 (d, J=8.34 Hz, 1H) 7.92 (m, 1H) 8.17 (d, J=9.09 Hz, 1H) 8.52 (d, J=5.31 Hz, 1H). LC/MS (APCI, pos.): 423.0 (M+H).

Example 117

Preparation of N-[5-(aminomethyl)pyridin-2-yl]-6-[(7-methoxyquinolin-4-yl)oxy]-2-methyl-1-benzofuran-3-carboxamide

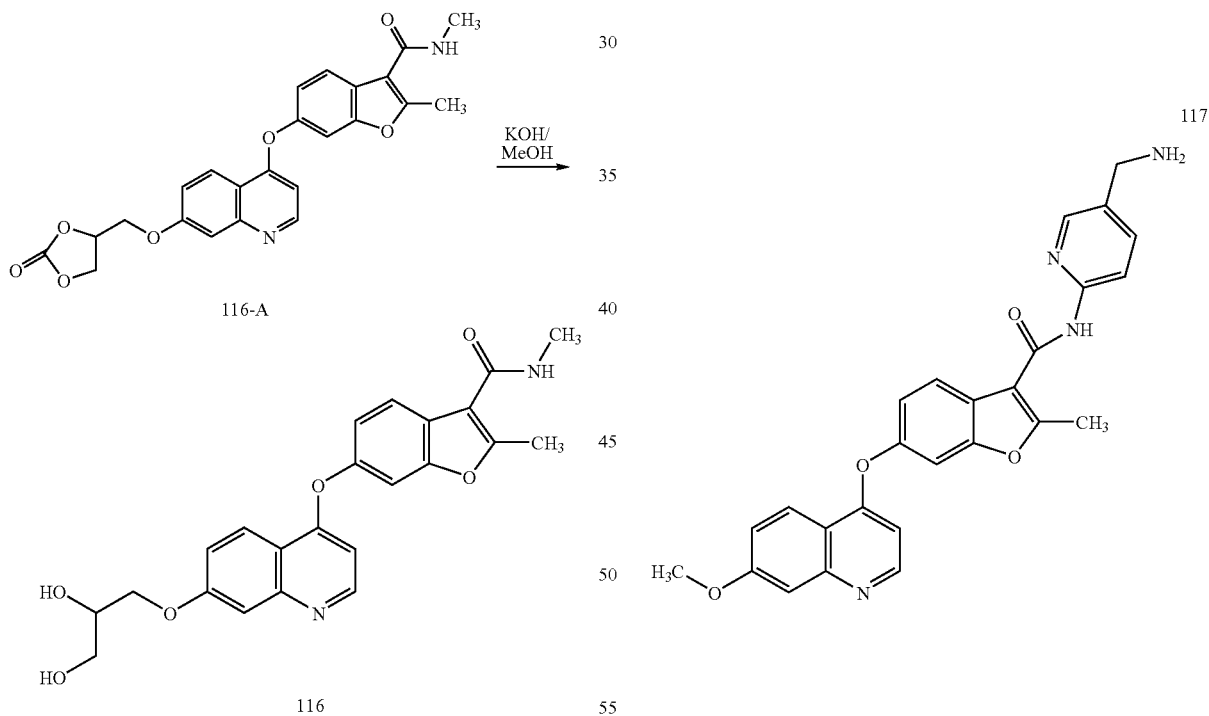

This compound was prepared according to the synthetic scheme depicted and described below.

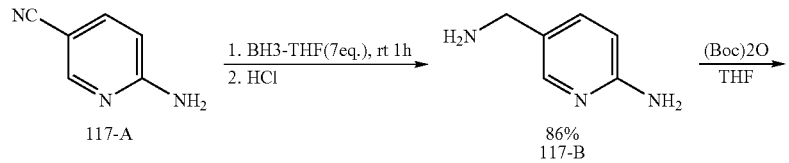

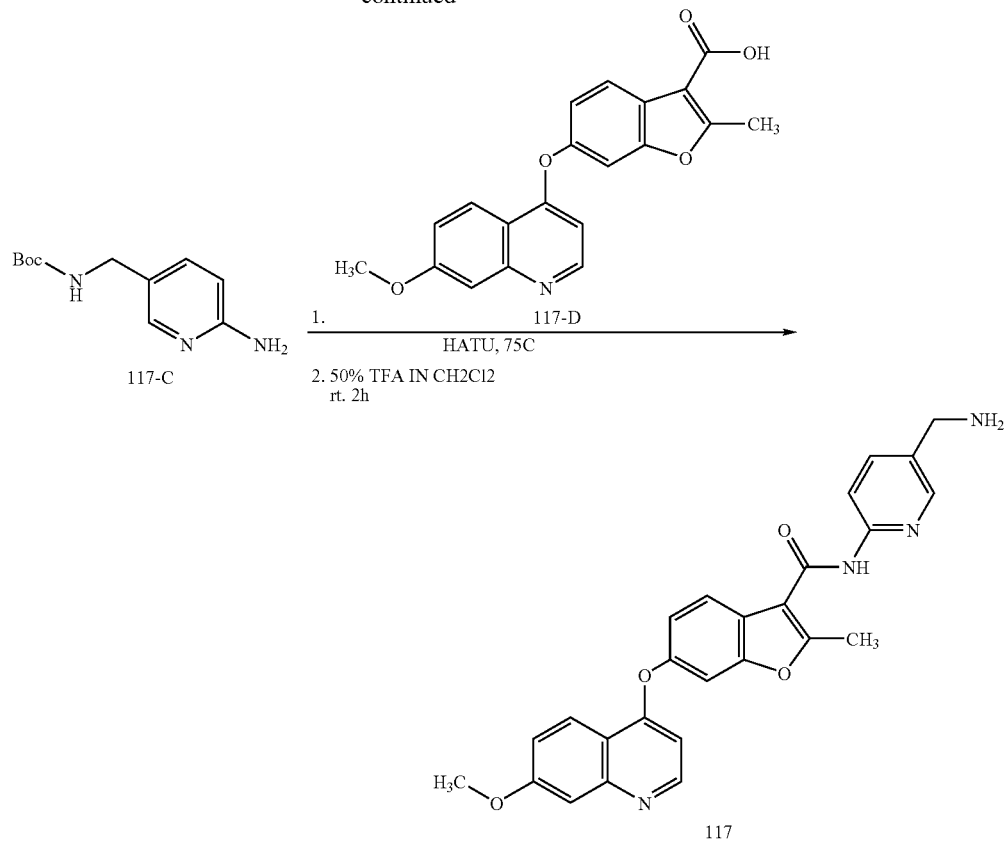

To a solution of 6-aminonicotinonitrile 117-A (5.0 g, 42 mmol) was added a solution of 1 M $BH_3$-THF (294 mL, 294 mmol) at 0° C. (prepared as in J. Org. Chem., Vol. 38, No. 5, 1973). The reaction was stirred at room temperature for 1 hour. The reaction mixture was then slowly pored into ice water. 100 mL 4N HCl was added and stirred for 20 min. The solution was basified with $NH_4OH$ to pH of about 11, and then concentrated. THF (300 mL×2) was added to the mixture followed by addition of solid KOH (excess). The suspension was stirred. The THF layer was collected by filtration and concentrated to give 5-(aminomethyl)pyridin-2-amine 117-B (4.3 g).

A solution of 117-B (4 g, 32.5 mmol), $(Boc)_2O$ (7 g, 32.5 mmol) and $Et_3N$ (6.5 g, 64.5 mmol) in THF (150 mL) was stirred at room temperature overnight. 2.1 g of tert-butyl (6-aminopyridin-3-yl)methylcarbamate 117-C was isolated by silica gel chromatography (0-5% $MeOH/CH_2Cl_2$).

117-C was coupled with 6-[(7-methoxyquinolin-4-yl)oxy]-2-methyl-1-benzofuran-3-carboxylic acid 117-D (as prepared in Scheme II discussed previously). After work up the mixture was treated with 50% TFA in $CH_2Cl_2$ to give N-[5-(aminomethyl)pyridin-2-yl]-6-[(7-methoxyquinolin-4-yl)oxy]-2-methyl-1-benzofuran-3-carboxamide 117-E.

$^1$H NMR (400 MHz, DMSO-D6) δ ppm 2.65 (s, 3H) 3.93 (d, J=10.61 Hz, 3H) 4.02 (q, J=5.56 Hz, 2H) 6.70 (d, J=6.32 Hz, 1H) 7.30 (dd, J=8.59, 2.02 Hz, 1H) 7.47 (m, 2H) 7.75 (d, J=2.02 Hz, 1H) 7.81 (d, J=8.34 Hz, 1H) 7.89 (dd, J=8.59, 2.27 Hz, 1H) 8.17 (m, 4H) 8.39 (m, 1H) 8.79 (d, J=6.06 Hz, 1H) 10.74 (s, 1H). LC/MS (APCI, pos.): 455.1 (M+H).

Example 118

Preparation of N-[6-(aminomethyl)pyridin-3-yl]-6-[(7-methoxyquinolin-4-yl)oxy]-2-methyl-1-benzofuran-3-carboxamide

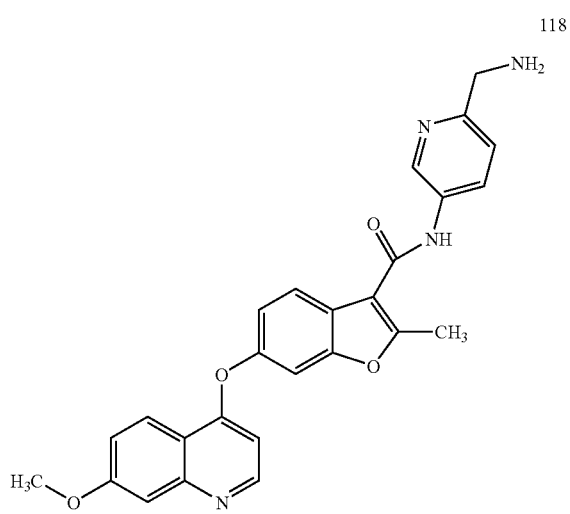

This compound was prepared according to methods analogous to those depicted and described in Example 117 using appropriate starting materials.

¹H NMR (400 MHz, DMSO-D6) δ ppm 2.65 (d, J=8.84 Hz, 3H) 3.94 (s, 3H) 4.13 (m, 2H) 6.65 (d, J=6.06 Hz, 1H) 7.31 (dd, J=8.46, 2.15 Hz, 1H) 7.45 (m, 3H) 7.76 (d, J=2.02 Hz, 1H) 7.86 (d, J=8.59 Hz, 1H) 8.15 (dd, J=8.34, 2.53 Hz, 1H) 8.22 (m, 2H) 8.36 (d, J=9.10 Hz, 1H) 8.78 (d, J=6.06 Hz, 1H) 8.91 (d, J=2.53 Hz, 1H) 10.41 (s, 1H) LC/MS (APCI, pos.): 455.1 (M+H).

Example 119

Preparation of 4-{[4-({2-methyl-3-[(methylamino)carbonyl]-1-benzofuran-6-yl}oxy)quinolin-7-yl]oxy}butanoic acid

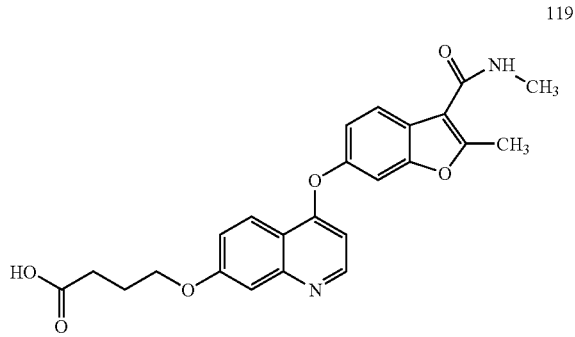

119

This compound was prepared according to the synthetic scheme depicted and described below.

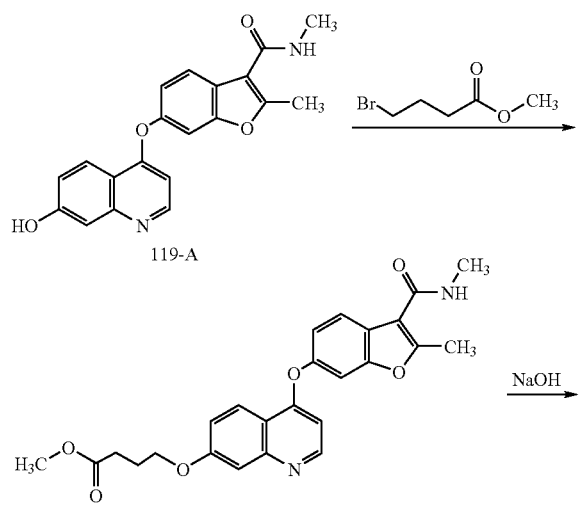

A solution of 6-[(7-hydroxyquinolin-4-yl)oxy]-N,2-dimethyl-1-benzofuran-3-carboxamide 119-A (200 mg, 0.57 mmol), methyl 4-bromobutanoate (155 mg, 0.85 mmol), and $Cs_2CO_3$ (433 mg, 1.14 mmol) in a mixed solvent of $CH_3CN$ (4 mL)/DMF (1 mL) was heated to 65° C. overnight. The reaction mixture was extracted with EtOAc, concentrated and dissolved in 5 mL of MeOH. To the solution was added 1N NaOH (1 mL). The solution was stirred at room temperature for 2 hours and then heated to 60° C. for 2 hours. The solution was acidified with AcOH to a pH of about 6 and extracted with EtOAc. The concentrated residue was purified by HPLC using 20-60% $CH_3CN/H_2O$ over 30 min. to give 4-{[4-({2-methyl-3-[(methylamino)carbonyl]-1-benzofuran-6-yl}oxy)quinolin-7-yl]oxy}butanoic acid 119.

¹H NMR (400 MHz, DMSO-D6) δ ppm 2.27 (m, 2H) 2.69 (t, J=7.20 Hz, 2H) 2.88 (s, 3H) 3.06 (d, J=4.55 Hz, 2H) 4.42 (t, J=6.44 Hz, 2H) 6.67 (d, J=5.31 Hz, 1H) 7.47 (dd, J=8.46, 2.15 Hz, 1H) 7.53 (dd, J=9.22, 2.40 Hz, 1H) 7.63 (d, J=2.53 Hz, 1H) 7.86 (d, J=2.27 Hz, 1H) 8.08 (d, J=8.34 Hz, 1H) 8.22 (d, J=4.55 Hz, 1H) 8.47 (d, J=9.10 Hz, 1H) 8.82 (d, J=5.31 Hz, 1H) 12.41 (s, 1H). LC/MS (APCI, pos.): 435.1 (M+H).

Example 120

Preparation of {[4-({2-methyl-3-[(methylamino)carbonyl]-1-benzofuran-6-yl}oxy)quinolin-7-yl]oxy}acetic acid

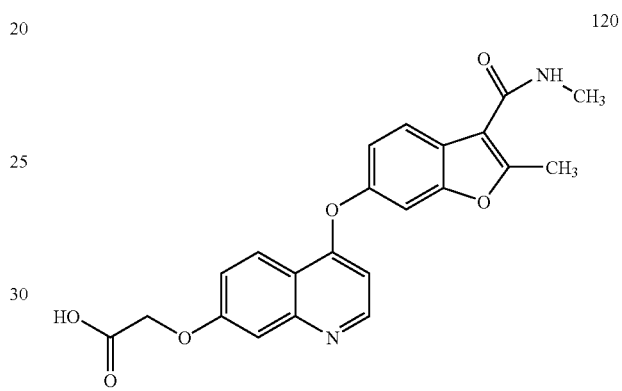

120

This compound was prepared according to methods analogous to those depicted and described in Example 119, except that methyl 2-bromoethanoate is used instead of methyl 4-bromobutanoate.

¹H NMR (400 MHz, CHLOROFORM-D) δ ppm 2.72 (s, 3H) 3.04 (d, J=4.04 Hz, 2H) 4.85 (s, 2H) 6.56 (m, 1H) 7.15 (dd, J=8.59, 2.02 Hz, 1H) 7.32 (d, J=2.02 Hz, 1H) 7.39 (m, 1H) 7.47 (dd, J=9.35, 2.27 Hz, 1H) 7.55 (d, J=2.27 Hz, 1H) 7.83 (d, J=8.34 Hz, 1H) 8.38 (m, 1H) 8.54 (m, 1H). LC/MS (APCI, pos.): 407.0 (M+H).

Example 121

Preparation of N-(4,6-dimethylpyridin-2-yl)-2-methyl-6-{[7-(2-pyrrolidin-1-ylethoxy)quinolin-4-yl]oxy}-1-benzofuran-3-carboxamide

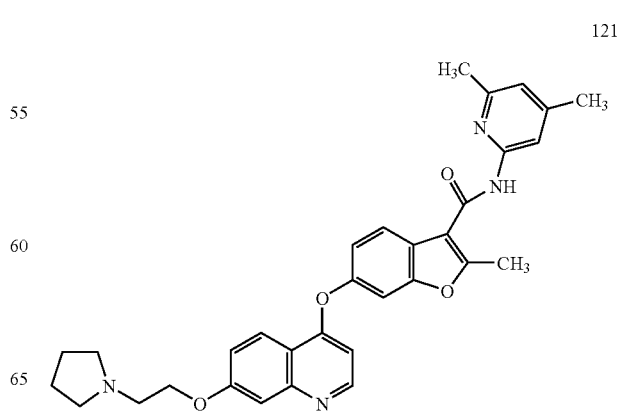

121

This compound was prepared according to the synthetic scheme depicted and described below.

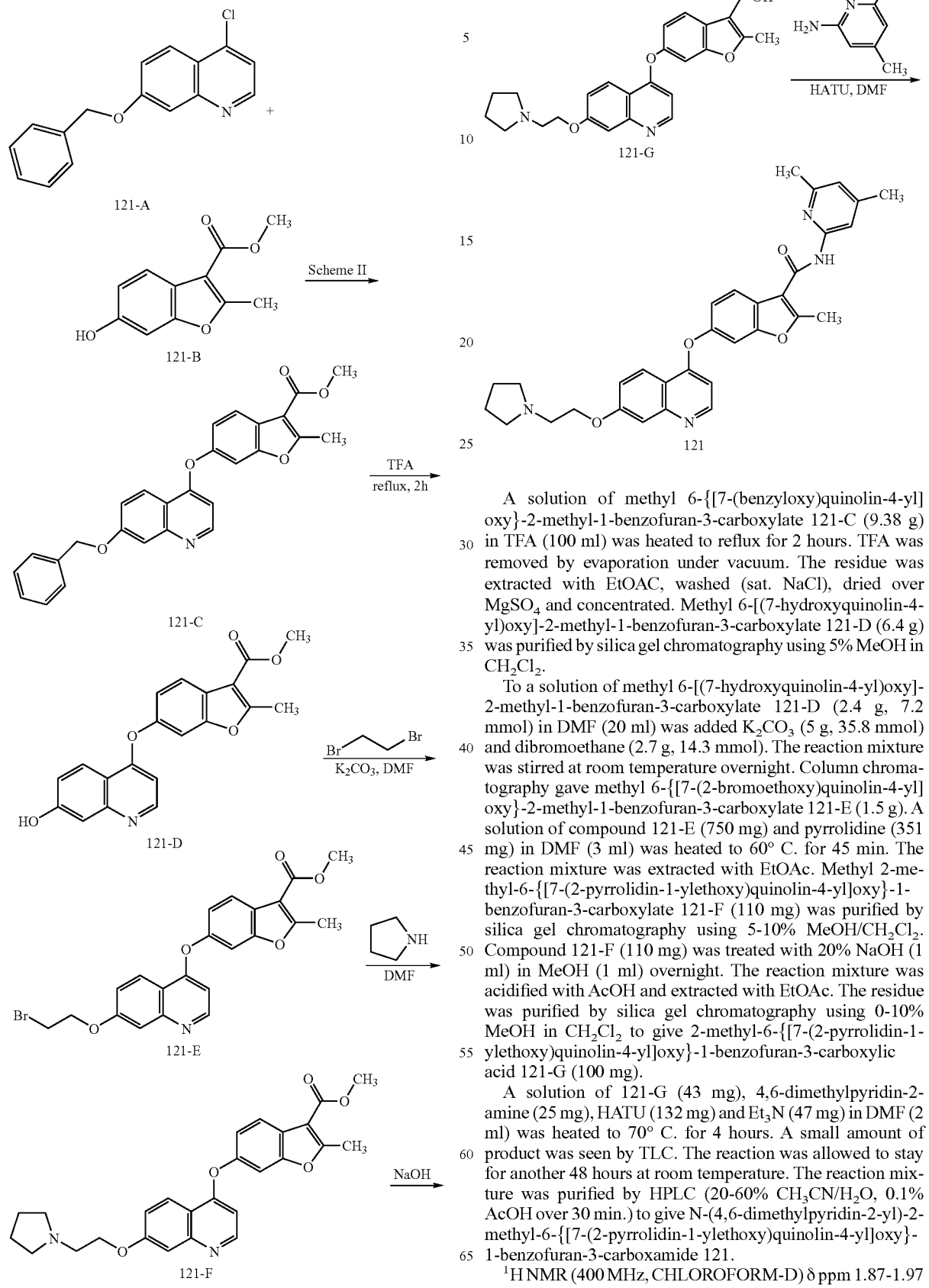

A solution of methyl 6-{[7-(benzyloxy)quinolin-4-yl]oxy}-2-methyl-1-benzofuran-3-carboxylate 121-C (9.38 g) in TFA (100 ml) was heated to reflux for 2 hours. TFA was removed by evaporation under vacuum. The residue was extracted with EtOAC, washed (sat. NaCl), dried over MgSO$_4$ and concentrated. Methyl 6-[(7-hydroxyquinolin-4-yl)oxy]-2-methyl-1-benzofuran-3-carboxylate 121-D (6.4 g) was purified by silica gel chromatography using 5% MeOH in CH$_2$Cl$_2$.

To a solution of methyl 6-[(7-hydroxyquinolin-4-yl)oxy]-2-methyl-1-benzofuran-3-carboxylate 121-D (2.4 g, 7.2 mmol) in DMF (20 ml) was added K$_2$CO$_3$ (5 g, 35.8 mmol) and dibromoethane (2.7 g, 14.3 mmol). The reaction mixture was stirred at room temperature overnight. Column chromatography gave methyl 6-{[7-(2-bromoethoxy)quinolin-4-yl]oxy}-2-methyl-1-benzofuran-3-carboxylate 121-E (1.5 g). A solution of compound 121-E (750 mg) and pyrrolidine (351 mg) in DMF (3 ml) was heated to 60° C. for 45 min. The reaction mixture was extracted with EtOAc. Methyl 2-methyl-6-{[7-(2-pyrrolidin-1-ylethoxy)quinolin-4-yl]oxy}-1-benzofuran-3-carboxylate 121-F (110 mg) was purified by silica gel chromatography using 5-10% MeOH/CH$_2$Cl$_2$. Compound 121-F (110 mg) was treated with 20% NaOH (1 ml) in MeOH (1 ml) overnight. The reaction mixture was acidified with AcOH and extracted with EtOAc. The residue was purified by silica gel chromatography using 0-10% MeOH in CH$_2$Cl$_2$ to give 2-methyl-6-{[7-(2-pyrrolidin-1-ylethoxy)quinolin-4-yl]oxy}-1-benzofuran-3-carboxylic acid 121-G (100 mg).

A solution of 121-G (43 mg), 4,6-dimethylpyridin-2-amine (25 mg), HATU (132 mg) and Et$_3$N (47 mg) in DMF (2 ml) was heated to 70° C. for 4 hours. A small amount of product was seen by TLC. The reaction was allowed to stay for another 48 hours at room temperature. The reaction mixture was purified by HPLC (20-60% CH$_3$CN/H$_2$O, 0.1% AcOH over 30 min.) to give N-(4,6-dimethylpyridin-2-yl)-2-methyl-6-{[7-(2-pyrrolidin-1-ylethoxy)quinolin-4-yl]oxy}-1-benzofuran-3-carboxamide 121.

$^1$H NMR (400 MHz, CHLOROFORM-D) δ ppm 1.87-1.97 (m, 4H) 2.38 (s, 3H) 2.45 (s, 3H) 2.82 (s, 3H) 2.79-2.89 (m, 4H) 3.08-3.20 (m, 2H) 4.35 (t, 2H) 6.45 (d, J=5.31 Hz, 1H) 6.80 (s, 1H) 7.21 (dd, J=8.46, 2.15 Hz, 1H) 7.29 (dd, 1H) 7.33 (d, J=2.02 Hz, 1H) 7.43 (d, J=2.53 Hz, 1H) 7.91 (d, J=8.34 Hz, 1H) 8.00 (s, 1H) 8.28 (d, J=9.35 Hz, 2H) 8.60 (d, J=5.31 Hz, 1H) LCMS: (APCI) m/z (M+1) 537.1 HRMS (Observed) 537.2492 (Calculated) 537.2497. Mass Error −0.92 ppm Example 122

Preparation of methyl 2-methyl-6-{[7-(2-morpholin-4-ylethoxy)quinolin-4-yl]oxy}-1-benzofuran-3-carboxylate

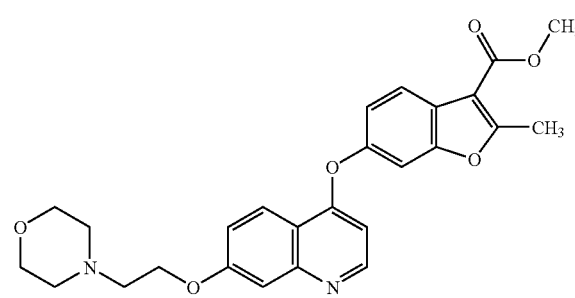

This compound was prepared according to the synthetic scheme depicted and described below.

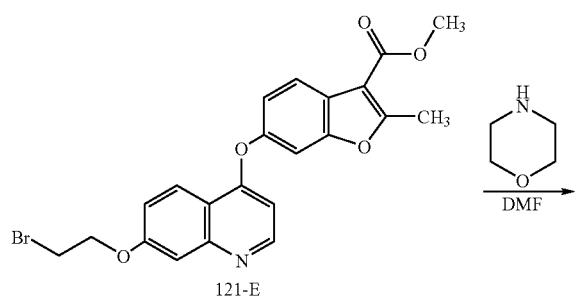

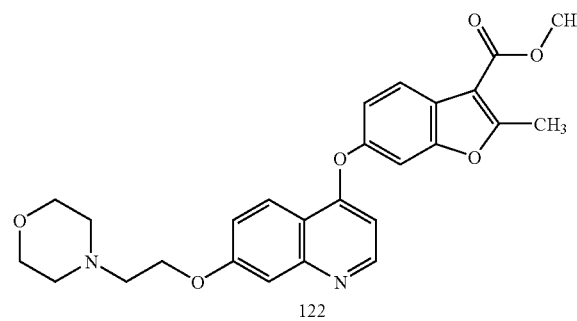

$^1$H NMR (400 MHz, CHLOROFORM-D) δ ppm 2.77-2.82 (m, 3H) 2.82-2.95 (m, 3H) 3.03-3.18 (m, 3H) 3.82-3.94 (m, 4H) 3.95-4.01 (m, 3H) 4.42-4.55 (m, 2H) 6.54 (d, J=5.81 Hz, 1H) 7.16 (dd, J=8.59, 2.02 Hz, 1H) 7.30 (d, J=2.53 Hz, 1H) 7.36 (d, J=4.55 Hz, 1H) 7.73 (s, 1H) 8.06 (d, J=8.59 Hz, 1H) 8.35 (d, J=9.35 Hz, 1H) 8.57 (d, J=6.06 Hz, 1H) LCMS: (APCI) m/z (M+1) 463.1

Example 123

Preparation of 6-({7-[2-hydroxy-3-(methylamino)propoxy]quinolin-4-yl}oxy)-N,2-dimethyl-1-benzofuran-3-carboxamide

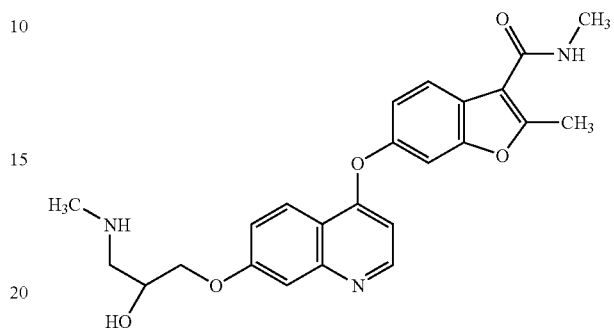

This compound was prepared according to the synthetic scheme depicted and described below.

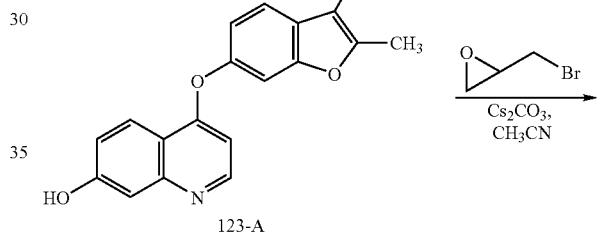

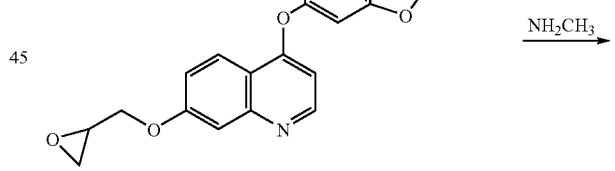

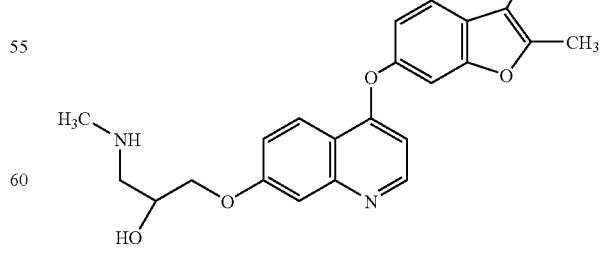

A solution of 6-[(7-hydroxyquinolin-4-yl)oxy]-N,2-dimethyl-1-benzofuran-3-carboxamide 123-A (1 g, 2.9 mmol), 2-(bromomethyl)oxirane (467 mg, 3.4 mmol) and Cs$_2$CO$_3$ (1.4 g, 4.2 mmol) in CH₃CN (25 ml) was heated to 65° C. for 3 hours. The solution was extracted with EtOAc. N,2-dimethyl-6-{[7-(oxiran-2-ylmethoxy)quinolin-4-yl]oxy}-1-benzofuran-3-carboxamide 123-B (1.1 g) was isolated by a silica gel column using 1-5% MeOH in CH₂Cl₂. To a solution of 123-B (150 mg, 0.35 mmol) in THF (5 ml) was added a solution of methylamine in MeOH (1N, 1 ml). The solution was heated to 65° C. for 2 hours. The crude product was purified by HPLC (10-40% CH₃CN/H₂O over 30 min.) to give 6-({7-[2-hydroxy-3-(methylamino)propoxy]quinolin-4-yl}oxy)-N,2-dimethyl-1-benzofuran-3-carboxamide 123.

¹H NMR (400 MHz, Solvent) δ ppm 1.80 (s, 3H) 2.56 (s, 3H) 2.88 (s, 3H) 3.03 (m, 2H) 3.21 (m, 3H) 4.10 (m, 2H) 4.22 (m, 1H) 6.42 (m, 1H) 7.09 (dd, J=8.46, 2.15 Hz, 1H) 7.28 (m, 3H) 7.74 (d, J=8.59 Hz, 1H) 8.23 (m, 1H) 8.44 (d, J=5.31 Hz, 1H). LC/MS (ACPI, pos.): 436.1 (M+H).

Example 124

Preparation of methyl 4-{[4-({2-methyl-3-[(methylamino)carbonyl]-1-benzofuran-6-yl}oxy)quinolin-7-yl]oxy}butanoate

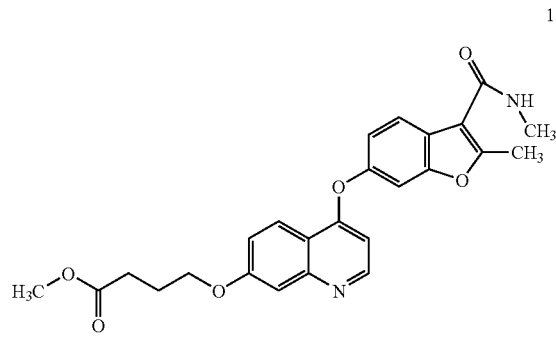

This compound was prepared according to the synthetic scheme depicted and described below.

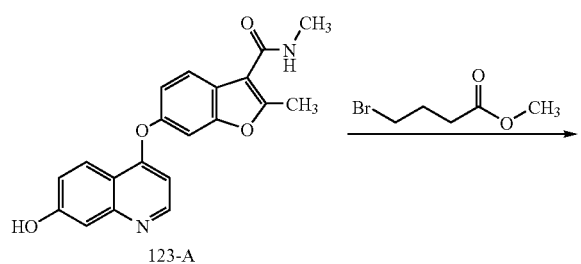

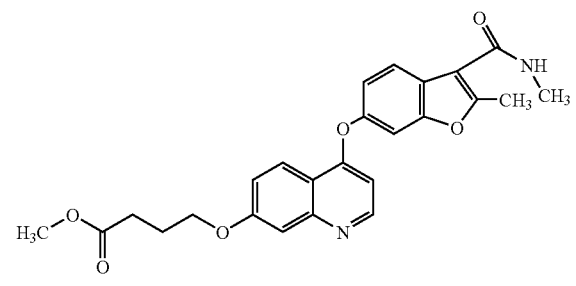

¹H NMR (400 MHz, DMSO-D6) δ ppm 2.03 (m, 2H) 2.49 (t, J=7.20 Hz, 2H) 2.59 (s, 3H) 2.76 (d, J=4.55 Hz, 3H) 3.56 (s, 3H) 4.17 (t, J=6.19 Hz, 2H) 6.62 (d, J=6.06 Hz, 1H) 7.24 (dd, J=8.59, 2.02 Hz, 1H) 7.40 (d, J=11.87 Hz, 1H) 7.41 (s, 1H) 7.66 (d, J=1.77 Hz, 1H) 7.83 (d, J=8.34 Hz, 1H) 7.93 (m, 1H) 8.34 (d, J=8.84 Hz, 1H) 8.72 (d, J=6.06 Hz, 1H). LC/MS (ACPI, pos.): 450.1 (M+H).

Example 125

Preparation of 7-Methoxy-4-(2-methyl-benzofuran-6-yloxy)-quinoline

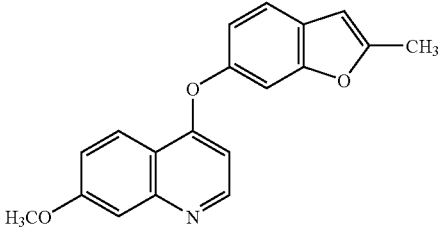

This compound was prepared according to the synthetic scheme described below.

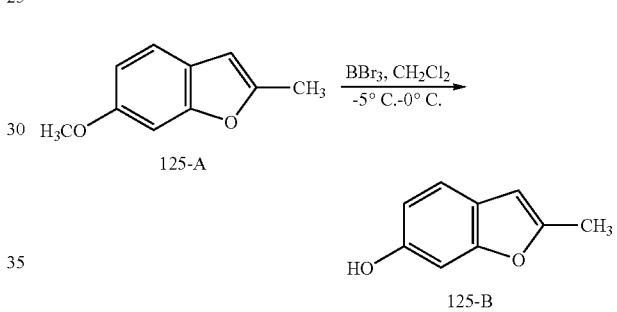

To a stirred solution of 6-Methoxy-2-methyl-benzofuran 125-A (1.76 g, 10.85 mmol) in 45 ml of CH₂Cl₂ at −5° C. was added BBr₃ (24 ml of 1M BBr₃ in CH₂Cl₂, 16.28 mmol). The reaction was allowed to warm to 0° C. and stirred at that temperature for 1.5 hr. The reaction was poured into a mixture of ice and saturated aqueous NaHCO₃ and layers were separated. The aqueous layer was re-extracted with CH₂Cl₂. The combined organic layers were dried (MgSO₄) and concentrated under reduced pressure to a brown oil. The residue was chromatographed on silica gel eluting CH₂Cl₂ to give 872 mg (54%) of 6-Hydroxy-2-methyl-benzofuran 125-B. Anal calc'd for C₉H₈O₂: C, 72.96; H, 5.44. Found: C, 72.72; H, 5.43.

¹H NMR (400 MHz, DMSO-D6) ⊓ ppm 9.31 (s, 1H) 7.24 (d, J=8.34 Hz, 1H) 6.81 (d, J=1.77 Hz, 1H) 6.64 (dd, J=8.34, 2.02 Hz, 1H) 6.38 (s, 1H) 2.35 (s, 3H).

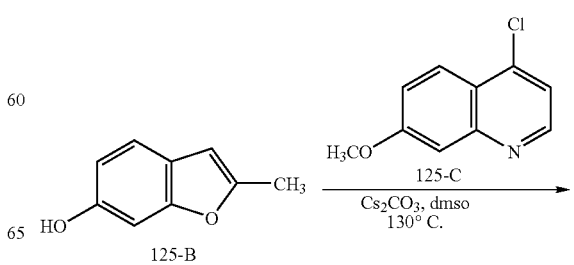

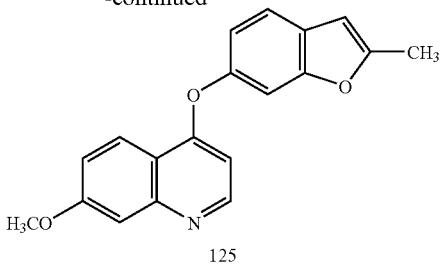

125

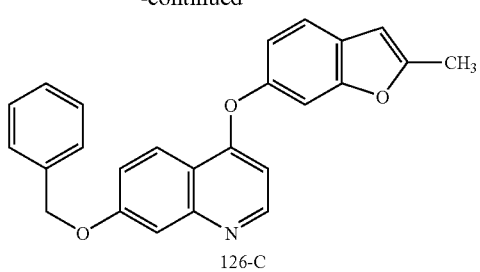

126-C

To a degassed solution of 4-Chloro-7-methoxy-quinoline 125-C (76 mg, 0.39 mmol) and 6-Hydroxy-2-methyl-benzofuran 125-B (58 mg, 0.39 mmol) in 1.5 ml of dmso, was added Cesium Carbonate (320 mg, 0.98 mmol). The reaction mixture was heated at 130° C. for 1.5 hr, cooled, poured into saturated aqueous NaCl solution, and extracted with EtOAc and Et$_2$O. The combined extracts washed again with saturated aqueous NaCl solution, dried (MgSO$_4$), and concentrated under reduced pressure. The residue was chromatographed on silica gel eluting a gradient of 9% to 10% of EtOAc in CH$_2$Cl$_2$. In this manner 7-Methoxy-4-(2-methyl-benzofuran-6-yloxy)-quinoline 125 was prepared as a yellow solid (70 mg, 58%).

$^1$H NMR (400 MHz, DMSO-D6) δ ppm 8.57 (d, J=5.05 Hz, 1H) 8.23 (d, J=9.35 Hz, 1H) 7.62 (d, J=8.34 Hz, 1H) 7.52 (d, J=1.77 Hz, 1H) 7.40 (d, J=2.53 Hz, 1H) 7.28 (dd, J=9.09, 2.53 Hz, 1H) 7.11 (dd, J=8.34, 2.02 Hz, 1H) 6.65 (s, 1H) 6.41 (d, J=5.31 Hz, 1H) 3.93 (s, 3H) 2.46 (s, 3H). The biological activity of this compound (125) is indicated by the following assay results: FLVK: 68% inhibition @ 1 µM; FGF: 32% inhibition @ 1 µM. See also the results shown in Table 1.

Example 126

Preparation of 4-(2-Methyl-benzofuran-6-yloxy)-7-(2-morpholin-4-yl-ethoxy)-quinoline

126

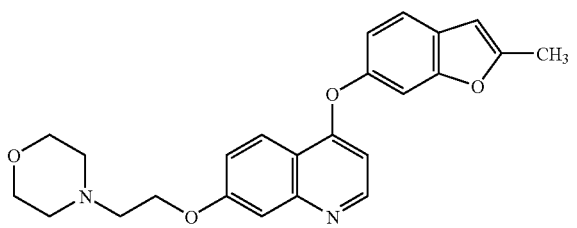

This compound was prepared according to the scheme described below.

Using the general procedure shown in Example 125, using 6-Hydroxy-2-methyl-benzofuran 126-A and 7-Benzyloxy-4-chloro-quinoline 126-B, 7-Benzyloxy-4-(2-methyl-benzofuran-6-yloxy)-quinoline 126-C was prepared in 82% yield.

$^1$H NMR (400 MHz, DMSO-D6) δ ppm 8.56 (d, J=5.31 Hz, 1H) 8.24 (d, J=9.35 Hz, 1H) 7.62 (d, J=8.34 Hz, 1H) 7.46-7.57 (m, 4H) 7.42 (t, J=7.33 Hz, 2H) 7.29-7.39 (m, 2H) 7.11 (dd, J=8.46, 2.15 Hz, 1H) 6.64 (s, 1H) 6.42 (d, J=5.31 Hz, 1H) 5.31 (s, 2H) 2.45 (s, 3H).

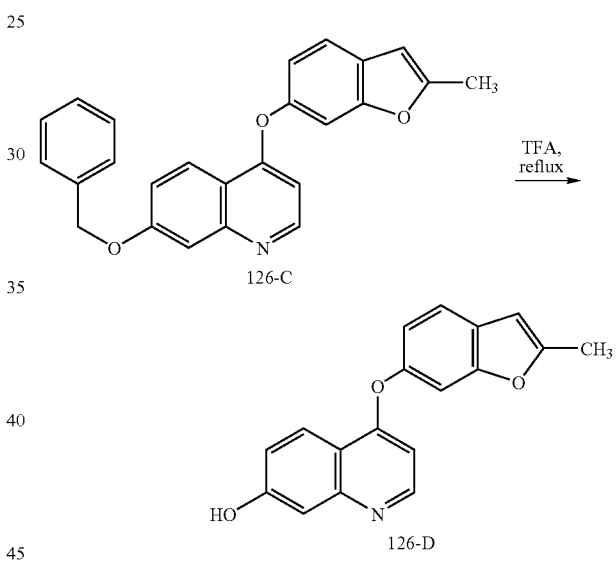

A solution of 7-Benzyloxy-4-(2-methyl-benzofuran-6-yloxy)-quinoline 126-C (349 mg, 0.91 mmol) in TFA (1.5 ml) was heated to reflux for 2 hr. The volatiles were removed under reduced pressure, the residue dissolved in EtOAc, and washed sequentially with saturated aqueous NaHCO$_3$ then brine. The organic layer was dried (MgSO$_4$) and concentrated under reduced pressure. The residue was triturated with TBME and used without further purification in the next step.

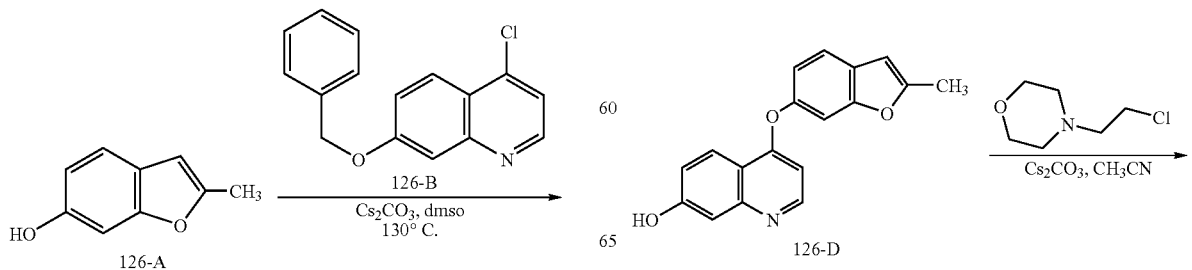

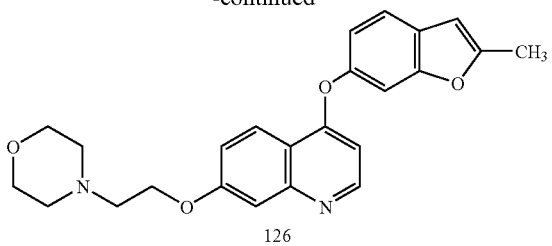

126

A suspension of 4-(2-Chloro-ethyl)-morpholine hydrochloride (153 mg, 0.82 mmol) and Cesium Carbonate (537 mg, 1.65 mmol) in CH$_3$CN (2 ml) was stirred at room temperature for 1 hr. The 4-(2-Methyl-benzofuran-6-yloxy)-quinolin-7-ol 126-D (120 mg, 0.41 mmol) in CH$_3$CN (2 ml) was added and the reaction was heated to reflux for 2 hr. The bright yellow reaction was cooled, poured into brine, and extracted with EtOAc (2 times). The combined organic layers were washed with brine, dried (MgSO$_4$), and concentrated under reduced pressure. The residue was chromatographed on silica gel eluting with 10% MeOH in EtOAc/CH$_2$Cl$_2$ (1:1). This gave slightly impure material which was re-purified by HPLC to give 110 mg (42%) of 4-(2-Methyl-benzofuran-6-yloxy)-7-(2-morpholin-4-yl-ethoxy)-quinoline 126 as the bis TFA salt.

$^1$H NMR (400 MHz, DMSO-D6) δ ppm 9.77-10.27 (broad s, 2H) 8.85 (none, 1H) 8.76 (d, J=5.56 Hz, 1H) 8.42 (d, J=9.09 Hz, 1H) 7.68 (d, J=8.34 Hz, 1H) 7.56 (d, J=2.27 Hz, 1H) 7.47 (d, 1H) 7.17 (dd, J=8.34, 2.02 Hz, 1H) 6.61-6.73 (m, 2H) 4.60 (d, J=4.29 Hz, 2H) 3.06-4.18 (m, 10H) 2.38-2.49 (m, 3H).

The biological activity of this compound (126) is indicated by the following assay results: FLVK: Ki=32 nM; FGF: 38% inhibition @ 1 µM.

Biological Testing—Enzyme Assays

The stimulation of cell proliferation by growth factors such as VEGF, FGF, and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

(i) VEGF-R2 Construct for Assay:

This construct determines the ability of a test compound to inhibit tyrosine kinase activity. A construct (VEGF-R2D50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2D50 contains residues 806-939 and 990-1171, and also one point mutation (E990V) within the kinase insert domain relative to wild-type VEGF-R2. Autophosphorylation of the purified construct was performed by incubation of the enzyme at a concentration of 4 mM in the presence of 3 mM ATP and 40 mM MgCl$_2$ in 100 mM HEPES, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., Biochemistry, 37, 16788-16801 (1998).

(ii) FGF-R1 Construct for Assay:

The intracellular kinase domain of human FGF-R1 was expressed using the baculovirus vector expression system starting from the endogenous methionine residue 456 to glutamate 766, according to the residue numbering system of Mohammadi et al., Mol. Cell. Biol., 16, 977-989 (1996). In addition, the construct also has the following 3 amino acid substitutions: L457V, C488A, and C584S.

Example A

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm (e$_{340}$=6.22 cm$^{-1}$ mM$^{-1}$) using a Beckman DU 650 spectrophotometer. Assay conditions for phosphorylated VEGF-R2D50 (indicated as FLVK-P in the tables below) were the following: 1 mM PEP; 250 mM NADH; 50 units of LDH/mL; 20 units of PK/mL; 5 mM DTT; 5.1 mM poly(E$_4$Y$_1$); 1 mM ATP; and 25 mM MgCl$_2$ in 200 mM HEPES, pH 7.5. Assay conditions for unphosphorylated VEGF-R2D50 (indicated as FLVK in the tables) were the following: 1 mM PEP; 250 mM NADH; 50 units of LDH/mL; 20 units of PK/mL; 5 mM DTT; 20 mM poly(E$_4$Y$_1$); 3 mM ATP; and 60 mM MgCl$_2$ and 2 mM MnCl$_2$ in 200 mM HEPES, pH 7.5. Assays were initiated with 5 to 40 nM of enzyme. K$_i$ values were determined by measuring enzyme activity in the presence of varying concentrations of test compounds. The percent inhibition at 50 nM (% inhibition @ 50 nM) was determined by linear least-squares regression analysis of absorbance as a function of time. The binding inhibitions were fitted to equation as described by Morrison. The data were analyzed using Enzyme Kinetic and Kaleidagraph software.

Example B

FGF-R Assay

The spectrophotometric assay was carried out as described above for VEGF-R2, except for the following changes in concentration: FGF-R=50 nM, ATP=2 mM, and poly (E4Y1)=15 mM.

Example C

HUVEC+VEGF Proliferation Assay

This assay determines the ability of a test compound to inhibit the growth factor-stimulated proliferation of human umbilical vein endothelial cells ("HUVEC"). HUVEC cells (passage 3-4, Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 mg/mL endothelial cell growth supplement (ECGS), and 0.1 mg/mL heparin). Exponentially-growing HUVEC cells were used in experiments thereafter. Ten to twelve thousand HUVEC cells were plated in 96-well dishes in 100 ml of rich, culture medium (described above). The cells were allowed to attach for 24 hours in this medium. The medium was then removed by aspiration and 105 ml of starvation media (F12K+1% FBS) was added to each well. After 24 hours, 15 ml of test agent dissolved in 1% DMSO in starvation medium or this vehicle alone was added into each treatment well; the final DMSO concentration was 0.1%. One hour later, 30 ml of VEGF (30 ng/mL) in starvation media was added to all wells except those containing untreated controls; the final VEGF concentration was 6 ng/mL. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595 nm was determined on a 96-well spectrophotometer plate reader.

Example D

Mouse PK Assay

The pharmacokinetics (e.g., absorption and elimination) of drugs in mice were analyzed using the following experiment. Test compounds were formulated as a suspension in a 30:70 (PEG 400: acidified $H_2O$) vehicle. This solution was administered orally (p.o.) and intraperitoneally (i.p.) at 50 mg/kg to two distinct groups (n=4) of B6 female mice. Blood samples were collected via an orbital bleed at time points: 0 hour (pre-dose), 0.5 hr, 1.0 hr, 2.0 hr, and 4.0 hr post dose. Plasma was obtained from each sample by centrifugation at 2500 rpm for 5 min. Test compound was extracted from the plasma by an organic protein precipitation method. For each time bleed, 50 μL of plasma was combined with 1.0 mL of acetonitrile, vortexed for 2 min. and then spun at 4000 rpm for 15 min. to precipitate the protein and extract out the test compound. Next, the acetonitrile supernatant (the extract containing test compound) was poured into new test tubes and evaporated on a hot plate (25° C.) under a steam of $N_2$ gas. To each tube containing the dried test compound extract, 125 μL of mobile phase (60:40, 0.025 M $NH_4H_2PO_4$+2.5 mL/L TEA:acetonitrile) was added. The test compound was resuspended in the mobile phase by vortexing and more protein was removed by centrifugation at 4000 rpm for 5 min. Each sample was poured into an HPLC vial for test compound analysis on an Hewlett Packard 1100 series HPLC with UV detection. From each sample, 95 μL was injected onto a Phenomenex-Prodigy reverse phase C-18, 150×3.2 mm column and eluted with a 45-50% acetonitrile gradient run over 10 min. Test-compound plasma concentrations (μg/mL) were determined by a comparison to standard curve (peak area vs. conc. μg/mL) using known concentrations of test compound extracted from plasma samples in the manner described above. Along with the standards and unknowns, three groups (n=4) of quality controls (0.25 μg/mL, 1.5 μg/mL, and 7.5 μg/mL) were run to insure the consistency of the analysis. The standard curve had an $R_2$>0.99 and the quality controls were all within 10% of their expected values. The quantitated test samples were plotted for visual display using Kalidagraph software and their pharmacokinetic parameters were determined using WIN NONLIN software.

Example E

Human Liver Microsome (HLM) Assay

Compound metabolism in human liver microsomes was measured by LC-MS analytical assay procedures as follows. First, human liver microsomes (HLM) were thawed and diluted to 5 mg/mL with cold 100 mM potassium phosphate ($KPO_4$) buffer. Appropriate amounts of $KPO_4$ buffer, NADPH-regenerating solution (containing B-NADP, glucose-6-phosphate, glucose-6-phosphate dehydrogenase, and $MgCl_2$), and HLM were preincubated in 13×100 mm glass tubes at 37° C. for 10 min. (3 tubes per test compound—triplicate). Test compound (5 μM final) was added to each tube to initiate reaction and was mixed by gentle vortexing, followed by incubation at 37° C. At t=0, and 2 h, a 250-uL sample was removed from each incubation tube to separate 12×75 mm glass tubes containing 1 mL ice-cold acetonitrile with 0.05 μM reserpine. Samples were centrifuged at 4000 rpm for 20 min. to precipitate proteins and salt (Beckman Allegra 6KR, S/N ALK98D06, #634). Supernatant was transferred to new 12×75 mm glass tubes and evaporated by Speed-Vac centrifugal vacuum evaporator. Samples were reconstituted in 200 μL 0.1% formic acid/acetonitrile (90/10) and vortexed vigorously to dissolve. The samples were then transferred to separate polypropylene microcentrifuge tubes and centrifuged at 14000×g for 10 min. (Fisher Micro 14, S/N M0017580). For each replicate (#1-3) at each timepoint (0 and 2 h), an aliquot sample of each test compound was combined into a single HPLC vial insert (6 total samples) for LC-MS analysis, which is described below.

The combined compound samples were injected into the LC-MS system, composed of a Hewlett-Packard HP1100 diode array HPLC and a Micromass Quattro II triple quadruple mass spectrometer operating in positive electrospray SIR mode (programmed to scan specifically for the molecular ion of each test compound). Each test compound peak was integrated at each timepoint. For each compound, peak area at each timepoint (n=3) was averaged, and this mean peak area at 2 h was divided by the average peak area at time 0 hour to obtain the percent test compound remaining at 2 h.

Example F

KDR (VEGFR2) Phosphorylation in PAE-KDR Cells Assay

This assay determines the ability of a test compound to inhibit the autophosphorylation of KDR in porcine aorta endothelial (PAE)-KDR cells. PAE cells that overexpress human KDR were used in this assay. The cells were cultured in Ham's F12 media supplemented with 10% fetal bovine serum (FBS) and 400 μg/mL G418. Thirty thousands cells were seeded into each well of a 96-well plate in 75 mL of growth media and allowed to attach for 6 hours at 37° C. Cells were then exposed to the starvation media (Ham's F12 media supplemented with 0.1% FBS) for 16 hours. After the starvation period was over, 10 mL of test agent in 5% DMSO in starvation media were added to the test wells and 10 mL of the vehicle (5% DMSO in starvation media) were added into the control wells. The final DMSO concentration in each well was 0.5%. Plates were incubated at 37° C. for 1 hour and the cells were then stimulated with 500 ng/ml VEGF (commercially available from R & D System) in the presence of 2 mM $Na_3VO_4$ for 8 minutes. The cells were washed once with 1 mm $Na_3VO_4$ in HBSS and lysed by adding 50 mL per well of lysis buffer. One hundred mL of dilution buffer were then added to each well and the diluted cell lysate was transferred to a 96-well goat ant-rabbit coated plate (commercially available from Pierce) which was pre-coated with Rabbit anti Human Anti-flk-1 C-20 antibody (commercially available from Santa Cruz). The plates were incubated at room temperature for 2 hours and washed seven times with 1% Tween 20 in PBS. HRP-PY20 (commercially available from Santa Cruz) was diluted and added to the plate for a 30-minute incubation. Plates were then washed again and TMB peroxidase substrate (commercially available from Kirkegaard & Perry) was added for a 10-minute incubation. One hundred mL of 0.09 N $H_2SO_4$ was added to each well of the 96-well plates to stop the reaction. Phosphorylation status was assessed by spectrophotometer reading at 450 nm. $IC_{50}$ values were calculated by curve fitting using a four-parameter analysis.

Example G

PAE-PDGFRb Phosphorylation in PAE-PDGFRB Cells Assay

This assay determines the ability of a test compound to inhibit the autophosphorylation of PDGFRb in porcine aorta endothelial (PAE)-PDGFRb cells. PAE cells that overexpress human PDGFRb were used in this assay. The cells were cultured in Ham's F12 media supplemented with 10% fetal bovine serum (FBS) and 400 ug/ml G418. Twenty thousands cells were seeded in each well of a 96-well plate in 50 mL of growth media and allowed to attach for 6 hours at 37° C. Cells were then exposed to the starvation media (Ham's F12 media supplemented with 0.1% FBS) for 16 hours. After the starvation period was over, 10 mL of test agent in 5% DMSO in starvation media were added to the test wells and 10 mL of the vehicle (5% DMSO in starvation media) were added into the control wells. The final DMSO concentration in each well was 0.5%. Plates were incubated at 37° C. for 1 hour and the cells were then stimulated with 1 mg/mL PDGF-BB (R & D System) in the presence of 2 mM $Na_3VO_4$ for 8 minutes. The cells were washed once with 1 mm $Na_3VO_4$ in HBSS and lysed by adding 50 mL per well of lysis buffer. One hundred mL of dilution buffer were then added to each well and the diluted cell lysate was transferred to a 96-well goat ant-rabbit coated plate (Pierce), which was pre-coated with Rabbit anti Human PDGFRb antibody (Santa Cruz). The plates were incubated at room temperature for 2 hours and washed seven times with 1% Tween 20 in PBS. HRP-PY20 (Santa Cruz) was diluted and added to the plate for a 30-minute incubation. Plates were then washed again and TMB peroxidase substrate (Kirkegaard & Perry) was added for a 10-minute incubation. One hundred mL of 0.09 N $H_2SO_4$ was added into each well of the 96-well plate to stop the reaction. Phosphorylation status was assessed by spectrophotometer reading at 450 nm. $IC_{50}$ values were calculated by curve fitting using a four-parameter analysis.

The results of the testing of the compounds using various assays are summarized in Table 1.

| Example | FLVK Ki (nM) A = >10 nm B = 1-10 nm C = <1 nm NT = Not tested | HUVEC + VEGF IC50 (nM) AVG |
|---|---|---|
| 1 | NT | NT |
| 2 | NT | NT |
| 3 | NT | NT |
| 4 | NT | NT |
| 6 | B | B |
| 7 | C | NT |
| 8 | C | C |
| 9 | C | B |
| 10 | B | B |
| 11 | B | C |
| 12 | A | Nt |
| 13 | C | B |
| 14 | B | B |
| 15 | B | NT |
| 16 | A | NT |
| 17 | NT | NT |
| 18 | A | NT |
| 19 | B | B |
| 20 | A | NT |
| 21 | NT | NT |
| 22 | NT | NT |
| 23 | A | NT |
| 24 | B | NT |
| 25 | NT | NT |
| 26 | NT | NT |
| 27 | A | NT |
| 28 | NT | B |
| 29 | C | B |
| 30 | C | NT |
| 31 | B | C |
| 32 | NT | B |
| 33 | B | NT |
| 34 | C | B |
| 35 | NT | C |
| 36 | B | C |
| 37 | B | C |
| 38 | B | C |
| 39 | NT | C |
| 40 | NT | C |
| 41 | NT | B |
| 42 | NT | C |
| 43 | NT | B |
| 44 | B | C |
| 45 | B | B |
| 46 | B | C |
| 47 | B | C |
| 48 | B | B |
| 49 | A | NT |
| 50 | B | B |
| 51 | A | B |
| 52 | B | B |
| 53 | B | B |
| 54 | A | NT |
| 55 | A | NT |
| 56 | A | NT |
| 57 | A | NT |
| 58 | NT | NT |
| 59 | NT | NT |
| 60 | A | NT |
| 61 | A | NT |
| 62 | NT | A |
| 63 | NT | C |
| 64 | NT | B |
| 65 | NT | NT |
| 66 | A | B |
| 67 | B | B |
| 68 | NT | NT |
| 69 | NT | B |
| 70 | NT | NT |
| 71 | B | NT |
| 72 | NT | NT |
| 73 | B | B |
| 74 | NT | NT |
| 75 | A | NT |
| 76 | A | NT |
| 77 | A | NT |
| 78 | A | NT |
| 79 | A | NT |
| 80 | A | NT |
| 81 | A | NT |
| 82 | A | NT |
| 83 | C | NT |
| 84 | B | B |
| 85 | A | NT |
| 86 | B | B |
| 87 | A | NT |
| 88 | B | B |
| 89 | C | NT |
| 90 | C | NT |

-continued

| Example | FLVK Ki (nM) A = >10 nm B = 1-10 nm C = <1 nm NT = Not tested | HUVEC + VEGF IC50 (nM) AVG |
|---|---|---|
| 91 | C | Nt |
| 92 | C | NT |
| 93 | C | NT |
| 94 | C | NT |
| 95 | C | NT |
| 96 | C | NT |
| 97 | C | NT |
| 98 | C | NT |
| 99 | NT | NT |
| 100 | NT | B |
| 101 | NT | NT |
| 102 | NT | NT |
| 103 | NT | NT |
| 104 | NT | NT |
| 105 | NT | NT |
| 106 | NT | NT |
| 107 | NT | NT |
| 108 | NT | B |
| 109 | NT | A |
| 110 | NT | NT |
| 111 | NT | NT |
| 112 | NT | NT |
| 113 | NT | NT |
| 114 | NT | NT |
| 115 | NT | NT |
| 116 | NT | NT |
| 117 | NT | NT |
| 118 | NT | NT |
| 119 | NT | NT |
| 120 | NT | NT |
| 121 | NT | NT |
| 122 | NT | NT |
| 123 | NT | NT |
| 124 | NT | NT |
| 125 | NT | NT |
| 126 | A | NT |

Examples of Pharmaceutical Formulations

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The exemplary compounds described above may be formulated into pharmaceutical compositions according to the following general examples.

Example I

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example II

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

We claim:
1. A compound of formula

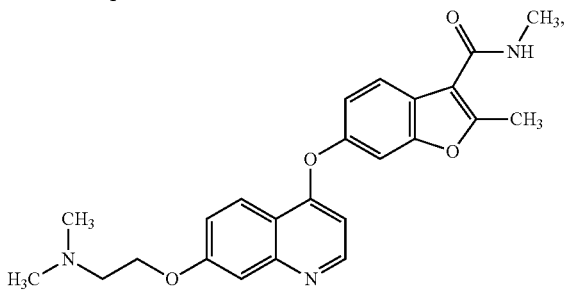

or a pharmaceutically acceptable salt thereof.

2. A pharmaceutical composition, comprising a therapeutically effective amount of a compound according to claim 1, or a pharmaceutically acceptable salt thereof, and a pharmaceutically acceptable carrier.

3. A method of treating a disease related to vasculogenesis or angiogenesis in a mammal, comprising administering to said mammal a therapeutically effective amount of a compound according to claim 1, or a pharmaceutically acceptable salt thereof, wherein said disease is age-related macular degeneration.

4. A method of treating a disease related to vasculogenesis or angiogenesis in a mammal, comprising administering to said mammal a therapeutically effective amount of a compound according to claim 1, or a pharmaceutically acceptable salt thereof, wherein said disease is diabetic retinopathy.

* * * * *